US008945589B2

(12) United States Patent
Telford et al.

(10) Patent No.: US 8,945,589 B2
(45) Date of Patent: Feb. 3, 2015

(54) IMMUNOGENIC COMPOSITIONS FOR *STREPTOCOCCUS AGALACTIAE*

(75) Inventors: John Telford, Monteriggioni (IT);
Guido Grandi, Milan (IT);
Immaculada Margarit Y Ros, Siena (IT); Domenico Maione, Castelnuovo Berardenga (IT)

(73) Assignee: Novartis Vaccines and Diagnostics, SRL, Siena (IT)

( * ) Notice: Subject to any disclaimer, the term of this patent is extended or adjusted under 35 U.S.C. 154(b) by 1843 days.

(21) Appl. No.: 10/568,422

(22) PCT Filed: Sep. 15, 2004

(86) PCT No.: PCT/US2004/030032
§ 371 (c)(1),
(2), (4) Date: Oct. 22, 2007

(87) PCT Pub. No.: WO2005/028618
PCT Pub. Date: Mar. 31, 2005

(65) Prior Publication Data
US 2008/0220010 A1   Sep. 11, 2008

Related U.S. Application Data

(63) Continuation-in-part of application No. PCT/US03/29167, filed on Sep. 15, 2003.

(60) Provisional application No. 60/548,789, filed on Feb. 26, 2004.

(51) Int. Cl.
*A61K 39/09* (2006.01)
*A61K 39/02* (2006.01)
*A61K 39/00* (2006.01)
*A61K 38/00* (2006.01)
*C07K 1/00* (2006.01)

(52) U.S. Cl.
CPC ............. *A61K 39/09* (2013.01); *Y10S 530/825* (2013.01)
USPC ................ 424/244.1; 424/192.1; 424/190.1; 424/234.1; 424/184.1; 514/1.1; 530/350; 530/300; 530/825

(58) Field of Classification Search
None
See application file for complete search history.

(56) References Cited

U.S. PATENT DOCUMENTS

| 4,454,121 | A | 6/1984 | Beachey |
|---|---|---|---|
| 5,098,827 | A | 3/1992 | Boyle et al. |
| 5,354,846 | A | 10/1994 | Kehoe |
| 5,378,620 | A | 1/1995 | Adams et al. |
| 5,391,712 | A | 2/1995 | Adams et al. |
| 5,445,820 | A | 8/1995 | Seidel et al. |
| 5,585,098 | A | 12/1996 | Coleman |
| 5,700,648 | A | 12/1997 | Kehoe |
| 5,821,088 | A | 10/1998 | Darzins et al. |
| 5,846,547 | A | 12/1998 | Cleary |
| 5,968,763 | A | 10/1999 | Fischetti et al. |
| 6,174,528 | B1 | 1/2001 | Cooper et al. |
| 6,372,222 | B1 | 4/2002 | Michon et al. |
| 6,406,883 | B1 | 6/2002 | Lutticken et al. |
| 6,420,152 | B1 | 7/2002 | Adams et al. |
| 6,426,074 | B1 | 7/2002 | Michel et al. |
| 6,579,711 | B1 | 6/2003 | Gaier et al. |
| 6,635,623 | B1 | 10/2003 | Hoogeveen et al. |
| 6,669,703 | B2 | 12/2003 | Shue |
| 6,737,521 | B1 | 5/2004 | Fischetti et al. |
| 6,747,437 | B2 | 6/2004 | Chiu |
| 6,777,547 | B1 | 8/2004 | Podbielski |
| 6,833,356 | B1 | 12/2004 | Koenig et al. |
| 6,936,252 | B2 | 8/2005 | Gilbert et al. |
| 7,033,765 | B1 | 4/2006 | Dime et al. |
| 7,041,814 | B1 | 5/2006 | Weinstock et al. |
| 7,098,182 | B2 | 8/2006 | Le Page et al. |
| 7,101,692 | B2 | 9/2006 | Schneewind et al. |
| 7,128,918 | B1 | 10/2006 | Hamel et al. |
| 7,128,919 | B2 | 10/2006 | Adderson et al. |
| 7,169,902 | B2 | 1/2007 | Podbielski |
| 7,247,308 | B2 | 7/2007 | Martin et al. |
| 7,348,006 | B2 | 3/2008 | Contorni et al. |
| 7,407,664 | B2 | 8/2008 | Beall et al. |
| 7,438,912 | B2 | 10/2008 | Meinke et al. |
| 7,485,710 | B2 | 2/2009 | Reinscheid et al. |
| 2002/0025516 | A1 | 2/2002 | Black et al. |

(Continued)

FOREIGN PATENT DOCUMENTS

| EP | 0369825 | 5/1990 |
|---|---|---|
| EP | 0613947 | 1/1994 |

(Continued)

OTHER PUBLICATIONS

Abbas et al., *Cellular and Molecular Immunology*, 4th ed., Chapter 15, pp. 360-362, 2000.
Amara et al., "Molecular detection of methionine in rat brain using specific antibodies," Neurosci. Lett. 185, 147-50, Feb. 13, 1995.
Areschoug et al., "Group B streptococcal surface proteins as targets for protective antibodies: identification of two novel proteins in strains of serotype V.," Inf. Immun. 67(12), 6350-57, Dec. 1999.
Banks et al., "Progress toward characterization of the Group A *Streptococcus* metagenome: Complete genome sequence of a macrolide-resistant serotype M6 strain," *J. Infectious Diseases* 190, 727-38, Aug. 15, 2004.
Barnett & Scott, "Differential recognition of surface proteins in *Streptococcus pyogenes* by two sortase gene homologs," J. Bacteriol. 184, 2181-91, 2002.

(Continued)

*Primary Examiner* — S. Devi
(74) *Attorney, Agent, or Firm* — Banner & Witcoff, Ltd.

(57) ABSTRACT

This application relates to Group B *Streptococcus* ("GBS") vaccines comprising combinations of GBS polypeptide antigens where the polypeptides contribute to the immunological response in a recipient. Preferably, the compositions of the invention comprise a combination of two or more GBS antigens, wherein said combination includes GBS 80 or a fragment thereof. In one embodiment, the combination may consist of two to thirteen GBS antigens selected from an antigen group consisting of GBS 80, GBS 91, GBS 104, GBS 184, GBS 276, GBS 305, GBS 322, GBS 330, GBS 338, GBS 361, GBS 404, GBS 690, and GBS 691.

10 Claims, No Drawings

(56) References Cited

U.S. PATENT DOCUMENTS

| | | |
|---|---|---|
| 2002/0045737 A1 | 4/2002 | Choi et al. |
| 2002/0061569 A1 | 5/2002 | Haselbeck et al. |
| 2002/0086023 A1 | 7/2002 | Dale |
| 2003/0035805 A1 | 2/2003 | Michel et al. |
| 2003/0109690 A1 | 6/2003 | Ruben et al. |
| 2003/0157122 A1 | 8/2003 | Dale |
| 2003/0171337 A1 | 9/2003 | Aylward et al. |
| 2004/0029129 A1 | 2/2004 | Wang et al. |
| 2004/0101536 A1 | 5/2004 | Teti et al. |
| 2004/0219639 A1 | 11/2004 | Potter et al. |
| 2004/0236072 A1 | 11/2004 | Olmsted et al. |
| 2005/0019345 A1 | 1/2005 | Podbielski |
| 2005/0020813 A1 | 1/2005 | Masignani et al. |
| 2005/0181388 A1 | 8/2005 | Edwards et al. |
| 2005/0214918 A1 | 9/2005 | Edwards et al. |
| 2005/0288866 A1 | 12/2005 | Sachdeva |
| 2006/0039922 A1 | 2/2006 | Mizzen et al. |
| 2006/0041961 A1 | 2/2006 | Abad et al. |
| 2006/0073530 A1 | 4/2006 | Schneewind et al. |
| 2006/0115479 A1 | 6/2006 | Reinscheid et al. |
| 2006/0160121 A1 | 7/2006 | Mounts et al. |
| 2006/0165716 A1 | 7/2006 | Telford et al. |
| 2006/0194751 A1 | 8/2006 | Meinke et al. |
| 2006/0210579 A1 | 9/2006 | Telford et al. |
| 2006/0210580 A1 | 9/2006 | Telford et al. |
| 2006/0210581 A1 | 9/2006 | Telford et al. |
| 2006/0210582 A1 | 9/2006 | Telford et al. |
| 2006/0258849 A1 | 11/2006 | Telford et al. |
| 2006/0269541 A1 | 11/2006 | Meinke et al. |
| 2006/0275315 A1 | 12/2006 | Telford et al. |
| 2007/0036828 A1 | 2/2007 | Rappuoli et al. |
| 2007/0053924 A1 | 3/2007 | Tettelin et al. |
| 2007/0065464 A1 | 3/2007 | Grandi et al. |
| 2007/0098737 A1 | 5/2007 | Dale |
| 2007/0116712 A1 | 5/2007 | Hamel et al. |
| 2007/0128210 A1 | 6/2007 | Olmsted et al. |
| 2007/0128211 A1 | 6/2007 | Olmsted et al. |
| 2007/0128229 A1 | 6/2007 | Olmsted et al. |
| 2007/0141635 A1 | 6/2007 | James |
| 2008/0038268 A1 | 2/2008 | Martin et al. |
| 2008/0220010 A1 | 9/2008 | Telford et al. |
| 2009/0022753 A1 | 1/2009 | Olmsted et al. |

FOREIGN PATENT DOCUMENTS

| | | |
|---|---|---|
| EP | 555438 | 1/1997 |
| EP | 555439 | 10/1997 |
| EP | 1770171 | 4/2007 |
| GB | 2233977 | 1/1991 |
| WO | WO906951 | 6/1990 |
| WO | WO9305155 | 3/1993 |
| WO | WO9305156 | 3/1993 |
| WO | WO9801561 | 1/1998 |
| WO | WO9818931 | 5/1998 |
| WO | WO9819689 | 5/1998 |
| WO | WO9823631 | 6/1998 |
| WO | WO9803677 | 8/1998 |
| WO | WO9913084 | 3/1999 |
| WO | WO9916882 | 4/1999 |
| WO | WO9926969 | 6/1999 |
| WO | WO9942588 | 8/1999 |
| WO | WO9954457 | 10/1999 |
| WO | WO0006736 | 2/2000 |
| WO | WO0006737 | 2/2000 |
| WO | WO0023456 | 4/2000 |
| WO | WO0078787 | 12/2000 |
| WO | WO0132882 | 5/2001 |
| WO | WO0212294 | 2/2002 |
| WO | WO0234771 | 5/2002 |
| WO | WO02075507 | 9/2002 |
| WO | WO02077183 | 10/2002 |
| WO | WO02092818 | 11/2002 |
| WO | WO03068813 | 8/2003 |
| WO | WO03087353 | 10/2003 |
| WO | WO03093306 | 11/2003 |
| WO | WO2004018646 | 3/2004 |
| WO | WO2004078907 | 9/2004 |
| WO | WO2004099242 | 11/2004 |
| WO | WO2005013666 | 2/2005 |
| WO | WO2005028618 | 3/2005 |
| WO | WO2005032582 | 4/2005 |
| WO | WO2005076010 | 8/2005 |
| WO | WO2005108419 | 11/2005 |
| WO | WO2006035311 | 4/2006 |
| WO | WO2006042027 | 4/2006 |
| WO | WO2006069200 | 6/2006 |
| WO | WO2006/078318 | 7/2006 |
| WO | WO2006078318 | 7/2006 |
| WO | WO2006082527 | 8/2006 |
| WO | WO2006082530 | 8/2006 |
| WO | WO2006130328 | 12/2006 |
| WO | WO2007018563 | 2/2007 |
| WO | WO2007039319 | 4/2007 |
| WO | WO2007052168 | 5/2007 |
| WO | WO2008020335 | 2/2008 |
| WO | WO2008108830 | 9/2008 |
| WO | WO2008003515 | 10/2008 |

OTHER PUBLICATIONS

Barnett et al., "A Novel Sortase, SrtC2, from *Streptococcus pyogenes* Anchors a Surface Protein Containing a QVPTGV Motif to the Cell Wall," *Journal of Bacteriology*, vol. 186, No. 17, pp. 5865-5875, Sep. 2004.

Beckmann et al., "Identification of Novel Adhesins from Group B Streptococci by Use of Phage Display Reveals that C5a Peptidase Mediates Fibronectin Binding," *Inf. Immun.* 70, 2869-76, Jun. 2002.

Bessen et al., "Genomic Localization of a T Serotype Locus to a Recombinatorial Zone Ending Extracellular Matrix-Binding Proteins in *Streptococcus pyogenes*," *Infection and Immunity*, vol. 70, No. 3, pp. 1159-1167, Mar. 2002.

Black et al: "*Streptococcus pneumoniae* polypeptide coding region"; Genbank Accession No. AAV42990, Nov. 9, 1998.

Blackburn et al., "The end of the (DNA) line," Nature Structural Biology 7, 847-49, Oct. 2000.

Bork et al., "Powers and pitfalls in sequence analysis: the 70% hurdle," Genome Research 10, 398-400, 2000.

Borovec et al., "Synthesis and assembly of hepatitis A virus-specific proteins in BS-C-1 cells," J. Virol. 67, 3095-301, Jun. 1993.

Bowie et al., "Deciphering the message in protein sequences: tolerance to amino acid substitution," Science 257, 1306-10, 1990.

Brodeur et al., "Identification of group B streptococcal Sip protein, which elicits cross-protective immunity," Inf. Immun. 68(10), 5610-8, Oct. 2000.

Burgess et al., "Possible dissociation of the heparin-binding and mitogenic activities of heparin-binding (acidic fibroblast) growth factor-1 from its receptor-binding activities by site-directed mutagenesis of a single lysine residue," J. Cell Biol. 111, 2129-38, 1990.

Chung et al., "chlorosome protein," NCBI Accession No. 2115394F, Jul. 10, 1992.

Clancy et al., "Cloning and Characterization of a Novel Macrolide Efflux Gene, mreA, from *Streptococcus agalactiae*," Antimicrobial Agents and Chemotherapy 41, 2719-23, 1997.

Collins et al., "Mutation of the principal sigma factor causes loss of virulence in a strain of the *Mycobacterium tuberculosis* complex," Proc. Natl. Acad. Sci. USA 92, 8036-40, 1995.

Dale et al., "New Protective Antigen of Gorup A Streptococci," J. Clin. Invest. 103, 1261-68, May 1999.

Dale et al., "Recombinant, octavalent group A streptococcal M protein vaccine," Vaccine 14, 944-48, 1996.

Dale, "Group A Streptococcal Vaccines," Infectious Disease Clinics of North America 13, 227-43, Mar. 1999.

Dale, "Multivalent group A streptococcal vaccine designed to optimize the immunogenicity of six tandem M protein fragments," Vaccine 17, 193-200, 1999.

Database EMBL, Accession No. AAX13129, *Enterococcus faecalis* genome contig SEQ ID No. 192, Mar. 19, 1999.

Database EPO Proteins, EBI Accession No. AX605513, "Sequence 3442 from WO0209818," Feb. 17, 2003.

(56) References Cited

OTHER PUBLICATIONS

Database Geneseq, "Group B *Streptococcus* protein sequence SEQ ID No. 49," EBI Accession No. GSP:AAY91320, May 30, 2000.
Database Geneseq, "*Streptococcus agalactiae* protein, SEQ ID 2382," EBI Accession No. GSP:ADV81242, Feb. 24, 2005.
Database Geneseq, "Fibrinogen-binding polypeptide, SEQ ID No. 17," EBI Accession No. GSP: ADS93952, Dec. 2, 2004; revised in 2007.
Database Geneseq, EBI Accession No. GSP: ABP30134, "*Streptococcus* polypeptide SEQ ID No. 9444," Jul. 2, 2002.
Database Geneseq, EBI Accession No. GSP: ABP27285, "*Streptococcus* polypeptide SEQ ID No. 3746," Jul. 2, 2002; revised in 2007.
Database Genseq, "Protein encoded by Prokaryotic essential gene #319788," Accession No. ABU46451, Jun. 13, 2003.
Database JPO Proteins, "Nucleic acid and protein originating in group B *Streptococcus*," EBI Accession No. JPOP:BD629260, Jul. 17, 2003.
Database SWISSPROT[Online] Oct. 1, 2002, accession No. EBI, Database accession No. Q9PGX9, Hypothetical protein XF0167.
Database UniProt [Online] Mar. 1, 2003, "Cell wall surface anchor family protein," retrieved from EBI accession No. UNIPROT: Q8DYR5, Database accession No. Q8DYR5, 87.2% identity with SEQ ID No. 20906.
Database UniProt [Online], Nov. 22, 2005, "Cell wall surface anchor family protein," retrieved from EBI accession No. UNIPROT: Q3D2D6; 100% identity with SEQ ID No. 20906; abstract.
De Boever et al., "*Enterococcus faecalis* conjugative plasmid pAM373. Complete nucleotide sequence and genetic analyses of sec phermone response," Mol. Microbiol. 37, 1327-41, 2000.
Dittmer et al., "Treatment of infectious diseases with immunostimulatory oligodeoxynucleotides containing CpG motifs," Curr. Opinion Microbiol. 6, 472-77, Oct. 2003.
Duez, "*Enterococcus hirae* mraR, pbp3s, mraY, murD, murG, ftsQ and ftsA genes, mraW, yllC and ftsZ partial genes," Genbank Accession No. Y13922, Apr. 18, 2005.
Ellis, *Vaccines*, Chapter 29, Plotkin et al., eds., W.B. Saunders Company (Philadelphia), pp. 568-575, 1988.
Examination Report for NZ 560966, Mar. 4, 2009, 2 pages.
Ferretti et al., "Complete genome sequence of an M1 strain of *Streptococcus pyogenes*," Proc. Natl. Acad. Sci. USA 98, 4658-63, Apr. 10, 2001.
Guzman et al., "Protective immune response against *Streptococcus pyogenes* in mice after intranasal vaccination with the fibronectin-binding protein Sfbl," J. Infectious Disease 179, 901-06, 1999.
Holmes, "PSMA specific antibodies and their diagnostic and therapeutic use," Exp. Opin. Invest. Drugs 10, 511-10, 2001.
Hong, "unnamed protein product [*Streptococcus pyogenes*]," NCBI Accession No. BAB1603, one page, Oct. 3, 2000.
Horvath et al., "Toward the development of a synthetic group a streptococcal vaccine of high purity and broad protective coverage," J Med Chem. Jul. 29, 2004;47(16):4100-4.
Hughs et al., "Identification of Major Outer surface Proteins of *Streptococcus agalactiae*," Inf. Immun. 70, 1254-59, Mar. 2002.
International Preliminary Examination Report for PCT/GB01/04789 (published as WO 02/34771) dated Feb. 17, 2003.
International Preliminary Examination Report for PCT/GB2003/001882 (published as WO 03/093306) dated Aug. 18, 2004.
International Preliminary Examination Report for PCT/IB2005/036009 (published as WO 06/042027) dated Apr. 11, 2007.
International Preliminary Examination Report for PCT/US2003/029167 (published as WO 04/041157) dated Mar. 5, 2005.
International Preliminary Examination Report for PCT/US2004/024868 (published as WO 05/032582) dated Feb. 6, 2006.
International Preliminary Examination Report for PCT/US2004/030032 (published as WO 05/028618) dated Mar. 16, 2006.
International Search Report for PCT/GB01/04789 (published as WO 02/34771) dated Aug. 27, 2002.
International Search Report for PCT/GB2003/001882 (published as WO 03/093306) dated Nov. 14, 2002.
International Search Report for PCT/IB2005/036009 (published as WO 06/042027) dated Jun. 20, 2006.
International Search Report for PCT/US05/046491 dated Jun. 26, 2007 (published as WO 2006/069200).
International Search Report for PCT/US2003/029167 (published as WO 04/041157) dated Aug. 2, 2004.
International Search Report for PCT/US2004/024868 (published as WO 05/032582) dated Oct. 28, 2005.
International Search Report for PCT/US2004/030032 (published as WO 05/028618) dated Dec. 6, 2005.
International Search Report for PCT/US2005/027239 (published as WO 06/078318) dated Aug. 25, 2008.
International Search Report for PCT/US2007/022838 (published as WO 08/108830) dated Oct. 9, 2008.
Jobling et al., "Analysis of structure and function of the B subunit of cholera toxin by the use of site-directed mutagenesis," Mol. Microbiol. 5, 1755-67, 1991.
Kalman et al., "Comparative genomes of *Chlamydia pneumoniae* and *C. trachomatis*," Nature Genetics 21, 385-89, Apr. 1999.
Kehoe et al., "Nucleotide Sequence of the Streptolysin O (SLO) Gene: Structural Homologies between SLO and Other Membrane-Damaging, Thiol-Activated Toxins," Inf. Immun. 55, 3228-32, Dec. 1987.
Koch et al., "Complexity and expression patterns of the desmosomal adherins," Proc. Natl. Acad. Sci. USA 89, 353-57, Jan. 1992.
Kunst et al., "The complete genome sequence of the Gram positive bacterium *Bacillus subtilis*," NCBI Accession No. CAB14964, Nov. 20, 1997.
Lachenauer et al., "A protective surface protein from the Type V Group B *Streptococcus* shares N-terminal sequence homology with the Alpha C Protein," Inf. Immun. 64, 4255-60, Oct. 1996.
Larsson et al., "Protection against experimental infection with group B *Streptococcus* by immunization with a bivalent protein vaccine," *Vaccine* 17, 454-58, 1999.
Lauer et al., "Genome Analysis Reveals Pili in Group B *Streptococcus*," *Science* 309, 105, Jul. 1, 2005.
Lazar et al., "Transforming growth factor alpha: mutation of aspartic acid 47 and leucine 48 results in different biological activities," Mol. Cell. Biol. 8, 1247-52, 1988.
Le Page et al., *Streptococcus agalactiae* sequence 217 from WO 01/32882, Genbank Accession No. AX134653, May 29, 2001.
Lei et al., "Identification and immunogenicity of group A *Streptococcus* culture supernatant proteins," Inf. Immunity 68, 6807-18, 2000.
Lewis, "Riddle of Biofilm Resistance," *Antimicrobial Agents and Chemotherapy*, vol. 45, No. 4, pp. 999-1007, Apr. 2001.
Lindahl et al., "Surface proteins of *Streptococcus agalactiae* and related proteins in other bacterial pathogens," Clinical Microbiol. Rev. 18(1), 102-07, Jan. 2005.
Madoff et al., "Maternal Immunization of Mice with Group B Streptococcal Type III Polysaccharide-Beta C Protein Conjugate Elicits Protective Antibody to Multiple Serotypes," J. Clinical Invest. 94, 286-92, 1994.
Maione et al., "Identification of a Universal Group B *Streptococcus* Vaccine by Multiple Genome Screen," *Science* 309, 148-50, Jul. 1, 2005.
McMillan et al., "Identification and assessment of new vaccine candidates for group A streptococcal infections," *Vaccine* 22, 2783-90, 2004.
McMillan et al., "Prospecting for new group A streptococcal vaccine candidates," *Indian J. Med. Res*. 119, 121-25, May 2004.
Meehan & Owen, "Sequence 1 from Patent WO9801561," Genbank Accession No. A68631, May 6, 1999.
Meinke et al., "*S. pyogenes* hyperimmune system reactive antigen Spy0269," EBI Accession No. ADR83896, Dec. 2, 2004; revised Jun. 15, 2007.
Michel et al: "Cloned alpha and beta C-protein antigens of group B Streptococci elicit protective immunity"; Infection and Immunity; vol. 59, No. 6, Jun. 1991; pp. 2023-2028.
Molling et al., "Naked DNA for vaccine or therapy," J. Mol. Med. 75, 242-46, 1997.
Mora et al., "Group A *Streptococcus* produce pilus-like structures containing protective antigens and Lancefield T antigens," Proc. Natl. Acad. Sci. USA 102, 15641-46, Oct. 25, 2005.

(56) References Cited

OTHER PUBLICATIONS

Musser, "The Next Chapter in Reverse Vaccinology," Nat. Biotechnol. 24, 157-58, 2006.
Nakagawa et al., "Genome sequence of an M3 strain of *Streptococcus pyogenes* reveals a large-scale genomic rearrangement in invasive strains and new insights into phage evolution," Genome Res. 13, 1042-55, Jun. 2003.
Nakata et al., "MsmR, a specific positive regulator of the *Streptococcus pyogenes* FCT pathogenicity region and cytolysin-mediated translocation system genes," Mol. Microbiol. 57, 786-803, 2005.
Navarre et al., "Surface Proteins of Gram-Positive Bacteria and Mechanisms of Their Targeting to the Cell Wall Envelope," Microbiology and Molecular Biology Reviews, vol. 63, No. 1, pp. 174-229, Mar. 1999.
NCBI News, table on p. 4, "Microbial Genomes Available for BLAST Search," Jul. 1998.
Olive et al., "Protection of mice from group A streptococcal infection by intranasal immunization with a peptide vaccine that contains a conserved M protein B cell epitope and lacks a T cell autoepitope," Vaccine 20, 2816-25, 2002.
Orefici et al., "Possible virulence marker for *Streptococcus agalactiae* (Lancefiled Group B)," J. Clin. Microbiol. Infectious Diseases 7, 302-05, 1988.
Paoletti et al., "Neonatal mouse protection against infection with multiple group B streptococcal (GBS) serotypes by maternal immunization with a tetravalent GBS polysaccharide-tetanus toxoid conjugate vaccine," Inf. Immun. 62, 3236-43, 1994.
Paoletti, "Surface structure of group B *Streptoccoccus* important in human immunity," in *Gram Positive Pathogens*, Fischetti et al., eds., Chapter 14, pp. 137-153, 2000.
Pournaras et al., "Pheromone responses and high-level aminoglycoside resistance of conjugative plasmids of *Enterococcus faecalis* from Greece," J. Antimicrobial Chemotherapy 46, 1013-16, 2000.
Pritzlaff et al., "Genetic basis for the beta-haemolytic cytolitic activity of group B *Streptococcus*," Mol. Microbiol. 39, 236-48, 2001.
Pritzlaff et al., "*Streptococcus agalactiae* cyl gene cluster, partial sequence," Genbank Accession No. AF157015, Feb. 8, 2001.
Proft et al., "Identification and Characterization of Novel Superantigens from *Streptococcus pyogenes*," J. Exp. Med. 189, 89-101, Jan. 4, 1999.
Pucci et al., "*Enterococcus faecalis* strain A24836 cell wall/cell division gene cluster, yllB, yllc, yllD, pbpC, mraY, murD, murG, divlB, ftsA and fitsZ genes, complete cds," Genbank Accession No. U94707, Sep. 10, 1997.
Quinn, "The response of rheumatic and non-rheumatic children to streptolysin O concentrate," J. Clin. Invest. 36, 793-802, Jun. 1957.
Ramachandran et al., "Two Distinct Genotypes of *prtF2*, Encoding a Fibronectin Binding Protein, and Evolution of the Gene Family in *Streptococcus pyogenes*," Journal of Bacteriology, vol. 186, No. 22, pp. 7601-7609, Nov. 2004.
Rodewald et al., "Neonatal mouse model of group b streptococcal infection," J. Infectious Diseases 166, 635-39, 1992.
Rodriguez-Ortega et al., "Characterization and identification of vaccine candidate proteins through analysis of the group A *Streptococcus* surface proteome," Nature Biotechnol. 24, 191-97, 2006.
Roitt et al., Structure of Antigens, *Immunology*, 4th ed., Mosby, London, pp. 7.7 and 7.8, 1998.
Rosini et al., "Identification of novel genomic islands coding for antigenic pilus-like structures in *Streptococcus agalactiae*," Mol. Microbiol. 61, 126-41, 2006.
Rudenko et al., "Selection for activation of a new variant surface glycoprotein gene expression site in *Trypanosoma brucei* can result in deletion of the old one," Mol. Biochem. Parisitol. 95, 97-109, 1998; NCBI Accession No. CAD21770.
Rudinger et al., "Characteristics of the amino acids as components of a peptide hormone sequence," in *Peptide Hormones*, Parsons, ed., University Park Press, Jun. 1976, pp. 1-7.
Schneewind et al., "Sequence and Structural Characteristics of the Trypsin-Resistant T6 Surface Protein of Group A Streptococci," Journal of Bacteriology, vol. 172, No. 6, pp. 3310-3317, Jun. 1990.
Schneewind, "Structure of the Cell Wall anchor of Surface Proteins in *Staphylococcus aureus*," Science 268, 103-06, Apr. 7, 1995.
Segura et al., "*Streptococcus suis* and group B *Streptococcus* differ in their interactions with murine macrophages," FEMS Immunol. Med. Microbiol. 21, 189-95, 1998.
Seizen, "Multi-domain, cell envelope proteases of lactic acid bacteria," Antonie von Leeuwenhoek 76, 139-55, 1999.
Simpson et al., "*Xylella fastidiosa* 9a5c, section 136 of 229 of the complete genome," Genbank Accession No. AE003990, Jun. 4, 2004.
Smoot et al., "Genome sequence and comparative microarray analysis of serotype M18 group A *Streptococcus* strains associated with acute rheumatic fever outbreaks," Proc. Natl. Acad. Sci. USA 99, 4668-73, Apr. 2, 2002.
Spellerberg et al., "*Streptococcus agalactiae* cyl gene cluster, complete sequence," Genbank Accession No. AF093787, Jul. 31, 2000.
Spellerberg et al: "Identification of genetic determinants for the hemolytic activity of *Streptococcus agalactiae* by ISSI transposition"; J. Bacteriol.; vol. 181, No. 10, May 1999; pp. 3212-3219.
Stalhammar-Carlemalm et al: "The R28 Protein of *Streptococcus pyogenes* is related to several group B streptococcal surface proteins, confer protective immunity and promotes binding to human epithelial cells"; Mol. Microbiol. 1, Jul. 1999, pp. 208-219.
Stephenson et al., "The Fap1 fimbrial adhesin is a glycoprotein: antibodies specific for the glycan moiety block the adhesion of *Streptococcus parasanguis* in an in vitro tooth model," Mol. Microbiol. 43, 147-57, 2002.
Su et al., "Identification of a Xenopus cDNA that prevents mitotic catastrophe in the fission yeast *Schizosaccharomyces pombe*," Gene 145, 155-56, 1994.
Supplementary Search report for EP 03799822 (corresponding to WO 04/041157) dated Jan. 21, 2008.
Surovov & Ferretti, "Physical and Genetic Chromosomal Map of an M Type 1 Strain of *Streptococcus pyogenes*," J. Bacteriol. 178, 5546-49, Sep. 1996.
Takami et al., "Two component sensor histidine kinase involved in phosphate regulation," NCBI Accession No. NP_244022.1, Sep. 10, 2001.
Telford et al., Sequence 7466 from WO 02/34771, EBI Accession No. CQ650509, Feb. 2, 2004; modified May 31, 2006.
Telford et al., "*Streptococcus* polypeptide SEQ ID No. 9188" of WO 02/34771, EBI Accession No. ABP300006, Jul. 2, 2002; revised Jun. 15, 1007.
Tettelin et al., "Complete genome sequence and comparative genomic analysis of an emerging human pathogen, serotype V *Streptococcus agalactiae*," Proc. Natl. Acad. Sci. USA 99, 12391-96, Sep. 17, 2002.
Tettelin et al., "Complete genome sequence of a virulent isolate of *Streptococcus pneumoniae*," Science 293, 498-506, 2001.
Tettelin et al., Database EMBL, Accession No. AE014193, *Streptococcus agalactiae* 2603V/R section 3 of 100 of the complete genome, Sep. 2, 2002.
Tettelin et al., Swiss-Prot Accession No. Q3DV91 for *Streptococcus agalactiae* strain 18R21, Nov. 22, 2005.
Tighe et al., "Gene vaccination: plasmid DNA is more than just a blueprint," Immunology Today 19, 89-97, Feb. 1998.
Todd, "Antigenic Streptococcal Hemolysin," J. Exp. Med. 55, 267-80, 1932.
Ton-That & Schneewind, "Assembly of pili on the surface of *Corynebacterium diphtheriae*," Mol. Microbiol. 50, 1429-38, 2003.
Ton-That et al., "Sortases and pilin elements involved in pilus assembly of *Corynebacterium diphtheriae*," Mol. Microbiol. 53, 251-61, 2004.
UniProt Accession No. A7CNQ7, Jul. 5, 2004.
UniProt Accession No. Q5XEL1, Nov. 23, 2004.
UniProt Accession No. Q8P318, Oct. 1, 2002.
Vallet et al., "The chaperone/usher pathways of *Pseudomonas aeruginosa*: Identification of fimbrial gene clusters (cup) and their involvement in biofilm formation," PNAS, vol. 98, No. 12, pp. 6911-6916, Jun. 2001.

(56) References Cited

OTHER PUBLICATIONS

Wang et al., "Protein encoded by prokaryotic essential gene #31978," EBI Accession No. ABU46451, Jun. 19, 2003; revised Jun. 15, 2007.
Watnick et al., "Steps in the development of a *Vibrio cholerae* El Tor biofilm," *Molecular Microbiology*, vol. 34, No. 3, pp. 586-595, 1999.
Wessels et al., "Stimulation of protective antibodies against type 1a and 1b group B streptococci by a type 1a polysaccharide-tetanus toxoid conjugate vaccine," Inf. Immun. 61, 4760-66, 1993.
Woodson et al., "Analysis of a ribose transport operon from *Bacillus subtilis*," Microbiology 140, 1829-38, 1994.
Zhong et al., "Hypothetical protein of *Arabidopsis thaliana*," NCBI Accession No. AAD29767, May 11, 1999.
Colman, "Effects of Amino Acid Sequence Changes on Antibody-Antigen Interactions," Research in Immunology, 1994, vol. 145, pp. 33-36, col. 2, p. 35, col. 1.
Database Geneseq (Online), "SCPB peptidase (wild type sequence)," EBI accession No. AAB01265, Sep. 25, 2000.
Database EMBL (Online), "*Streptococcus pyogenes* gene, partial cds, LPXT(A)G motif containing protein," EBI accession No. AB030812, Oct. 3, 2000.
Gaspar and Ton-That, Assembly of Distinct Pilus Structures on the Surface of *Corynebacterium diphtheriae*, J. Bacteriol., Feb. 2006, vol. 188, pp. 1526-1533.
Harlow and Lane., "Antibodies A Laboratory Manual," Cold Spring Harbor Laboratory Press, Inc., 1988, pp. 23-25, 27-33.
Houghten et al., "New Approaches to Immunization. Developing Vaccines Against Parasitic, Bacterial, or Viral Diseases," Vaccines 86, Cold Spring Habor Laboratory, 1986, pp. 21-25.
Krishnan et al., "An IgG-like Domain in the Minor Pilin GBS52 of *Streptococcus agalactiae* Mediates Lung Epithelial Cell Adhesion," Structure 15, Aug. 2007 (provided as NIH Public Access manuscript), pp. 893-903.
Maione et al., pending claims of U.S. Appl. No. 12/304,018 as amended Aug. 29, 2013.
New England Biolabs Catalog, Random primers, 1996/1997, p. 111.
Rubens et al., "Identification of cpsD, a gene essential for type III capsule expression in group B streptococci," Molecular Microbiology, 1993, vol. 8, No. 5, pp. 843-855.
Sequence alignment result for U.S. Appl. No. 10/415,182, Apr. 8, 2008, 8 pages.
Verdonck et al., "Oral immunization of piglets with recombinant F4 fimbrial adhesin FaeG monomers induces a mucosal and systemic F4-specific immune response," Vaccine 22, Oct. 22, 2004, pp. 4291-4299.
Ferretti et al., "Putative surface exclusion protein," Genbank Accession No. Q9A1H3, Oct. 31, 2006.
Ferretti et al: "*Streptococcus pyogenes* M1 Gas strain SF370, Section 87 of 167 of the complete genome" Database Accession No. AE006558.
Glaser et al., "Genome sequence of *Streptococcus agalactiae*, a pathogen causing invasive neonatal disease," Mol. Moicrobiol. 45, 1499-1513, 2002.
Grandi & Zagursky, "The impact of genomics in vaccine discovery: achievements and lessons," Expert. Rev. Vaccines 3, 621-23, 2004.
Grandi, "Genomics and Proteomics in Reverse Vaccines," in *Microbial Proteomics: Functional Biology of Whole Organisms*, Humphery-Smith & Hecker, eds., John Wiley & Sons, chapter 20, 2006.
Greenspan et al., "Defining epitopes: Its not as easy as it seems," Nature Biotechnol. 7, 936-37, 1999.
Gutekunst et al., "Analysis of RogB-Controlled Virulence Mechanisms and Gene Expression in *Streptococcus agalactiae*," *Inf. Immun.* 71, 5056-64, Sep. 2003.
Gutierrez et al., "insertional Mutagenesis and Recovery of Interrupted Genes of *Streptococcus* mutans by Using Transposon Tn917: Preliminary Characterization of Mutants Displaying Acid Sensitivity and Nutritional Requirements," J. Bacteriol. 178, 4166-75, Jul. 1996.
Guttierez et al., "*Streptococcus* mutans ProX (pouABC) gene, partial cds; YlxM (ylxM) gene, complete cds; Ffh (ffh) gene, complete cds, alternatively spliced; SatC (satC) and SatD (satD) gene, complete cds; and SatE (satE) gene, partical cds," Genbank Accession No. U88582, Apr. 3, 2001.

SEQUENCE LISTING

```
<160> NUMBER OF SEQ ID NOS: 93

<210> SEQ ID NO 1
<211> LENGTH: 1662
<212> TYPE: DNA
<213> ORGANISM: Streptococcus agalactiae

<400> SEQUENCE: 1
atgaaattat cgaagaagtt attgttttcg gctgctgttt taacaatggt ggcggggtca      60
actgttgaac cagtagctca gtttgcgact ggaatgagta ttgtaagagc tgcagaagtg     120
tcacaagaac gcccagcgaa aacaacagta aatatctata aattacaagc tgatagttat     180
aaatcggaaa ttacttctaa tggtggtatc gagaataaag acggcgaagt aatatctaac     240
tatgctaaac ttggtgacaa tgtaaaaggt ttgcaaggtg tacagtttaa acgttataaa     300
gtcaagacgg atatttctgt tgatgaattg aaaaaattga caacagttga agcagcagat     360
gcaaaagttg gaacgattct tgaagaaggt gtcagtctac ctcaaaaaac taatgctcaa     420
ggtttggtcg tcgatgctct ggattcaaaa agtaatgtga gatacttgta tgtagaagat     480
ttaaagaatt caccttcaaa cattaccaaa gcttatgctg taccgtttgt gttggaatta     540
ccagttgcta actctacagg tacaggtttc ctttctgaaa ttaatattta ccctaaaaac     600
gttgtaactg atgaaccaaa aacagataaa gatgttaaaa aattaggtca ggacgatgca     660
ggttatacga ttggtgaaga attcaaatgg ttcttgaaat ctacaatccc tgccaattta     720
ggtgactatg aaaaatttga aattactgat aaatttgcag atggcttgac ttataaatct     780
```

```
gttggaaaaa tcaagattgg ttcgaaaaca ctgaatagag atgagcacta cactattgat    840
gaaccaacag ttgataacca aaatacatta aaaattacgt ttaaaccaga gaaatttaaa    900
gaaattgctg agctacttaa aggaatgacc cttgttaaaa atcaagatgc tcttgataaa    960
gctactgcaa atacagatga tgcggcattt ttggaaattc cagttgcatc aactattaat   1020
gaaaaagcag ttttaggaaa agcaattgaa atactttg aacttcaata tgaccatact    1080
cctgataaag ctgacaatcc aaaccatct aatcctccaa gaaaaccaga agttcatact   1140
ggtgggaaac gatttgtaaa gaaagactca acagaaacac aaacactagg tggtgctgag   1200
tttgatttgt tggcttctga tgggacagca gtaaaatgga cagatgctct tattaaagcg   1260
aatactaata aaaactatat tgctggagaa gctgttactg ggcaaccaat caaattgaaa   1320
tcacatacag acggtacgtt tgagattaaa ggtttggctt atgcagttga tgcgaatgca   1380
gagggtacag cagtaactta caaattaaaa gaaacaaaag caccagaagg ttatgtaatc   1440
cctgataaag aaatcgagtt tacagtatca caaacatctt ataatacaaa accaactgac   1500
atcacggttg atagtgctga tgcaacacct gatacaatta aaaacaacaa acgtccttca   1560
atccctaata ctggtggtat tggtacggct atctttgtcg ctatcggtgc tgcggtgatg   1620
gcttttgctg ttaaggggat gaagcgtcgt acaaaagata ac                     1662
```

<210> SEQ ID NO 2
<211> LENGTH: 554
<212> TYPE: PRT
<213> ORGANISM: Streptococcus agalactiae

<400> SEQUENCE: 2

```
Met Lys Leu Ser Lys Lys Leu Leu Phe Ser Ala Ala Val Leu Thr Met
 1               5                  10                  15

Val Ala Gly Ser Thr Val Glu Pro Val Ala Gln Phe Ala Thr Gly Met
            20                  25                  30

Ser Ile Val Arg Ala Ala Glu Val Ser Gln Glu Arg Pro Ala Lys Thr
        35                  40                  45

Thr Val Asn Ile Tyr Lys Leu Gln Ala Asp Ser Tyr Lys Ser Glu Ile
    50                  55                  60

Thr Ser Asn Gly Gly Ile Glu Asn Lys Asp Gly Glu Val Ile Ser Asn
65                  70                  75                  80

Tyr Ala Lys Leu Gly Asp Asn Val Lys Gly Leu Gln Gly Val Gln Phe
                85                  90                  95

Lys Arg Tyr Lys Val Lys Thr Asp Ile Ser Val Asp Glu Leu Lys Lys
            100                 105                 110

Leu Thr Thr Val Glu Ala Ala Asp Ala Lys Val Gly Thr Ile Leu Glu
        115                 120                 125

Glu Gly Val Ser Leu Pro Gln Lys Thr Asn Ala Gln Gly Leu Val Val
    130                 135                 140

Asp Ala Leu Asp Ser Lys Ser Asn Val Arg Tyr Leu Tyr Val Glu Asp
145                 150                 155                 160

Leu Lys Asn Ser Pro Ser Asn Ile Thr Lys Ala Tyr Ala Val Pro Phe
                165                 170                 175

Val Leu Glu Leu Pro Val Ala Asn Ser Thr Gly Thr Gly Phe Leu Ser
            180                 185                 190

Glu Ile Asn Ile Tyr Pro Lys Asn Val Val Thr Asp Glu Pro Lys Thr
        195                 200                 205

Asp Lys Asp Val Lys Lys Leu Gly Gln Asp Asp Ala Gly Tyr Thr Ile
```

```
                210                 215                 220
Gly Glu Glu Phe Lys Trp Phe Leu Lys Ser Thr Ile Pro Ala Asn Leu
225                 230                 235                 240

Gly Asp Tyr Glu Lys Phe Glu Ile Thr Asp Lys Phe Ala Asp Gly Leu
                245                 250                 255

Thr Tyr Lys Ser Val Gly Lys Ile Lys Ile Gly Ser Lys Thr Leu Asn
                    260                 265                 270

Arg Asp Glu His Tyr Thr Ile Asp Glu Pro Thr Val Asp Asn Gln Asn
                275                 280                 285

Thr Leu Lys Ile Thr Phe Lys Pro Glu Lys Phe Lys Glu Ile Ala Glu
            290                 295                 300

Leu Leu Lys Gly Met Thr Leu Val Lys Asn Gln Asp Ala Leu Asp Lys
305                 310                 315                 320

Ala Thr Ala Asn Thr Asp Asp Ala Ala Phe Leu Glu Ile Pro Val Ala
                    325                 330                 335

Ser Thr Ile Asn Glu Lys Ala Val Leu Gly Lys Ala Ile Glu Asn Thr
                340                 345                 350

Phe Glu Leu Gln Tyr Asp His Thr Pro Asp Lys Ala Asp Asn Pro Lys
            355                 360                 365

Pro Ser Asn Pro Pro Arg Lys Pro Glu Val His Thr Gly Gly Lys Arg
        370                 375                 380

Phe Val Lys Lys Asp Ser Thr Glu Thr Gln Thr Leu Gly Gly Ala Glu
385                 390                 395                 400

Phe Asp Leu Leu Ala Ser Asp Gly Thr Ala Val Lys Trp Thr Asp Ala
                    405                 410                 415

Leu Ile Lys Ala Asn Thr Asn Lys Asn Tyr Ile Ala Gly Glu Ala Val
                420                 425                 430

Thr Gly Gln Pro Ile Lys Leu Lys Ser His Thr Asp Gly Thr Phe Glu
            435                 440                 445

Ile Lys Gly Leu Ala Tyr Ala Val Asp Ala Asn Ala Glu Gly Thr Ala
        450                 455                 460

Val Thr Tyr Lys Leu Lys Glu Thr Lys Ala Pro Glu Gly Tyr Val Ile
465                 470                 475                 480

Pro Asp Lys Glu Ile Glu Phe Thr Val Ser Gln Thr Ser Tyr Asn Thr
                    485                 490                 495

Lys Pro Thr Asp Ile Thr Val Asp Ser Ala Asp Ala Thr Pro Asp Thr
                500                 505                 510

Ile Lys Asn Asn Lys Arg Pro Ser Ile Pro Asn Thr Gly Gly Ile Gly
            515                 520                 525

Thr Ala Ile Phe Val Ala Ile Gly Ala Ala Val Met Ala Phe Ala Val
        530                 535                 540

Lys Gly Met Lys Arg Arg Thr Lys Asp Asn
545                 550

<210> SEQ ID NO 3
<211> LENGTH: 517
<212> TYPE: PRT
<213> ORGANISM: Streptococcus agalactiae

<400> SEQUENCE: 3

Ala Glu Val Ser Gln Glu Arg Pro Ala Lys Thr Thr Val Asn Ile Tyr
1               5                   10                  15

Lys Leu Gln Ala Asp Ser Tyr Lys Ser Glu Ile Thr Ser Asn Gly Gly
            20                  25                  30
```

-continued

```
Ile Glu Asn Lys Asp Gly Glu Val Ile Ser Asn Tyr Ala Lys Leu Gly
         35                  40                  45

Asp Asn Val Lys Gly Leu Gln Gly Val Gln Phe Lys Arg Tyr Lys Val
 50                  55                  60

Lys Thr Asp Ile Ser Val Asp Glu Leu Lys Lys Leu Thr Thr Val Glu
 65                  70                  75                  80

Ala Ala Asp Ala Lys Val Gly Thr Ile Leu Glu Glu Gly Val Ser Leu
                 85                  90                  95

Pro Gln Lys Thr Asn Ala Gln Gly Leu Val Val Asp Ala Leu Asp Ser
            100                 105                 110

Lys Ser Asn Val Arg Tyr Leu Tyr Val Glu Asp Leu Lys Asn Ser Pro
            115                 120                 125

Ser Asn Ile Thr Lys Ala Tyr Ala Val Pro Phe Val Leu Glu Leu Pro
130                 135                 140

Val Ala Asn Ser Thr Gly Thr Gly Phe Leu Ser Glu Ile Asn Ile Tyr
145                 150                 155                 160

Pro Lys Asn Val Val Thr Asp Glu Pro Lys Thr Asp Lys Asp Val Lys
                165                 170                 175

Lys Leu Gly Gln Asp Asp Ala Gly Tyr Thr Ile Gly Glu Glu Phe Lys
            180                 185                 190

Trp Phe Leu Lys Ser Thr Ile Pro Ala Asn Leu Gly Asp Tyr Glu Lys
            195                 200                 205

Phe Glu Ile Thr Asp Lys Phe Ala Asp Gly Leu Thr Tyr Lys Ser Val
210                 215                 220

Gly Lys Ile Lys Ile Gly Ser Lys Thr Leu Asn Arg Asp Glu His Tyr
225                 230                 235                 240

Thr Ile Asp Glu Pro Thr Val Asp Asn Gln Asn Thr Leu Lys Ile Thr
                245                 250                 255

Phe Lys Pro Glu Lys Phe Lys Glu Ile Ala Glu Leu Leu Lys Gly Met
            260                 265                 270

Thr Leu Val Lys Asn Gln Asp Ala Leu Asp Lys Ala Thr Ala Asn Thr
            275                 280                 285

Asp Asp Ala Ala Phe Leu Glu Ile Pro Val Ala Ser Thr Ile Asn Glu
290                 295                 300

Lys Ala Val Leu Gly Lys Ala Ile Glu Asn Thr Phe Glu Leu Gln Tyr
305                 310                 315                 320

Asp His Thr Pro Asp Lys Ala Asp Asn Pro Lys Pro Ser Asn Pro Pro
                325                 330                 335

Arg Lys Pro Glu Val His Thr Gly Gly Lys Arg Phe Val Lys Lys Asp
            340                 345                 350

Ser Thr Glu Thr Gln Thr Leu Gly Gly Ala Glu Phe Asp Leu Leu Ala
            355                 360                 365

Ser Asp Gly Thr Ala Val Lys Trp Thr Asp Ala Leu Ile Lys Ala Asn
370                 375                 380

Thr Asn Lys Asn Tyr Ile Ala Gly Glu Ala Val Thr Gly Gln Pro Ile
385                 390                 395                 400

Lys Leu Lys Ser His Thr Asp Gly Thr Phe Glu Ile Lys Gly Leu Ala
                405                 410                 415

Tyr Ala Val Asp Ala Asn Ala Glu Gly Thr Ala Val Thr Tyr Lys Leu
            420                 425                 430

Lys Glu Thr Lys Ala Pro Glu Gly Tyr Val Ile Pro Asp Lys Glu Ile
            435                 440                 445

Glu Phe Thr Val Ser Gln Thr Ser Tyr Asn Thr Lys Pro Thr Asp Ile
```

```
                450                 455                 460
Thr Val Asp Ser Ala Asp Ala Thr Pro Asp Thr Ile Lys Asn Asn Lys
465                 470                 475                 480

Arg Pro Ser Ile Pro Asn Thr Gly Gly Ile Gly Thr Ala Ile Phe Val
                485                 490                 495

Ala Ile Gly Ala Ala Val Met Ala Phe Ala Val Lys Gly Met Lys Arg
                500                 505                 510

Arg Thr Lys Asp Asn
        515

<210> SEQ ID NO 4
<211> LENGTH: 525
<212> TYPE: PRT
<213> ORGANISM: Streptococcus agalactiae

<400> SEQUENCE: 4

Met Lys Leu Ser Lys Lys Leu Leu Phe Ser Ala Ala Val Leu Thr Met
 1               5                  10                  15

Val Ala Gly Ser Thr Val Glu Pro Val Ala Gln Phe Ala Thr Gly Met
                20                  25                  30

Ser Ile Val Arg Ala Ala Glu Val Ser Gln Glu Arg Pro Ala Lys Thr
            35                  40                  45

Thr Val Asn Ile Tyr Lys Leu Gln Ala Asp Ser Tyr Lys Ser Glu Ile
        50                  55                  60

Thr Ser Asn Gly Gly Ile Glu Asn Lys Asp Gly Glu Val Ile Ser Asn
65                  70                  75                  80

Tyr Ala Lys Leu Gly Asp Asn Val Lys Gly Leu Gln Gly Val Gln Phe
                85                  90                  95

Lys Arg Tyr Lys Val Lys Thr Asp Ile Ser Val Asp Glu Leu Lys Lys
                100                 105                 110

Leu Thr Thr Val Glu Ala Ala Asp Ala Lys Val Gly Thr Ile Leu Glu
            115                 120                 125

Glu Gly Val Ser Leu Pro Gln Lys Thr Asn Ala Gln Gly Leu Val Val
        130                 135                 140

Asp Ala Leu Asp Ser Lys Ser Asn Val Arg Tyr Leu Tyr Val Glu Asp
145                 150                 155                 160

Leu Lys Asn Ser Pro Ser Asn Ile Thr Lys Ala Tyr Ala Val Pro Phe
                165                 170                 175

Val Leu Glu Leu Pro Val Ala Asn Ser Thr Gly Thr Gly Phe Leu Ser
                180                 185                 190

Glu Ile Asn Ile Tyr Pro Lys Asn Val Val Thr Asp Glu Pro Lys Thr
            195                 200                 205

Asp Lys Asp Val Lys Lys Leu Gly Gln Asp Asp Ala Gly Tyr Thr Ile
        210                 215                 220

Gly Glu Glu Phe Lys Trp Phe Leu Lys Ser Thr Ile Pro Ala Asn Leu
225                 230                 235                 240

Gly Asp Tyr Glu Lys Phe Glu Ile Thr Asp Lys Phe Ala Asp Gly Leu
                245                 250                 255

Thr Tyr Lys Ser Val Gly Lys Ile Lys Ile Gly Ser Lys Thr Leu Asn
                260                 265                 270

Arg Asp Glu His Tyr Thr Ile Asp Glu Pro Thr Val Asp Asn Gln Asn
            275                 280                 285

Thr Leu Lys Ile Thr Phe Lys Pro Glu Lys Phe Lys Glu Ile Ala Glu
        290                 295                 300
```

```
Leu Leu Lys Gly Met Thr Leu Val Lys Asn Gln Asp Ala Leu Asp Lys
305                 310                 315                 320

Ala Thr Ala Asn Thr Asp Asp Ala Ala Phe Leu Glu Ile Pro Val Ala
            325                 330                 335

Ser Thr Ile Asn Glu Lys Ala Val Leu Gly Lys Ala Ile Glu Asn Thr
            340                 345                 350

Phe Glu Leu Gln Tyr Asp His Thr Pro Asp Lys Ala Asp Asn Pro Lys
        355                 360                 365

Pro Ser Asn Pro Pro Arg Lys Pro Glu Val His Thr Gly Gly Lys Arg
    370                 375                 380

Phe Val Lys Lys Asp Ser Thr Glu Thr Gln Thr Leu Gly Gly Ala Glu
385                 390                 395                 400

Phe Asp Leu Leu Ala Ser Asp Gly Thr Ala Val Lys Trp Thr Asp Ala
            405                 410                 415

Leu Ile Lys Ala Asn Thr Asn Lys Asn Tyr Ile Ala Gly Glu Ala Val
            420                 425                 430

Thr Gly Gln Pro Ile Lys Leu Lys Ser His Thr Asp Gly Thr Phe Glu
        435                 440                 445

Ile Lys Gly Leu Ala Tyr Ala Val Asp Ala Asn Ala Glu Gly Thr Ala
    450                 455                 460

Val Thr Tyr Lys Leu Lys Glu Thr Lys Ala Pro Glu Gly Tyr Val Ile
465                 470                 475                 480

Pro Asp Lys Glu Ile Glu Phe Thr Val Ser Gln Thr Ser Tyr Asn Thr
            485                 490                 495

Lys Pro Thr Asp Ile Thr Val Asp Ser Ala Asp Ala Thr Pro Asp Thr
            500                 505                 510

Ile Lys Asn Asn Lys Arg Pro Ser Ile Pro Asn Thr Gly
        515                 520                 525

<210> SEQ ID NO 5
<211> LENGTH: 5
<212> TYPE: PRT
<213> ORGANISM: Streptococcus agalactiae

<400> SEQUENCE: 5

Ile Pro Asn Thr Gly
1               5

<210> SEQ ID NO 6
<211> LENGTH: 520
<212> TYPE: PRT
<213> ORGANISM: Streptococcus agalactiae

<400> SEQUENCE: 6

Met Lys Leu Ser Lys Lys Leu Leu Phe Ser Ala Ala Val Leu Thr Met
1               5                   10                  15

Val Ala Gly Ser Thr Val Glu Pro Val Ala Gln Phe Ala Thr Gly Met
            20                  25                  30

Ser Ile Val Arg Ala Ala Glu Val Ser Gln Glu Arg Pro Ala Lys Thr
        35                  40                  45

Thr Val Asn Ile Tyr Lys Leu Gln Ala Asp Ser Tyr Lys Ser Glu Ile
    50                  55                  60

Thr Ser Asn Gly Gly Ile Glu Asn Lys Asp Gly Glu Val Ile Ser Asn
65                  70                  75                  80

Tyr Ala Lys Leu Gly Asp Asn Val Lys Gly Leu Gln Gly Val Gln Phe
            85                  90                  95
```

```
Lys Arg Tyr Lys Val Lys Thr Asp Ile Ser Val Asp Glu Leu Lys Lys
                100                 105                 110

Leu Thr Thr Val Glu Ala Ala Asp Ala Lys Val Gly Thr Ile Leu Glu
        115                 120                 125

Glu Gly Val Ser Leu Pro Gln Lys Thr Asn Ala Gln Gly Leu Val Val
    130                 135                 140

Asp Ala Leu Asp Ser Lys Ser Asn Val Arg Tyr Leu Tyr Val Glu Asp
145                 150                 155                 160

Leu Lys Asn Ser Pro Ser Asn Ile Thr Lys Ala Tyr Ala Val Pro Phe
                165                 170                 175

Val Leu Glu Leu Pro Val Ala Asn Ser Thr Gly Thr Gly Phe Leu Ser
            180                 185                 190

Glu Ile Asn Ile Tyr Pro Lys Asn Val Val Thr Asp Glu Pro Lys Thr
        195                 200                 205

Asp Lys Asp Val Lys Lys Leu Gly Gln Asp Asp Ala Gly Tyr Thr Ile
    210                 215                 220

Gly Glu Glu Phe Lys Trp Phe Leu Lys Ser Thr Ile Pro Ala Asn Leu
225                 230                 235                 240

Gly Asp Tyr Glu Lys Phe Glu Ile Thr Asp Lys Phe Ala Asp Gly Leu
                245                 250                 255

Thr Tyr Lys Ser Val Gly Lys Ile Lys Ile Gly Ser Lys Thr Leu Asn
            260                 265                 270

Arg Asp Glu His Tyr Thr Ile Asp Glu Pro Thr Val Asp Asn Gln Asn
        275                 280                 285

Thr Leu Lys Ile Thr Phe Lys Pro Glu Lys Phe Lys Glu Ile Ala Glu
    290                 295                 300

Leu Leu Lys Gly Met Thr Leu Val Lys Asn Gln Asp Ala Leu Asp Lys
305                 310                 315                 320

Ala Thr Ala Asn Thr Asp Asp Ala Ala Phe Leu Glu Ile Pro Val Ala
                325                 330                 335

Ser Thr Ile Asn Glu Lys Ala Val Leu Gly Lys Ala Ile Glu Asn Thr
            340                 345                 350

Phe Glu Leu Gln Tyr Asp His Thr Pro Asp Lys Ala Asp Asn Pro Lys
        355                 360                 365

Pro Ser Asn Pro Pro Arg Lys Pro Glu Val His Thr Gly Gly Lys Arg
    370                 375                 380

Phe Val Lys Lys Asp Ser Thr Glu Thr Gln Thr Leu Gly Gly Ala Glu
385                 390                 395                 400

Phe Asp Leu Leu Ala Ser Asp Gly Thr Ala Val Lys Trp Thr Asp Ala
                405                 410                 415

Leu Ile Lys Ala Asn Thr Asn Lys Asn Tyr Ile Ala Gly Glu Ala Val
            420                 425                 430

Thr Gly Gln Pro Ile Lys Leu Lys Ser His Thr Asp Gly Thr Phe Glu
        435                 440                 445

Ile Lys Gly Leu Ala Tyr Ala Val Asp Ala Asn Ala Glu Gly Thr Ala
    450                 455                 460

Val Thr Tyr Lys Leu Lys Glu Thr Lys Ala Pro Glu Gly Tyr Val Ile
465                 470                 475                 480

Pro Asp Lys Glu Ile Glu Phe Thr Val Ser Gln Thr Ser Tyr Asn Thr
                485                 490                 495

Lys Pro Thr Asp Ile Thr Val Asp Ser Ala Asp Ala Thr Pro Asp Thr
            500                 505                 510

Ile Lys Asn Asn Lys Arg Pro Ser
```

-continued

```
            515                 520

<210> SEQ ID NO 7
<211> LENGTH: 483
<212> TYPE: PRT
<213> ORGANISM: Streptococcus agalactiae

<400> SEQUENCE: 7

Ala Glu Val Ser Gln Glu Arg Pro Ala Lys Thr Thr Val Asn Ile Tyr
 1               5                  10                  15

Lys Leu Gln Ala Asp Ser Tyr Lys Ser Glu Ile Thr Ser Asn Gly Gly
             20                  25                  30

Ile Glu Asn Lys Asp Gly Glu Val Ile Ser Asn Tyr Ala Lys Leu Gly
         35                  40                  45

Asp Asn Val Lys Gly Leu Gln Gly Val Gln Phe Lys Arg Tyr Lys Val
     50                  55                  60

Lys Thr Asp Ile Ser Val Asp Glu Leu Lys Lys Leu Thr Thr Val Glu
 65                  70                  75                  80

Ala Ala Asp Ala Lys Val Gly Thr Ile Leu Glu Glu Gly Val Ser Leu
                 85                  90                  95

Pro Gln Lys Thr Asn Ala Gln Gly Leu Val Val Asp Ala Leu Asp Ser
            100                 105                 110

Lys Ser Asn Val Arg Tyr Leu Tyr Val Glu Asp Leu Lys Asn Ser Pro
        115                 120                 125

Ser Asn Ile Thr Lys Ala Tyr Ala Val Pro Phe Val Leu Glu Leu Pro
    130                 135                 140

Val Ala Asn Ser Thr Gly Thr Gly Phe Leu Ser Glu Ile Asn Ile Tyr
145                 150                 155                 160

Pro Lys Asn Val Val Thr Asp Glu Pro Lys Thr Asp Lys Asp Val Lys
                165                 170                 175

Lys Leu Gly Gln Asp Asp Ala Gly Tyr Thr Ile Gly Glu Glu Phe Lys
            180                 185                 190

Trp Phe Leu Lys Ser Thr Ile Pro Ala Asn Leu Gly Asp Tyr Glu Lys
        195                 200                 205

Phe Glu Ile Thr Asp Lys Phe Ala Asp Gly Leu Thr Tyr Lys Ser Val
    210                 215                 220

Gly Lys Ile Lys Ile Gly Ser Lys Thr Leu Asn Arg Asp Glu His Tyr
225                 230                 235                 240

Thr Ile Asp Glu Pro Thr Val Asp Asn Gln Asn Thr Leu Lys Ile Thr
                245                 250                 255

Phe Lys Pro Glu Lys Phe Lys Glu Ile Ala Glu Leu Leu Lys Gly Met
            260                 265                 270

Thr Leu Val Lys Asn Gln Asp Ala Leu Asp Lys Ala Thr Ala Asn Thr
        275                 280                 285

Asp Asp Ala Ala Phe Leu Glu Ile Pro Val Ala Ser Thr Ile Asn Glu
    290                 295                 300

Lys Ala Val Leu Gly Lys Ala Ile Glu Asn Thr Phe Glu Leu Gln Tyr
305                 310                 315                 320

Asp His Thr Pro Asp Lys Ala Asp Asn Pro Lys Pro Ser Asn Pro
                325                 330                 335

Arg Lys Pro Glu Val His Thr Gly Gly Lys Arg Phe Val Lys Lys Asp
            340                 345                 350

Ser Thr Glu Thr Gln Thr Leu Gly Gly Ala Glu Phe Asp Leu Leu Ala
        355                 360                 365
```

```
Ser Asp Gly Thr Ala Val Lys Trp Thr Asp Ala Leu Ile Lys Ala Asn
    370                 375                 380

Thr Asn Lys Asn Tyr Ile Ala Gly Glu Ala Val Thr Gly Gln Pro Ile
385                 390                 395                 400

Lys Leu Lys Ser His Thr Asp Gly Thr Phe Glu Ile Lys Gly Leu Ala
                405                 410                 415

Tyr Ala Val Asp Ala Asn Ala Glu Gly Thr Ala Val Thr Tyr Lys Leu
            420                 425                 430

Lys Glu Thr Lys Ala Pro Glu Gly Tyr Val Ile Pro Asp Lys Glu Ile
        435                 440                 445

Glu Phe Thr Val Ser Gln Thr Ser Tyr Asn Thr Lys Pro Thr Asp Ile
    450                 455                 460

Thr Val Asp Ser Ala Asp Ala Thr Pro Asp Thr Ile Lys Asn Asn Lys
465                 470                 475                 480

Arg Pro Ser

<210> SEQ ID NO 8
<211> LENGTH: 271
<212> TYPE: PRT
<213> ORGANISM: Streptococcus agalactiae

<400> SEQUENCE: 8

Ala Glu Val Ser Gln Glu Arg Pro Ala Lys Thr Thr Val Asn Ile Tyr
1               5                   10                  15

Lys Leu Gln Ala Asp Ser Tyr Lys Ser Glu Ile Thr Ser Asn Gly Gly
            20                  25                  30

Ile Glu Asn Lys Asp Gly Glu Val Ile Ser Asn Tyr Ala Lys Leu Gly
        35                  40                  45

Asp Asn Val Lys Gly Leu Gln Gly Val Gln Phe Lys Arg Tyr Lys Val
    50                  55                  60

Lys Thr Asp Ile Ser Val Asp Glu Leu Lys Lys Leu Thr Thr Val Glu
65                  70                  75                  80

Ala Ala Asp Ala Lys Val Gly Thr Ile Leu Glu Glu Gly Val Ser Leu
                85                  90                  95

Pro Gln Lys Thr Asn Ala Gln Gly Leu Val Val Asp Ala Leu Asp Ser
            100                 105                 110

Lys Ser Asn Val Arg Tyr Leu Tyr Val Glu Asp Leu Lys Asn Ser Pro
        115                 120                 125

Ser Asn Ile Thr Lys Ala Tyr Ala Val Pro Phe Val Leu Glu Leu Pro
    130                 135                 140

Val Ala Asn Ser Thr Gly Thr Gly Phe Leu Ser Glu Ile Asn Ile Tyr
145                 150                 155                 160

Pro Lys Asn Val Val Thr Asp Glu Pro Lys Thr Asp Lys Asp Val Lys
                165                 170                 175

Lys Leu Gly Gln Asp Asp Ala Gly Tyr Thr Ile Gly Glu Glu Phe Lys
            180                 185                 190

Trp Phe Leu Lys Ser Thr Ile Pro Ala Asn Leu Gly Asp Tyr Glu Lys
        195                 200                 205

Phe Glu Ile Thr Asp Lys Phe Ala Asp Gly Leu Thr Tyr Lys Ser Val
    210                 215                 220

Gly Lys Ile Lys Ile Gly Ser Lys Thr Leu Asn Arg Asp Glu His Tyr
225                 230                 235                 240

Thr Ile Asp Glu Pro Thr Val Asp Asn Gln Asn Thr Leu Lys Ile Thr
                245                 250                 255
```

```
Phe Lys Pro Glu Lys Phe Lys Glu Ile Ala Glu Leu Leu Lys Gly
            260                 265                 270

<210> SEQ ID NO 9
<211> LENGTH: 212
<212> TYPE: PRT
<213> ORGANISM: Streptococcus agalactiae

<400> SEQUENCE: 9

Met Thr Leu Val Lys Asn Gln Asp Ala Leu Asp Lys Ala Thr Ala Asn
 1               5                  10                  15

Thr Asp Asp Ala Ala Phe Leu Glu Ile Pro Val Ala Ser Thr Ile Asn
                20                  25                  30

Glu Lys Ala Val Leu Gly Lys Ala Ile Glu Asn Thr Phe Glu Leu Gln
            35                  40                  45

Tyr Asp His Thr Pro Asp Lys Ala Asp Asn Pro Lys Pro Ser Asn Pro
        50                  55                  60

Pro Arg Lys Pro Glu Val His Thr Gly Gly Lys Arg Phe Val Lys Lys
65                  70                  75                  80

Asp Ser Thr Glu Thr Gln Thr Leu Gly Gly Ala Glu Phe Asp Leu Leu
                85                  90                  95

Ala Ser Asp Gly Thr Ala Val Lys Trp Thr Asp Ala Leu Ile Lys Ala
            100                 105                 110

Asn Thr Asn Lys Asn Tyr Ile Ala Gly Glu Ala Val Thr Gly Gln Pro
        115                 120                 125

Ile Lys Leu Lys Ser His Thr Asp Gly Thr Phe Glu Ile Lys Gly Leu
    130                 135                 140

Ala Tyr Ala Val Asp Ala Asn Ala Glu Gly Thr Ala Val Thr Tyr Lys
145                 150                 155                 160

Leu Lys Glu Thr Lys Ala Pro Glu Gly Tyr Val Ile Pro Asp Lys Glu
                165                 170                 175

Ile Glu Phe Thr Val Ser Gln Thr Ser Tyr Asn Thr Lys Pro Thr Asp
            180                 185                 190

Ile Thr Val Asp Ser Ala Asp Ala Thr Pro Asp Thr Ile Lys Asn Asn
        195                 200                 205

Lys Arg Pro Ser
    210

<210> SEQ ID NO 10
<211> LENGTH: 1629
<212> TYPE: DNA
<213> ORGANISM: Streptococcus agalactiae

<400> SEQUENCE: 10
atgaaaaaag acaagtaaa tgatactaag caatcttact ctctacgtaa atataaattt      60
ggtttagcat cagtaatttt agggtcattc ataatggtca caagtcctgt ttttgcggat    120
caaactacat cggttcaagt taataatcag acaggcacta gtgtggatgc taataattct    180
tccaatgaga caagtgcgtc aagtgtgatt acttccaata tgatagtgt tcaagcgtct    240 gataaagttg taaatagtca aaatacggca acaaggaca ttactactcc tttagtagag    300
acaaagccaa tggtggaaaa acattacct gaacaaggga attatgttta tagcaaagaa    360
accgaggtga aaaatacacc ttcaaaatca gccccagtag cttttctatgc aaagaaaggt    420 gataaagttt tctatgacca agtatttaat aaagataatg tgaaatggat ttcatataag    480 tcttttttgtg gcgtacgtcg atacgcagct attgagtcac tagatccatc aggaggttca    540
```

```
gagactaaag cacctactcc tgtaacaaat tcaggaagca ataatcaaga gaaaatagca    600
acgcaaggaa attatacatt ttcacataaa gtagaagtaa aaaatgaagc taaggtagcg    660
agtccaactc aatttacatt ggacaaagga gacagaattt tttacgacca atactaact    720 attgaaggaa atcagtggtt atctatataaa tcattcaatg gtgttcgtcg ttttgttttg    780
ctaggtaaag catcttcagt agaaaaaact gaagataaag aaaaagtgtc tcctcaacca    840
caagcccgta ttactaaaac tggtagacta actatttcta acgaaacaac tacaggtttt    900
gatattttaa ttacgaatat taaagatgat aacggtatcg ctgctgttaa ggtaccggtt    960
tggactgaac aaggagggca agatgatatt aaatggtata cagctgtaac tactggggat   1020
ggcaactaca aagtagctgt atcatttgct gaccataaga atgagaaggg tctttataat   1080
attcatttat actaccaaga agctagtggg acacttgtag gtgtaacagg aactaaagtg   1140
acagtagctg gaactaattc ttctcaagaa cctattgaaa atggtttagc aaagactggt   1200
gtttataata ttatcggaag tactgaagta aaaaatgaag ctaaaatatc aagtcagacc   1260
caatttactt tagaaaaagg tgacaaaata aattatgatc aagtattgac agcagatggt   1320
taccagtgga tttcttacaa atcttatagt ggtgttcgtc gctatattcc tgtgaaaaag   1380
ctaactacaa gtagtgaaaa agcgaaagat gaggcgacta aaccgactag ttatcccaac   1440
ttacctaaaa caggtaccta tacattact aaaactgtag atgtgaaaag tcaacctaaa   1500
gtatcaagtc cagtggaatt taattttcaa aagggtgaaa aaatacatta tgatcaagtg   1560
ttagtagtag atggtcatca gtggatttca tacaagagtt attccggtat tcgtcgctat   1620
attgaaatt                                                           1629
```

<210> SEQ ID NO 11
<211> LENGTH: 543
<212> TYPE: PRT
<213> ORGANISM: Streptococcus agalactiae

<400> SEQUENCE: 11

```
Met Lys Lys Gly Gln Val Asn Asp Thr Lys Gln Ser Tyr Ser Leu Arg
1               5                   10                  15

Lys Tyr Lys Phe Gly Leu Ala Ser Val Ile Leu Gly Ser Phe Ile Met
            20                  25                  30

Val Thr Ser Pro Val Phe Ala Asp Gln Thr Thr Ser Val Gln Val Asn
        35                  40                  45

Asn Gln Thr Gly Thr Ser Val Asp Ala Asn Asn Ser Ser Asn Glu Thr
    50                  55                  60

Ser Ala Ser Ser Val Ile Thr Ser Asn Asn Asp Ser Val Gln Ala Ser
65                  70                  75                  80

Asp Lys Val Val Asn Ser Gln Asn Thr Ala Thr Lys Asp Ile Thr Thr
                85                  90                  95

Pro Leu Val Glu Thr Lys Pro Met Val Glu Lys Thr Leu Pro Glu Gln
            100                 105                 110

Gly Asn Tyr Val Tyr Ser Lys Glu Thr Glu Val Lys Asn Thr Pro Ser
        115                 120                 125

Lys Ser Ala Pro Val Ala Phe Tyr Ala Lys Gly Asp Lys Val Phe
    130                 135                 140

Tyr Asp Gln Val Phe Asn Lys Asp Asn Val Lys Trp Ile Ser Tyr Lys
145                 150                 155                 160

Ser Phe Cys Gly Val Arg Arg Tyr Ala Ala Ile Glu Ser Leu Asp Pro
                165                 170                 175
```

```
Ser Gly Gly Ser Glu Thr Lys Ala Pro Thr Pro Val Thr Asn Ser Gly
            180                 185                 190

Ser Asn Asn Gln Glu Lys Ile Ala Thr Gln Gly Asn Tyr Thr Phe Ser
        195                 200                 205

His Lys Val Glu Val Lys Asn Glu Ala Lys Val Ala Ser Pro Thr Gln
    210                 215                 220

Phe Thr Leu Asp Lys Gly Asp Arg Ile Phe Tyr Asp Gln Ile Leu Thr
225                 230                 235                 240

Ile Glu Gly Asn Gln Trp Leu Ser Tyr Lys Ser Phe Asn Gly Val Arg
                245                 250                 255

Arg Phe Val Leu Leu Gly Lys Ala Ser Ser Val Glu Lys Thr Glu Asp
            260                 265                 270

Lys Glu Lys Val Ser Pro Gln Pro Gln Ala Arg Ile Thr Lys Thr Gly
        275                 280                 285

Arg Leu Thr Ile Ser Asn Glu Thr Thr Thr Gly Phe Asp Ile Leu Ile
    290                 295                 300

Thr Asn Ile Lys Asp Asp Asn Gly Ile Ala Ala Val Lys Val Pro Val
305                 310                 315                 320

Trp Thr Glu Gln Gly Gly Gln Asp Asp Ile Lys Trp Tyr Thr Ala Val
                325                 330                 335

Thr Thr Gly Asp Gly Asn Tyr Lys Val Ala Val Ser Phe Ala Asp His
            340                 345                 350

Lys Asn Glu Lys Gly Leu Tyr Asn Ile His Leu Tyr Tyr Gln Glu Ala
        355                 360                 365

Ser Gly Thr Leu Val Gly Val Thr Gly Thr Lys Val Thr Val Ala Gly
    370                 375                 380

Thr Asn Ser Ser Gln Glu Pro Ile Glu Asn Gly Leu Ala Lys Thr Gly
385                 390                 395                 400

Val Tyr Asn Ile Ile Gly Ser Thr Glu Val Lys Asn Glu Ala Lys Ile
                405                 410                 415

Ser Ser Gln Thr Gln Phe Thr Leu Glu Lys Gly Asp Lys Ile Asn Tyr
            420                 425                 430

Asp Gln Val Leu Thr Ala Asp Gly Tyr Gln Trp Ile Ser Tyr Lys Ser
        435                 440                 445

Tyr Ser Gly Val Arg Arg Tyr Ile Pro Val Lys Lys Leu Thr Thr Ser
    450                 455                 460

Ser Glu Lys Ala Lys Asp Glu Ala Thr Lys Pro Thr Ser Tyr Pro Asn
465                 470                 475                 480

Leu Pro Lys Thr Gly Thr Tyr Thr Phe Thr Lys Thr Val Asp Val Lys
                485                 490                 495

Ser Gln Pro Lys Val Ser Ser Pro Val Glu Phe Asn Phe Gln Lys Gly
            500                 505                 510

Glu Lys Ile His Tyr Asp Gln Val Leu Val Val Asp Gly His Gln Trp
        515                 520                 525

Ile Ser Tyr Lys Ser Tyr Ser Gly Ile Arg Arg Tyr Ile Glu Ile
    530                 535                 540

<210> SEQ ID NO 12
<211> LENGTH: 504
<212> TYPE: PRT
<213> ORGANISM: Streptococcus agalactiae

<400> SEQUENCE: 12

Asp Gln Thr Thr Ser Val Gln Val Asn Asn Gln Thr Gly Thr Ser Val
1               5                   10                  15
```

```
Asp Ala Asn Asn Ser Ser Asn Glu Thr Ser Ala Ser Ser Val Ile Thr
            20                  25                  30

Ser Asn Asn Asp Ser Val Gln Ala Ser Asp Lys Val Val Asn Ser Gln
        35                  40                  45

Asn Thr Ala Thr Lys Asp Ile Thr Thr Pro Leu Val Glu Thr Lys Pro
    50                  55                  60

Met Val Glu Lys Thr Leu Pro Glu Gln Gly Asn Tyr Val Tyr Ser Lys
65                  70                  75                  80

Glu Thr Glu Val Lys Asn Thr Pro Ser Lys Ser Ala Pro Val Ala Phe
                85                  90                  95

Tyr Ala Lys Lys Gly Asp Lys Val Phe Tyr Asp Gln Val Phe Asn Lys
            100                 105                 110

Asp Asn Val Lys Trp Ile Ser Tyr Lys Ser Phe Cys Gly Val Arg Arg
        115                 120                 125

Tyr Ala Ala Ile Glu Ser Leu Asp Pro Ser Gly Gly Ser Glu Thr Lys
    130                 135                 140

Ala Pro Thr Pro Val Thr Asn Ser Gly Ser Asn Asn Gln Glu Lys Ile
145                 150                 155                 160

Ala Thr Gln Gly Asn Tyr Thr Phe Ser His Lys Val Glu Val Lys Asn
                165                 170                 175

Glu Ala Lys Val Ala Ser Pro Thr Gln Phe Thr Leu Asp Lys Gly Asp
            180                 185                 190

Arg Ile Phe Tyr Asp Gln Ile Leu Thr Ile Glu Gly Asn Gln Trp Leu
        195                 200                 205

Ser Tyr Lys Ser Phe Asn Gly Val Arg Arg Phe Val Leu Leu Gly Lys
    210                 215                 220

Ala Ser Ser Val Glu Lys Thr Glu Asp Lys Glu Lys Val Ser Pro Gln
225                 230                 235                 240

Pro Gln Ala Arg Ile Thr Lys Thr Gly Arg Leu Thr Ile Ser Asn Glu
                245                 250                 255

Thr Thr Thr Gly Phe Asp Ile Leu Ile Thr Asn Ile Lys Asp Asp Asn
            260                 265                 270

Gly Ile Ala Ala Val Lys Val Pro Val Trp Thr Glu Gln Gly Gly Gln
        275                 280                 285

Asp Asp Ile Lys Trp Tyr Thr Ala Val Thr Thr Gly Asp Gly Asn Tyr
    290                 295                 300

Lys Val Ala Val Ser Phe Ala Asp His Lys Asn Glu Lys Gly Leu Tyr
305                 310                 315                 320

Asn Ile His Leu Tyr Tyr Gln Glu Ala Ser Gly Thr Leu Val Gly Val
                325                 330                 335

Thr Gly Thr Lys Val Thr Val Ala Gly Thr Asn Ser Ser Gln Glu Pro
            340                 345                 350

Ile Glu Asn Gly Leu Ala Lys Thr Gly Val Tyr Asn Ile Ile Gly Ser
        355                 360                 365

Thr Glu Val Lys Asn Glu Ala Lys Ile Ser Ser Gln Thr Gln Phe Thr
    370                 375                 380

Leu Glu Lys Gly Asp Lys Ile Asn Tyr Asp Gln Val Leu Thr Ala Asp
385                 390                 395                 400

Gly Tyr Gln Trp Ile Ser Tyr Lys Ser Tyr Ser Gly Val Arg Arg Tyr
                405                 410                 415

Ile Pro Val Lys Lys Leu Thr Ser Ser Glu Lys Ala Lys Asp Glu
            420                 425                 430
```

```
Ala Thr Lys Pro Thr Ser Tyr Pro Asn Leu Pro Lys Thr Gly Thr Tyr
            435                 440                 445

Thr Phe Thr Lys Thr Val Asp Val Lys Ser Gln Pro Lys Val Ser Ser
450                 455                 460

Pro Val Glu Phe Asn Phe Gln Lys Gly Glu Lys Ile His Tyr Asp Gln
465                 470                 475                 480

Val Leu Val Val Asp Gly His Gln Trp Ile Ser Tyr Lys Ser Tyr Ser
                485                 490                 495

Gly Ile Arg Arg Tyr Ile Glu Ile
                500

<210> SEQ ID NO 13
<211> LENGTH: 485
<212> TYPE: PRT
<213> ORGANISM: Streptococcus agalactiae

<400> SEQUENCE: 13

Met Lys Lys Gly Gln Val Asn Asp Thr Lys Gln Ser Tyr Ser Leu Arg
1               5                   10                  15

Lys Tyr Lys Phe Gly Leu Ala Ser Val Ile Leu Gly Ser Phe Ile Met
                20                  25                  30

Val Thr Ser Pro Val Phe Ala Asp Gln Thr Thr Ser Val Gln Val Asn
            35                  40                  45

Asn Gln Thr Gly Thr Ser Val Asp Ala Asn Asn Ser Ser Asn Glu Thr
        50                  55                  60

Ser Ala Ser Ser Val Ile Thr Ser Asn Asn Asp Ser Val Gln Ala Ser
65                  70                  75                  80

Asp Lys Val Val Asn Ser Gln Asn Thr Ala Thr Lys Asp Ile Thr Thr
                85                  90                  95

Pro Leu Val Glu Thr Lys Pro Met Val Glu Lys Thr Leu Pro Glu Gln
            100                 105                 110

Gly Asn Tyr Val Tyr Ser Lys Glu Thr Glu Val Lys Asn Thr Pro Ser
        115                 120                 125

Lys Ser Ala Pro Val Ala Phe Tyr Ala Lys Lys Gly Asp Lys Val Phe
130                 135                 140

Tyr Asp Gln Val Phe Asn Lys Asp Asn Val Lys Trp Ile Ser Tyr Lys
145                 150                 155                 160

Ser Phe Cys Gly Val Arg Arg Tyr Ala Ala Ile Glu Ser Leu Asp Pro
                165                 170                 175

Ser Gly Gly Ser Glu Thr Lys Ala Pro Thr Pro Val Thr Asn Ser Gly
            180                 185                 190

Ser Asn Asn Gln Glu Lys Ile Ala Thr Gln Gly Asn Tyr Thr Phe Ser
        195                 200                 205

His Lys Val Glu Val Lys Asn Glu Ala Lys Val Ala Ser Pro Thr Gln
    210                 215                 220

Phe Thr Leu Asp Lys Gly Asp Arg Ile Phe Tyr Asp Gln Ile Leu Thr
225                 230                 235                 240

Ile Glu Gly Asn Gln Trp Leu Ser Tyr Lys Ser Phe Asn Gly Val Arg
                245                 250                 255

Arg Phe Val Leu Leu Gly Lys Ala Ser Ser Val Glu Lys Thr Glu Asp
            260                 265                 270

Lys Glu Lys Val Ser Pro Gln Pro Gln Ala Arg Ile Thr Lys Thr Gly
        275                 280                 285

Arg Leu Thr Ile Ser Asn Glu Thr Thr Thr Gly Phe Asp Ile Leu Ile
    290                 295                 300
```

```
Thr Asn Ile Lys Asp Asp Asn Gly Ile Ala Ala Val Lys Val Pro Val
305                 310                 315                 320

Trp Thr Glu Gln Gly Gly Gln Asp Asp Ile Lys Trp Tyr Thr Ala Val
                325                 330                 335

Thr Thr Gly Asp Gly Asn Tyr Lys Val Ala Val Ser Phe Ala Asp His
                340                 345                 350

Lys Asn Glu Lys Gly Leu Tyr Asn Ile His Leu Tyr Tyr Gln Glu Ala
                355                 360                 365

Ser Gly Thr Leu Val Gly Val Thr Gly Thr Lys Val Thr Val Ala Gly
            370                 375                 380

Thr Asn Ser Ser Gln Glu Pro Ile Glu Asn Gly Leu Ala Lys Thr Gly
385                 390                 395                 400

Val Tyr Asn Ile Ile Gly Ser Thr Glu Val Lys Asn Glu Ala Lys Ile
                405                 410                 415

Ser Ser Gln Thr Gln Phe Thr Leu Glu Lys Gly Asp Lys Ile Asn Tyr
                420                 425                 430

Asp Gln Val Leu Thr Ala Asp Gly Tyr Gln Trp Ile Ser Tyr Lys Ser
            435                 440                 445

Tyr Ser Gly Val Arg Arg Tyr Ile Pro Val Lys Lys Leu Thr Thr Ser
450                 455                 460

Ser Glu Lys Ala Lys Asp Glu Ala Thr Lys Pro Thr Ser Tyr Pro Asn
465                 470                 475                 480

Leu Pro Lys Thr Gly
                485

<210> SEQ ID NO 14
<211> LENGTH: 5
<212> TYPE: PRT
<213> ORGANISM: Streptococcus agalactiae

<400> SEQUENCE: 14

Leu Thr Lys Thr Gly
1               5

<210> SEQ ID NO 15
<211> LENGTH: 480
<212> TYPE: PRT
<213> ORGANISM: Streptococcus agalactiae

<400> SEQUENCE: 15

Met Lys Lys Gly Gln Val Asn Asp Thr Lys Gln Ser Tyr Ser Leu Arg
1               5                   10                  15

Lys Tyr Lys Phe Gly Leu Ala Ser Val Ile Leu Gly Ser Phe Ile Met
                20                  25                  30

Val Thr Ser Pro Val Phe Ala Asp Gln Thr Thr Ser Val Gln Val Asn
                35                  40                  45

Asn Gln Thr Gly Thr Ser Val Asp Ala Asn Asn Ser Ser Asn Glu Thr
            50                  55                  60

Ser Ala Ser Ser Val Ile Thr Ser Asn Asn Asp Ser Val Gln Ala Ser
65              70                  75                  80

Asp Lys Val Val Asn Ser Gln Asn Thr Ala Thr Lys Asp Ile Thr Thr
                85                  90                  95

Pro Leu Val Glu Thr Lys Pro Met Val Glu Lys Thr Leu Pro Glu Gln
                100                 105                 110

Gly Asn Tyr Val Tyr Ser Lys Glu Thr Glu Val Lys Asn Thr Pro Ser
                115                 120                 125
```

Lys Ser Ala Pro Val Ala Phe Tyr Ala Lys Gly Asp Lys Val Phe
              130                 135                 140

Tyr Asp Gln Val Phe Asn Lys Asp Asn Val Lys Trp Ile Ser Tyr Lys
145                 150                 155                 160

Ser Phe Cys Gly Val Arg Arg Tyr Ala Ala Ile Glu Ser Leu Asp Pro
                165                 170                 175

Ser Gly Gly Ser Glu Thr Lys Ala Pro Thr Pro Val Thr Asn Ser Gly
                180                 185                 190

Ser Asn Asn Gln Glu Lys Ile Ala Thr Gln Gly Asn Tyr Thr Phe Ser
            195                 200                 205

His Lys Val Glu Val Lys Asn Glu Ala Lys Val Ala Ser Pro Thr Gln
            210                 215                 220

Phe Thr Leu Asp Lys Gly Asp Arg Ile Phe Tyr Asp Gln Ile Leu Thr
225                 230                 235                 240

Ile Glu Gly Asn Gln Trp Leu Ser Tyr Lys Ser Phe Asn Gly Val Arg
                245                 250                 255

Arg Phe Val Leu Leu Gly Lys Ala Ser Ser Val Glu Lys Thr Glu Asp
                260                 265                 270

Lys Glu Lys Val Ser Pro Gln Pro Gln Ala Arg Ile Thr Lys Thr Gly
                275                 280                 285

Arg Leu Thr Ile Ser Asn Glu Thr Thr Gly Phe Asp Ile Leu Ile
                290                 295                 300

Thr Asn Ile Lys Asp Asp Asn Gly Ile Ala Ala Val Lys Val Pro Val
305                 310                 315                 320

Trp Thr Glu Gln Gly Gly Gln Asp Asp Ile Lys Trp Tyr Thr Ala Val
                325                 330                 335

Thr Thr Gly Asp Gly Asn Tyr Lys Val Ala Val Ser Phe Ala Asp His
                340                 345                 350

Lys Asn Glu Lys Gly Leu Tyr Asn Ile His Leu Tyr Tyr Gln Glu Ala
                355                 360                 365

Ser Gly Thr Leu Val Gly Val Thr Gly Thr Lys Val Thr Val Ala Gly
                370                 375                 380

Thr Asn Ser Ser Gln Glu Pro Ile Glu Asn Gly Leu Ala Lys Thr Gly
385                 390                 395                 400

Val Tyr Asn Ile Ile Gly Ser Thr Glu Val Lys Asn Glu Ala Lys Ile
                405                 410                 415

Ser Ser Gln Thr Gln Phe Thr Leu Glu Lys Gly Asp Lys Ile Asn Tyr
                420                 425                 430

Asp Gln Val Leu Thr Ala Asp Gly Tyr Gln Trp Ile Ser Tyr Lys Ser
                435                 440                 445

Tyr Ser Gly Val Arg Arg Tyr Ile Pro Val Lys Lys Leu Thr Thr Ser
                450                 455                 460

Ser Glu Lys Ala Lys Asp Glu Ala Thr Lys Pro Thr Ser Tyr Pro Asn
465                 470                 475                 480

<210> SEQ ID NO 16
<211> LENGTH: 446
<212> TYPE: PRT
<213> ORGANISM: Streptococcus agalactiae

<400> SEQUENCE: 16

Asp Gln Thr Thr Ser Val Gln Val Asn Asn Gln Thr Gly Thr Ser Val
1               5                   10                  15

Asp Ala Asn Asn Ser Ser Asn Glu Thr Ser Ala Ser Ser Val Ile Thr

-continued

```
                20                  25                  30
Ser Asn Asn Asp Ser Val Gln Ala Ser Asp Lys Val Val Asn Ser Gln
                35                  40                  45

Asn Thr Ala Thr Lys Asp Ile Thr Thr Pro Leu Val Glu Thr Lys Pro
 50                  55                  60

Met Val Glu Lys Thr Leu Pro Glu Gln Gly Asn Tyr Val Tyr Ser Lys
 65                  70                  75                  80

Glu Thr Glu Val Lys Asn Thr Pro Ser Lys Ser Ala Pro Val Ala Phe
                85                  90                  95

Tyr Ala Lys Lys Gly Asp Lys Val Phe Tyr Asp Gln Val Phe Asn Lys
                100                 105                 110

Asp Asn Val Lys Trp Ile Ser Tyr Lys Ser Phe Cys Gly Val Arg Arg
                115                 120                 125

Tyr Ala Ala Ile Glu Ser Leu Asp Pro Ser Gly Gly Ser Glu Thr Lys
                130                 135                 140

Ala Pro Thr Pro Val Thr Asn Ser Gly Ser Asn Asn Gln Glu Lys Ile
145                 150                 155                 160

Ala Thr Gln Gly Asn Tyr Thr Phe Ser His Lys Val Glu Val Lys Asn
                165                 170                 175

Glu Ala Lys Val Ala Ser Pro Thr Gln Phe Thr Leu Asp Lys Gly Asp
                180                 185                 190

Arg Ile Phe Tyr Asp Gln Ile Leu Thr Ile Glu Gly Asn Gln Trp Leu
                195                 200                 205

Ser Tyr Lys Ser Phe Asn Gly Val Arg Arg Phe Val Leu Leu Gly Lys
                210                 215                 220

Ala Ser Ser Val Glu Lys Thr Glu Asp Lys Glu Lys Val Ser Pro Gln
225                 230                 235                 240

Pro Gln Ala Arg Ile Thr Lys Thr Gly Arg Leu Thr Ile Ser Asn Glu
                245                 250                 255

Thr Thr Thr Gly Phe Asp Ile Leu Ile Thr Asn Ile Lys Asp Asp Asn
                260                 265                 270

Gly Ile Ala Ala Val Lys Val Pro Val Trp Thr Glu Gln Gly Gly Gln
                275                 280                 285

Asp Asp Ile Lys Trp Tyr Thr Ala Val Thr Thr Gly Asp Gly Asn Tyr
                290                 295                 300

Lys Val Ala Val Ser Phe Ala Asp His Lys Asn Glu Lys Gly Leu Tyr
305                 310                 315                 320

Asn Ile His Leu Tyr Tyr Gln Glu Ala Ser Gly Thr Leu Val Gly Val
                325                 330                 335

Thr Gly Thr Lys Val Thr Val Ala Gly Thr Asn Ser Ser Gln Glu Pro
                340                 345                 350

Ile Glu Asn Gly Leu Ala Lys Thr Gly Val Tyr Asn Ile Ile Gly Ser
                355                 360                 365

Thr Glu Val Lys Asn Glu Ala Lys Ile Ser Ser Gln Thr Gln Phe Thr
                370                 375                 380

Leu Glu Lys Gly Asp Lys Ile Asn Tyr Asp Gln Val Leu Thr Ala Asp
385                 390                 395                 400

Gly Tyr Gln Trp Ile Ser Tyr Ser Tyr Ser Gly Val Arg Arg Tyr
                405                 410                 415

Ile Pro Val Lys Lys Leu Thr Thr Ser Ser Glu Lys Ala Lys Asp Glu
                420                 425                 430

Ala Thr Lys Pro Thr Ser Tyr Pro Asn Leu Pro Lys Thr Gly
                435                 440                 445
```

<210> SEQ ID NO 17
<211> LENGTH: 441
<212> TYPE: PRT
<213> ORGANISM: Streptococcus agalactiae

<400> SEQUENCE: 17

```
Asp Gln Thr Thr Ser Val Gln Val Asn Asn Gln Thr Gly Thr Ser Val
  1               5                  10                  15

Asp Ala Asn Asn Ser Ser Asn Glu Thr Ser Ala Ser Ser Val Ile Thr
             20                  25                  30

Ser Asn Asn Asp Ser Val Gln Ala Ser Asp Lys Val Val Asn Ser Gln
         35                  40                  45

Asn Thr Ala Thr Lys Asp Ile Thr Thr Pro Leu Val Glu Thr Lys Pro
     50                  55                  60

Met Val Glu Lys Thr Leu Pro Glu Gln Gly Asn Tyr Val Tyr Ser Lys
 65                  70                  75                  80

Glu Thr Glu Val Lys Asn Thr Pro Ser Lys Ser Ala Pro Val Ala Phe
                 85                  90                  95

Tyr Ala Lys Lys Gly Asp Lys Val Phe Tyr Asp Gln Val Phe Asn Lys
            100                 105                 110

Asp Asn Val Lys Trp Ile Ser Tyr Lys Ser Phe Cys Gly Val Arg Arg
        115                 120                 125

Tyr Ala Ala Ile Glu Ser Leu Asp Pro Ser Gly Gly Ser Glu Thr Lys
    130                 135                 140

Ala Pro Thr Pro Val Thr Asn Ser Gly Ser Asn Asn Gln Glu Lys Ile
145                 150                 155                 160

Ala Thr Gln Gly Asn Tyr Thr Phe Ser His Lys Val Glu Val Lys Asn
                165                 170                 175

Glu Ala Lys Val Ala Ser Pro Thr Gln Phe Thr Leu Asp Lys Gly Asp
            180                 185                 190

Arg Ile Phe Tyr Asp Gln Ile Leu Thr Ile Glu Gly Asn Gln Trp Leu
        195                 200                 205

Ser Tyr Lys Ser Phe Asn Gly Val Arg Arg Phe Val Leu Leu Gly Lys
    210                 215                 220

Ala Ser Ser Val Glu Lys Thr Glu Asp Lys Glu Lys Val Ser Pro Gln
225                 230                 235                 240

Pro Gln Ala Arg Ile Thr Lys Thr Gly Arg Leu Thr Ile Ser Asn Glu
                245                 250                 255

Thr Thr Thr Gly Phe Asp Ile Leu Ile Thr Asn Ile Lys Asp Asp Asn
            260                 265                 270

Gly Ile Ala Ala Val Lys Val Pro Val Trp Thr Glu Gln Gly Gly Gln
        275                 280                 285

Asp Asp Ile Lys Trp Tyr Thr Ala Val Thr Thr Gly Asp Gly Asn Tyr
    290                 295                 300

Lys Val Ala Val Ser Phe Ala Asp His Lys Asn Glu Lys Gly Leu Tyr
305                 310                 315                 320

Asn Ile His Leu Tyr Tyr Gln Glu Ala Ser Gly Thr Leu Val Gly Val
                325                 330                 335

Thr Gly Thr Lys Val Thr Val Ala Gly Thr Asn Ser Ser Gln Glu Pro
            340                 345                 350

Ile Glu Asn Gly Leu Ala Lys Thr Gly Val Tyr Asn Ile Ile Gly Ser
        355                 360                 365

Thr Glu Val Lys Asn Glu Ala Lys Ile Ser Ser Gln Thr Gln Phe Thr
```

```
                370              375              380
Leu Glu Lys Gly Asp Lys Ile Asn Tyr Asp Gln Val Leu Thr Ala Asp
385                 390                  395                  400

Gly Tyr Gln Trp Ile Ser Tyr Lys Ser Tyr Ser Gly Val Arg Arg Tyr
                    405                  410                  415

Ile Pro Val Lys Lys Leu Thr Thr Ser Ser Glu Lys Ala Lys Asp Glu
                420                  425                  430

Ala Thr Lys Pro Thr Ser Tyr Pro Asn
                435                  440

<210> SEQ ID NO 18
<211> LENGTH: 2670
<212> TYPE: DNA
<213> ORGANISM: Streptococcus agalactiae

<400> SEQUENCE: 18
```

| | | | | | |
|---|---|---|---|---|---|
| atgaaaaaga | gacaaaaaat | atggagaggg | ttatcagtta | ctttactaat | cctgtcccaa | 60 |
| attccatttg | gtatattggt | acaaggtgaa | acccaagata | ccaatcaagc | acttggaaaa | 120 |
| gtaattgtta | aaaaaacggg | agacaatgct | acaccattag | gcaaagcgac | ttttgtgtta | 180 |
| aaaaatgaca | atgataagtc | agaaacaagt | cacgaaacgg | tagagggttc | tggagaagca | 240 |
| acctttgaaa | cataaaaacc | tggagactac | acattaagag | aagaaacagc | accaattggt | 300 |
| tataaaaaaa | ctgataaaac | ctggaaagtt | aaagttgcag | ataacggagc | aacaataatc | 360 |
| gagggtatgg | atgcagataa | agcagagaaa | cgaaagaag | ttttgaatgc | ccaatatcca | 420 |
| aaatcagcta | tttatgagga | tacaaaagaa | aattacccat | tagttaatgt | agagggttcc | 480 |
| aaagttggtg | aacaatacaa | agcattgaat | ccaataaatg | gaaagatgg | tcgaagagag | 540 |
| attgctgaag | gttggttatc | aaaaaaaatt | acagggtca | atgatctcga | taagaataaa | 600 |
| tataaaattg | aattaactgt | tgagggtaaa | accactgttg | aaacgaaaga | acttaatcaa | 660 |
| ccactagatg | tcgttgtgct | attagataat | tcaaatagta | tgaataatga | aagagccaat | 720 |
| aattctcaaa | gagcattaaa | agctggggaa | gcagttgaaa | agctgattga | taaaattaca | 780 |
| tcaaataaag | acaatagagt | agctcttgtg | acatatgcct | caaccatttt | tgatggtact | 840 |
| gaagcgaccg | tatcaaaggg | agttgccgat | caaaatggta | aagcgctgaa | tgatagtgta | 900 |
| tcatgggatt | atcataaaac | tacttttaca | gcaactacac | ataattacag | ttatttaaat | 960 |
| ttaacaaatg | atgctaacga | agttaatatt | ctaaagtcaa | gaattccaaa | ggaagcggag | 1020 |
| catataaatg | gggatcgcac | gctctatcaa | tttggtgcga | catttactca | aaaagctcta | 1080 |
| atgaaagcaa | atgaaatttt | agagacacaa | agttctaatg | ctagaaaaaa | acttattttt | 1140 |
| cacgtaactg | atggtgtccc | tacgatgtct | tatgccataa | attttaatcc | ttatatatca | 1200 |
| acatcttacc | aaaaccagtt | taattctttt | ttaaataaaa | taccagatag | aagtggtatt | 1260 |
| ctccaagagg | attttataat | caatggtgat | gattatcaaa | tagtaaaagg | agatggagag | 1320 |
| agttttaaac | tgttttcgga | tagaaaagtt | cctgttactg | gaggaacgac | acaagcagct | 1380 |
| tatcgagtac | cgcaaaatca | actctctgta | atgagtaatg | agggatatgc | aattaatagt | 1440 |
| ggatatattt | atctctattg | gagagattac | aactgggtct | atccatttga | tcctaagaca | 1500 |
| aagaaagttt | ctgcaacgaa | acaaatcaaa | actcatggtg | agccaacaac | attatacttt | 1560 |
| aatggaaata | taagacctaa | aggttatgac | attttttactg | ttgggattgg | tgtaaacgga | 1620 |
| gatcctggtg | caactcctct | tgaagctgag | aaatttatgc | aatcaatatc | aagtaaaaca | 1680 |
| gaaaattata | ctaatgttga | tgatacaaat | aaaatttatg | atgagctaaa | taaatacttt | 1740 |

```
aaaacaattg ttgaggaaaa acattctatt gttgatggaa atgtgactga tcctatggga   1800
gagatgattg aattccaatt aaaaaatggt caaagtttta cacatgatga ttacgttttg   1860
gttggaaatg atggcagtca attaaaaaat ggtgtggctc ttggtggacc aaacagtgat   1920
gggggaattt taaaagatgt tacagtgact tatgataaga catctcaaac catcaaaatc   1980
aatcatttga acttaggaag tggacaaaaa gtagttctta cctatgatgt acgtttaaaa   2040
gataactata taagtaacaa attttacaat acaaataatc gtacaacgct aagtccgaag   2100
agtgaaaaag aaccaaatac tattcgtgat ttcccaattc ccaaaattcg tgatgttcgt   2160
gagtttccgg tactaaccat cagtaatcag aagaaaatgg gtgaggttga atttattaaa   2220
gttaataaag acaaacattc agaatcgctt ttgggagcta agtttcaact tcagatagaa   2280
aaagattttt ctgggtataa gcaatttgtt ccagagggaa gtgatgttac aacaaagaat   2340
gatggtaaaa tttattttaa agcacttcaa gatggtaact ataaattata tgaaatttca   2400
agtccagatg gctatataga ggttaaaacg aaacctgttg tgacatttac aattcaaaat   2460
ggagaagtta cgaacctgaa agcagatcca aatgctaata aaaatcaaat cgggtatctt   2520
gaaggaaatg gtaaacatct tattaccaac actcccaaac gcccaccagg tgttttttcct  2580
aaaacagggg gaattggtac aattgtctat atattagttg gttctacttt tatgatactt   2640
accatttgtt ctttccgtcg taaacaattg                                    2670

<210> SEQ ID NO 19
<211> LENGTH: 890
<212> TYPE: PRT
<213> ORGANISM: Streptococcus agalactiae

<400> SEQUENCE: 19

Met Lys Lys Arg Gln Lys Ile Trp Arg Gly Leu Ser Val Thr Leu Leu
  1               5                  10                  15

Ile Leu Ser Gln Ile Pro Phe Gly Ile Leu Val Gln Gly Glu Thr Gln
             20                  25                  30

Asp Thr Asn Gln Ala Leu Gly Lys Val Ile Val Lys Lys Thr Gly Asp
         35                  40                  45

Asn Ala Thr Pro Leu Gly Lys Ala Thr Phe Val Leu Lys Asn Asp Asn
     50                  55                  60

Asp Lys Ser Glu Thr Ser His Glu Thr Val Glu Gly Ser Gly Glu Ala
 65                  70                  75                  80

Thr Phe Glu Asn Ile Lys Pro Gly Asp Tyr Thr Leu Arg Glu Glu Thr
                 85                  90                  95

Ala Pro Ile Gly Tyr Lys Lys Thr Asp Lys Thr Trp Lys Val Lys Val
            100                 105                 110

Ala Asp Asn Gly Ala Thr Ile Ile Glu Gly Met Asp Ala Asp Lys Ala
        115                 120                 125

Glu Lys Arg Lys Glu Val Leu Asn Ala Gln Tyr Pro Lys Ser Ala Ile
    130                 135                 140

Tyr Glu Asp Thr Lys Glu Asn Tyr Pro Leu Val Asn Val Glu Gly Ser
145                 150                 155                 160

Lys Val Gly Glu Gln Tyr Lys Ala Leu Asn Pro Ile Asn Gly Lys Asp
                165                 170                 175

Gly Arg Arg Glu Ile Ala Glu Gly Trp Leu Ser Lys Lys Ile Thr Gly
            180                 185                 190

Val Asn Asp Leu Asp Lys Asn Lys Tyr Lys Ile Glu Leu Thr Val Glu
        195                 200                 205
```

-continued

```
Gly Lys Thr Thr Val Glu Thr Lys Glu Leu Asn Gln Pro Leu Asp Val
    210                 215                 220

Val Val Leu Leu Asp Asn Ser Asn Ser Met Asn Asn Glu Arg Ala Asn
225                 230                 235                 240

Asn Ser Gln Arg Ala Leu Lys Ala Gly Glu Ala Val Glu Lys Leu Ile
                245                 250                 255

Asp Lys Ile Thr Ser Asn Lys Asp Asn Arg Val Ala Leu Val Thr Tyr
                260                 265                 270

Ala Ser Thr Ile Phe Asp Gly Thr Glu Ala Thr Val Ser Lys Gly Val
                275                 280                 285

Ala Asp Gln Asn Gly Lys Ala Leu Asn Asp Ser Val Ser Trp Asp Tyr
    290                 295                 300

His Lys Thr Thr Phe Thr Ala Thr Thr His Asn Tyr Ser Tyr Leu Asn
305                 310                 315                 320

Leu Thr Asn Asp Ala Asn Glu Val Asn Ile Leu Lys Ser Arg Ile Pro
                325                 330                 335

Lys Glu Ala Glu His Ile Asn Gly Asp Arg Thr Leu Tyr Gln Phe Gly
                340                 345                 350

Ala Thr Phe Thr Gln Lys Ala Leu Met Lys Ala Asn Glu Ile Leu Glu
                355                 360                 365

Thr Gln Ser Ser Asn Ala Arg Lys Lys Leu Ile Phe His Val Thr Asp
    370                 375                 380

Gly Val Pro Thr Met Ser Tyr Ala Ile Asn Phe Asn Pro Tyr Ile Ser
385                 390                 395                 400

Thr Ser Tyr Gln Asn Gln Phe Asn Ser Phe Leu Asn Lys Ile Pro Asp
                405                 410                 415

Arg Ser Gly Ile Leu Gln Glu Asp Phe Ile Ile Asn Gly Asp Asp Tyr
                420                 425                 430

Gln Ile Val Lys Gly Asp Gly Glu Ser Phe Lys Leu Phe Ser Asp Arg
    435                 440                 445

Lys Val Pro Val Thr Gly Gly Thr Thr Gln Ala Ala Tyr Arg Val Pro
450                 455                 460

Gln Asn Gln Leu Ser Val Met Ser Asn Glu Gly Tyr Ala Ile Asn Ser
465                 470                 475                 480

Gly Tyr Ile Tyr Leu Tyr Trp Arg Asp Tyr Asn Trp Val Tyr Pro Phe
                485                 490                 495

Asp Pro Lys Thr Lys Lys Val Ser Ala Thr Lys Gln Ile Lys Thr His
                500                 505                 510

Gly Glu Pro Thr Thr Leu Tyr Phe Asn Gly Asn Ile Arg Pro Lys Gly
    515                 520                 525

Tyr Asp Ile Phe Thr Val Gly Ile Gly Val Asn Gly Asp Pro Gly Ala
530                 535                 540

Thr Pro Leu Glu Ala Glu Lys Phe Met Gln Ser Ile Ser Ser Lys Thr
545                 550                 555                 560

Glu Asn Tyr Thr Asn Val Asp Asp Thr Asn Lys Ile Tyr Asp Glu Leu
                565                 570                 575

Asn Lys Tyr Phe Lys Thr Ile Val Glu Glu Lys His Ser Ile Val Asp
                580                 585                 590

Gly Asn Val Thr Asp Pro Met Gly Glu Met Ile Glu Phe Gln Leu Lys
    595                 600                 605

Asn Gly Gln Ser Phe Thr His Asp Asp Tyr Val Leu Val Gly Asn Asp
610                 615                 620
```

```
Gly Ser Gln Leu Lys Asn Gly Val Ala Leu Gly Pro Asn Ser Asp
625                 630                 635                 640

Gly Gly Ile Leu Lys Asp Val Thr Val Thr Tyr Asp Lys Thr Ser Gln
            645                 650                 655

Thr Ile Lys Ile Asn His Leu Asn Leu Gly Ser Gly Gln Lys Val Val
                660                 665                 670

Leu Thr Tyr Asp Val Arg Leu Lys Asp Asn Tyr Ile Ser Asn Lys Phe
            675                 680                 685

Tyr Asn Thr Asn Asn Arg Thr Thr Leu Ser Pro Lys Ser Glu Lys Glu
            690                 695                 700

Pro Asn Thr Ile Arg Asp Phe Pro Ile Pro Lys Ile Arg Asp Val Arg
705                 710                 715                 720

Glu Phe Pro Val Leu Thr Ile Ser Asn Gln Lys Lys Met Gly Glu Val
                725                 730                 735

Glu Phe Ile Lys Val Asn Lys Asp Lys His Ser Glu Ser Leu Leu Gly
                740                 745                 750

Ala Lys Phe Gln Leu Gln Ile Glu Lys Asp Phe Ser Gly Tyr Lys Gln
            755                 760                 765

Phe Val Pro Glu Gly Ser Asp Val Thr Thr Lys Asn Asp Gly Lys Ile
770                 775                 780

Tyr Phe Lys Ala Leu Gln Asp Gly Asn Tyr Lys Leu Tyr Glu Ile Ser
785                 790                 795                 800

Ser Pro Asp Gly Tyr Ile Glu Val Lys Thr Lys Pro Val Val Thr Phe
                805                 810                 815

Thr Ile Gln Asn Gly Glu Val Thr Asn Leu Lys Ala Asp Pro Asn Ala
            820                 825                 830

Asn Lys Asn Gln Ile Gly Tyr Leu Glu Gly Asn Gly Lys His Leu Ile
            835                 840                 845

Thr Asn Thr Pro Lys Arg Pro Pro Gly Val Phe Pro Lys Thr Gly Gly
            850                 855                 860

Ile Gly Thr Ile Val Tyr Ile Leu Val Gly Ser Thr Phe Met Ile Leu
865                 870                 875                 880

Thr Ile Cys Ser Phe Arg Arg Lys Gln Leu
            885                 890

<210> SEQ ID NO 20
<211> LENGTH: 862
<212> TYPE: PRT
<213> ORGANISM: Streptococcus agalactiae

<400> SEQUENCE: 20

Gly Glu Thr Gln Asp Thr Asn Gln Ala Leu Gly Lys Val Ile Val Lys
1               5                   10                  15

Lys Thr Gly Asp Asn Ala Thr Pro Leu Gly Lys Ala Thr Phe Val Leu
            20                  25                  30

Lys Asn Asp Asn Asp Lys Ser Glu Thr Ser His Glu Thr Val Glu Gly
        35                  40                  45

Ser Gly Glu Ala Thr Phe Glu Asn Ile Lys Pro Gly Asp Tyr Thr Leu
    50                  55                  60

Arg Glu Glu Thr Ala Pro Ile Gly Tyr Lys Lys Thr Asp Lys Thr Trp
65                  70                  75                  80

Lys Val Lys Val Ala Asp Asn Gly Ala Thr Ile Ile Glu Gly Met Asp
                85                  90                  95

Ala Asp Lys Ala Glu Lys Arg Lys Glu Val Leu Asn Ala Gln Tyr Pro
            100                 105                 110
```

```
Lys Ser Ala Ile Tyr Glu Asp Thr Lys Glu Asn Tyr Pro Leu Val Asn
        115                 120                 125

Val Glu Gly Ser Lys Val Gly Glu Gln Tyr Lys Ala Leu Asn Pro Ile
        130                 135                 140

Asn Gly Lys Asp Gly Arg Arg Glu Ile Ala Glu Gly Trp Leu Ser Lys
145                 150                 155                 160

Lys Ile Thr Gly Val Asn Asp Leu Asp Lys Asn Lys Tyr Lys Ile Glu
                165                 170                 175

Leu Thr Val Glu Gly Lys Thr Thr Val Glu Thr Lys Glu Leu Asn Gln
            180                 185                 190

Pro Leu Asp Val Val Leu Leu Asp Asn Ser Asn Ser Met Asn Asn
        195                 200                 205

Glu Arg Ala Asn Asn Ser Gln Arg Ala Leu Lys Ala Gly Glu Ala Val
        210                 215                 220

Glu Lys Leu Ile Asp Lys Ile Thr Ser Asn Lys Asp Asn Arg Val Ala
225                 230                 235                 240

Leu Val Thr Tyr Ala Ser Thr Ile Phe Asp Gly Thr Glu Ala Thr Val
                245                 250                 255

Ser Lys Gly Val Ala Asp Gln Asn Gly Lys Ala Leu Asn Asp Ser Val
            260                 265                 270

Ser Trp Asp Tyr His Lys Thr Thr Phe Thr Ala Thr Thr His Asn Tyr
        275                 280                 285

Ser Tyr Leu Asn Leu Thr Asn Asp Ala Asn Glu Val Asn Ile Leu Lys
        290                 295                 300

Ser Arg Ile Pro Lys Glu Ala Glu His Ile Asn Gly Asp Arg Thr Leu
305                 310                 315                 320

Tyr Gln Phe Gly Ala Thr Phe Thr Gln Lys Ala Leu Met Lys Ala Asn
                325                 330                 335

Glu Ile Leu Glu Thr Gln Ser Ser Asn Ala Arg Lys Lys Leu Ile Phe
            340                 345                 350

His Val Thr Asp Gly Val Pro Thr Met Ser Tyr Ala Ile Asn Phe Asn
        355                 360                 365

Pro Tyr Ile Ser Thr Ser Tyr Gln Asn Gln Phe Asn Ser Phe Leu Asn
        370                 375                 380

Lys Ile Pro Asp Arg Ser Gly Ile Leu Gln Glu Asp Phe Ile Ile Asn
385                 390                 395                 400

Gly Asp Asp Tyr Gln Ile Val Lys Gly Asp Gly Glu Ser Phe Lys Leu
                405                 410                 415

Phe Ser Asp Arg Lys Val Pro Val Thr Gly Thr Thr Gln Ala Ala
            420                 425                 430

Tyr Arg Val Pro Gln Asn Gln Leu Ser Val Met Ser Asn Glu Gly Tyr
        435                 440                 445

Ala Ile Asn Ser Gly Tyr Ile Tyr Leu Tyr Trp Arg Asp Tyr Asn Trp
        450                 455                 460

Val Tyr Pro Phe Asp Pro Lys Thr Lys Lys Val Ser Ala Thr Lys Gln
465                 470                 475                 480

Ile Lys Thr His Gly Glu Pro Thr Thr Leu Tyr Phe Asn Gly Asn Ile
                485                 490                 495

Arg Pro Lys Gly Tyr Asp Ile Phe Thr Val Gly Ile Gly Val Asn Gly
            500                 505                 510

Asp Pro Gly Ala Thr Pro Leu Glu Ala Glu Lys Phe Met Gln Ser Ile
        515                 520                 525
```

```
Ser Ser Lys Thr Glu Asn Tyr Thr Asn Val Asp Asp Thr Asn Lys Ile
    530                 535                 540

Tyr Asp Glu Leu Asn Lys Tyr Phe Lys Thr Ile Val Glu Glu Lys His
545                 550                 555                 560

Ser Ile Val Asp Gly Asn Val Thr Asp Pro Met Gly Glu Met Ile Glu
                565                 570                 575

Phe Gln Leu Lys Asn Gly Gln Ser Phe Thr His Asp Asp Tyr Val Leu
            580                 585                 590

Val Gly Asn Asp Gly Ser Gln Leu Lys Asn Gly Val Ala Leu Gly Gly
        595                 600                 605

Pro Asn Ser Asp Gly Gly Ile Leu Lys Asp Val Thr Val Thr Tyr Asp
    610                 615                 620

Lys Thr Ser Gln Thr Ile Lys Ile Asn His Leu Asn Leu Gly Ser Gly
625                 630                 635                 640

Gln Lys Val Val Leu Thr Tyr Asp Val Arg Leu Lys Asp Asn Tyr Ile
                645                 650                 655

Ser Asn Lys Phe Tyr Asn Thr Asn Asn Arg Thr Thr Leu Ser Pro Lys
            660                 665                 670

Ser Glu Lys Glu Pro Asn Thr Ile Arg Asp Phe Pro Ile Pro Lys Ile
        675                 680                 685

Arg Asp Val Arg Glu Phe Pro Val Leu Thr Ile Ser Asn Gln Lys Lys
    690                 695                 700

Met Gly Glu Val Glu Phe Ile Lys Val Asn Lys Asp Lys His Ser Glu
705                 710                 715                 720

Ser Leu Leu Gly Ala Lys Phe Gln Leu Gln Ile Glu Lys Asp Phe Ser
                725                 730                 735

Gly Tyr Lys Gln Phe Val Pro Glu Gly Ser Asp Val Thr Thr Lys Asn
            740                 745                 750

Asp Gly Lys Ile Tyr Phe Lys Ala Leu Gln Asp Gly Asn Tyr Lys Leu
        755                 760                 765

Tyr Glu Ile Ser Ser Pro Asp Gly Tyr Ile Glu Val Lys Thr Lys Pro
    770                 775                 780

Val Val Thr Phe Thr Ile Gln Asn Gly Glu Val Thr Asn Leu Lys Ala
785                 790                 795                 800

Asp Pro Asn Ala Asn Lys Asn Gln Ile Gly Tyr Leu Glu Gly Asn Gly
                805                 810                 815

Lys His Leu Ile Thr Asn Thr Pro Lys Arg Pro Pro Gly Val Phe Pro
            820                 825                 830

Lys Thr Gly Gly Ile Gly Thr Ile Val Tyr Ile Leu Val Gly Ser Thr
        835                 840                 845

Phe Met Ile Leu Thr Ile Cys Ser Phe Arg Arg Lys Gln Leu
    850                 855                 860

<210> SEQ ID NO 21
<211> LENGTH: 851
<212> TYPE: PRT
<213> ORGANISM: Streptococcus agalactiae

<400> SEQUENCE: 21

Met Lys Lys Arg Gln Lys Ile Trp Arg Gly Leu Ser Thr Leu Leu
 1               5                  10                  15

Ile Leu Ser Gln Ile Pro Phe Gly Ile Leu Val Gln Gly Glu Thr Gln
                20                  25                  30

Asp Thr Asn Gln Ala Leu Gly Lys Val Ile Val Lys Lys Thr Gly Asp
            35                  40                  45
```

```
Asn Ala Thr Pro Leu Gly Lys Ala Thr Phe Val Leu Lys Asn Asp Asn
     50                  55                  60

Asp Lys Ser Glu Thr Ser His Glu Thr Val Glu Gly Ser Gly Glu Ala
 65                  70                  75                  80

Thr Phe Glu Asn Ile Lys Pro Gly Asp Tyr Thr Leu Arg Glu Glu Thr
                     85                  90                  95

Ala Pro Ile Gly Tyr Lys Lys Thr Asp Lys Thr Trp Lys Val Lys Val
                100                 105                 110

Ala Asp Asn Gly Ala Thr Ile Ile Glu Gly Met Asp Ala Asp Lys Ala
            115                 120                 125

Glu Lys Arg Lys Glu Val Leu Asn Ala Gln Tyr Pro Lys Ser Ala Ile
        130                 135                 140

Tyr Glu Asp Thr Lys Glu Asn Tyr Pro Leu Val Asn Val Glu Gly Ser
145                 150                 155                 160

Lys Val Gly Glu Gln Tyr Lys Ala Leu Asn Pro Ile Asn Gly Lys Asp
                165                 170                 175

Gly Arg Arg Glu Ile Ala Glu Gly Trp Leu Ser Lys Lys Ile Thr Gly
            180                 185                 190

Val Asn Asp Leu Asp Lys Asn Lys Tyr Lys Ile Glu Leu Thr Val Glu
        195                 200                 205

Gly Lys Thr Thr Val Glu Thr Lys Glu Leu Asn Gln Pro Leu Asp Val
210                 215                 220

Val Val Leu Leu Asp Asn Ser Asn Ser Met Asn Asn Glu Arg Ala Asn
225                 230                 235                 240

Asn Ser Gln Arg Ala Leu Lys Ala Gly Glu Ala Val Glu Lys Leu Ile
                245                 250                 255

Asp Lys Ile Thr Ser Asn Lys Asp Asn Arg Val Ala Leu Val Thr Tyr
            260                 265                 270

Ala Ser Thr Ile Phe Asp Gly Thr Glu Ala Thr Val Ser Lys Gly Val
        275                 280                 285

Ala Asp Gln Asn Gly Lys Ala Leu Asn Asp Ser Val Ser Trp Asp Tyr
290                 295                 300

His Lys Thr Thr Phe Thr Ala Thr Thr His Asn Tyr Ser Tyr Leu Asn
305                 310                 315                 320

Leu Thr Asn Asp Ala Asn Glu Val Asn Ile Leu Lys Ser Arg Ile Pro
                325                 330                 335

Lys Glu Ala Glu His Ile Asn Gly Asp Arg Thr Leu Tyr Gln Phe Gly
            340                 345                 350

Ala Thr Phe Thr Gln Lys Ala Leu Met Lys Ala Asn Glu Ile Leu Glu
        355                 360                 365

Thr Gln Ser Ser Asn Ala Arg Lys Lys Leu Ile Phe His Val Thr Asp
370                 375                 380

Gly Val Pro Thr Met Ser Tyr Ala Ile Asn Phe Asn Pro Tyr Ile Ser
385                 390                 395                 400

Thr Ser Tyr Gln Asn Gln Phe Asn Ser Phe Leu Asn Lys Ile Pro Asp
                405                 410                 415

Arg Ser Gly Ile Leu Gln Glu Asp Phe Ile Ile Asn Gly Asp Asp Tyr
            420                 425                 430

Gln Ile Val Lys Gly Asp Gly Glu Ser Phe Lys Leu Phe Ser Asp Arg
        435                 440                 445

Lys Val Pro Val Thr Gly Gly Thr Thr Gln Ala Ala Tyr Arg Val Pro
450                 455                 460
```

```
Gln Asn Gln Leu Ser Val Met Ser Asn Glu Gly Tyr Ala Ile Asn Ser
465                 470                 475                 480

Gly Tyr Ile Tyr Leu Tyr Trp Arg Asp Tyr Asn Trp Val Tyr Pro Phe
            485                 490                 495

Asp Pro Lys Thr Lys Lys Val Ser Ala Thr Lys Gln Ile Lys Thr His
        500                 505                 510

Gly Glu Pro Thr Thr Leu Tyr Phe Asn Gly Asn Ile Arg Pro Lys Gly
    515                 520                 525

Tyr Asp Ile Phe Thr Val Gly Ile Gly Val Asn Gly Asp Pro Gly Ala
530                 535                 540

Thr Pro Leu Glu Ala Glu Lys Phe Met Gln Ser Ile Ser Ser Lys Thr
545                 550                 555                 560

Glu Asn Tyr Thr Asn Val Asp Asp Thr Asn Lys Ile Tyr Asp Glu Leu
            565                 570                 575

Asn Lys Tyr Phe Lys Thr Ile Val Glu Glu Lys His Ser Ile Val Asp
        580                 585                 590

Gly Asn Val Thr Asp Pro Met Gly Glu Met Ile Glu Phe Gln Leu Lys
    595                 600                 605

Asn Gly Gln Ser Phe Thr His Asp Asp Tyr Val Leu Val Gly Asn Asp
610                 615                 620

Gly Ser Gln Leu Lys Asn Gly Val Ala Leu Gly Pro Asn Ser Asp
625                 630                 635                 640

Gly Gly Ile Leu Lys Asp Val Thr Val Thr Tyr Asp Lys Thr Ser Gln
            645                 650                 655

Thr Ile Lys Ile Asn His Leu Asn Leu Gly Ser Gly Gln Lys Val Val
        660                 665                 670

Leu Thr Tyr Asp Val Arg Leu Lys Asp Asn Tyr Ile Ser Asn Lys Phe
    675                 680                 685

Tyr Asn Thr Asn Asn Arg Thr Thr Leu Ser Pro Lys Ser Glu Lys Glu
690                 695                 700

Pro Asn Thr Ile Arg Asp Phe Pro Ile Pro Lys Ile Arg Asp Val Arg
705                 710                 715                 720

Glu Phe Pro Val Leu Thr Ile Ser Asn Gln Lys Lys Met Gly Glu Val
            725                 730                 735

Glu Phe Ile Lys Val Asn Lys Asp Lys His Ser Glu Ser Leu Leu Gly
        740                 745                 750

Ala Lys Phe Gln Leu Gln Ile Glu Lys Asp Phe Ser Gly Tyr Lys Gln
    755                 760                 765

Phe Val Pro Glu Gly Ser Asp Val Thr Thr Lys Asn Asp Gly Lys Ile
770                 775                 780

Tyr Phe Lys Ala Leu Gln Asp Gly Asn Tyr Lys Leu Tyr Glu Ile Ser
785                 790                 795                 800

Ser Pro Asp Gly Tyr Ile Glu Val Lys Thr Lys Pro Val Val Thr Phe
            805                 810                 815

Thr Ile Gln Asn Gly Glu Val Thr Asn Leu Lys Ala Asp Pro Asn Ala
        820                 825                 830

Asn Lys Asn Gln Ile Gly Tyr Leu Glu Gly Asn Gly Lys His Leu Ile
    835                 840                 845

Thr Asn Thr
    850

<210> SEQ ID NO 22
<211> LENGTH: 823
<212> TYPE: PRT
```

<213> ORGANISM: Streptococcus agalactiae

<400> SEQUENCE: 22

```
Gly Glu Thr Gln Asp Thr Asn Gln Ala Leu Gly Lys Val Ile Val Lys
  1               5                  10                  15

Lys Thr Gly Asp Asn Ala Thr Pro Leu Gly Lys Ala Thr Phe Val Leu
             20                  25                  30

Lys Asn Asp Asn Asp Lys Ser Glu Thr Ser His Glu Thr Val Glu Gly
         35                  40                  45

Ser Gly Glu Ala Thr Phe Glu Asn Ile Lys Pro Gly Asp Tyr Thr Leu
     50                  55                  60

Arg Glu Glu Thr Ala Pro Ile Gly Tyr Lys Lys Thr Asp Lys Thr Trp
 65                  70                  75                  80

Lys Val Lys Val Ala Asp Asn Gly Ala Thr Ile Ile Glu Gly Met Asp
                 85                  90                  95

Ala Asp Lys Ala Glu Lys Arg Lys Glu Val Leu Asn Ala Gln Tyr Pro
            100                 105                 110

Lys Ser Ala Ile Tyr Glu Asp Thr Lys Glu Asn Tyr Pro Leu Val Asn
            115                 120                 125

Val Glu Gly Ser Lys Val Gly Glu Gln Tyr Lys Ala Leu Asn Pro Ile
130                 135                 140

Asn Gly Lys Asp Gly Arg Arg Glu Ile Ala Glu Gly Trp Leu Ser Lys
145                 150                 155                 160

Lys Ile Thr Gly Val Asn Asp Leu Asp Lys Asn Lys Tyr Lys Ile Glu
                165                 170                 175

Leu Thr Val Glu Gly Lys Thr Thr Val Glu Thr Lys Glu Leu Asn Gln
            180                 185                 190

Pro Leu Asp Val Val Val Leu Leu Asp Asn Ser Asn Ser Met Asn Asn
            195                 200                 205

Glu Arg Ala Asn Asn Ser Gln Arg Ala Leu Lys Ala Gly Glu Ala Val
            210                 215                 220

Glu Lys Leu Ile Asp Lys Ile Thr Ser Asn Lys Asp Asn Arg Val Ala
225                 230                 235                 240

Leu Val Thr Tyr Ala Ser Thr Ile Phe Asp Gly Thr Glu Ala Thr Val
                245                 250                 255

Ser Lys Gly Val Ala Asp Gln Asn Gly Lys Ala Leu Asn Asp Ser Val
            260                 265                 270

Ser Trp Asp Tyr His Lys Thr Thr Phe Thr Ala Thr Thr His Asn Tyr
            275                 280                 285

Ser Tyr Leu Asn Leu Thr Asn Asp Ala Asn Glu Val Asn Ile Leu Lys
            290                 295                 300

Ser Arg Ile Pro Lys Glu Ala Glu His Ile Asn Gly Asp Arg Thr Leu
305                 310                 315                 320

Tyr Gln Phe Gly Ala Thr Phe Thr Gln Lys Ala Leu Met Lys Ala Asn
                325                 330                 335

Glu Ile Leu Glu Thr Gln Ser Ser Asn Ala Arg Lys Lys Leu Ile Phe
            340                 345                 350

His Val Thr Asp Gly Val Pro Thr Met Ser Tyr Ala Ile Asn Phe Asn
            355                 360                 365

Pro Tyr Ile Ser Thr Ser Tyr Gln Asn Gln Phe Asn Ser Phe Leu Asn
            370                 375                 380

Lys Ile Pro Asp Arg Ser Gly Ile Leu Gln Glu Asp Phe Ile Ile Asn
385                 390                 395                 400
```

```
Gly Asp Asp Tyr Gln Ile Val Lys Gly Asp Gly Glu Ser Phe Lys Leu
                405                 410                 415

Phe Ser Asp Arg Lys Val Pro Val Thr Gly Thr Thr Gln Ala Ala
        420                 425                 430

Tyr Arg Val Pro Gln Asn Gln Leu Ser Val Met Ser Asn Glu Gly Tyr
            435                 440                 445

Ala Ile Asn Ser Gly Tyr Ile Tyr Leu Tyr Trp Arg Asp Tyr Asn Trp
450                 455                 460

Val Tyr Pro Phe Asp Pro Lys Thr Lys Val Ser Ala Thr Lys Gln
465                 470                 475                 480

Ile Lys Thr His Gly Glu Pro Thr Thr Leu Tyr Phe Asn Gly Asn Ile
                485                 490                 495

Arg Pro Lys Gly Tyr Asp Ile Phe Thr Val Gly Ile Gly Val Asn Gly
            500                 505                 510

Asp Pro Gly Ala Thr Pro Leu Glu Ala Glu Lys Phe Met Gln Ser Ile
        515                 520                 525

Ser Ser Lys Thr Glu Asn Tyr Thr Asn Val Asp Asp Thr Asn Lys Ile
    530                 535                 540

Tyr Asp Glu Leu Asn Lys Tyr Phe Lys Thr Ile Val Glu Glu Lys His
545                 550                 555                 560

Ser Ile Val Asp Gly Asn Val Thr Asp Pro Met Gly Glu Met Ile Glu
                565                 570                 575

Phe Gln Leu Lys Asn Gly Gln Ser Phe Thr His Asp Asp Tyr Val Leu
            580                 585                 590

Val Gly Asn Asp Gly Ser Gln Leu Lys Asn Gly Val Ala Leu Gly Gly
        595                 600                 605

Pro Asn Ser Asp Gly Gly Ile Leu Lys Asp Val Thr Val Thr Tyr Asp
    610                 615                 620

Lys Thr Ser Gln Thr Ile Lys Ile Asn His Leu Asn Leu Gly Ser Gly
625                 630                 635                 640

Gln Lys Val Val Leu Thr Tyr Asp Val Arg Leu Lys Asp Asn Tyr Ile
                645                 650                 655

Ser Asn Lys Phe Tyr Asn Thr Asn Asn Arg Thr Thr Leu Ser Pro Lys
            660                 665                 670

Ser Glu Lys Glu Pro Asn Thr Ile Arg Asp Phe Pro Ile Pro Lys Ile
        675                 680                 685

Arg Asp Val Arg Glu Phe Pro Val Leu Thr Ile Ser Asn Gln Lys Lys
    690                 695                 700

Met Gly Glu Val Glu Phe Ile Lys Val Asn Lys Asp Lys His Ser Glu
705                 710                 715                 720

Ser Leu Leu Gly Ala Lys Phe Gln Leu Gln Ile Glu Lys Asp Phe Ser
                725                 730                 735

Gly Tyr Lys Gln Phe Val Pro Glu Gly Ser Asp Val Thr Thr Lys Asn
            740                 745                 750

Asp Gly Lys Ile Tyr Phe Lys Ala Leu Gln Asp Gly Asn Tyr Lys Leu
        755                 760                 765

Tyr Glu Ile Ser Ser Pro Asp Gly Tyr Ile Glu Val Lys Thr Lys Pro
    770                 775                 780

Val Val Thr Phe Thr Ile Gln Asn Gly Glu Val Thr Asn Leu Lys Ala
785                 790                 795                 800

Asp Pro Asn Ala Asn Lys Asn Gln Ile Gly Tyr Leu Glu Gly Asn Gly
                805                 810                 815

Lys His Leu Ile Thr Asn Thr
```

<210> SEQ ID NO 23
<211> LENGTH: 549
<212> TYPE: DNA
<213> ORGANISM: Streptococcus agalactiae

<400> SEQUENCE: 23

```
atgaaaaaac aaaaactatt actgcttatt ggaggcttat taataatgat aatgatgaca      60
gcatgtaagg attcaaaaat cccagaaaac cgcacaaagg aagagtacca agctgaacaa     120
aattttaaac cgttttttga gttttttagca caaaaagata aagatttgag caaaatacaa    180
aaatacttac tattagtatc ggattcaggt gatgcattag atttagaata tttctatagt    240
attcaagatt taaaaaaaaa taaggattta gggaagtttg aaacaagaaa aagtcaaata    300
gaaaagccgg gtggctataa tgagttagaa aataaagagg tcccatttga atattttaaa    360
aataatatag tttatccaaa aggaaaaccg aatattacat ttgatgactt tattatcgga    420
gcaatggata ctaaagaatt aaaagaatta aaaaaattaa aagtaaaaag ttatttatta    480
aaacatccgg aaactgagtt gaaagatata acatatgaat tgccgacaca gtcgaagctt    540
attaaaaaa                                                            549
```

<210> SEQ ID NO 24
<211> LENGTH: 183
<212> TYPE: PRT
<213> ORGANISM: Streptococcus agalactiae

<400> SEQUENCE: 24

```
Met Lys Lys Gln Lys Leu Leu Leu Ile Gly Gly Leu Leu Ile Met
  1               5                  10                  15

Ile Met Met Thr Ala Cys Lys Asp Ser Lys Ile Pro Glu Asn Arg Thr
             20                  25                  30

Lys Glu Glu Tyr Gln Ala Glu Gln Asn Phe Lys Pro Phe Phe Glu Phe
         35                  40                  45

Leu Ala Gln Lys Asp Lys Asp Leu Ser Lys Ile Gln Lys Tyr Leu Leu
     50                  55                  60

Leu Val Ser Asp Ser Gly Asp Ala Leu Asp Leu Glu Tyr Phe Tyr Ser
 65                  70                  75                  80

Ile Gln Asp Leu Lys Lys Asn Lys Asp Leu Gly Lys Phe Glu Thr Arg
                 85                  90                  95

Lys Ser Gln Ile Glu Lys Pro Gly Gly Tyr Asn Glu Leu Glu Asn Lys
            100                 105                 110

Glu Val Pro Phe Glu Tyr Phe Lys Asn Asn Ile Val Tyr Pro Lys Gly
        115                 120                 125

Lys Pro Asn Ile Thr Phe Asp Asp Phe Ile Ile Gly Ala Met Asp Thr
    130                 135                 140

Lys Glu Leu Lys Glu Leu Lys Lys Leu Lys Val Lys Ser Tyr Leu Leu
145                 150                 155                 160

Lys His Pro Glu Thr Glu Leu Lys Asp Ile Thr Tyr Glu Leu Pro Thr
                165                 170                 175

Gln Ser Lys Leu Ile Lys Lys
            180
```

<210> SEQ ID NO 25
<211> LENGTH: 161
<212> TYPE: PRT
<213> ORGANISM: Streptococcus agalactiae

<400> SEQUENCE: 25

```
Lys Asp Ser Lys Ile Pro Glu Asn Arg Thr Lys Glu Glu Tyr Gln Ala
1               5                   10                  15

Glu Gln Asn Phe Lys Pro Phe Phe Glu Phe Leu Ala Gln Lys Asp Lys
            20                  25                  30

Asp Leu Ser Lys Ile Gln Lys Tyr Leu Leu Leu Val Ser Asp Ser Gly
        35                  40                  45

Asp Ala Leu Asp Leu Glu Tyr Phe Tyr Ser Ile Gln Asp Leu Lys Lys
    50                  55                  60

Asn Lys Asp Leu Gly Lys Phe Glu Thr Arg Lys Ser Gln Ile Glu Lys
65                  70                  75                  80

Pro Gly Gly Tyr Asn Glu Leu Glu Asn Lys Glu Val Pro Phe Glu Tyr
                85                  90                  95

Phe Lys Asn Asn Ile Val Tyr Pro Lys Gly Lys Pro Asn Ile Thr Phe
            100                 105                 110

Asp Asp Phe Ile Ile Gly Ala Met Asp Thr Lys Glu Leu Lys Glu Leu
        115                 120                 125

Lys Lys Leu Lys Val Lys Ser Tyr Leu Leu Lys His Pro Glu Thr Glu
    130                 135                 140

Leu Lys Asp Ile Thr Tyr Glu Leu Pro Thr Gln Ser Lys Leu Ile Lys
145                 150                 155                 160

Lys
```

<210> SEQ ID NO 26
<211> LENGTH: 3402
<212> TYPE: DNA
<213> ORGANISM: Streptococcus agalactiae

<400> SEQUENCE: 26

```
ttgcgtaaaa aacaaaaact accatttgat aaacttgcca ttgcgcttat atctacgagc      60
atcttgctca atgcacaatc agacattaaa gcaaatactg tgacagaaga cactcctgct     120
accgaacaag ccgtagaacc cccacaacca atagcagttt ctgaggaatc acgatcatca     180
aaggaaacta aaacctcaca aactcctagt gatgtaggag aaacagtagc agatgacgct     240
aatgatctag cccctcaagc tcctgctaaa actgctgata caccagcaac ctcaaaagcg     300
actattaggg atttgaacga cccttctcat gtcaaaaccc tgcaggaaaa agcaggcaag     360
ggagctggga ccgttgttgc agtgattgat gctggttttg ataaaaatca tgaagcgtgg     420
cgcttaacag acaaaactaa agcacgttac caatcaaaag aaaatcttga aaagctaaa      480
aaagagcacg gtattaccta tgcgagtgg gtcaatgata aggttgctta ttaccacgac     540
tatagtaaag atggtaaaaa cgctgttgat caagaacacg gcacacacgt gtcagggatc     600
ttgtcaggaa atgctccatc tgaaatgaaa gaaccttacc gcctagaagg tgcgatgcct     660
gaggctcaat tgctttttga tgcgtgtcgaa attgtaaatg gactagcaga ctatgctcgt     720
aactacgctc aagctatcag agatgctgtc aacttgggag ctaaggtgat taatatgagc     780
tttggtaatg ctgcactagc ttacgccaac cttccagacg aaaccaaaaa agcctttgac     840
tatgccaaat caaaggtgt tagcattgtg acctcagctg gtaatgatag tagctttggg     900
ggcaagcccc gtctacctct agcagatcat cctgattatg gggtggttgg gacacctgca     960
gcggcagatt caacattgac agttgcttct tacagcccag ataaacagct cactgaaact    1020
gctacggtca aacagacga tcatcaagat aaagaaatgc tgttatttc aacaaaccgt    1080
```

```
tttgagccaa acaaggctta cgactatgct tatgctaatc gtggtacgaa agaggatgat    1140
tttaaggatg tcgaaggtaa gattgcccct attgaacgtg gcgatattga tttcaaagat    1200
aagattgcaa acgctaaaaa agctggtgct gtaggggtct tgatctatga caatcaagac    1260
aagggcttcc cgattgaatt gccaaatgtt gaccagatgc ctgcggcctt tatcagtcga    1320
agagacggtc tcttattaaa agacaatccc ccaaaaacca ttaccttcaa tgcgacacct    1380
aaggtattgc caacagcaag tggcaccaaa ctaagccgct tctcaagctg gggtctgaca    1440
gctgacggca atattaaacc ggatattgca gcacccggcc aagatatttt gtcatcagtg    1500
gctaacaaca agtatgccaa actttctgga actagtatgt ctgcaccatt ggtagcgggt    1560
atcatgggac tgttgcaaaa gcaatatgag acacagtatc ctgatatgac accatcagag    1620
cgtcttgatt tagctaagaa agtattgatg agctcagcaa ctgccctata tgatgaagat    1680
gaaaaagctt attttttctcc tcgccaacag ggagcaggag cagtcgatgc taaaaaagct    1740
tcagcagcaa cgatgtatgt aacagataag gacaatacct caagcaaggt tcacctgaac    1800
aatgtttctg ataaatttga agtaacagta acagttcaca acaaatctga taaacctcaa    1860
gagttgtatt accaagtaac tgttcaaaca gataaagtag atggaaaaca ctttgccttg    1920
gctcctaaag cattgtatga gacatcatgg caaaaaatca caattccagc caatagcagc    1980
aaacaagtca ccgttccaat cgatgctagt cgatttagca aggacttgct tgcccaaatg    2040
aaaaatggct atttcttaga aggttttgtt cgtttcaaac aagatcctac aaaagaagag    2100
cttatgagca ttccatatat tggtttccga ggtgattttg gcaatctgtc agccttagaa    2160
aaaccaatct atgatagcaa agacggtagc agctactatc atgaagcaaa tagtgatgcc    2220
aaagaccaat tagatggtga tggattacag ttttacgctc tgaaaaataa ctttacagca    2280
cttaccacag agtctaaccc atggacgatt attaaagctg tcaaagaagg ggttgaaaac    2340
atagaggata tcgaatcttc agagatcaca gaaaccattt ttgcaggtac ttttgcaaaa    2400
caagacgatg atagccacta ctatatccac cgtcacgcta atggcaaacc atatgctgcg    2460
atctctccaa atggggacgg taacagagat tatgtccaat tccaaggtac tttcttgcgt    2520
aatgctaaaa accttgtggc tgaagtcttg gacaaagaag gaaatgttgt ttggacaagt    2580
gaggtaaccg agcaagttgt taaaaactac aacaatgact tggcaagcac acttggttca    2640
acccgttttg aaaaaacgcg tttgggacggt aaagataaag acggcaaagt tgttgctaac    2700
ggaacctaca cctatcgtgt tcgctacacg ccgattagct caggtgcaaa agaacaacac    2760
actgattttg atgtgattgt agacaatacg acacctgaag tcgcaacatc ggcaacattc    2820
tcaacagaag atagtcgttt gacacttgca tctaaaccaa aaaccagcca accggtttac    2880
cgtgagcgta ttgcttacac ttatatggat gaggatctgc caacaacaga gtatatttct    2940
ccaaatgaag atggtaccct tactcttcct gaagaggctg aaacaatgga aggcgctact    3000
gttccattga aaatgtcaga ctttacttat gttgttgaag atatggctgg taacatcact    3060
tatacaccag tgactaagct attggaggc cactctaata agccagaaca agacggttca    3120
gatcaagcac cagacaagaa accagaagct aaaccagaac aagacggttc aggtcaaaca    3180
ccagataaaa aaaagaaac taaaccgaaa aagatagtt caggtcaaac accaggtaaa    3240
actcctcaaa aaggtcaatc ttctcgtact ctagagaaac gatcttctaa gcgtgcttta    3300
gctacaaaag catcaacaag agatcagtta ccaacgacta atgacaagga tacaaatcgt    3360
ttacatctcc ttaagttagt tatgaccact ttcttcttgg ga                      3402
```

```
<210> SEQ ID NO 27
<211> LENGTH: 1134
<212> TYPE: PRT
<213> ORGANISM: Streptococcus agalactiae

<400> SEQUENCE: 27

Met Arg Lys Lys Gln Lys Leu Pro Phe Asp Lys Leu Ala Ile Ala Leu
 1               5                  10                  15

Ile Ser Thr Ser Ile Leu Leu Asn Ala Gln Ser Asp Ile Lys Ala Asn
             20                  25                  30

Thr Val Thr Glu Asp Thr Pro Ala Thr Glu Gln Ala Val Glu Pro Pro
         35                  40                  45

Gln Pro Ile Ala Val Ser Glu Glu Ser Arg Ser Lys Glu Thr Lys
     50                  55                  60

Thr Ser Gln Thr Pro Ser Asp Val Gly Glu Thr Val Ala Asp Asp Ala
 65                  70                  75                  80

Asn Asp Leu Ala Pro Gln Ala Pro Ala Lys Thr Ala Asp Thr Pro Ala
                 85                  90                  95

Thr Ser Lys Ala Thr Ile Arg Asp Leu Asn Asp Pro Ser His Val Lys
            100                 105                 110

Thr Leu Gln Glu Lys Ala Gly Lys Gly Ala Gly Thr Val Val Ala Val
        115                 120                 125

Ile Asp Ala Gly Phe Asp Lys Asn His Glu Ala Trp Arg Leu Thr Asp
130                 135                 140

Lys Thr Lys Ala Arg Tyr Gln Ser Lys Glu Asn Leu Glu Lys Ala Lys
145                 150                 155                 160

Lys Glu His Gly Ile Thr Tyr Gly Glu Trp Val Asn Asp Lys Val Ala
                165                 170                 175

Tyr Tyr His Asp Tyr Ser Lys Asp Gly Lys Asn Ala Val Asp Gln Glu
            180                 185                 190

His Gly Thr His Val Ser Gly Ile Leu Ser Gly Asn Ala Pro Ser Glu
        195                 200                 205

Met Lys Glu Pro Tyr Arg Leu Glu Gly Ala Met Pro Glu Ala Gln Leu
    210                 215                 220

Leu Leu Met Arg Val Glu Ile Val Asn Gly Leu Ala Asp Tyr Ala Arg
225                 230                 235                 240

Asn Tyr Ala Gln Ala Ile Arg Asp Ala Val Asn Leu Gly Ala Lys Val
                245                 250                 255

Ile Asn Met Ser Phe Gly Asn Ala Ala Leu Ala Tyr Ala Asn Leu Pro
            260                 265                 270

Asp Glu Thr Lys Lys Ala Phe Asp Tyr Ala Lys Ser Lys Gly Val Ser
        275                 280                 285

Ile Val Thr Ser Ala Gly Asn Asp Ser Ser Phe Gly Gly Lys Pro Arg
    290                 295                 300

Leu Pro Leu Ala Asp His Pro Asp Tyr Gly Val Val Gly Thr Pro Ala
305                 310                 315                 320

Ala Ala Asp Ser Thr Leu Thr Val Ala Ser Tyr Ser Pro Asp Lys Gln
                325                 330                 335

Leu Thr Glu Thr Ala Thr Val Lys Thr Asp Asp His Gln Asp Lys Glu
            340                 345                 350

Met Pro Val Ile Ser Thr Asn Arg Phe Glu Pro Asn Lys Ala Tyr Asp
        355                 360                 365

Tyr Ala Tyr Ala Asn Arg Gly Thr Lys Glu Asp Asp Phe Lys Asp Val
    370                 375                 380
```

```
Glu Gly Lys Ile Ala Leu Ile Glu Arg Gly Asp Ile Asp Phe Lys Asp
385                 390                 395                 400

Lys Ile Ala Asn Ala Lys Lys Ala Gly Ala Val Gly Val Leu Ile Tyr
            405                 410                 415

Asp Asn Gln Asp Lys Gly Phe Pro Ile Glu Leu Pro Asn Val Asp Gln
        420                 425                 430

Met Pro Ala Ala Phe Ile Ser Arg Arg Asp Gly Leu Leu Leu Lys Asp
        435                 440                 445

Asn Pro Pro Lys Thr Ile Thr Phe Asn Ala Thr Pro Lys Val Leu Pro
    450                 455                 460

Thr Ala Ser Gly Thr Lys Leu Ser Arg Phe Ser Ser Trp Gly Leu Thr
465                 470                 475                 480

Ala Asp Gly Asn Ile Lys Pro Asp Ile Ala Ala Pro Gly Gln Asp Ile
            485                 490                 495

Leu Ser Ser Val Ala Asn Asn Lys Tyr Ala Lys Leu Ser Gly Thr Ser
        500                 505                 510

Met Ser Ala Pro Leu Val Ala Gly Ile Met Gly Leu Leu Gln Lys Gln
    515                 520                 525

Tyr Glu Thr Gln Tyr Pro Asp Met Thr Pro Ser Glu Arg Leu Asp Leu
530                 535                 540

Ala Lys Lys Val Leu Met Ser Ser Ala Thr Ala Leu Tyr Asp Glu Asp
545                 550                 555                 560

Glu Lys Ala Tyr Phe Ser Pro Arg Gln Gln Gly Ala Gly Ala Val Asp
            565                 570                 575

Ala Lys Lys Ala Ser Ala Ala Thr Met Tyr Val Thr Asp Lys Asp Asn
        580                 585                 590

Thr Ser Ser Lys Val His Leu Asn Asn Val Ser Asp Lys Phe Glu Val
    595                 600                 605

Thr Val Thr Val His Asn Lys Ser Asp Lys Pro Gln Glu Leu Tyr Tyr
610                 615                 620

Gln Val Thr Val Gln Thr Asp Lys Val Asp Gly Lys His Phe Ala Leu
625                 630                 635                 640

Ala Pro Lys Ala Leu Tyr Glu Thr Ser Trp Gln Lys Ile Thr Ile Pro
            645                 650                 655

Ala Asn Ser Ser Lys Gln Val Thr Val Pro Ile Asp Ala Ser Arg Phe
        660                 665                 670

Ser Lys Asp Leu Leu Ala Gln Met Lys Asn Gly Tyr Phe Leu Glu Gly
    675                 680                 685

Phe Val Arg Phe Lys Gln Asp Pro Thr Lys Glu Glu Leu Met Ser Ile
690                 695                 700

Pro Tyr Ile Gly Phe Arg Gly Asp Phe Gly Asn Leu Ser Ala Leu Glu
705                 710                 715                 720

Lys Pro Ile Tyr Asp Ser Lys Asp Gly Ser Ser Tyr His Glu Ala
            725                 730                 735

Asn Ser Asp Ala Lys Asp Gln Leu Asp Gly Asp Gly Leu Gln Phe Tyr
        740                 745                 750

Ala Leu Lys Asn Asn Phe Thr Ala Leu Thr Thr Glu Ser Asn Pro Trp
    755                 760                 765

Thr Ile Ile Lys Ala Val Lys Glu Gly Val Glu Asn Ile Glu Asp Ile
770                 775                 780

Glu Ser Ser Glu Ile Thr Glu Thr Ile Phe Ala Gly Thr Phe Ala Lys
785                 790                 795                 800

Gln Asp Asp Asp Ser His Tyr Tyr Ile His Arg His Ala Asn Gly Lys
```

Pro Tyr Ala Ala Ile Ser Pro Asn Gly Asp Gly Asn Arg Asp Tyr Val
                805                 810                 815

Gln Phe Gln Gly Thr Phe Leu Arg Asn Ala Lys Asn Leu Val Ala Glu
        820                 825                 830

Val Leu Asp Lys Glu Gly Asn Val Val Trp Thr Ser Glu Val Thr Glu
        835                 840                 845

Gln Val Val Lys Asn Tyr Asn Asn Asp Leu Ala Ser Thr Leu Gly Ser
865                 870                 875                 880

Thr Arg Phe Glu Lys Thr Arg Trp Asp Gly Lys Asp Lys Asp Gly Lys
                885                 890                 895

Val Val Ala Asn Gly Thr Tyr Thr Tyr Arg Val Arg Tyr Thr Pro Ile
                900                 905                 910

Ser Ser Gly Ala Lys Glu Gln His Thr Asp Phe Asp Val Ile Val Asp
                915                 920                 925

Asn Thr Thr Pro Glu Val Ala Thr Ser Ala Thr Phe Ser Thr Glu Asp
                930                 935                 940

Ser Arg Leu Thr Leu Ala Ser Lys Pro Lys Thr Ser Gln Pro Val Tyr
945                 950                 955                 960

Arg Glu Arg Ile Ala Tyr Thr Tyr Met Asp Glu Asp Leu Pro Thr Thr
                965                 970                 975

Glu Tyr Ile Ser Pro Asn Glu Asp Gly Thr Phe Thr Leu Pro Glu Glu
                980                 985                 990

Ala Glu Thr Met Glu Gly Ala Thr Val Pro Leu Lys Met Ser Asp Phe
                995                 1000                1005

Thr Tyr Val Val Glu Asp Met Ala Gly Asn Ile Thr Tyr Thr Pro Val
                1010                1015                1020

Thr Lys Leu Leu Glu Gly His Ser Asn Lys Pro Glu Gln Asp Gly Ser
1025                1030                1035                1040

Asp Gln Ala Pro Asp Lys Lys Pro Glu Ala Lys Pro Glu Gln Asp Gly
                1045                1050                1055

Ser Gly Gln Thr Pro Asp Lys Lys Glu Thr Lys Pro Glu Lys Asp
                1060                1065                1070

Ser Ser Gly Gln Thr Pro Gly Lys Thr Pro Gln Lys Gly Gln Ser Ser
        1075                1080                1085

Arg Thr Leu Glu Lys Arg Ser Ser Lys Arg Ala Leu Ala Thr Lys Ala
        1090                1095                1100

Ser Thr Arg Asp Gln Leu Pro Thr Thr Asn Asp Lys Asp Thr Asn Arg
1105                1110                1115                1120

Leu His Leu Leu Lys Leu Val Met Thr Thr Phe Phe Leu Gly
                1125                1130

<210> SEQ ID NO 28
<211> LENGTH: 1109
<212> TYPE: PRT
<213> ORGANISM: Streptococcus agalactiae

<400> SEQUENCE: 28

Gln Ser Asp Ile Lys Ala Asn Thr Val Thr Glu Asp Thr Pro Ala Thr
1               5                   10                  15

Glu Gln Ala Val Glu Pro Pro Gln Pro Ile Ala Val Ser Glu Glu Ser
                20                  25                  30

Arg Ser Ser Lys Glu Thr Lys Ser Gln Thr Pro Ser Asp Val Gly
        35                  40                  45

Glu Thr Val Ala Asp Asp Ala Asn Asp Leu Ala Pro Gln Ala Pro Ala
    50                  55                  60

Lys Thr Ala Asp Thr Pro Ala Thr Ser Lys Ala Thr Ile Arg Asp Leu
 65                  70                  75                  80

Asn Asp Pro Ser His Val Lys Thr Leu Gln Glu Lys Ala Gly Lys Gly
                 85                  90                  95

Ala Gly Thr Val Val Ala Val Ile Asp Ala Gly Phe Asp Lys Asn His
                100                 105                 110

Glu Ala Trp Arg Leu Thr Asp Lys Thr Lys Ala Arg Tyr Gln Ser Lys
            115                 120                 125

Glu Asn Leu Glu Lys Ala Lys Lys Glu His Gly Ile Thr Tyr Gly Glu
        130                 135                 140

Trp Val Asn Asp Lys Val Ala Tyr Tyr His Asp Tyr Ser Lys Asp Gly
145                 150                 155                 160

Lys Asn Ala Val Asp Gln Glu His Gly Thr His Val Ser Gly Ile Leu
                165                 170                 175

Ser Gly Asn Ala Pro Ser Glu Met Lys Glu Pro Tyr Arg Leu Glu Gly
            180                 185                 190

Ala Met Pro Glu Ala Gln Leu Leu Met Arg Val Glu Ile Val Asn
        195                 200                 205

Gly Leu Ala Asp Tyr Ala Arg Asn Tyr Ala Gln Ala Ile Arg Asp Ala
    210                 215                 220

Val Asn Leu Gly Ala Lys Val Ile Asn Met Ser Phe Gly Asn Ala Ala
225                 230                 235                 240

Leu Ala Tyr Ala Asn Leu Pro Asp Glu Thr Lys Lys Ala Phe Asp Tyr
                245                 250                 255

Ala Lys Ser Lys Gly Val Ser Ile Val Thr Ser Ala Gly Asn Asp Ser
            260                 265                 270

Ser Phe Gly Gly Lys Pro Arg Leu Pro Leu Ala Asp His Pro Asp Tyr
        275                 280                 285

Gly Val Val Gly Thr Pro Ala Ala Ala Asp Ser Thr Leu Thr Val Ala
    290                 295                 300

Ser Tyr Ser Pro Asp Lys Gln Leu Thr Glu Thr Ala Thr Val Lys Thr
305                 310                 315                 320

Asp Asp His Gln Asp Lys Glu Met Pro Val Ile Ser Thr Asn Arg Phe
                325                 330                 335

Glu Pro Asn Lys Ala Tyr Asp Tyr Ala Tyr Ala Asn Arg Gly Thr Lys
            340                 345                 350

Glu Asp Asp Phe Lys Asp Val Glu Gly Lys Ile Ala Leu Ile Glu Arg
        355                 360                 365

Gly Asp Ile Asp Phe Lys Asp Lys Ile Ala Asn Ala Lys Lys Ala Gly
    370                 375                 380

Ala Val Gly Val Leu Ile Tyr Asp Asn Gln Asp Lys Gly Phe Pro Ile
385                 390                 395                 400

Glu Leu Pro Asn Val Asp Gln Met Pro Ala Ala Phe Ile Ser Arg Arg
                405                 410                 415

Asp Gly Leu Leu Leu Lys Asp Asn Pro Pro Lys Thr Ile Thr Phe Asn
            420                 425                 430

Ala Thr Pro Lys Val Leu Pro Thr Ala Ser Gly Thr Lys Leu Ser Arg
        435                 440                 445

Phe Ser Ser Trp Gly Leu Thr Ala Asp Gly Asn Ile Lys Pro Asp Ile
450                 455                 460

Ala Ala Pro Gly Gln Asp Ile Leu Ser Ser Val Ala Asn Asn Lys Tyr

-continued

```
            465                 470                 475                 480
        Ala Lys Leu Ser Gly Thr Ser Met Ser Ala Pro Leu Val Ala Gly Ile
                            485                 490                 495
        Met Gly Leu Leu Gln Lys Gln Tyr Glu Thr Gln Tyr Pro Asp Met Thr
                            500                 505                 510
        Pro Ser Glu Arg Leu Asp Leu Ala Lys Lys Val Leu Met Ser Ser Ala
                            515                 520                 525
        Thr Ala Leu Tyr Asp Glu Asp Glu Lys Ala Tyr Phe Ser Pro Arg Gln
                530                 535                 540
        Gln Gly Ala Gly Ala Val Asp Ala Lys Lys Ala Ser Ala Ala Thr Met
        545                 550                 555                 560
        Tyr Val Thr Asp Lys Asp Asn Thr Ser Ser Lys Val His Leu Asn Asn
                            565                 570                 575
        Val Ser Asp Lys Phe Glu Val Thr Val Thr Val His Asn Lys Ser Asp
                            580                 585                 590
        Lys Pro Gln Glu Leu Tyr Tyr Gln Val Thr Val Gln Thr Asp Lys Val
                            595                 600                 605
        Asp Gly Lys His Phe Ala Leu Ala Pro Lys Ala Leu Tyr Glu Thr Ser
                610                 615                 620
        Trp Gln Lys Ile Thr Ile Pro Ala Asn Ser Ser Lys Gln Val Thr Val
        625                 630                 635                 640
        Pro Ile Asp Ala Ser Arg Phe Ser Lys Asp Leu Leu Ala Gln Met Lys
                            645                 650                 655
        Asn Gly Tyr Phe Leu Glu Gly Phe Val Arg Phe Lys Gln Asp Pro Thr
                            660                 665                 670
        Lys Glu Glu Leu Met Ser Ile Pro Tyr Ile Gly Phe Arg Gly Asp Phe
                            675                 680                 685
        Gly Asn Leu Ser Ala Leu Glu Lys Pro Ile Tyr Asp Ser Lys Asp Gly
                690                 695                 700
        Ser Ser Tyr Tyr His Glu Ala Asn Ser Asp Ala Lys Asp Gln Leu Asp
        705                 710                 715                 720
        Gly Asp Gly Leu Gln Phe Tyr Ala Leu Lys Asn Asn Phe Thr Ala Leu
                            725                 730                 735
        Thr Thr Glu Ser Asn Pro Trp Thr Ile Ile Lys Ala Val Lys Glu Gly
                            740                 745                 750
        Val Glu Asn Ile Glu Asp Ile Glu Ser Glu Ile Thr Glu Thr Ile
                            755                 760                 765
        Phe Ala Gly Thr Phe Ala Lys Gln Asp Asp Ser His Tyr Tyr Ile
                770                 775                 780
        His Arg His Ala Asn Gly Lys Pro Tyr Ala Ala Ile Ser Pro Asn Gly
        785                 790                 795                 800
        Asp Gly Asn Arg Asp Tyr Val Gln Phe Gln Gly Thr Phe Leu Arg Asn
                            805                 810                 815
        Ala Lys Asn Leu Val Ala Glu Val Leu Asp Lys Glu Gly Asn Val Val
                            820                 825                 830
        Trp Thr Ser Glu Val Thr Glu Gln Val Val Lys Asn Tyr Asn Asn Asp
                            835                 840                 845
        Leu Ala Ser Thr Leu Gly Ser Thr Arg Phe Glu Lys Thr Arg Trp Asp
                            850                 855                 860
        Gly Lys Asp Lys Asp Gly Lys Val Val Ala Asn Gly Thr Tyr Thr Tyr
        865                 870                 875                 880
        Arg Val Arg Tyr Thr Pro Ile Ser Ser Gly Ala Lys Glu Gln His Thr
                            885                 890                 895
```

```
Asp Phe Asp Val Ile Val Asp Asn Thr Thr Pro Glu Val Ala Thr Ser
            900                 905                 910

Ala Thr Phe Ser Thr Glu Asp Ser Arg Leu Thr Leu Ala Ser Lys Pro
            915                 920                 925

Lys Thr Ser Gln Pro Val Tyr Arg Glu Arg Ile Ala Tyr Thr Tyr Met
            930                 935                 940

Asp Glu Asp Leu Pro Thr Thr Glu Tyr Ile Ser Pro Asn Glu Asp Gly
945                 950                 955                 960

Thr Phe Thr Leu Pro Glu Glu Ala Glu Thr Met Glu Gly Ala Thr Val
                965                 970                 975

Pro Leu Lys Met Ser Asp Phe Thr Tyr Val Val Glu Asp Met Ala Gly
            980                 985                 990

Asn Ile Thr Tyr Thr Pro Val Thr Lys Leu Leu Glu Gly His Ser Asn
            995                 1000                1005

Lys Pro Glu Gln Asp Gly Ser Asp Gln Ala Pro Asp Lys Lys Pro Glu
            1010                1015                1020

Ala Lys Pro Glu Gln Asp Gly Ser Gly Gln Thr Pro Asp Lys Lys Lys
1025                1030                1035                1040

Glu Thr Lys Pro Glu Lys Asp Ser Ser Gly Gln Thr Pro Gly Lys Thr
            1045                1050                1055

Pro Gln Lys Gly Gln Ser Ser Arg Thr Leu Glu Lys Arg Ser Ser Lys
            1060                1065                1070

Arg Ala Leu Ala Thr Lys Ala Ser Thr Arg Asp Gln Leu Pro Thr Thr
            1075                1080                1085

Asn Asp Lys Asp Thr Asn Arg Leu His Leu Leu Lys Leu Val Met Thr
            1090                1095                1100

Thr Phe Phe Leu Gly
1105

<210> SEQ ID NO 29
<211> LENGTH: 1103
<212> TYPE: PRT
<213> ORGANISM: Streptococcus agalactiae

<400> SEQUENCE: 29

Met Arg Lys Lys Gln Lys Leu Pro Phe Asp Lys Leu Ala Ile Ala Leu
1               5                   10                  15

Ile Ser Thr Ser Ile Leu Leu Asn Ala Gln Ser Asp Ile Lys Ala Asn
                20                  25                  30

Thr Val Thr Glu Asp Thr Pro Ala Thr Glu Gln Ala Val Glu Pro Pro
            35                  40                  45

Gln Pro Ile Ala Val Ser Glu Glu Ser Arg Ser Ser Lys Glu Thr Lys
50                  55                  60

Thr Ser Gln Thr Pro Ser Asp Val Gly Glu Thr Val Ala Asp Asp Ala
65                  70                  75                  80

Asn Asp Leu Ala Pro Gln Ala Pro Ala Lys Thr Ala Asp Thr Pro Ala
                85                  90                  95

Thr Ser Lys Ala Thr Ile Arg Asp Leu Asn Asp Pro Ser His Val Lys
            100                 105                 110

Thr Leu Gln Glu Lys Ala Gly Lys Gly Ala Gly Thr Val Val Ala Val
            115                 120                 125

Ile Asp Ala Gly Phe Asp Lys Asn His Glu Ala Trp Arg Leu Thr Asp
            130                 135                 140

Lys Thr Lys Ala Arg Tyr Gln Ser Lys Glu Asn Leu Glu Lys Ala Lys
```

-continued

```
               145                 150                 155                 160
        Lys Glu His Gly Ile Thr Tyr Gly Glu Trp Val Asn Asp Lys Val Ala
                        165                 170                 175

Tyr Tyr His Asp Tyr Ser Lys Asp Gly Lys Asn Ala Val Asp Gln Glu
                        180                 185                 190

His Gly Thr His Val Ser Gly Ile Leu Ser Gly Asn Ala Pro Ser Glu
                        195                 200                 205

Met Lys Glu Pro Tyr Arg Leu Glu Gly Ala Met Pro Glu Ala Gln Leu
                210                 215                 220

Leu Leu Met Arg Val Glu Ile Val Asn Gly Leu Ala Asp Tyr Ala Arg
        225                 230                 235                 240

Asn Tyr Ala Gln Ala Ile Arg Asp Ala Val Asn Leu Gly Ala Lys Val
                        245                 250                 255

Ile Asn Met Ser Phe Gly Asn Ala Ala Leu Ala Tyr Ala Asn Leu Pro
                        260                 265                 270

Asp Glu Thr Lys Lys Ala Phe Asp Tyr Ala Lys Ser Lys Gly Val Ser
                        275                 280                 285

Ile Val Thr Ser Ala Gly Asn Asp Ser Ser Phe Gly Gly Lys Pro Arg
                        290                 295                 300

Leu Pro Leu Ala Asp His Pro Asp Tyr Gly Val Val Gly Thr Pro Ala
        305                 310                 315                 320

Ala Ala Asp Ser Thr Leu Thr Val Ala Ser Tyr Ser Pro Asp Lys Gln
                        325                 330                 335

Leu Thr Glu Thr Ala Thr Val Lys Thr Asp Asp His Gln Asp Lys Glu
                        340                 345                 350

Met Pro Val Ile Ser Thr Asn Arg Phe Glu Pro Asn Lys Ala Tyr Asp
                        355                 360                 365

Tyr Ala Tyr Ala Asn Arg Gly Thr Lys Glu Asp Asp Phe Lys Asp Val
                        370                 375                 380

Glu Gly Lys Ile Ala Leu Ile Glu Arg Gly Asp Ile Asp Phe Lys Asp
        385                 390                 395                 400

Lys Ile Ala Asn Ala Lys Lys Ala Gly Ala Val Gly Val Leu Ile Tyr
                        405                 410                 415

Asp Asn Gln Asp Lys Gly Phe Pro Ile Glu Leu Pro Asn Val Asp Gln
                        420                 425                 430

Met Pro Ala Ala Phe Ile Ser Arg Arg Asp Gly Leu Leu Leu Lys Asp
                        435                 440                 445

Asn Pro Pro Lys Thr Ile Thr Phe Asn Ala Thr Pro Lys Val Leu Pro
                450                 455                 460

Thr Ala Ser Gly Thr Lys Leu Ser Arg Phe Ser Ser Trp Gly Leu Thr
        465                 470                 475                 480

Ala Asp Gly Asn Ile Lys Pro Asp Ile Ala Ala Pro Gly Gln Asp Ile
                        485                 490                 495

Leu Ser Ser Val Ala Asn Asn Lys Tyr Ala Lys Leu Ser Gly Thr Ser
                        500                 505                 510

Met Ser Ala Pro Leu Val Ala Gly Ile Met Gly Leu Leu Gln Lys Gln
                        515                 520                 525

Tyr Glu Thr Gln Tyr Pro Asp Met Thr Pro Ser Glu Arg Leu Asp Leu
                        530                 535                 540

Ala Lys Lys Val Leu Met Ser Ser Ala Thr Ala Leu Tyr Asp Glu Asp
        545                 550                 555                 560

Glu Lys Ala Tyr Phe Ser Pro Arg Gln Gln Gly Ala Gly Ala Val Asp
                        565                 570                 575
```

```
Ala Lys Lys Ala Ser Ala Ala Thr Met Tyr Val Thr Asp Lys Asp Asn
            580                 585                 590

Thr Ser Ser Lys Val His Leu Asn Asn Val Ser Asp Lys Phe Glu Val
        595                 600                 605

Thr Val Thr Val His Asn Lys Ser Asp Lys Pro Gln Glu Leu Tyr Tyr
    610                 615                 620

Gln Val Thr Val Gln Thr Asp Lys Val Asp Gly Lys His Phe Ala Leu
625                 630                 635                 640

Ala Pro Lys Ala Leu Tyr Glu Thr Ser Trp Gln Lys Ile Thr Ile Pro
                645                 650                 655

Ala Asn Ser Ser Lys Gln Val Thr Val Pro Ile Asp Ala Ser Arg Phe
            660                 665                 670

Ser Lys Asp Leu Leu Ala Gln Met Lys Asn Gly Tyr Phe Leu Glu Gly
        675                 680                 685

Phe Val Arg Phe Lys Gln Asp Pro Thr Lys Glu Glu Leu Met Ser Ile
    690                 695                 700

Pro Tyr Ile Gly Phe Arg Gly Asp Phe Gly Asn Leu Ser Ala Leu Glu
705                 710                 715                 720

Lys Pro Ile Tyr Asp Ser Lys Asp Gly Ser Tyr Tyr His Glu Ala
                725                 730                 735

Asn Ser Asp Ala Lys Asp Gln Leu Asp Gly Asp Gly Leu Gln Phe Tyr
            740                 745                 750

Ala Leu Lys Asn Asn Phe Thr Ala Leu Thr Thr Glu Ser Asn Pro Trp
        755                 760                 765

Thr Ile Ile Lys Ala Val Lys Glu Gly Val Glu Asn Ile Glu Asp Ile
    770                 775                 780

Glu Ser Ser Glu Ile Thr Glu Thr Ile Phe Ala Gly Thr Phe Ala Lys
785                 790                 795                 800

Gln Asp Asp Asp Ser His Tyr Tyr Ile His Arg His Ala Asn Gly Lys
                805                 810                 815

Pro Tyr Ala Ala Ile Ser Pro Asn Gly Asp Gly Asn Arg Asp Tyr Val
            820                 825                 830

Gln Phe Gln Gly Thr Phe Leu Arg Asn Ala Lys Asn Leu Val Ala Glu
        835                 840                 845

Val Leu Asp Lys Glu Gly Asn Val Val Trp Thr Ser Glu Val Thr Glu
    850                 855                 860

Gln Val Val Lys Asn Tyr Asn Asn Asp Leu Ala Ser Thr Leu Gly Ser
865                 870                 875                 880

Thr Arg Phe Glu Lys Thr Arg Trp Asp Gly Lys Asp Lys Asp Gly Lys
                885                 890                 895

Val Val Ala Asn Gly Thr Tyr Tyr Tyr Arg Val Arg Tyr Thr Pro Ile
            900                 905                 910

Ser Ser Gly Ala Lys Glu Gln His Thr Asp Phe Asp Val Ile Val Asp
        915                 920                 925

Asn Thr Thr Pro Glu Val Ala Thr Ser Ala Thr Phe Ser Thr Glu Asp
    930                 935                 940

Ser Arg Leu Thr Leu Ala Ser Lys Pro Lys Thr Ser Gln Pro Val Tyr
945                 950                 955                 960

Arg Glu Arg Ile Ala Tyr Thr Tyr Met Asp Glu Asp Leu Pro Thr Thr
                965                 970                 975

Glu Tyr Ile Ser Pro Asn Glu Asp Gly Thr Phe Thr Leu Pro Glu Glu
            980                 985                 990
```

```
Ala Glu Thr Met Glu Gly Ala Thr Val Pro Leu Lys Met Ser Asp Phe
            995                 1000                1005

Thr Tyr Val Val Glu Asp Met Ala Gly Asn Ile Thr Tyr Thr Pro Val
    1010                1015                1020

Thr Lys Leu Leu Glu Gly His Ser Asn Lys Pro Glu Gln Asp Gly Ser
1025                1030                1035                1040

Asp Gln Ala Pro Asp Lys Lys Pro Glu Ala Lys Pro Glu Gln Asp Gly
                1045                1050                1055

Ser Gly Gln Thr Pro Asp Lys Lys Glu Thr Lys Pro Glu Lys Asp
                1060                1065                1070

Ser Ser Gly Gln Thr Pro Gly Lys Thr Pro Gln Lys Gly Gln Ser Ser
                1075                1080                1085

Arg Thr Leu Glu Lys Arg Ser Ser Lys Arg Ala Leu Ala Thr Lys
    1090                1095                1100

<210> SEQ ID NO 30
<211> LENGTH: 1078
<212> TYPE: PRT
<213> ORGANISM: Streptococcus agalactiae

<400> SEQUENCE: 30

Gln Ser Asp Ile Lys Ala Asn Thr Val Thr Glu Asp Thr Pro Ala Thr
1               5                   10                  15

Glu Gln Ala Val Glu Pro Pro Gln Pro Ile Ala Val Ser Glu Glu Ser
                20                  25                  30

Arg Ser Ser Lys Glu Thr Lys Thr Ser Gln Thr Pro Ser Asp Val Gly
            35                  40                  45

Glu Thr Val Ala Asp Asp Ala Asn Asp Leu Ala Pro Gln Ala Pro Ala
50                  55                  60

Lys Thr Ala Asp Thr Pro Ala Thr Ser Lys Ala Thr Ile Arg Asp Leu
65                  70                  75                  80

Asn Asp Pro Ser His Val Lys Thr Leu Gln Glu Lys Ala Gly Lys Gly
                85                  90                  95

Ala Gly Thr Val Val Ala Val Ile Asp Ala Gly Phe Asp Lys Asn His
                100                 105                 110

Glu Ala Trp Arg Leu Thr Asp Lys Thr Lys Ala Arg Tyr Gln Ser Lys
            115                 120                 125

Glu Asn Leu Glu Lys Ala Lys Lys Glu His Gly Ile Thr Tyr Gly Glu
        130                 135                 140

Trp Val Asn Asp Lys Val Ala Tyr Tyr His Asp Tyr Ser Lys Asp Gly
145                 150                 155                 160

Lys Asn Ala Val Asp Gln Glu His Gly Thr His Val Ser Gly Ile Leu
                165                 170                 175

Ser Gly Asn Ala Pro Ser Glu Met Lys Glu Pro Tyr Arg Leu Glu Gly
                180                 185                 190

Ala Met Pro Glu Ala Gln Leu Leu Met Arg Val Glu Ile Val Asn
            195                 200                 205

Gly Leu Ala Asp Tyr Ala Arg Asn Tyr Ala Gln Ala Ile Arg Asp Ala
        210                 215                 220

Val Asn Leu Gly Ala Lys Val Ile Asn Met Ser Phe Gly Asn Ala Ala
225                 230                 235                 240

Leu Ala Tyr Ala Asn Leu Pro Asp Glu Thr Lys Lys Ala Phe Asp Tyr
                245                 250                 255

Ala Lys Ser Lys Gly Val Ser Ile Val Thr Ser Ala Gly Asn Asp Ser
                260                 265                 270
```

```
Ser Phe Gly Gly Lys Pro Arg Leu Pro Leu Ala Asp His Pro Asp Tyr
    275                 280                 285

Gly Val Val Gly Thr Pro Ala Ala Asp Ser Thr Leu Thr Val Ala
290                 295                 300

Ser Tyr Ser Pro Asp Lys Gln Leu Thr Glu Thr Ala Thr Val Lys Thr
305                 310                 315                 320

Asp Asp His Gln Asp Lys Glu Met Pro Val Ile Ser Thr Asn Arg Phe
                325                 330                 335

Glu Pro Asn Lys Ala Tyr Asp Tyr Ala Tyr Ala Asn Arg Gly Thr Lys
                340                 345                 350

Glu Asp Asp Phe Lys Asp Val Glu Gly Lys Ile Ala Leu Ile Glu Arg
            355                 360                 365

Gly Asp Ile Asp Phe Lys Asp Lys Ile Ala Asn Ala Lys Lys Ala Gly
        370                 375                 380

Ala Val Gly Val Leu Ile Tyr Asp Asn Gln Asp Lys Gly Phe Pro Ile
385                 390                 395                 400

Glu Leu Pro Asn Val Asp Gln Met Pro Ala Ala Phe Ile Ser Arg Arg
                405                 410                 415

Asp Gly Leu Leu Leu Lys Asp Asn Pro Pro Lys Thr Ile Thr Phe Asn
                420                 425                 430

Ala Thr Pro Lys Val Leu Pro Thr Ala Ser Gly Thr Lys Leu Ser Arg
            435                 440                 445

Phe Ser Ser Trp Gly Leu Thr Ala Asp Gly Asn Ile Lys Pro Asp Ile
        450                 455                 460

Ala Ala Pro Gly Gln Asp Ile Leu Ser Ser Val Ala Asn Asn Lys Tyr
465                 470                 475                 480

Ala Lys Leu Ser Gly Thr Ser Met Ser Ala Pro Leu Val Ala Gly Ile
                485                 490                 495

Met Gly Leu Leu Gln Lys Gln Tyr Glu Thr Gln Tyr Pro Asp Met Thr
                500                 505                 510

Pro Ser Glu Arg Leu Asp Leu Ala Lys Lys Val Leu Met Ser Ser Ala
            515                 520                 525

Thr Ala Leu Tyr Asp Glu Asp Glu Lys Ala Tyr Phe Ser Pro Arg Gln
        530                 535                 540

Gln Gly Ala Gly Ala Val Asp Ala Lys Lys Ala Ser Ala Ala Thr Met
545                 550                 555                 560

Tyr Val Thr Asp Lys Asp Asn Thr Ser Ser Lys Val His Leu Asn Asn
                565                 570                 575

Val Ser Asp Lys Phe Glu Val Thr Val Thr His Asn Lys Ser Asp
                580                 585                 590

Lys Pro Gln Glu Leu Tyr Tyr Gln Val Thr Val Gln Thr Asp Lys Val
            595                 600                 605

Asp Gly Lys His Phe Ala Leu Ala Pro Lys Ala Leu Tyr Glu Thr Ser
        610                 615                 620

Trp Gln Lys Ile Thr Ile Pro Ala Asn Ser Ser Lys Gln Val Thr Val
625                 630                 635                 640

Pro Ile Asp Ala Ser Arg Phe Ser Lys Asp Leu Leu Ala Gln Met Lys
                645                 650                 655

Asn Gly Tyr Phe Leu Glu Gly Phe Val Arg Phe Lys Gln Asp Pro Thr
                660                 665                 670

Lys Glu Glu Leu Met Ser Ile Pro Tyr Ile Gly Phe Arg Gly Asp Phe
            675                 680                 685
```

```
Gly Asn Leu Ser Ala Leu Glu Lys Pro Ile Tyr Asp Ser Lys Asp Gly
    690                 695                 700

Ser Ser Tyr Tyr His Glu Ala Asn Ser Asp Ala Lys Asp Gln Leu Asp
705                 710                 715                 720

Gly Asp Gly Leu Gln Phe Tyr Ala Leu Lys Asn Asn Phe Thr Ala Leu
                725                 730                 735

Thr Thr Glu Ser Asn Pro Trp Thr Ile Ile Lys Ala Val Lys Glu Gly
            740                 745                 750

Val Glu Asn Ile Glu Asp Ile Glu Ser Ser Ile Thr Glu Thr Ile
            755                 760                 765

Phe Ala Gly Thr Phe Ala Lys Gln Asp Asp Ser His Tyr Tyr Ile
770                 775                 780

His Arg His Ala Asn Gly Lys Pro Tyr Ala Ala Ile Ser Pro Asn Gly
785                 790                 795                 800

Asp Gly Asn Arg Asp Tyr Val Gln Phe Gln Gly Thr Phe Leu Arg Asn
                805                 810                 815

Ala Lys Asn Leu Val Ala Glu Val Leu Asp Lys Glu Gly Asn Val Val
            820                 825                 830

Trp Thr Ser Glu Val Thr Glu Gln Val Val Lys Asn Tyr Asn Asn Asp
        835                 840                 845

Leu Ala Ser Thr Leu Gly Ser Thr Arg Phe Glu Lys Thr Arg Trp Asp
850                 855                 860

Gly Lys Asp Lys Asp Gly Lys Val Val Ala Asn Gly Thr Tyr Thr Tyr
865                 870                 875                 880

Arg Val Arg Tyr Thr Pro Ile Ser Ser Gly Ala Lys Glu Gln His Thr
                885                 890                 895

Asp Phe Asp Val Ile Val Asp Asn Thr Thr Pro Glu Val Ala Thr Ser
                900                 905                 910

Ala Thr Phe Ser Thr Glu Asp Ser Arg Leu Thr Leu Ala Ser Lys Pro
        915                 920                 925

Lys Thr Ser Gln Pro Val Tyr Arg Glu Arg Ile Ala Tyr Thr Tyr Met
    930                 935                 940

Asp Glu Asp Leu Pro Thr Thr Glu Tyr Ile Ser Pro Asn Glu Asp Gly
945                 950                 955                 960

Thr Phe Thr Leu Pro Glu Glu Ala Glu Thr Met Glu Gly Ala Thr Val
                965                 970                 975

Pro Leu Lys Met Ser Asp Phe Thr Tyr Val Val Glu Asp Met Ala Gly
            980                 985                 990

Asn Ile Thr Tyr Thr Pro Val Thr Lys Leu Leu Glu Gly His Ser Asn
        995                 1000                1005

Lys Pro Glu Gln Asp Gly Ser Asp Gln Ala Pro Asp Lys Lys Pro Glu
    1010                1015                1020

Ala Lys Pro Glu Gln Asp Gly Ser Gly Gln Thr Pro Asp Lys Lys
1025                1030                1035                1040

Glu Thr Lys Pro Glu Lys Asp Ser Ser Gly Thr Pro Gly Lys Thr
    1045                1050                1055

Pro Gln Lys Gly Gln Ser Ser Arg Thr Leu Glu Lys Arg Ser Ser Lys
                1060                1065                1070

Arg Ala Leu Ala Thr Lys
        1075

<210> SEQ ID NO 31
<211> LENGTH: 1365
<212> TYPE: DNA
```

<213> ORGANISM: Streptococcus agalactiae

<400> SEQUENCE: 31

```
atgggacgag taatgaaaac aataacaaca tttgaaaata aaaaagtttt agtccttggt      60
ttagcacgat ctggagaagc tgctgcacgt ttgttagcta agttaggagc aatagtgaca     120
gttaatgatg gcaaaccatt tgatgaaaat ccaacagcac agtctttgtt ggaagagggt     180
attaaagtgg tttgtggtag tcatccttta gaattgttag atgaggattt ttgttacatg     240
attaaaaatc caggaatacc ttataacaat cctatggtca aaaaagcatt agaaaaacaa     300
atccctgttt tgactgaagt ggaattagca tacttagttt cagaatctca gctaataggt     360
attacaggct ctaacgggaa aacgacaacg acaacgatga ttgcagaagt cttaaatgct     420
ggaggtcaga gaggttttgtt agctgggaat atcggctttc ctgctagtga agttgttcag     480
gctgcgaatg ataaagatac tctagttatg gaattatcaa gttttcagct aatgggagtt     540
aaggaatttc gtcctcatat tgcagtaatt actaatttaa tgccaactca tttagattat     600
catgggtctt tgaagattat tgttgctgca aaatggaata tccaaaatca aatgtcttca     660
tctgattttt tggtacttaa ttttaatcaa ggtatttcta aagagttagc taaaactact     720
aaagcaacaa tcgttccttt ctctactacg gaaaaagttg atggtgctta cgtacaagac     780
aagcaacttt tctataaagg ggagaatatt atgtcagtag atgacattgg tgtcccagga     840
agccataacg tagagaatgc tctagcaact attgcgttg ctaaactggc tggtatcagt       900
aatcaagtta ttagagaaac tttaagcaat tttggaggtg taaacaccg cttgcaatca     960
ctcggtaagg ttcatggtat tagtttctat aacgacagca agtcaactaa tatattggca    1020
actcaaaaag cattatctgg ctttgataat actaaagtta tcctaattgc aggaggtctt    1080
gatcgcggta atgagtttga tgaattgata ccagatatca ctggacttaa acatatggtt    1140
gttttaggg aatcggcatc tcgagtaaaa cgtgctgcac aaaaagcagg agtaacttat    1200
agcgatgctt tagatgttag agatgcggta cataaagctt atgaggtggc acaacagggc    1260
gatgttatct tgctaagtcc tgcaaatgca tcatgggaca tgtataagaa tttcgaagtc    1320
cgtggtgatg aattcattga tactttcgaa agtcttagag gagag                    1365
```

<210> SEQ ID NO 32
<211> LENGTH: 455
<212> TYPE: PRT
<213> ORGANISM: Streptococcus agalactiae

<400> SEQUENCE: 32

```
Met Gly Arg Val Met Lys Thr Ile Thr Thr Phe Glu Asn Lys Lys Val
1               5                   10                  15
Leu Val Leu Gly Leu Ala Arg Ser Gly Glu Ala Ala Ala Arg Leu Leu
            20                  25                  30
Ala Lys Leu Gly Ala Ile Val Thr Val Asn Asp Gly Lys Pro Phe Asp
        35                  40                  45
Glu Asn Pro Thr Ala Gln Ser Leu Leu Glu Glu Gly Ile Lys Val Val
    50                  55                  60
Cys Gly Ser His Pro Leu Glu Leu Leu Asp Glu Asp Phe Cys Tyr Met
65                  70                  75                  80
Ile Lys Asn Pro Gly Ile Pro Tyr Asn Asn Pro Met Val Lys Lys Ala
                85                  90                  95
Leu Glu Lys Gln Ile Pro Val Leu Thr Glu Val Glu Leu Ala Tyr Leu
            100                 105                 110
```

Val Ser Glu Ser Gln Leu Ile Gly Ile Thr Gly Ser Asn Gly Lys Thr
            115                 120                 125

Thr Thr Thr Thr Met Ile Ala Glu Val Leu Asn Ala Gly Gly Gln Arg
130                 135                 140

Gly Leu Leu Ala Gly Asn Ile Gly Phe Pro Ala Ser Glu Val Val Gln
145                 150                 155                 160

Ala Ala Asn Asp Lys Asp Thr Leu Val Met Glu Leu Ser Ser Phe Gln
            165                 170                 175

Leu Met Gly Val Lys Glu Phe Arg Pro His Ile Ala Val Ile Thr Asn
            180                 185                 190

Leu Met Pro Thr His Leu Asp Tyr His Gly Ser Phe Glu Asp Tyr Val
            195                 200                 205

Ala Ala Lys Trp Asn Ile Gln Asn Gln Met Ser Ser Ser Asp Phe Leu
            210                 215                 220

Val Leu Asn Phe Asn Gln Gly Ile Ser Lys Glu Leu Ala Lys Thr Thr
225                 230                 235                 240

Lys Ala Thr Ile Val Pro Phe Ser Thr Thr Glu Lys Val Asp Gly Ala
            245                 250                 255

Tyr Val Gln Asp Lys Gln Leu Phe Tyr Lys Gly Glu Asn Ile Met Ser
            260                 265                 270

Val Asp Asp Ile Gly Val Pro Gly Ser His Asn Val Glu Asn Ala Leu
            275                 280                 285

Ala Thr Ile Ala Val Ala Lys Leu Ala Gly Ile Ser Asn Gln Val Ile
            290                 295                 300

Arg Glu Thr Leu Ser Asn Phe Gly Gly Val Lys His Arg Leu Gln Ser
305                 310                 315                 320

Leu Gly Lys Val His Gly Ile Ser Phe Tyr Asn Asp Ser Lys Ser Thr
            325                 330                 335

Asn Ile Leu Ala Thr Gln Lys Ala Leu Ser Gly Phe Asp Asn Thr Lys
            340                 345                 350

Val Ile Leu Ile Ala Gly Gly Leu Asp Arg Gly Asn Glu Phe Asp Glu
            355                 360                 365

Leu Ile Pro Asp Ile Thr Gly Leu Lys His Met Val Val Leu Gly Glu
            370                 375                 380

Ser Ala Ser Arg Val Lys Arg Ala Ala Gln Lys Ala Gly Val Thr Tyr
385                 390                 395                 400

Ser Asp Ala Leu Asp Val Arg Asp Ala Val His Lys Ala Tyr Glu Val
            405                 410                 415

Ala Gln Gln Gly Asp Val Ile Leu Leu Ser Pro Ala Asn Ala Ser Trp
            420                 425                 430

Asp Met Tyr Lys Asn Phe Glu Val Arg Gly Asp Glu Phe Ile Asp Thr
            435                 440                 445

Phe Glu Ser Leu Arg Gly Glu
    450                 455

<210> SEQ ID NO 33
<211> LENGTH: 448
<212> TYPE: PRT
<213> ORGANISM: Streptococcus agalactiae

<400> SEQUENCE: 33

Ile Thr Thr Phe Glu Asn Lys Lys Val Leu Val Leu Gly Leu Ala Arg
1               5                   10                  15

Ser Gly Glu Ala Ala Ala Arg Leu Leu Ala Lys Leu Gly Ala Ile Val
            20                  25                  30

```
Thr Val Asn Asp Gly Lys Pro Phe Asp Glu Asn Pro Thr Ala Gln Ser
         35                  40                  45

Leu Leu Glu Glu Gly Ile Lys Val Val Cys Gly Ser His Pro Leu Glu
 50                  55                  60

Leu Leu Asp Glu Asp Phe Cys Tyr Met Ile Lys Asn Pro Gly Ile Pro
 65                  70                  75                  80

Tyr Asn Asn Pro Met Val Lys Lys Ala Leu Glu Lys Gln Ile Pro Val
                 85                  90                  95

Leu Thr Glu Val Glu Leu Ala Tyr Leu Val Ser Glu Ser Gln Leu Ile
                100                 105                 110

Gly Ile Thr Gly Ser Asn Gly Lys Thr Thr Thr Thr Met Ile Ala
                115                 120                 125

Glu Val Leu Asn Ala Gly Gly Gln Arg Gly Leu Leu Ala Gly Asn Ile
130                 135                 140

Gly Phe Pro Ala Ser Glu Val Val Gln Ala Ala Asn Asp Lys Asp Thr
145                 150                 155                 160

Leu Val Met Glu Leu Ser Ser Phe Gln Leu Met Gly Val Lys Glu Phe
                165                 170                 175

Arg Pro His Ile Ala Val Ile Thr Asn Leu Met Pro Thr His Leu Asp
                180                 185                 190

Tyr His Gly Ser Phe Glu Asp Tyr Val Ala Ala Lys Trp Asn Ile Gln
                195                 200                 205

Asn Gln Met Ser Ser Ser Asp Phe Leu Val Leu Asn Phe Asn Gln Gly
                210                 215                 220

Ile Ser Lys Glu Leu Ala Lys Thr Thr Lys Ala Thr Ile Val Pro Phe
225                 230                 235                 240

Ser Thr Thr Glu Lys Val Asp Gly Ala Tyr Val Gln Asp Lys Gln Leu
                245                 250                 255

Phe Tyr Lys Gly Glu Asn Ile Met Ser Val Asp Asp Ile Gly Val Pro
                260                 265                 270

Gly Ser His Asn Val Glu Asn Ala Leu Ala Thr Ile Ala Val Ala Lys
                275                 280                 285

Leu Ala Gly Ile Ser Asn Gln Val Ile Arg Glu Thr Leu Ser Asn Phe
                290                 295                 300

Gly Gly Val Lys His Arg Leu Gln Ser Leu Gly Lys Val His Gly Ile
305                 310                 315                 320

Ser Phe Tyr Asn Asp Ser Lys Ser Thr Asn Ile Leu Ala Thr Gln Lys
                325                 330                 335

Ala Leu Ser Gly Phe Asp Asn Thr Lys Val Ile Leu Ile Ala Gly Gly
                340                 345                 350

Leu Asp Arg Gly Asn Glu Phe Asp Glu Leu Ile Pro Asp Ile Thr Gly
                355                 360                 365

Leu Lys His Met Val Val Leu Gly Glu Ser Ala Ser Arg Val Lys Arg
                370                 375                 380

Ala Ala Gln Lys Ala Gly Val Thr Tyr Ser Asp Ala Leu Asp Val Arg
385                 390                 395                 400

Asp Ala Val His Lys Ala Tyr Glu Val Ala Gln Gln Gly Asp Val Ile
                405                 410                 415

Leu Leu Ser Pro Ala Asn Ala Ser Trp Asp Met Tyr Lys Asn Phe Glu
                420                 425                 430

Val Arg Gly Asp Glu Phe Ile Asp Thr Phe Glu Ser Leu Arg Gly Glu
                435                 440                 445
```

<210> SEQ ID NO 34
<211> LENGTH: 334
<212> TYPE: PRT
<213> ORGANISM: Streptococcus agalactiae

<400> SEQUENCE: 34

Met Gly Arg Val Met Lys Thr Ile Thr Thr Phe Glu Asn Lys Lys Val
1               5                   10                  15

Leu Val Leu Gly Leu Ala Arg Ser Gly Glu Ala Ala Ala Arg Leu Leu
            20                  25                  30

Ala Lys Leu Gly Ala Ile Val Thr Val Asn Asp Gly Lys Pro Phe Asp
        35                  40                  45

Glu Asn Pro Thr Ala Gln Ser Leu Leu Glu Glu Gly Ile Lys Val Val
    50                  55                  60

Cys Gly Ser His Pro Leu Glu Leu Leu Asp Glu Asp Phe Cys Tyr Met
65                  70                  75                  80

Ile Lys Asn Pro Gly Ile Pro Tyr Asn Asn Pro Met Val Lys Lys Ala
                85                  90                  95

Leu Glu Lys Gln Ile Pro Val Leu Thr Glu Val Glu Leu Ala Tyr Leu
            100                 105                 110

Val Ser Glu Ser Gln Leu Ile Gly Ile Thr Gly Ser Asn Gly Lys Thr
        115                 120                 125

Thr Thr Thr Thr Met Ile Ala Glu Val Leu Asn Ala Gly Gly Gln Arg
    130                 135                 140

Gly Leu Leu Ala Gly Asn Ile Gly Phe Pro Ala Ser Glu Val Val Gln
145                 150                 155                 160

Ala Ala Asn Asp Lys Asp Thr Leu Val Met Glu Leu Ser Ser Phe Gln
                165                 170                 175

Leu Met Gly Val Lys Glu Phe Arg Pro His Ile Ala Val Ile Thr Asn
            180                 185                 190

Leu Met Pro Thr His Leu Asp Tyr His Gly Ser Phe Glu Asp Tyr Val
        195                 200                 205

Ala Ala Lys Trp Asn Ile Gln Asn Gln Met Ser Ser Ser Asp Phe Leu
    210                 215                 220

Val Leu Asn Phe Asn Gln Gly Ile Ser Lys Glu Leu Ala Lys Thr Thr
225                 230                 235                 240

Lys Ala Thr Ile Val Pro Phe Ser Thr Thr Glu Lys Val Asp Gly Ala
                245                 250                 255

Tyr Val Gln Asp Lys Gln Leu Phe Tyr Lys Gly Glu Asn Ile Met Ser
            260                 265                 270

Val Asp Asp Ile Gly Val Pro Gly Ser His Asn Val Glu Asn Ala Leu
        275                 280                 285

Ala Thr Ile Ala Val Ala Lys Leu Ala Gly Ile Ser Asn Gln Val Ile
    290                 295                 300

Arg Glu Thr Leu Ser Asn Phe Gly Gly Val Lys His Arg Leu Gln Ser
305                 310                 315                 320

Leu Gly Lys Val His Gly Ile Ser Phe Tyr Asn Asp Ser Lys
                325                 330

<210> SEQ ID NO 35
<211> LENGTH: 327
<212> TYPE: PRT
<213> ORGANISM: Streptococcus agalactiae

<400> SEQUENCE: 35

```
Ile Thr Thr Phe Glu Asn Lys Lys Val Leu Val Leu Gly Leu Ala Arg
 1               5                  10                  15

Ser Gly Glu Ala Ala Arg Leu Leu Ala Lys Leu Gly Ala Ile Val
             20                  25                  30

Thr Val Asn Asp Gly Lys Pro Phe Asp Glu Asn Pro Thr Ala Gln Ser
             35                  40                  45

Leu Leu Glu Glu Gly Ile Lys Val Val Cys Gly Ser His Pro Leu Glu
 50                  55                  60

Leu Leu Asp Glu Asp Phe Cys Tyr Met Ile Lys Asn Pro Gly Ile Pro
 65                  70                  75                  80

Tyr Asn Asn Pro Met Val Lys Lys Ala Leu Glu Lys Gln Ile Pro Val
                 85                  90                  95

Leu Thr Glu Val Glu Leu Ala Tyr Leu Val Ser Glu Ser Gln Leu Ile
                100                 105                 110

Gly Ile Thr Gly Ser Asn Gly Lys Thr Thr Thr Thr Met Ile Ala
            115                 120                 125

Glu Val Leu Asn Ala Gly Gly Gln Arg Gly Leu Leu Ala Gly Asn Ile
130                 135                 140

Gly Phe Pro Ala Ser Glu Val Val Gln Ala Ala Asn Asp Lys Asp Thr
145                 150                 155                 160

Leu Val Met Glu Leu Ser Ser Phe Gln Leu Met Gly Val Lys Glu Phe
                165                 170                 175

Arg Pro His Ile Ala Val Ile Thr Asn Leu Met Pro Thr His Leu Asp
                180                 185                 190

Tyr His Gly Ser Phe Glu Asp Tyr Val Ala Ala Lys Trp Asn Ile Gln
            195                 200                 205

Asn Gln Met Ser Ser Ser Asp Phe Leu Val Leu Asn Phe Asn Gln Gly
        210                 215                 220

Ile Ser Lys Glu Leu Ala Lys Thr Thr Lys Ala Thr Ile Val Pro Phe
225                 230                 235                 240

Ser Thr Thr Glu Lys Val Asp Gly Ala Tyr Val Gln Asp Lys Gln Leu
                245                 250                 255

Phe Tyr Lys Gly Glu Asn Ile Met Ser Val Asp Asp Ile Gly Val Pro
                260                 265                 270

Gly Ser His Asn Val Glu Asn Ala Leu Ala Thr Ile Ala Val Ala Lys
            275                 280                 285

Leu Ala Gly Ile Ser Asn Gln Val Ile Arg Glu Thr Leu Ser Asn Phe
        290                 295                 300

Gly Gly Val Lys His Arg Leu Gln Ser Leu Gly Lys Val His Gly Ile
305                 310                 315                 320

Ser Phe Tyr Asn Asp Ser Lys
                325
```

<210> SEQ ID NO 36
<211> LENGTH: 1376
<212> TYPE: DNA
<213> ORGANISM: Streptococcus agalactiae

<400> SEQUENCE: 36

```
atgaataaaa aggtactatt gacatcgaca atggcagctt cgctattatc agtcgcaagt      60
gttcaagcac aagaaacaga tacgacgtgg acagcacgta ctgtttcaga ggtaaaggct     120
gatttggtaa agcaagacaa taatcatca tatactgtga atatggtga tacactaagc      180 gttatttcag aagcaatgtc aattgatatg aatgtcttag caaaaataaa taacattgca     240
```

```
gatatcaatc ttatttatcc tgagacaaca ctgacagtaa cttacgatca gaagagtcat    300
actgccactt caatgaaaat agaaacacca gcaacaaatg ctgctggtca acaacagct    360 actgtggatt tgaaaaccaa tcaagtttct gttgcagacc aaaaagtttc tctcaataca    420
atttcggaag gtatgacacc agaagcagca acaacgattg tttcgccaat gaagacatat    480
tcttctgcgc cagctttgaa atcaaaagaa gtattagcac aagagcaagc tgttagtcaa    540
gcagcagcta atgaacaggt atcaccagct cctgtgaagt cgattacttc agaagttcca    600
gcagctaaag aggaagttaa accaactcag acgtcagtca gtcagtcaac aacagtatca    660
ccagcttctg ttgccgctga acaccagct ccagtagcta agtagcacc ggtaagaact    720 gtagcagccc ctagagtggc aagtgttaaa gtagtcactc ctaaagtaga aactggtgca    780
tcaccagagc atgtatcagc tccagcagtt cctgtgacta cgacttcacc agctacagac    840
agtaagttac aagcgactga agttaagagc gttccggtag cacaaaaagc tccaacagca    900
acaccggtag cacaaccagc ttcaacaaca aatgcagtag ctgcacatcc tgaaaatgca    960
gggctccaac ctcatgttgc agcttataaa gaaaaagtag cgtcaactta tggagttaat   1020
gaattcagta cataccgtgc gggagatcca ggtgatcatg gtaaaggttt agcagttgac   1080
tttattgtag gtactaatca agcacttggt aataaagttg cacagtactc tacacaaaat   1140
atggcagcaa ataacatttc atatgttatc tggcaacaaa gtttttactc aaatacaaac   1200
agtatttatg gacctgctaa tacttggaat gcaatgccag atcgtggtgg cgttactgcc   1260
aaccactatg accacgttca cgtatcattt aacaaataat ataaaaaagg aagctatttg   1320
gcttcttttt tatatgcctt gaatagactt tcaaggttct tatataattt ttatta        1376
```

<210> SEQ ID NO 37
<211> LENGTH: 432
<212> TYPE: PRT
<213> ORGANISM: Streptococcus agalactiae

<400> SEQUENCE: 37

```
Met Asn Lys Lys Val Leu Leu Thr Ser Thr Met Ala Ala Ser Leu Leu
 1               5                  10                  15

Ser Val Ala Ser Val Gln Ala Gln Glu Thr Asp Thr Thr Trp Thr Ala
             20                  25                  30

Arg Thr Val Ser Glu Val Lys Ala Asp Leu Val Lys Gln Asp Asn Lys
         35                  40                  45

Ser Ser Tyr Thr Val Lys Tyr Gly Asp Thr Leu Ser Val Ile Ser Glu
     50                  55                  60

Ala Met Ser Ile Asp Met Asn Val Leu Ala Lys Ile Asn Asn Ile Ala
 65                  70                  75                  80

Asp Ile Asn Leu Ile Tyr Pro Glu Thr Thr Leu Thr Val Thr Tyr Asp
                 85                  90                  95

Gln Lys Ser His Thr Ala Thr Ser Met Lys Ile Glu Thr Pro Ala Thr
            100                 105                 110

Asn Ala Ala Gly Gln Thr Thr Ala Thr Val Asp Leu Lys Thr Asn Gln
        115                 120                 125

Val Ser Val Ala Asp Gln Lys Val Ser Leu Asn Thr Ile Ser Glu Gly
    130                 135                 140

Met Thr Pro Glu Ala Ala Thr Thr Ile Val Ser Pro Met Lys Thr Tyr
145                 150                 155                 160

Ser Ser Ala Pro Ala Leu Lys Ser Lys Glu Val Leu Ala Gln Glu Gln
                165                 170                 175
```

Ala Val Ser Gln Ala Ala Asn Glu Gln Val Ser Pro Ala Pro Val
                180                 185                 190

Lys Ser Ile Thr Ser Glu Val Pro Ala Lys Glu Glu Val Lys Pro
        195                 200                 205

Thr Gln Thr Ser Val Ser Gln Ser Thr Thr Val Ser Pro Ala Ser Val
    210                 215                 220

Ala Ala Glu Thr Pro Ala Pro Val Ala Lys Val Ala Pro Val Arg Thr
225                 230                 235                 240

Val Ala Ala Pro Arg Val Ala Ser Val Lys Val Val Thr Pro Lys Val
                245                 250                 255

Glu Thr Gly Ala Ser Pro Glu His Val Ser Ala Pro Ala Val Pro Val
            260                 265                 270

Thr Thr Thr Ser Pro Ala Thr Asp Ser Lys Leu Gln Ala Thr Glu Val
        275                 280                 285

Lys Ser Val Pro Val Ala Gln Lys Ala Pro Thr Ala Thr Pro Val Ala
    290                 295                 300

Gln Pro Ala Ser Thr Thr Asn Ala Val Ala Ala His Pro Glu Asn Ala
305                 310                 315                 320

Gly Leu Gln Pro His Val Ala Ala Tyr Lys Glu Lys Val Ala Ser Thr
                325                 330                 335

Tyr Gly Val Asn Glu Phe Ser Thr Tyr Arg Ala Gly Asp Pro Gly Asp
            340                 345                 350

His Gly Lys Gly Leu Ala Val Asp Phe Ile Val Gly Thr Asn Gln Ala
        355                 360                 365

Leu Gly Asn Lys Val Ala Gln Tyr Ser Thr Gln Asn Met Ala Ala Asn
370                 375                 380

Asn Ile Ser Tyr Val Ile Trp Gln Gln Lys Phe Tyr Ser Asn Thr Asn
385                 390                 395                 400

Ser Ile Tyr Gly Pro Ala Asn Thr Trp Asn Ala Met Pro Asp Arg Gly
                405                 410                 415

Gly Val Thr Ala Asn His Tyr Asp His Val His Val Ser Phe Asn Lys
            420                 425                 430

<210> SEQ ID NO 38
<211> LENGTH: 392
<212> TYPE: PRT
<213> ORGANISM: Streptococcus agalactiae

<400> SEQUENCE: 38

Asp Leu Val Lys Gln Asp Asn Lys Ser Ser Tyr Thr Val Lys Tyr Gly
1               5                   10                  15

Asp Thr Leu Ser Val Ile Ser Glu Ala Met Ser Ile Asp Met Asn Val
            20                  25                  30

Leu Ala Lys Ile Asn Asn Ile Ala Asp Ile Asn Leu Ile Tyr Pro Glu
        35                  40                  45

Thr Thr Leu Thr Val Thr Tyr Asp Gln Lys Ser His Thr Ala Thr Ser
    50                  55                  60

Met Lys Ile Glu Thr Pro Ala Thr Asn Ala Ala Gly Gln Thr Thr Ala
65                  70                  75                  80

Thr Val Asp Leu Lys Thr Asn Gln Val Ser Val Ala Asp Gln Lys Val
                85                  90                  95

Ser Leu Asn Thr Ile Ser Glu Gly Met Thr Pro Glu Ala Ala Thr Thr
            100                 105                 110

Ile Val Ser Pro Met Lys Thr Tyr Ser Ser Ala Pro Ala Leu Lys Ser
        115                 120                 125

```
Lys Glu Val Leu Ala Gln Glu Ala Val Ser Gln Ala Ala Asn
        130                 135                 140

Glu Gln Val Ser Pro Ala Pro Val Lys Ser Ile Thr Ser Glu Val Pro
145                 150                 155                 160

Ala Ala Lys Glu Glu Val Lys Pro Thr Gln Thr Ser Val Ser Gln Ser
                165                 170                 175

Thr Thr Val Ser Pro Ala Ser Val Ala Ala Glu Thr Pro Ala Pro Val
            180                 185                 190

Ala Lys Val Ala Pro Val Arg Thr Val Ala Ala Pro Arg Val Ala Ser
        195                 200                 205

Val Lys Val Val Thr Pro Lys Val Glu Thr Gly Ala Ser Pro Glu His
    210                 215                 220

Val Ser Ala Pro Ala Val Pro Val Thr Thr Thr Ser Pro Ala Thr Asp
225                 230                 235                 240

Ser Lys Leu Gln Ala Thr Glu Val Lys Ser Val Pro Val Ala Gln Lys
                245                 250                 255

Ala Pro Thr Ala Thr Pro Val Ala Gln Pro Ala Ser Thr Thr Asn Ala
            260                 265                 270

Val Ala Ala His Pro Glu Asn Ala Gly Leu Gln Pro His Val Ala Ala
        275                 280                 285

Tyr Lys Glu Lys Val Ala Ser Thr Tyr Gly Val Asn Glu Phe Ser Thr
    290                 295                 300

Tyr Arg Ala Gly Asp Pro Gly Asp His Gly Lys Gly Leu Ala Val Asp
305                 310                 315                 320

Phe Ile Val Gly Thr Asn Gln Ala Leu Gly Asn Lys Val Ala Gln Tyr
                325                 330                 335

Ser Thr Gln Asn Met Ala Ala Asn Asn Ile Ser Tyr Val Ile Trp Gln
            340                 345                 350

Gln Lys Phe Tyr Ser Asn Thr Asn Ser Ile Tyr Gly Pro Ala Asn Thr
        355                 360                 365

Trp Asn Ala Met Pro Asp Arg Gly Gly Val Thr Ala Asn His Tyr Asp
    370                 375                 380

His Val His Val Ser Phe Asn Lys
385                 390

<210> SEQ ID NO 39
<211> LENGTH: 1500
<212> TYPE: DNA
<213> ORGANISM: Streptococcus agalactiae

<400> SEQUENCE: 39
atgaataaac gcgtaaaaat cgttgcaaca cttggtcctg cggttgaatt ccgtggtggt      60
aagaagtttg gtgagtctgg atactggggt gaaagccttg acgtagaagc ttcagcagaa     120
aaaattgctc aattgattaa agaaggtgct aacgttttcc gtttcaactt ctcacatgga     180
gatcatgctg agcaaggagc tcgtatggct actgttcgta agcagaagag gattgcagga     240
caaaaagttg gcttcctcct tgatactaaa ggacctgaaa ttcgtacaga acttttgaa      300 gatggtgcag atttccattc atatacaaca ggtacaaaat acgtgttgc tactaagcaa      360 ggtatcaaat caactccaga agtgattgca ttgaatgttg ctggtggact tgacatcttt     420
gatgacgttg aagttggtaa gcaaatcctt gttgatgatg gtaaactagg tcttactgtg     480
tttgcaaaag ataagacac tcgtgaattt gaagtagttg ttgagaatga tggccttatt     540
ggtaaacaaa aagtgtaaa catccccttat actaaaattc ctttcccagc acttgcagaa     600
```

```
cgcgataatg ctgatatccg ttttggactt gagcaaggac ttaactttat tgctatctca    660
tttgtacgta ctgctaaaga tgttaatgaa gttcgtgcta tttgtgaaga aactggsmat    720
ggacacgtta agttgtttgc taaaattgaa aatcaacaag gtatcgataa tattgatgag    780
attatcgaag cagcagatgg tattatgatt gctcgtggtg atatgggtat cgaagttcca    840
tttgaaatgg ttccagttta ccaaaaaatg atcattacta agttaatgc agctggtaaa      900 gcagttatta cagcaacaaa tatgcttgaa acaatgacta taaaccacg tcgactcgt       960 tcagaagtat ctgatgtctt caatgctgtt attgatggta ctgatgctac aatgctttca    1020
ggtgagtcag ctaatggtaa atacccagtt gagtcagttc gtacaatggc tactattgat    1080
aaaaatgctc aaacattact caatgagtat ggtcgcttag actcatctgc attcccacgt    1140
aataacaaaa ctgatgttat tgcatctgcg gttaaagatg caacacactc aatggatatc    1200
aaacttgttg taacaattac tgaaacaggt aatacagctc gtgccattc taaattccgt      1260 ccagatgcag acatttggc tgttacattt gatgaaaaag tacaacgttc attgatgatt      1320
aactggggtg ttatccctgt ccttgcagac aaaccagcat ctacagatga tatgtttgag    1380
gttgcagaac gtgtagcact tgaagcagga tttgttgaat caggcgataa tatcgttatc    1440
gttgcaggtg ttcctgtagg tacaggtgga actaacacaa tgcgtgttcg tactgttaaa    1500

<210> SEQ ID NO 40
<211> LENGTH: 500
<212> TYPE: PRT
<213> ORGANISM: Streptococcus agalactiae
<220> FEATURE:
<221> NAME/KEY: VARIANT
<222> LOCATION: (1)...(500)
<223> OTHER INFORMATION: Xaa = Any Amino Acid

<400> SEQUENCE: 40

Met Asn Lys Arg Val Lys Ile Val Ala Thr Leu Gly Pro Ala Val Glu
 1               5                  10                  15

Phe Arg Gly Gly Lys Lys Phe Gly Glu Ser Gly Tyr Trp Gly Glu Ser
                20                  25                  30

Leu Asp Val Glu Ala Ser Ala Glu Lys Ile Ala Gln Leu Ile Lys Glu
            35                  40                  45

Gly Ala Asn Val Phe Arg Phe Asn Phe Ser His Gly Asp His Ala Glu
        50                  55                  60

Gln Gly Ala Arg Met Ala Thr Val Arg Lys Ala Glu Glu Ile Ala Gly
    65                  70                  75                  80

Gln Lys Val Gly Phe Leu Leu Asp Thr Lys Gly Pro Glu Ile Arg Thr
                85                  90                  95

Glu Leu Phe Glu Asp Gly Ala Asp Phe His Ser Tyr Thr Thr Gly Thr
                100                 105                 110

Lys Leu Arg Val Ala Thr Lys Gln Gly Ile Lys Ser Thr Pro Glu Val
            115                 120                 125

Ile Ala Leu Asn Val Ala Gly Gly Leu Asp Ile Phe Asp Asp Val Glu
        130                 135                 140

Val Gly Lys Gln Ile Leu Val Asp Asp Gly Lys Leu Gly Leu Thr Val
    145                 150                 155                 160

Phe Ala Lys Asp Lys Asp Thr Arg Glu Phe Glu Val Val Glu Asn
                165                 170                 175

Asp Gly Leu Ile Gly Lys Gln Lys Gly Val Asn Ile Pro Tyr Thr Lys
            180                 185                 190
```

```
Ile Pro Phe Pro Ala Leu Ala Glu Arg Asp Asn Ala Asp Ile Arg Phe
            195                 200                 205

Gly Leu Glu Gln Gly Leu Asn Phe Ile Ala Ile Ser Phe Val Arg Thr
        210                 215                 220

Ala Lys Asp Val Asn Glu Val Arg Ala Ile Cys Glu Glu Thr Gly Xaa
225                 230                 235                 240

Gly His Val Lys Leu Phe Ala Lys Ile Glu Asn Gln Gln Gly Ile Asp
                245                 250                 255

Asn Ile Asp Glu Ile Ile Glu Ala Ala Asp Gly Ile Met Ile Ala Arg
            260                 265                 270

Gly Asp Met Gly Ile Glu Val Pro Phe Glu Met Val Pro Val Tyr Gln
        275                 280                 285

Lys Met Ile Ile Thr Lys Val Asn Ala Ala Gly Lys Ala Val Ile Thr
290                 295                 300

Ala Thr Asn Met Leu Glu Thr Met Thr Asp Lys Pro Arg Ala Thr Arg
305                 310                 315                 320

Ser Glu Val Ser Asp Val Phe Asn Ala Val Ile Asp Gly Thr Asp Ala
                325                 330                 335

Thr Met Leu Ser Gly Glu Ser Ala Asn Gly Lys Tyr Pro Val Glu Ser
            340                 345                 350

Val Arg Thr Met Ala Thr Ile Asp Lys Asn Ala Gln Thr Leu Leu Asn
        355                 360                 365

Glu Tyr Gly Arg Leu Asp Ser Ser Ala Phe Pro Arg Asn Asn Lys Thr
    370                 375                 380

Asp Val Ile Ala Ser Ala Val Lys Asp Ala Thr His Ser Met Asp Ile
385                 390                 395                 400

Lys Leu Val Val Thr Ile Thr Glu Thr Gly Asn Thr Ala Arg Ala Ile
                405                 410                 415

Ser Lys Phe Arg Pro Asp Ala Asp Ile Leu Ala Val Thr Phe Asp Glu
            420                 425                 430

Lys Val Gln Arg Ser Leu Met Ile Asn Trp Gly Val Ile Pro Val Leu
        435                 440                 445

Ala Asp Lys Pro Ala Ser Thr Asp Asp Met Phe Glu Val Ala Glu Arg
    450                 455                 460

Val Ala Leu Glu Ala Gly Phe Val Glu Ser Gly Asp Asn Ile Val Ile
465                 470                 475                 480

Val Ala Gly Val Pro Val Gly Thr Gly Gly Thr Asn Thr Met Arg Val
                485                 490                 495

Arg Thr Val Lys
            500

<210> SEQ ID NO 41
<211> LENGTH: 720
<212> TYPE: DNA
<213> ORGANISM: Streptococcus agalactiae

<400> SEQUENCE: 41
ttgtctgcta ataagacaa aaaggtggtg atatttatgt atttagcatt aatcggtgat      60
atcattaatt caaaacagat acttgaacgt gaaactttcc aacagtcttt tcagcaacta    120
atgaccgaac tatctgatgt atatggtgaa gagctgattt ctccattcac tattacagct    180
ggtgatgaat tcaagctttt attgaaacca tcaaaaaagg tatttcaaat tattgaccat    240
attcaactag ctctaaaacc tgttaatgta aggttcggcc tcggtacagg aaacattata    300
acatccatca attcaaatga agtatcggt gctgatggtc ctgcctactg gcatgctcgc    360
```

```
tcagctatta atcatataca tgataaaaat gattatggaa cagttcaagt agctatttgc    420
cttgatgatg aagaccaaaa ccttgaatta acactaaata gtctcatttc agctggtgat    480
tttatcaagt caaaatggac tacaaaccat tttcaaatgc ttgagcactt aatacttcaa    540
gataattatc aagaacaatt tcaacatcaa agttagccca actggaaaaa tattgaacct    600
agtgcgctga ctaaacgcct taaagcaagc ggtctgaaga tttacttaag aacgagaaca    660
caggcagccg atctattagt taaagttgc actcaaacta aaggggaag ctatgatttc     720
```

<210> SEQ ID NO 42
<211> LENGTH: 240
<212> TYPE: PRT
<213> ORGANISM: Streptococcus agalactiae

<400> SEQUENCE: 42

Met Ser Ala Ile Ile Asp Lys Lys Val Val Ile Phe Met Tyr Leu Ala
1               5                   10                  15

Leu Ile Gly Asp Ile Ile Asn Ser Lys Gln Ile Leu Glu Arg Glu Thr
            20                  25                  30

Phe Gln Gln Ser Phe Gln Gln Leu Met Thr Glu Leu Ser Asp Val Tyr
        35                  40                  45

Gly Glu Glu Leu Ile Ser Pro Phe Thr Ile Thr Ala Gly Asp Glu Phe
    50                  55                  60

Gln Ala Leu Leu Lys Pro Ser Lys Lys Val Phe Gln Ile Ile Asp His
65                  70                  75                  80

Ile Gln Leu Ala Leu Lys Pro Val Asn Val Arg Phe Gly Leu Gly Thr
                85                  90                  95

Gly Asn Ile Ile Thr Ser Ile Asn Ser Asn Glu Ser Ile Gly Ala Asp
            100                 105                 110

Gly Pro Ala Tyr Trp His Ala Arg Ser Ala Ile Asn His Ile His Asp
        115                 120                 125

Lys Asn Asp Tyr Gly Thr Val Gln Val Ala Ile Cys Leu Asp Asp Glu
    130                 135                 140

Asp Gln Asn Leu Glu Leu Thr Leu Asn Ser Leu Ile Ser Ala Gly Asp
145                 150                 155                 160

Phe Ile Lys Ser Lys Trp Thr Thr Asn His Phe Gln Met Leu Glu His
                165                 170                 175

Leu Ile Leu Gln Asp Asn Tyr Gln Glu Gln Phe Gln His Gln Lys Leu
            180                 185                 190

Ala Gln Leu Glu Asn Ile Glu Pro Ser Ala Leu Thr Lys Arg Leu Lys
        195                 200                 205

Ala Ser Gly Leu Lys Ile Tyr Leu Arg Thr Arg Thr Gln Ala Ala Asp
    210                 215                 220

Leu Leu Val Lys Ser Cys Thr Gln Thr Lys Gly Gly Ser Tyr Asp Phe
225                 230                 235                 240

<210> SEQ ID NO 43
<211> LENGTH: 228
<212> TYPE: PRT
<213> ORGANISM: Streptococcus agalactiae

<400> SEQUENCE: 43

Met Tyr Leu Ala Leu Ile Gly Asp Ile Ile Asn Ser Lys Gln Ile Leu
1               5                   10                  15

Glu Arg Glu Thr Phe Gln Gln Ser Phe Gln Gln Leu Met Thr Glu Leu
            20                  25                  30

Ser Asp Val Tyr Gly Glu Glu Leu Ile Ser Pro Phe Thr Ile Thr Ala
        35                  40                  45

Gly Asp Glu Phe Gln Ala Leu Leu Lys Pro Ser Lys Lys Val Phe Gln
    50                  55                  60

Ile Ile Asp His Ile Gln Leu Ala Leu Lys Pro Val Asn Val Arg Phe
65                  70                  75                  80

Gly Leu Gly Thr Gly Asn Ile Ile Thr Ser Ile Asn Ser Asn Glu Ser
                85                  90                  95

Ile Gly Ala Asp Gly Pro Ala Tyr Trp His Ala Arg Ser Ala Ile Asn
            100                 105                 110

His Ile His Asp Lys Asn Asp Tyr Gly Thr Val Gln Val Ala Ile Cys
        115                 120                 125

Leu Asp Asp Glu Asp Gln Asn Leu Glu Leu Thr Leu Asn Ser Leu Ile
    130                 135                 140

Ser Ala Gly Asp Phe Ile Lys Ser Lys Trp Thr Thr Asn His Phe Gln
145                 150                 155                 160

Met Leu Glu His Leu Ile Leu Gln Asp Asn Tyr Gln Glu Gln Phe Gln
                165                 170                 175

His Gln Lys Leu Ala Gln Leu Glu Asn Ile Glu Pro Ser Ala Leu Thr
            180                 185                 190

Lys Arg Leu Lys Ala Ser Gly Leu Lys Ile Tyr Leu Arg Thr Arg Thr
        195                 200                 205

Gln Ala Ala Asp Leu Leu Val Lys Ser Cys Thr Gln Thr Lys Gly Gly
    210                 215                 220

Ser Tyr Asp Phe
225

<210> SEQ ID NO 44
<211> LENGTH: 2193
<212> TYPE: DNA
<213> ORGANISM: Streptococcus agalactiae

<400> SEQUENCE: 44
atgagcgtat atgttagtgg aataggaatt atttcttctt tgggaaagaa ttatagcgag      60
cataaacagc atctcttcga cttaaaagaa ggaatttcta acatttata taaaaatcac     120 gactctattt tagaatctta tacaggaagc ataactagtg acccagaggt tcctgagcaa     180
tacaaagatg agacacgtaa ttttaaattt gcttttaccg cttttgaaga ggctcttgct     240
tcttcaggtg ttaatttaaa agcttatcat aatattgctg tgtgtttagg gacctcactt     300
gggggaaaga gtgctggtca aaatgccttg tatcaatttg aagaaggaga gcgtcaagta     360
gatgctagtt tattagaaaa agcatctgtt taccatattg ctgatgaatt gatggcttat     420
catgatattg tgggagcttc gtatgttatt tcaaccgcct gttctgcaag taataatgcc     480
gtaatattag aacacaatt acttcaagat ggcgattgtg atttagctat ttgtggtggc     540
tgtgatgagt taagtgatat ttctttagca ggcttcacat cactaggagc tattaataca     600
gaaatggcat gtcagcccta ttcttctgga aaaggaatca atttgggtga gggcgctggt     660
tttgttgttc ttgtcaaaga tcagtcctta gctaaatatg gaaaaattat cggtggtctt     720
attacttcag atggttatca tataacagca cctaagccaa caggtgaagg ggcggcacag     780
attgcaaagc agctagtgac tcaagcaggt attgactaca gtgagattga ctatattaac     840
ggtcacggta caggtactca agctaatgat aaaatggaaa aaatatgta tggtaagttt     900 ttccccgacaa cgacattgat cagcagtacc aagggggcaaa cgggtcatac tctaggggct     960

```
gcaggtatta tcgaattgat taattgttta gcggcaatag aggaacagac tgtaccagca    1020
actaaaaatg agattgggat agaaggtttt ccagaaaatt ttgtctatca tcaaaagaga    1080
gaatacccaa taagaaatgc tttaaatttt tcgtttgctt ttggtggaaa taatagtggt    1140
gtcttattgt catctttaga ttcacctcta gaaacattac ctgctagaga aaatcttaaa    1200
atggctatct tatcatctgt tgcttccatt tctaagaatg aatcactttc tataacctat    1260 gaaaagttg ctagtaattt caacgacttt gaagcattac gctttaaagg ggctagacca    1320
cccaaaactg tcaacccagc acaatttagg aaaatggatg attttttccaa aatggttgcc    1380 gtaacaacag ctcaagcact aatagaaagc aatattaatc taaaaaaaca agatacttca    1440
aaagtaggaa ttgtatttac aacactttct ggaccagttg aggttgttga aggtattgaa    1500
aagcaaatca acacagaagg atatgcacat gtttctgctt cacgattccc gtttacagta    1560
atgaatgcag cagctggtat gctttctatc attttttaaaa taacaggtcc tttatctgtc    1620
atttcgacaa atagtggagc gcttgatggt atacaatatg ccaaggaaat gatgcgtaac    1680
gataatctag actatgtgat tcttgtttct gctaatcagt ggacagacat gagttttatg    1740
tggtggcaac aattaaacta tgatagtcaa atgtttgtcg ttctgatta ttgttcagca    1800 caagtcctct ctcgtcaagc attggataat tctcctataa tattaggtag taaacaatta    1860
aaatatagcc ataaaacatt cacagatgtg atgactattt tgatgctgc gcttcaaaat    1920 ttattatcag acttaggact aaccataaaa gatatcaaag gtttcgtttg gaatgagcgg    1980
aagaaggcag ttagttcaga ttatgatttc ttagcgaact tgtctgagta ttataatatg    2040
ccaaaccttg cttctggtca gtttggattt tcatctaatg gtgctggtga agaactggac    2100
tatactgtta atgaaagtat agaaaagggc tattatttag tcctatctta ttcgatcttc    2160
ggtggtatct cttttgctat tattgaaaaa agg                                 2193
```

<210> SEQ ID NO 45
<211> LENGTH: 731
<212> TYPE: PRT
<213> ORGANISM: Streptococcus agalactiae

<400> SEQUENCE: 45

```
Met Ser Val Tyr Val Ser Gly Ile Gly Ile Ile Ser Ser Leu Gly Lys
  1               5                  10                  15

Asn Tyr Ser Glu His Lys Gln His Leu Phe Asp Leu Lys Glu Gly Ile
             20                  25                  30

Ser Lys His Leu Tyr Lys Asn His Asp Ser Ile Leu Glu Ser Tyr Thr
         35                  40                  45

Gly Ser Ile Thr Ser Asp Pro Glu Val Pro Glu Gln Tyr Lys Asp Glu
     50                  55                  60

Thr Arg Asn Phe Lys Phe Ala Phe Thr Ala Phe Glu Glu Ala Leu Ala
 65                  70                  75                  80

Ser Ser Gly Val Asn Leu Lys Ala Tyr His Asn Ile Ala Val Cys Leu
                 85                  90                  95

Gly Thr Ser Leu Gly Gly Lys Ser Ala Gly Gln Asn Ala Leu Tyr Gln
            100                 105                 110

Phe Glu Glu Gly Glu Arg Gln Val Asp Ala Ser Leu Leu Glu Lys Ala
        115                 120                 125

Ser Val Tyr His Ile Ala Asp Glu Leu Met Ala Tyr His Asp Ile Val
    130                 135                 140

Gly Ala Ser Tyr Val Ile Ser Thr Ala Cys Ser Ala Ser Asn Asn Ala
```

```
            145                 150                 155                 160
        Val Ile Leu Gly Thr Gln Leu Leu Gln Asp Gly Asp Cys Asp Leu Ala
                        165                 170                 175
        Ile Cys Gly Gly Cys Asp Glu Leu Ser Asp Ile Ser Leu Ala Gly Phe
                        180                 185                 190
        Thr Ser Leu Gly Ala Ile Asn Thr Glu Met Ala Cys Gln Pro Tyr Ser
                        195                 200                 205
        Ser Gly Lys Gly Ile Asn Leu Gly Glu Gly Ala Gly Phe Val Val Leu
                        210                 215                 220
        Val Lys Asp Gln Ser Leu Ala Lys Tyr Gly Lys Ile Ile Gly Gly Leu
        225                 230                 235                 240
        Ile Thr Ser Asp Gly Tyr His Ile Thr Ala Pro Lys Pro Thr Gly Glu
                        245                 250                 255
        Gly Ala Ala Gln Ile Ala Lys Gln Leu Val Thr Gln Ala Gly Ile Asp
                        260                 265                 270
        Tyr Ser Glu Ile Asp Tyr Ile Asn Gly His Gly Thr Gly Thr Gln Ala
                        275                 280                 285
        Asn Asp Lys Met Glu Lys Asn Met Tyr Gly Lys Phe Phe Pro Thr Thr
        290                 295                 300
        Thr Leu Ile Ser Ser Thr Lys Gly Gln Thr Gly His Thr Leu Gly Ala
        305                 310                 315                 320
        Ala Gly Ile Ile Glu Leu Ile Asn Cys Leu Ala Ala Ile Glu Glu Gln
                        325                 330                 335
        Thr Val Pro Ala Thr Lys Asn Glu Ile Gly Ile Glu Gly Phe Pro Glu
                        340                 345                 350
        Asn Phe Val Tyr His Gln Lys Arg Glu Tyr Pro Ile Arg Asn Ala Leu
                        355                 360                 365
        Asn Phe Ser Phe Ala Phe Gly Gly Asn Asn Ser Gly Val Leu Leu Ser
                        370                 375                 380
        Ser Leu Asp Ser Pro Leu Glu Thr Leu Pro Ala Arg Glu Asn Leu Lys
        385                 390                 395                 400
        Met Ala Ile Leu Ser Ser Val Ala Ser Ile Ser Lys Asn Glu Ser Leu
                        405                 410                 415
        Ser Ile Thr Tyr Glu Lys Val Ala Ser Asn Phe Asn Asp Phe Glu Ala
                        420                 425                 430
        Leu Arg Phe Lys Gly Ala Arg Pro Pro Lys Thr Val Asn Pro Ala Gln
                        435                 440                 445
        Phe Arg Lys Met Asp Asp Phe Ser Lys Met Val Ala Val Thr Thr Ala
                        450                 455                 460
        Gln Ala Leu Ile Glu Ser Asn Ile Asn Leu Lys Lys Gln Asp Thr Ser
        465                 470                 475                 480
        Lys Val Gly Ile Val Phe Thr Thr Leu Ser Gly Pro Val Glu Val Val
                        485                 490                 495
        Glu Gly Ile Glu Lys Gln Ile Thr Thr Glu Gly Tyr Ala His Val Ser
                        500                 505                 510
        Ala Ser Arg Phe Pro Phe Thr Val Met Asn Ala Ala Ala Gly Met Leu
                        515                 520                 525
        Ser Ile Ile Phe Lys Ile Thr Gly Pro Leu Ser Val Ile Ser Thr Asn
                        530                 535                 540
        Ser Gly Ala Leu Asp Gly Ile Gln Tyr Ala Lys Glu Met Met Arg Asn
        545                 550                 555                 560
        Asp Asn Leu Asp Tyr Val Ile Leu Val Ser Ala Asn Gln Trp Thr Asp
                        565                 570                 575
```

```
Met Ser Phe Met Trp Trp Gln Gln Leu Asn Tyr Asp Ser Gln Met Phe
            580                 585                 590

Val Gly Ser Asp Tyr Cys Ser Ala Gln Val Leu Ser Arg Gln Ala Leu
            595                 600                 605

Asp Asn Ser Pro Ile Ile Leu Gly Ser Lys Gln Leu Lys Tyr Ser His
            610                 615                 620

Lys Thr Phe Thr Asp Val Met Thr Ile Phe Asp Ala Ala Leu Gln Asn
625                 630                 635                 640

Leu Leu Ser Asp Leu Gly Leu Thr Ile Lys Asp Ile Lys Gly Phe Val
                645                 650                 655

Trp Asn Glu Arg Lys Lys Ala Val Ser Ser Asp Tyr Asp Phe Leu Ala
                660                 665                 670

Asn Leu Ser Glu Tyr Tyr Asn Met Pro Asn Leu Ala Ser Gly Gln Phe
                675                 680                 685

Gly Phe Ser Ser Asn Gly Ala Gly Glu Glu Leu Asp Tyr Thr Val Asn
            690                 695                 700

Glu Ser Ile Glu Lys Gly Tyr Tyr Leu Val Leu Ser Tyr Ser Ile Phe
705                 710                 715                 720

Gly Gly Ile Ser Phe Ala Ile Ile Glu Lys Arg
                725                 730

<210> SEQ ID NO 46
<211> LENGTH: 727
<212> TYPE: PRT
<213> ORGANISM: Streptococcus agalactiae

<400> SEQUENCE: 46

Val Ser Gly Ile Gly Ile Ile Ser Ser Leu Gly Lys Asn Tyr Ser Glu
1               5                   10                  15

His Lys Gln His Leu Phe Asp Leu Lys Glu Gly Ile Ser Lys His Leu
                20                  25                  30

Tyr Lys Asn His Asp Ser Ile Leu Glu Ser Tyr Thr Gly Ser Ile Thr
                35                  40                  45

Ser Asp Pro Glu Val Pro Glu Gln Tyr Lys Asp Glu Thr Arg Asn Phe
50                  55                  60

Lys Phe Ala Phe Thr Ala Phe Glu Glu Ala Leu Ala Ser Ser Gly Val
65                  70                  75                  80

Asn Leu Lys Ala Tyr His Asn Ile Ala Val Cys Leu Gly Thr Ser Leu
                85                  90                  95

Gly Gly Lys Ser Ala Gly Gln Asn Ala Leu Tyr Gln Phe Glu Glu Gly
                100                 105                 110

Glu Arg Gln Val Asp Ala Ser Leu Leu Glu Lys Ala Ser Val Tyr His
                115                 120                 125

Ile Ala Asp Glu Leu Met Ala Tyr His Asp Ile Val Gly Ala Ser Tyr
            130                 135                 140

Val Ile Ser Thr Ala Cys Ser Ala Ser Asn Asn Ala Val Ile Leu Gly
145                 150                 155                 160

Thr Gln Leu Leu Gln Asp Gly Asp Cys Asp Leu Ala Ile Cys Gly Gly
                165                 170                 175

Cys Asp Glu Leu Ser Asp Ile Ser Leu Ala Gly Phe Thr Ser Leu Gly
                180                 185                 190

Ala Ile Asn Thr Glu Met Ala Cys Gln Pro Tyr Ser Ser Gly Lys Gly
                195                 200                 205

Ile Asn Leu Gly Glu Gly Ala Gly Phe Val Val Leu Val Lys Asp Gln
```

```
                  210                 215                 220
Ser Leu Ala Lys Tyr Gly Lys Ile Ile Gly Gly Leu Ile Thr Ser Asp
225                 230                 235                 240

Gly Tyr His Ile Thr Ala Pro Lys Pro Thr Gly Glu Gly Ala Ala Gln
                245                 250                 255

Ile Ala Lys Gln Leu Val Thr Gln Ala Gly Ile Asp Tyr Ser Glu Ile
            260                 265                 270

Asp Tyr Ile Asn Gly His Gly Thr Gly Thr Gln Ala Asn Asp Lys Met
        275                 280                 285

Glu Lys Asn Met Tyr Gly Lys Phe Phe Pro Thr Thr Thr Leu Ile Ser
    290                 295                 300

Ser Thr Lys Gly Gln Thr Gly His Thr Leu Gly Ala Ala Gly Ile Ile
305                 310                 315                 320

Glu Leu Ile Asn Cys Leu Ala Ala Ile Glu Glu Gln Thr Val Pro Ala
                325                 330                 335

Thr Lys Asn Glu Ile Gly Ile Glu Gly Phe Pro Glu Asn Phe Val Tyr
            340                 345                 350

His Gln Lys Arg Glu Tyr Pro Ile Arg Asn Ala Leu Asn Phe Ser Phe
        355                 360                 365

Ala Phe Gly Gly Asn Asn Ser Gly Val Leu Leu Ser Ser Leu Asp Ser
    370                 375                 380

Pro Leu Glu Thr Leu Pro Ala Arg Glu Asn Leu Lys Met Ala Ile Leu
385                 390                 395                 400

Ser Ser Val Ala Ser Ile Ser Lys Asn Glu Ser Leu Ser Ile Thr Tyr
                405                 410                 415

Glu Lys Val Ala Ser Asn Phe Asn Asp Phe Glu Ala Leu Arg Phe Lys
            420                 425                 430

Gly Ala Arg Pro Pro Lys Thr Val Asn Pro Ala Gln Phe Arg Lys Met
        435                 440                 445

Asp Asp Phe Ser Lys Met Val Ala Val Thr Thr Ala Gln Ala Leu Ile
    450                 455                 460

Glu Ser Asn Ile Asn Leu Lys Lys Gln Asp Thr Ser Lys Val Gly Ile
465                 470                 475                 480

Val Phe Thr Thr Leu Ser Gly Pro Val Glu Val Val Glu Gly Ile Glu
                485                 490                 495

Lys Gln Ile Thr Thr Glu Gly Tyr Ala His Val Ser Ala Ser Arg Phe
            500                 505                 510

Pro Phe Thr Val Met Asn Ala Ala Ala Gly Met Leu Ser Ile Ile Phe
        515                 520                 525

Lys Ile Thr Gly Pro Leu Ser Val Ile Ser Thr Asn Ser Gly Ala Leu
    530                 535                 540

Asp Gly Ile Gln Tyr Ala Lys Glu Met Met Arg Asn Asp Asn Leu Asp
545                 550                 555                 560

Tyr Val Ile Leu Val Ser Ala Asn Gln Trp Thr Asp Met Ser Phe Met
                565                 570                 575

Trp Trp Gln Gln Leu Asn Tyr Asp Ser Gln Met Phe Val Gly Ser Asp
            580                 585                 590

Tyr Cys Ser Ala Gln Val Leu Ser Arg Gln Ala Leu Asp Asn Ser Pro
        595                 600                 605

Ile Ile Leu Gly Ser Lys Gln Leu Lys Tyr Ser His Lys Thr Phe Thr
    610                 615                 620

Asp Val Met Thr Ile Phe Asp Ala Ala Leu Gln Asn Leu Leu Ser Asp
625                 630                 635                 640
```

Leu Gly Leu Thr Ile Lys Asp Ile Lys Gly Phe Val Trp Asn Glu Arg
                645                 650                 655

Lys Lys Ala Val Ser Ser Asp Tyr Asp Phe Leu Ala Asn Leu Ser Glu
            660                 665                 670

Tyr Tyr Asn Met Pro Asn Leu Ala Ser Gly Gln Phe Gly Phe Ser Ser
        675                 680                 685

Asn Gly Ala Gly Glu Glu Leu Asp Tyr Thr Val Asn Glu Ser Ile Glu
    690                 695                 700

Lys Gly Tyr Tyr Leu Val Leu Ser Tyr Ser Ile Phe Gly Gly Ile Ser
705                 710                 715                 720

Phe Ala Ile Ile Glu Lys Arg
                725

<210> SEQ ID NO 47
<211> LENGTH: 900
<212> TYPE: DNA
<213> ORGANISM: Streptococcus agalactiae

<400> SEQUENCE: 47
atgaaaatag atgacctaag aaaaagcgac aatgttgaag atcgtcgctc cagtagcgga      60
ggttcattct ctagcggagg aagtggatta ccgattcttc aacttttatt gctgcgaggg     120
agttggaaaa ccaagcttgt ggttttaatc atcttactgc tacttggcgg aggggggacta    180
accagcattt ttaatgactc atcctcacct tctagttacc aatctcagaa tgtctcacgt     240
tctgttgata tagcgcaac gagagaacaa atcgatttcg ttaataaagt ccttggctca     300
actgaggatt tctggtcaca agaattccaa acccaaggtt ttggaaatta taggaaccca     360
aaacttgttc tttacaccaa ttcaattcaa acaggttgtg gtataggtga atctgcttca     420
ggaccatttt attgttcagc agataaaaaa atctatcttg atatttcttt ttacaatgaa     480
ttatcacata aatatggtgc tactggtgat tttgctatgg cctacgtcat cgcccacgaa     540
gttggtcacc acattcaaac agagttaggc attatggata agtataatag aatgcgacac     600
ggacttacta agaaagaagc aaatgctttta aatgttcggc tagaacttca agcagattat     660
tatgcagggg tatgggctca ctacatcagg ggaaaaaatc tcttagaaca aggagacttt     720
gaagaggcca tgaatgctgc ccacgccgtc ggagacgata cccttcagaa agaaacctac     780
ggaaaattag tgcctgatag ctttacccat ggaacagctg aacaacgcca acgttggttt     840
aacaaaggct ttcaatatgg tgacatccaa cacggtgata ctttctccgt agaacatcta     900

<210> SEQ ID NO 48
<211> LENGTH: 300
<212> TYPE: PRT
<213> ORGANISM: Streptococcus agalactiae

<400> SEQUENCE: 48

Met Lys Ile Asp Asp Leu Arg Lys Ser Asp Asn Val Glu Asp Arg Arg
1               5                   10                  15

Ser Ser Ser Gly Gly Ser Phe Ser Ser Gly Gly Ser Gly Leu Pro Ile
            20                  25                  30

Leu Gln Leu Leu Leu Leu Arg Gly Ser Trp Lys Thr Lys Leu Val Val
        35                  40                  45

Leu Ile Ile Leu Leu Leu Gly Gly Gly Gly Leu Thr Ser Ile Phe
    50                  55                  60

Asn Asp Ser Ser Ser Pro Ser Ser Tyr Gln Ser Gln Asn Val Ser Arg
65                  70                  75                  80

```
Ser Val Asp Asn Ser Ala Thr Arg Glu Gln Ile Asp Phe Val Asn Lys
                85                  90                  95

Val Leu Gly Ser Thr Glu Asp Phe Trp Ser Gln Glu Phe Gln Thr Gln
            100                 105                 110

Gly Phe Gly Asn Tyr Lys Glu Pro Lys Leu Val Leu Tyr Thr Asn Ser
        115                 120                 125

Ile Gln Thr Gly Cys Gly Ile Gly Glu Ser Ala Ser Gly Pro Phe Tyr
    130                 135                 140

Cys Ser Ala Asp Lys Lys Ile Tyr Leu Asp Ile Ser Phe Tyr Asn Glu
145                 150                 155                 160

Leu Ser His Lys Tyr Gly Ala Thr Gly Asp Phe Ala Met Ala Tyr Val
                165                 170                 175

Ile Ala His Glu Val Gly His His Ile Gln Thr Glu Leu Gly Ile Met
            180                 185                 190

Asp Lys Tyr Asn Arg Met Arg His Gly Leu Thr Lys Lys Glu Ala Asn
        195                 200                 205

Ala Leu Asn Val Arg Leu Glu Leu Gln Ala Asp Tyr Tyr Ala Gly Val
    210                 215                 220

Trp Ala His Tyr Ile Arg Gly Lys Asn Leu Leu Glu Gln Gly Asp Phe
225                 230                 235                 240

Glu Glu Ala Met Asn Ala Ala His Ala Val Gly Asp Asp Thr Leu Gln
                245                 250                 255

Lys Glu Thr Tyr Gly Lys Leu Val Pro Asp Ser Phe Thr His Gly Thr
            260                 265                 270

Ala Glu Gln Arg Gln Arg Trp Phe Asn Lys Gly Phe Gln Tyr Gly Asp
        275                 280                 285

Ile Gln His Gly Asp Thr Phe Ser Val Glu His Leu
    290                 295                 300

<210> SEQ ID NO 49
<211> LENGTH: 1242
<212> TYPE: DNA
<213> ORGANISM: Streptococcus agalactiae

<400> SEQUENCE: 49
atgagtaaac gacaaaattt aggaattagt aaaaaaggag caattatatc agggctctca     60
gtggcactaa ttgtagtaat aggtggcttt ttatgggtac aatctcaacc taataagagt    120
gcagtaaaaa ctaactacaa agttttttaat gttagagaag aagtgtttc gtcctcaact    180 cttttgacag gaaaagctaa ggctaatcaa gaacagtatg tgtattttga tgctaataaa    240
ggtaatcgag caactgtcac agttaaagtg ggtgataaaa tcacagctgg tcagcagtta    300
gttcaatatg atacaacaac tgcacaagca gcctacgaca ctgctaatcg tcaattaaat    360
aaagtagcgc gtcagattaa taatctaaag acaacaggaa gtcttccagc tatggaatca    420
agtgatcaat cttcttcatc atcacaagga caagggactc aatcgactag tggtgcgacg    480
aatcgtctac agcaaaatta tcaaagtcaa gctaatgctt catacaacca acaacttcaa    540
gatttgaatg atgcttatgc agatgcacag gcagaagtaa ataaagcaca aaaagcattg    600
aatgatactg ttattacaag tgacgtatca gggacagttg ttgaagttaa tagtgatatt    660
gatccagctt caaaaactag tcaagtactt gtccatgtag caactgaagg taaactccaa    720
gtacaaggaa cgatgagtga gtatgatttg ctaatgttaa aaaagacca ggctgttaaa    780 ataaaatcta aggtctatcc tgacaaggaa tgggaaggta aaatttcata tatctcaaat    840
```

```
tatccagaag cagaagcaaa caacaatgac tctaataacg gctctagtgc tgtaaattat    900
aaatataaag tagatattac tagccctctc gatgcattaa acaaggtttt taccgtatca    960
gttgaagtag ttaatggaga taagcacctt attgtcccta caagttctgt gataaacaaa   1020
gataataaac actttgtttg gtatacaat gattctaatc gtaaaatttc caaagttgaa    1080
gtcaaaattg gtaaagctga tgctaagaca caagaaattt tatcaggttt gaaagcagga   1140
caaatcgtgg ttactaatcc aagtaaaacc ttcaaggatg ggcaaaaaat tgataatatt   1200
gaatcaatcg atcttaactc taataagaaa tcagaggtga aa                      1242
```

```
<210> SEQ ID NO 50
<211> LENGTH: 414
<212> TYPE: PRT
<213> ORGANISM: Streptococcus agalactiae

<400> SEQUENCE: 50

Met Ser Lys Arg Gln Asn Leu Gly Ile Ser Lys Gly Ala Ile Ile
  1               5                  10                  15

Ser Gly Leu Ser Val Ala Leu Ile Val Ile Gly Gly Phe Leu Trp
                 20                  25                  30

Val Gln Ser Gln Pro Asn Lys Ser Ala Val Lys Thr Asn Tyr Lys Val
                 35                  40                  45

Phe Asn Val Arg Glu Gly Ser Val Ser Ser Thr Leu Leu Thr Gly
 50                  55                  60

Lys Ala Lys Ala Asn Gln Glu Gln Tyr Val Tyr Phe Asp Ala Asn Lys
 65                  70                  75                  80

Gly Asn Arg Ala Thr Val Thr Val Lys Val Gly Asp Lys Ile Thr Ala
                 85                  90                  95

Gly Gln Gln Leu Val Gln Tyr Asp Thr Thr Thr Ala Gln Ala Ala Tyr
                100                 105                 110

Asp Thr Ala Asn Arg Gln Leu Asn Lys Val Ala Arg Gln Ile Asn Asn
                115                 120                 125

Leu Lys Thr Thr Gly Ser Leu Pro Ala Met Glu Ser Ser Asp Gln Ser
130                 135                 140

Ser Ser Ser Ser Gln Gly Gln Gly Thr Gln Ser Thr Ser Gly Ala Thr
145                 150                 155                 160

Asn Arg Leu Gln Gln Asn Tyr Gln Ser Gln Ala Asn Ala Ser Tyr Asn
                165                 170                 175

Gln Gln Leu Gln Asp Leu Asn Asp Ala Tyr Ala Asp Ala Gln Ala Glu
                180                 185                 190

Val Asn Lys Ala Gln Lys Ala Leu Asn Asp Thr Val Ile Thr Ser Asp
                195                 200                 205

Val Ser Gly Thr Val Val Glu Val Asn Ser Asp Ile Asp Pro Ala Ser
                210                 215                 220

Lys Thr Ser Gln Val Leu Val His Val Ala Thr Glu Gly Lys Leu Gln
225                 230                 235                 240

Val Gln Gly Thr Met Ser Glu Tyr Asp Leu Ala Asn Val Lys Lys Asp
                245                 250                 255

Gln Ala Val Lys Ile Lys Ser Lys Val Tyr Pro Asp Lys Glu Trp Glu
                260                 265                 270

Gly Lys Ile Ser Tyr Ile Ser Asn Tyr Pro Glu Ala Glu Ala Asn Asn
                275                 280                 285

Asn Asp Ser Asn Asn Gly Ser Ser Ala Val Asn Tyr Lys Tyr Lys Val
                290                 295                 300
```

```
Asp Ile Thr Ser Pro Leu Asp Ala Leu Lys Gln Gly Phe Thr Val Ser
305                 310                 315                 320

Val Glu Val Val Asn Gly Asp Lys His Leu Ile Val Pro Thr Ser Ser
                325                 330                 335

Val Ile Asn Lys Asp Asn Lys His Phe Val Trp Val Tyr Asn Asp Ser
                340                 345                 350

Asn Arg Lys Ile Ser Lys Val Glu Val Lys Ile Gly Lys Ala Asp Ala
                355                 360                 365

Lys Thr Gln Glu Ile Leu Ser Gly Leu Lys Ala Gly Gln Ile Val Val
                370                 375                 380

Thr Asn Pro Ser Lys Thr Phe Lys Asp Gly Gln Lys Ile Asp Asn Ile
385                 390                 395                 400

Glu Ser Ile Asp Leu Asn Ser Asn Lys Lys Ser Glu Val Lys
                405                 410

<210> SEQ ID NO 51
<211> LENGTH: 385
<212> TYPE: PRT
<213> ORGANISM: Streptococcus agalactiae

<400> SEQUENCE: 51

Phe Leu Trp Val Gln Ser Gln Pro Asn Lys Ser Ala Val Lys Thr Asn
1               5                   10                  15

Tyr Lys Val Phe Asn Val Arg Glu Gly Ser Val Ser Ser Ser Thr Leu
                20                  25                  30

Leu Thr Gly Lys Ala Lys Ala Asn Gln Glu Gln Tyr Val Tyr Phe Asp
                35                  40                  45

Ala Asn Lys Gly Asn Arg Ala Thr Val Thr Val Lys Val Gly Asp Lys
50                  55                  60

Ile Thr Ala Gly Gln Gln Leu Val Gln Tyr Asp Thr Thr Thr Ala Gln
65                  70                  75                  80

Ala Ala Tyr Asp Thr Ala Asn Arg Gln Leu Asn Lys Val Ala Arg Gln
                85                  90                  95

Ile Asn Asn Leu Lys Thr Thr Gly Ser Leu Pro Ala Met Glu Ser Ser
                100                 105                 110

Asp Gln Ser Ser Ser Ser Ser Gln Gly Gln Gly Thr Gln Ser Thr Ser
                115                 120                 125

Gly Ala Thr Asn Arg Leu Gln Gln Asn Tyr Gln Ser Gln Ala Asn Ala
                130                 135                 140

Ser Tyr Asn Gln Gln Leu Gln Asp Leu Asn Asp Ala Tyr Ala Asp Ala
145                 150                 155                 160

Gln Ala Glu Val Asn Lys Ala Gln Lys Ala Leu Asn Asp Thr Val Ile
                165                 170                 175

Thr Ser Asp Val Ser Gly Thr Val Val Glu Val Asn Ser Asp Ile Asp
                180                 185                 190

Pro Ala Ser Lys Thr Ser Gln Val Leu Val His Val Ala Thr Glu Gly
                195                 200                 205

Lys Leu Gln Val Gln Gly Thr Met Ser Glu Tyr Asp Leu Ala Asn Val
                210                 215                 220

Lys Lys Asp Gln Ala Val Lys Ile Lys Ser Lys Val Tyr Pro Asp Lys
225                 230                 235                 240

Glu Trp Glu Gly Lys Ile Ser Tyr Ile Ser Asn Tyr Pro Glu Ala Glu
                245                 250                 255

Ala Asn Asn Asn Asp Ser Asn Asn Gly Ser Ser Ala Val Asn Tyr Lys
                260                 265                 270
```

Tyr Lys Val Asp Ile Thr Ser Pro Leu Asp Ala Leu Lys Gln Gly Phe
            275                 280                 285

Thr Val Ser Val Glu Val Asn Gly Asp Lys His Leu Ile Val Pro
        290                 295                 300

Thr Ser Ser Val Ile Asn Lys Asp Asn Lys His Phe Val Trp Val Tyr
305                 310                 315                 320

Asn Asp Ser Asn Arg Lys Ile Ser Lys Val Glu Val Lys Ile Gly Lys
                325                 330                 335

Ala Asp Ala Lys Thr Gln Glu Ile Leu Ser Gly Leu Lys Ala Gly Gln
            340                 345                 350

Ile Val Val Thr Asn Pro Ser Lys Thr Phe Lys Asp Gly Gln Lys Ile
            355                 360                 365

Asp Asn Ile Glu Ser Ile Asp Leu Asn Ser Asn Lys Lys Ser Glu Val
            370                 375                 380

Lys
385

<210> SEQ ID NO 52
<211> LENGTH: 930
<212> TYPE: DNA
<213> ORGANISM: Streptococcus agalactiae

<400> SEQUENCE: 52
atgaaaaaaa ttggaattat tgtcctcaca ctactgacct tcttttttggt atcttgcgga      60 caacaaacta acaagaaag cactaaaaca actatttcta aaatgcctaa aattgaaggc       120
ttcacctatt atggaaaaat tcctgaaaat ccgaaaaaag taattaattt tacatattct     180
tacactgggt atttattaaa actaggtgtt aatgtttcaa gttacagttt agacttagaa     240
aaagatagcc ccgttttttgg taaacaactg aaagaagcta aaaaattaac tgctgatgat   300
acagaagcta ttgccgcaca aaaacctgat ttaatcatgg ttttcgatca agatccaaac   360
atcaatactc tgaaaaaaat tgcaccaact ttagttatta aatatggtgc acaaaattat   420
ttagatatga tgccagcctt ggggaaagta ttcggtaaag aaaaagaagc taatcagtgg   480
gttagccaat ggaaaactaa aactctcgct gtcaaaaaag atttacacca tatcttaaag   540
cctaacacta ctttttactat tatggatttt tatgataaaa atatctattt atatggtaat   600
aattttggac gcggtggaga actaatctat gattcactag ttatgctgc cccagaaaaa     660 gtcaaaaaag atgtctttaa aaagggtgg tttaccgttt cgcaagaagc aatcggtgat   720
tacgttggag attatgcccct tgttaatata aacaaaacga ctaaaaaagc agcttcatca   780
cttaaagaaa gtgatgtctg gaagaattta ccagctgtca aaaagggca catcatagaa     840 agtaactacg acgtgtttta tttctctgac cctctatctt tagaagctca attaaaatca   900
tttacaaagg ctatcaaaga aaatacaaat                                                              930

<210> SEQ ID NO 53
<211> LENGTH: 310
<212> TYPE: PRT
<213> ORGANISM: Streptococcus agalactiae

<400> SEQUENCE: 53

Met Lys Lys Ile Gly Ile Ile Val Leu Thr Leu Leu Thr Phe Phe Leu
1               5                   10                  15

Val Ser Cys Gly Gln Gln Thr Lys Gln Glu Ser Thr Lys Thr Thr Ile
            20                  25                  30

```
Ser Lys Met Pro Lys Ile Glu Gly Phe Thr Tyr Tyr Gly Lys Ile Pro
         35                  40                  45

Glu Asn Pro Lys Lys Val Ile Asn Phe Thr Tyr Ser Tyr Thr Gly Tyr
 50                  55                  60

Leu Leu Lys Leu Gly Val Asn Val Ser Ser Tyr Ser Leu Asp Leu Glu
 65                  70                  75                  80

Lys Asp Ser Pro Val Phe Gly Lys Gln Leu Lys Glu Ala Lys Lys Leu
                 85                  90                  95

Thr Ala Asp Asp Thr Glu Ala Ile Ala Ala Gln Lys Pro Asp Leu Ile
            100                 105                 110

Met Val Phe Asp Gln Asp Pro Asn Ile Asn Thr Leu Lys Lys Ile Ala
            115                 120                 125

Pro Thr Leu Val Ile Lys Tyr Gly Ala Gln Asn Tyr Leu Asp Met Met
        130                 135                 140

Pro Ala Leu Gly Lys Val Phe Gly Lys Glu Lys Glu Ala Asn Gln Trp
145                 150                 155                 160

Val Ser Gln Trp Lys Thr Lys Thr Leu Ala Val Lys Lys Asp Leu His
                165                 170                 175

His Ile Leu Lys Pro Asn Thr Thr Phe Thr Ile Met Asp Phe Tyr Asp
            180                 185                 190

Lys Asn Ile Tyr Leu Tyr Gly Asn Asn Phe Gly Arg Gly Gly Glu Leu
        195                 200                 205

Ile Tyr Asp Ser Leu Gly Tyr Ala Ala Pro Glu Lys Val Lys Lys Asp
        210                 215                 220

Val Phe Lys Lys Gly Trp Phe Thr Val Ser Gln Glu Ala Ile Gly Asp
225                 230                 235                 240

Tyr Val Gly Asp Tyr Ala Leu Val Asn Ile Asn Lys Thr Thr Lys Lys
                245                 250                 255

Ala Ala Ser Ser Leu Lys Glu Ser Asp Val Trp Lys Asn Leu Pro Ala
            260                 265                 270

Val Lys Lys Gly His Ile Ile Glu Ser Asn Tyr Asp Val Phe Tyr Phe
        275                 280                 285

Ser Asp Pro Leu Ser Leu Glu Ala Gln Leu Lys Ser Phe Thr Lys Ala
        290                 295                 300

Ile Lys Glu Asn Thr Asn
305                 310

<210> SEQ ID NO 54
<211> LENGTH: 272
<212> TYPE: PRT
<213> ORGANISM: Streptococcus agalactiae

<400> SEQUENCE: 54

Glu Gly Phe Thr Tyr Tyr Gly Lys Ile Pro Glu Asn Pro Lys Lys Val
  1               5                  10                  15

Ile Asn Phe Thr Tyr Ser Tyr Thr Gly Tyr Leu Leu Lys Leu Gly Val
             20                  25                  30

Asn Val Ser Ser Tyr Ser Leu Asp Leu Glu Lys Asp Ser Pro Val Phe
         35                  40                  45

Gly Lys Gln Leu Lys Glu Ala Lys Lys Leu Thr Ala Asp Asp Thr Glu
     50                  55                  60

Ala Ile Ala Ala Gln Lys Pro Asp Leu Ile Met Val Phe Asp Gln Asp
 65                  70                  75                  80

Pro Asn Ile Asn Thr Leu Lys Lys Ile Ala Pro Thr Leu Val Ile Lys
                 85                  90                  95
```

```
Tyr Gly Ala Gln Asn Tyr Leu Asp Met Met Pro Ala Leu Gly Lys Val
            100                 105                 110

Phe Gly Lys Glu Lys Glu Ala Asn Gln Trp Val Ser Gln Trp Lys Thr
        115                 120                 125

Lys Thr Leu Ala Val Lys Asp Leu His His Ile Leu Lys Pro Asn
    130                 135                 140

Thr Thr Phe Thr Ile Met Asp Phe Tyr Asp Lys Asn Ile Tyr Leu Tyr
145                 150                 155                 160

Gly Asn Asn Phe Gly Arg Gly Gly Glu Leu Ile Tyr Asp Ser Leu Gly
                165                 170                 175

Tyr Ala Ala Pro Glu Lys Val Lys Lys Asp Val Phe Lys Lys Gly Trp
                180                 185                 190

Phe Thr Val Ser Gln Glu Ala Ile Gly Asp Tyr Val Gly Asp Tyr Ala
                195                 200                 205

Leu Val Asn Ile Asn Lys Thr Thr Lys Ala Ala Ser Ser Leu Lys
    210                 215                 220

Glu Ser Asp Val Trp Lys Asn Leu Pro Ala Val Lys Lys Gly His Ile
225                 230                 235                 240

Ile Glu Ser Asn Tyr Asp Val Phe Tyr Phe Ser Asp Pro Leu Ser Leu
                245                 250                 255

Glu Ala Gln Leu Lys Ser Phe Thr Lys Ala Ile Lys Glu Asn Thr Asn
                260                 265                 270

<210> SEQ ID NO 55
<211> LENGTH: 302
<212> TYPE: PRT
<213> ORGANISM: Streptococcus agalactiae

<400> SEQUENCE: 55

Met Lys Lys Ile Gly Ile Ile Val Leu Thr Leu Leu Thr Phe Phe Leu
 1               5                  10                  15

Val Ser Cys Gly Gln Gln Thr Lys Gln Glu Ser Thr Lys Thr Thr Ile
                20                  25                  30

Ser Lys Met Pro Lys Ile Glu Gly Phe Thr Tyr Tyr Gly Lys Ile Pro
            35                  40                  45

Glu Asn Pro Lys Lys Val Ile Asn Phe Thr Tyr Ser Tyr Thr Gly Tyr
 50                  55                  60

Leu Leu Lys Leu Gly Val Asn Val Ser Ser Tyr Ser Leu Asp Leu Glu
65                  70                  75                  80

Lys Asp Ser Pro Val Phe Gly Lys Gln Leu Lys Glu Ala Lys Lys Leu
                85                  90                  95

Thr Ala Asp Asp Thr Glu Ala Ile Ala Ala Gln Lys Pro Asp Leu Ile
            100                 105                 110

Met Val Phe Asp Gln Asp Pro Asn Ile Asn Thr Leu Lys Lys Ile Ala
        115                 120                 125

Pro Thr Leu Val Ile Lys Tyr Gly Ala Gln Asn Tyr Leu Asp Met Met
    130                 135                 140

Pro Ala Leu Gly Lys Val Phe Gly Lys Glu Lys Glu Ala Asn Gln Trp
145                 150                 155                 160

Val Ser Gln Trp Lys Thr Lys Thr Leu Ala Val Lys Lys Asp Leu His
                165                 170                 175

His Ile Leu Lys Pro Asn Thr Thr Phe Thr Ile Met Asp Phe Tyr Asp
            180                 185                 190

Lys Asn Ile Tyr Leu Tyr Gly Asn Asn Phe Gly Arg Gly Gly Glu Leu
```

```
                195                 200                 205
Ile Tyr Asp Ser Leu Gly Tyr Ala Ala Pro Glu Lys Val Lys Lys Asp
210                 215                 220

Val Phe Lys Lys Gly Trp Phe Thr Val Ser Gln Glu Ala Ile Gly Asp
225                 230                 235                 240

Tyr Val Gly Asp Tyr Ala Leu Val Asn Ile Asn Lys Thr Thr Lys Lys
                245                 250                 255

Ala Ala Ser Ser Leu Lys Glu Ser Asp Val Trp Lys Asn Leu Pro Ala
                260                 265                 270

Val Lys Lys Gly His Ile Ile Glu Ser Asn Tyr Asp Val Phe Tyr Phe
                275                 280                 285

Ser Asp Pro Leu Ser Leu Glu Ala Gln Leu Lys Ser Phe Thr
                290                 295                 300

<210> SEQ ID NO 56
<211> LENGTH: 264
<212> TYPE: PRT
<213> ORGANISM: Streptococcus agalactiae

<400> SEQUENCE: 56

Glu Gly Phe Thr Tyr Tyr Gly Lys Ile Pro Glu Asn Pro Lys Lys Val
1               5                   10                  15

Ile Asn Phe Thr Tyr Ser Tyr Thr Gly Tyr Leu Leu Lys Leu Gly Val
                20                  25                  30

Asn Val Ser Ser Tyr Ser Leu Asp Leu Glu Lys Asp Ser Pro Val Phe
            35                  40                  45

Gly Lys Gln Leu Lys Glu Ala Lys Lys Leu Thr Ala Asp Asp Thr Glu
        50                  55                  60

Ala Ile Ala Ala Gln Lys Pro Asp Leu Ile Met Val Phe Asp Gln Asp
65                  70                  75                  80

Pro Asn Ile Asn Thr Leu Lys Lys Ile Ala Pro Thr Leu Val Ile Lys
                85                  90                  95

Tyr Gly Ala Gln Asn Tyr Leu Asp Met Met Pro Ala Leu Gly Lys Val
            100                 105                 110

Phe Gly Lys Glu Lys Glu Ala Asn Gln Trp Val Ser Gln Trp Lys Thr
        115                 120                 125

Lys Thr Leu Ala Val Lys Lys Asp Leu His His Ile Leu Lys Pro Asn
130                 135                 140

Thr Thr Phe Thr Ile Met Asp Phe Tyr Asp Lys Asn Ile Tyr Leu Tyr
145                 150                 155                 160

Gly Asn Asn Phe Gly Arg Gly Gly Glu Leu Ile Tyr Asp Ser Leu Gly
                165                 170                 175

Tyr Ala Pro Glu Lys Val Lys Lys Asp Val Phe Lys Lys Gly Trp
            180                 185                 190

Phe Thr Val Ser Gln Glu Ala Ile Gly Asp Tyr Val Gly Asp Tyr Ala
        195                 200                 205

Leu Val Asn Ile Asn Lys Thr Thr Lys Lys Ala Ala Ser Ser Leu Lys
    210                 215                 220

Glu Ser Asp Val Trp Lys Asn Leu Pro Ala Val Lys Lys Gly His Ile
225                 230                 235                 240

Ile Glu Ser Asn Tyr Asp Val Phe Tyr Phe Ser Asp Pro Leu Ser Leu
                245                 250                 255

Glu Ala Gln Leu Lys Ser Phe Thr
            260
```

<210> SEQ ID NO 57
<211> LENGTH: 576
<212> TYPE: DNA
<213> ORGANISM: Streptococcus agalactiae

<400> SEQUENCE: 57

```
atgaaagtga aaataagat tttaacgatg gtagcactta ctgtcttaac atgtgctact      60
tattcatcaa tcggttatgc tgatacaagt gataagaata ctgacacgag tgtcgtgact    120
acgaccttat ctgaggagaa aagatcagat gaactagacc agtctagtac tggttcttct    180
tctgaaaatg aatcgagttc atcaagtgaa ccagaaacaa atccgtcaac taatccacct    240
acaacagaac catcgcaacc ctcacctagt gaagagaaca agcctgatgg tagaacgaag    300
acagaaattg gcaataataa ggatatttct agtggaacaa aagtattaat ttcagaagat    360
agtattaaga attttagtaa agcaagtagt gatcaagaag aagtggatcg cgatgaatca    420
tcatcttcaa aagcaaatga tgggaaaaaa ggccacagta agcctaaaaa ggaacttcct    480
aaaacaggag atagccactc agatactgta atagcatcta cgggagggat tattctgtta    540
tcattaagtt tttacaataa gaaaatgaaa ctttat                              576
```

<210> SEQ ID NO 58
<211> LENGTH: 192
<212> TYPE: PRT
<213> ORGANISM: Streptococcus agalactiae

<400> SEQUENCE: 58

```
Met Lys Val Lys Asn Lys Ile Leu Thr Met Val Ala Leu Thr Val Leu
  1               5                  10                  15

Thr Cys Ala Thr Tyr Ser Ser Ile Gly Tyr Ala Asp Thr Ser Asp Lys
             20                  25                  30

Asn Thr Asp Thr Ser Val Val Thr Thr Thr Leu Ser Glu Glu Lys Arg
         35                  40                  45

Ser Asp Glu Leu Asp Gln Ser Ser Thr Gly Ser Ser Ser Glu Asn Glu
     50                  55                  60

Ser Ser Ser Ser Glu Pro Glu Thr Asn Pro Ser Thr Asn Pro Pro
 65                  70                  75                  80

Thr Thr Glu Pro Ser Gln Pro Ser Pro Ser Glu Glu Asn Lys Pro Asp
                 85                  90                  95

Gly Arg Thr Lys Thr Glu Ile Gly Asn Asn Lys Asp Ile Ser Ser Gly
            100                 105                 110

Thr Lys Val Leu Ile Ser Glu Asp Ser Ile Lys Asn Phe Ser Lys Ala
        115                 120                 125

Ser Ser Asp Gln Glu Glu Val Asp Arg Asp Glu Ser Ser Ser Ser Lys
    130                 135                 140

Ala Asn Asp Gly Lys Lys Gly His Ser Lys Pro Lys Lys Glu Leu Pro
145                 150                 155                 160

Lys Thr Gly Asp Ser His Ser Asp Thr Val Ile Ala Ser Thr Gly Gly
                165                 170                 175

Ile Ile Leu Leu Ser Leu Ser Phe Tyr Asn Lys Lys Met Lys Leu Tyr
            180                 185                 190
```

<210> SEQ ID NO 59
<211> LENGTH: 165
<212> TYPE: PRT
<213> ORGANISM: Streptococcus agalactiae

<400> SEQUENCE: 59

```
Asp Thr Ser Asp Lys Asn Thr Asp Thr Ser Val Val Thr Thr Thr Leu
1               5                   10                  15

Ser Glu Glu Lys Arg Ser Asp Glu Leu Asp Gln Ser Ser Thr Gly Ser
            20                  25                  30

Ser Ser Glu Asn Glu Ser Ser Ser Ser Glu Pro Glu Thr Asn Pro
        35                  40                  45

Ser Thr Asn Pro Pro Thr Thr Glu Pro Ser Gln Pro Ser Pro Ser Glu
    50                  55                  60

Glu Asn Lys Pro Asp Gly Arg Thr Lys Thr Glu Ile Gly Asn Asn Lys
65              70                  75                  80

Asp Ile Ser Ser Gly Thr Lys Val Leu Ile Ser Glu Asp Ser Ile Lys
                85                  90                  95

Asn Phe Ser Lys Ala Ser Ser Asp Gln Glu Glu Val Asp Arg Asp Glu
                100                 105                 110

Ser Ser Ser Ser Lys Ala Asn Asp Gly Lys Lys Gly His Ser Lys Pro
            115                 120                 125

Lys Lys Glu Leu Pro Lys Thr Gly Asp Ser His Ser Asp Thr Val Ile
        130                 135                 140

Ala Ser Thr Gly Gly Ile Ile Leu Leu Ser Leu Ser Phe Tyr Asn Lys
145                 150                 155                 160

Lys Met Lys Leu Tyr
                165

<210> SEQ ID NO 60
<211> LENGTH: 140
<212> TYPE: PRT
<213> ORGANISM: Streptococcus agalactiae

<400> SEQUENCE: 60

Asp Gln Ser Ser Thr Gly Ser Ser Ser Glu Asn Glu Ser Ser Ser Ser
1               5                   10                  15

Ser Glu Pro Glu Thr Asn Pro Ser Thr Asn Pro Pro Thr Thr Glu Pro
            20                  25                  30

Ser Gln Pro Ser Pro Ser Glu Glu Asn Lys Pro Asp Gly Arg Thr Lys
        35                  40                  45

Thr Glu Ile Gly Asn Asn Lys Asp Ile Ser Ser Gly Thr Lys Val Leu
    50                  55                  60

Ile Ser Glu Asp Ser Ile Lys Asn Phe Ser Lys Ala Ser Ser Asp Gln
65              70                  75                  80

Glu Glu Val Asp Arg Asp Glu Ser Ser Ser Ser Lys Ala Asn Asp Gly
                85                  90                  95

Lys Lys Gly His Ser Lys Pro Lys Lys Glu Leu Pro Lys Thr Gly Asp
                100                 105                 110

Ser His Ser Asp Thr Val Ile Ala Ser Thr Gly Gly Ile Ile Leu Leu
            115                 120                 125

Ser Leu Ser Phe Tyr Asn Lys Lys Met Lys Leu Tyr
        130                 135                 140

<210> SEQ ID NO 61
<211> LENGTH: 158
<212> TYPE: PRT
<213> ORGANISM: Streptococcus agalactiae

<400> SEQUENCE: 61

Met Lys Val Lys Asn Lys Ile Leu Thr Met Val Ala Leu Thr Val Leu
1               5                   10                  15
```

Thr Cys Ala Thr Tyr Ser Ser Ile Gly Tyr Ala Asp Thr Ser Asp Lys
            20                  25                  30

Asn Thr Asp Thr Ser Val Val Thr Thr Leu Ser Glu Glu Lys Arg
        35                  40                  45

Ser Asp Glu Leu Asp Gln Ser Ser Thr Gly Ser Ser Glu Asn Glu
50                  55                  60

Ser Ser Ser Ser Ser Glu Pro Glu Thr Asn Pro Ser Thr Asn Pro Pro
65                  70                  75                  80

Thr Thr Glu Pro Ser Gln Pro Ser Pro Ser Glu Glu Asn Lys Pro Asp
                85                  90                  95

Gly Arg Thr Lys Thr Glu Ile Gly Asn Asn Lys Asp Ile Ser Ser Gly
                100                 105                 110

Thr Lys Val Leu Ile Ser Glu Asp Ser Ile Lys Asn Phe Ser Lys Ala
            115                 120                 125

Ser Ser Asp Gln Glu Glu Val Asp Arg Asp Glu Ser Ser Ser Ser Lys
            130                 135                 140

Ala Asn Asp Gly Lys Lys Gly His Ser Lys Pro Lys Lys Glu
145                 150                 155

<210> SEQ ID NO 62
<211> LENGTH: 131
<212> TYPE: PRT
<213> ORGANISM: Streptococcus agalactiae

<400> SEQUENCE: 62

Asp Thr Ser Asp Lys Asn Thr Asp Thr Ser Val Val Thr Thr Thr Leu
1               5                   10                  15

Ser Glu Glu Lys Arg Ser Asp Glu Leu Asp Gln Ser Ser Thr Gly Ser
            20                  25                  30

Ser Ser Glu Asn Glu Ser Ser Ser Ser Ser Glu Pro Glu Thr Asn Pro
        35                  40                  45

Ser Thr Asn Pro Pro Thr Thr Glu Pro Ser Gln Pro Ser Pro Ser Glu
    50                  55                  60

Glu Asn Lys Pro Asp Gly Arg Thr Lys Thr Glu Ile Gly Asn Asn Lys
65                  70                  75                  80

Asp Ile Ser Ser Gly Thr Lys Val Leu Ile Ser Glu Asp Ser Ile Lys
                85                  90                  95

Asn Phe Ser Lys Ala Ser Ser Asp Gln Glu Glu Val Asp Arg Asp Glu
            100                 105                 110

Ser Ser Ser Ser Lys Ala Asn Asp Gly Lys Lys Gly His Ser Lys Pro
        115                 120                 125

Lys Lys Glu
    130

<210> SEQ ID NO 63
<211> LENGTH: 106
<212> TYPE: PRT
<213> ORGANISM: Streptococcus agalactiae

<400> SEQUENCE: 63

Asp Gln Ser Ser Thr Gly Ser Ser Glu Asn Glu Ser Ser Ser Ser Ser
1               5                   10                  15

Ser Glu Pro Glu Thr Asn Pro Ser Thr Asn Pro Pro Thr Thr Glu Pro
            20                  25                  30

Ser Gln Pro Ser Pro Ser Glu Glu Asn Lys Pro Asp Gly Arg Thr Lys
        35                  40                  45

Thr Glu Ile Gly Asn Asn Lys Asp Ile Ser Ser Gly Thr Lys Val Leu
    50                  55                  60

Ile Ser Glu Asp Ser Ile Lys Asn Phe Ser Lys Ala Ser Ser Asp Gln
65                  70                  75                  80

Glu Glu Val Asp Arg Asp Glu Ser Ser Ser Lys Ala Asn Asp Gly
                85                  90                  95

Lys Lys Gly His Ser Lys Pro Lys Lys Glu
            100                 105

<210> SEQ ID NO 64
<211> LENGTH: 924
<212> TYPE: DNA
<213> ORGANISM: Streptococcus agalactiae

<400> SEQUENCE: 64

| | |
|---|---|
| atgaaaagga tacggaaaag ccttattttt gttctcggag tagttaccct aatttgctta | 60 |
| tgtgcttgta ctaaacaaag ccagcaaaaa aatggcttgt cagtagtgac tagcttttat | 120 |
| ccagtatatt ccattacaaa agcagtttct ggtgatttga atgatattaa aatgattcga | 180 |
| tcacagtcag gtattcatgg ttttgaaccc tcatcaagtg atgttgctgc catttatgat | 240 |
| gctgatctat ttctttatca ttcgcacaca ctagaagctt gggcgagacg tttggaacct | 300 |
| agtttgcatc actctaaagt atctgtaatt gaagcttcaa aaggtatgac tttggataaa | 360 |
| gttcatggct agaagatgt agaggcagaa aaaggagtag atgagtcaac cttgtatgac | 420 |
| cctcacactt ggaatgaccc tgtaaaagta tctgaggaag cacaactcat cgctacacaa | 480 |
| ttagctaaaa aggatcctaa aaacgctaag gtttatcaaa aaaatgctga tcaatttagt | 540 |
| gacaaggcaa tggctattgc agagaagtat aagccaaaat ttaaagctgc aaagtctaaa | 600 |
| tactttgtga cttcacatac agcattctca tacttagcta agcgatacgg attgactcag | 660 |
| ttaggtattg caggtgtctc aaccgagcaa gaacctagtg ctaaaaaatt agccgaaatt | 720 |
| caggagtttg tgaaaacata taaggttaag actattttttg ttgaagaagg agtctcacct | 780 |
| aaattagctc aagcagtagc ttcagctact cgagttaaaa ttgcaagttt aagtccttta | 840 |
| raagcagttc ccaaaaacaa taagattac ttagaaaatt tggaaactaa tcttaaggta | 900 |
| cttgtcaaat cgttaaatca atag | 924 |

<210> SEQ ID NO 65
<211> LENGTH: 307
<212> TYPE: PRT
<213> ORGANISM: Streptococcus agalactiae
<220> FEATURE:
<221> NAME/KEY: VARIANT
<222> LOCATION: (1)...(307)
<223> OTHER INFORMATION: Xaa = Any Amino Acid

<400> SEQUENCE: 65

Met Lys Arg Ile Arg Lys Ser Leu Ile Phe Val Leu Gly Val Val Thr
1                   5                   10                  15

Leu Ile Cys Leu Cys Ala Cys Thr Lys Gln Ser Gln Gln Lys Asn Gly
                20                  25                  30

Leu Ser Val Val Thr Ser Phe Tyr Pro Val Tyr Ser Ile Thr Lys Ala
            35                  40                  45

Val Ser Gly Asp Leu Asn Asp Ile Lys Met Ile Arg Ser Gln Ser Gly
        50                  55                  60

Ile His Gly Phe Glu Pro Ser Ser Ser Asp Val Ala Ala Ile Tyr Asp
65                  70                  75                  80

```
Ala Asp Leu Phe Leu Tyr His Ser His Thr Leu Glu Ala Trp Ala Arg
            85                  90                  95
Arg Leu Glu Pro Ser Leu His His Ser Lys Val Ser Val Ile Glu Ala
            100                 105                 110
Ser Lys Gly Met Thr Leu Asp Lys Val His Gly Leu Glu Asp Val Glu
        115                 120                 125
Ala Glu Lys Gly Val Asp Glu Ser Thr Leu Tyr Asp Pro His Thr Trp
    130                 135                 140
Asn Asp Pro Val Lys Val Ser Glu Glu Ala Gln Leu Ile Ala Thr Gln
145                 150                 155                 160
Leu Ala Lys Lys Asp Pro Lys Asn Ala Lys Val Tyr Gln Lys Asn Ala
                165                 170                 175
Asp Gln Phe Ser Asp Lys Ala Met Ala Ile Ala Glu Lys Tyr Lys Pro
            180                 185                 190
Lys Phe Lys Ala Ala Lys Ser Lys Tyr Phe Val Thr Ser His Thr Ala
        195                 200                 205
Phe Ser Tyr Leu Ala Lys Arg Tyr Gly Leu Thr Gln Leu Gly Ile Ala
    210                 215                 220
Gly Val Ser Thr Glu Gln Glu Pro Ser Ala Lys Lys Leu Ala Glu Ile
225                 230                 235                 240
Gln Glu Phe Val Lys Thr Tyr Lys Val Lys Thr Ile Phe Val Glu Glu
                245                 250                 255
Gly Val Ser Pro Lys Leu Ala Gln Ala Val Ala Ser Ala Thr Arg Val
            260                 265                 270
Lys Ile Ala Ser Leu Ser Pro Leu Xaa Ala Val Pro Lys Asn Asn Lys
        275                 280                 285
Asp Tyr Leu Glu Asn Leu Glu Thr Asn Leu Lys Val Leu Val Lys Ser
    290                 295                 300
Leu Asn Gln
305

<210> SEQ ID NO 66
<211> LENGTH: 1134
<212> TYPE: DNA
<213> ORGANISM: Streptococcus agalactiae

<400> SEQUENCE: 66
atgcctaaga gaaatcaga taccccagaa aaagaagaag ttgtcttaac ggaatggcaa      60
aagcgtaacc ttgaatttt aaaaaaacgc aaagaagatg aagaagaaca aaaacgtatt     120
aacgaaaaat tacgcttaga taaagaagt aaattaaata tttcttctcc tgaagaacct     180
caaaatacta ctaaaattaa gaagcttcat tttccaaaga tttcaagacc taagattgaa     240
aagaaacaga aaaagaaaa aatagtcaac agcttagcca aaactaatcg cattagaact     300
gcacctatat tgtagtagc attcctagtc attttagttt ccgtttttcct actaactcct     360 tttagtaagc aaaaaacaat aacagttagt ggaaatcagc atacacctga tgatatttg     420 atagagaaaa cgaatattca aaaaaacgat tatttctttt ctttaatttt taaacataaa     480
gctattgaac aacgtttagc tgcagaagat gtatgggtaa aaacagctca gatgactat     540 caatttccca ataagtttca tattcaagtt caagaaaata agattattgc atatgcacat     600
acaaagcaag gatatcaacc tgtcttggaa actggaaaaa aggctgatcc tgtaaatagt     660
tcagagctac caaagcactt cttaacaatt aaccttgata ggaagatag tattaagcta     720 ttaattaaag atttaaaggc tttagaccct gatttaataa gtgagattca ggtgataagt     780
```

```
ttagctgatt ctaaaacgac acctgacctc ctgctgttag atatgcacga tggaaatagt   840
attagaatac cattatctaa atttaaagaa agacttcctt tttacaaaca aattaagaag   900
aaccttaagg aaccttctat tgttgatatg gaagtgggag tttacacaac aacaaatacc   960
attgaatcaa cccctgttaa agcagaagat acaaaaaata aatcaactga taaaacacaa  1020
acacaaaatg gtcaggttgc ggaaaatagt caaggacaaa caaataactc aaatactaat  1080
caacaaggac aacagatagc aacagagcag gcacctaacc ctcaaaatgt taat         1134
```

<210> SEQ ID NO 67
<211> LENGTH: 378
<212> TYPE: PRT
<213> ORGANISM: Streptococcus agalactiae

<400> SEQUENCE: 67

```
Met Pro Lys Lys Lys Ser Asp Thr Pro Glu Lys Glu Glu Val Val Leu
1               5                   10                  15

Thr Glu Trp Gln Lys Arg Asn Leu Glu Phe Leu Lys Lys Arg Lys Glu
            20                  25                  30

Asp Glu Glu Glu Gln Lys Arg Ile Asn Glu Lys Leu Arg Leu Asp Lys
        35                  40                  45

Arg Ser Lys Leu Asn Ile Ser Ser Pro Glu Glu Pro Gln Asn Thr Thr
    50                  55                  60

Lys Ile Lys Lys Leu His Phe Pro Lys Ile Ser Arg Pro Lys Ile Glu
65                  70                  75                  80

Lys Lys Gln Lys Lys Glu Lys Ile Val Asn Ser Leu Ala Lys Thr Asn
                85                  90                  95

Arg Ile Arg Thr Ala Pro Ile Phe Val Val Ala Phe Leu Val Ile Leu
            100                 105                 110

Val Ser Val Phe Leu Leu Thr Pro Phe Ser Lys Gln Lys Thr Ile Thr
        115                 120                 125

Val Ser Gly Asn Gln His Thr Pro Asp Asp Ile Leu Ile Glu Lys Thr
    130                 135                 140

Asn Ile Gln Lys Asn Asp Tyr Phe Phe Ser Leu Ile Phe Lys His Lys
145                 150                 155                 160

Ala Ile Glu Gln Arg Leu Ala Ala Glu Asp Val Trp Val Lys Thr Ala
                165                 170                 175

Gln Met Thr Tyr Gln Phe Pro Asn Lys Phe His Ile Gln Val Gln Glu
            180                 185                 190

Asn Lys Ile Ile Ala Tyr Ala His Thr Lys Gln Gly Tyr Gln Pro Val
        195                 200                 205

Leu Glu Thr Gly Lys Lys Ala Asp Pro Val Asn Ser Ser Glu Leu Pro
    210                 215                 220

Lys His Phe Leu Thr Ile Asn Leu Asp Lys Glu Asp Ser Ile Lys Leu
225                 230                 235                 240

Leu Ile Lys Asp Leu Lys Ala Leu Asp Pro Asp Leu Ile Ser Glu Ile
                245                 250                 255

Gln Val Ile Ser Leu Ala Asp Ser Lys Thr Thr Pro Asp Leu Leu Leu
            260                 265                 270

Leu Asp Met His Asp Gly Asn Ser Ile Arg Ile Pro Leu Ser Lys Phe
        275                 280                 285

Lys Glu Arg Leu Pro Phe Tyr Lys Gln Ile Lys Asn Leu Lys Glu
    290                 295                 300

Pro Ser Ile Val Asp Met Glu Val Gly Val Tyr Thr Thr Thr Asn Thr
```

```
                305                 310                 315                 320
Ile Ser Thr Pro Val Lys Ala Glu Asp Thr Lys Asn Lys Ser Thr
                325                 330                 335

Asp Lys Thr Gln Thr Gln Asn Gly Gln Val Ala Glu Asn Ser Gln Gly
            340                 345                 350

Gln Thr Asn Asn Ser Asn Thr Asn Gln Gln Gly Gln Gln Ile Ala Thr
                355                 360                 365

Glu Gln Ala Pro Asn Pro Gln Asn Val Asn
            370                 375

<210> SEQ ID NO 68
<211> LENGTH: 3699
<212> TYPE: DNA
<213> ORGANISM: Streptococcus agalactiae

<400> SEQUENCE: 68
```

| | | | | | |
|---|---|---|---|---|---|
| gtggataaac | atcactcaaa | aaaggctatt | ttaaagttaa | cacttataac | aactagtatt | 60 |
| ttattaatgc | atagcaatca | agtgaatgca | gaggagcaag | aattaaaaaa | ccaagagcaa | 120 |
| tcacctgtaa | ttgctaatgt | tgctcaacag | ccatcgccat | cggtaactac | taatactgtt | 180 |
| gaaaaaacat | ctgtaacagc | tgcttctgct | agtaatacag | cgaaagaaat | gggtgataca | 240 |
| tctgtaaaaa | atgacaaaac | agaagatgaa | ttattagaag | agttatctaa | aaaccttgat | 300 |
| acgtctaatt | tgggggctga | tcttgaagaa | gaatatccct | ctaaaccaga | gacaaccaac | 360 |
| aataagaaa | gcaatgtagt | aacaaatgct | tcaactgcaa | tagcacagaa | agttccctca | 420 |
| gcatatgaag | aggtgaagcc | agaaagcaag | tcatcgcttg | ctgttcttga | tacatctaaa | 480 |
| ataacaaaat | tacaagccat | aacccaaaga | ggaaagggaa | atgtagtagc | tattattgat | 540 |
| actggctttg | atattaacca | tgatattttt | cgtttagata | gcccaaaaga | tgataagcac | 600 |
| agctttaaaa | ctaagacaga | atttgaggaa | ttaaagcaa | acataatat | cacttatggg | 660 |
| aaatggggtta | acgataagat | tgttttttgca | cataactacg | ccaacaatac | agaaacggtg | 720 |
| gctgatattg | cagcagctat | gaaagatggt | tatggttcag | aagcaaagaa | tatttcgcat | 780 |
| ggtacacacg | ttgctggtat | ttttgtaggt | aatagtaaac | gtccagcaat | caatggtctt | 840 |
| cttttagaag | gtgcagcgcc | aaatgctcaa | gtcttattaa | tgcgtattcc | agataaaatt | 900 |
| gattcggaca | aatttggtga | agcatatgct | aaagcaatca | cagacgctgt | taatctagga | 960 |
| gcaaaaacga | ttaatatgag | tattggaaaa | acagctgatt | ctttaattgc | tctcaatgat | 1020 |
| aaagttaaat | tagcacttaa | attagcttct | gagaagggcg | ttgcagttgt | tgtggctgcc | 1080 |
| ggaaatgaag | gcgcatttgg | tatggattat | agcaaaccat | tatcaactaa | tcctgactac | 1140 |
| ggtacggtta | atagtccagc | tatttctgaa | gatactttga | gtgttgctag | ctatgaatca | 1200 |
| cttaaaacta | tcagtgaggt | cgttgaaaca | actattgaag | gtaagttagt | taagttgccg | 1260 |
| attgtgactt | ctaaaccttt | tgacaaaggt | aaggcctacg | atgtggttta | tgccaattat | 1320 |
| ggtgcaaaaa | aagactttga | aggtaaggac | tttaaaggta | agattgcatt | aattgagcgt | 1380 |
| ggtggtggac | ttgattttat | gactaaaatc | actcatgcta | caaatgcagg | tgttgttggt | 1440 |
| atcgttattt | ttaacgatca | agaaaaacgt | ggaaattttc | taattcctta | ccgtgaatta | 1500 |
| cctgtgggga | ttattagtaa | agtagatggc | gagcgtataa | aaaatacttc | aagtcagtta | 1560 |
| acatttaacc | agagttttga | agtagttgat | agccaaggtg | gtaatcgtat | gctggaacaa | 1620 |
| tcaagttggg | gcgtgacagc | tgaaggagca | atcaagcctg | atgtaacagc | ttctggcttt | 1680 |
| gaaatttatt | cttcaacccta | taataatcaa | taccaaacaa | tgtctggtac | aagtatggct | 1740 |

```
tcaccacatg ttgcaggatt aatgacaatg cttcaaagtc atttggctga gaaatataaa    1800
gggatgaatt tagattctaa aaaattgcta gaattgtcta aaaacatcct catgagctca    1860
gcaacagcat tatatagtga agaggataag gcgttttatt caccacgtca gcaaggtgca    1920
ggtgtagttg atgctgaaaa agctatccaa gctcaatatt atattactgg aaacgatggc    1980
aaagctaaaa ttaatctcaa acgaatggga gataaatttg atatcacagt tacaattcat    2040
aaacttgtag aaggtgtcaa agaattgtat tatcaagcta atgtagcaac agaacaagta    2100
aataaaggta aatttgccct taaaccacaa gccttgctag atactaattg gcagaaagta    2160
attcttcgtg ataaagaaac acaagttcga tttactattg atgctagtca atttagtcag    2220
aaattaaaag aacagatggc aaatggttat ttcttagaag gttttgtacg ttttaaagaa    2280
gccaaggata gtaatcagga gttaatgagt attcctttg taggatttaa tggtgatttt    2340
gcgaacttac aagcacttga acaccgatt tataagacgc tttctaaagg tagtttctac    2400
tataaaccaa atgatacaac tcataaagac caattggagt acaatgaatc agctcctttt    2460
gaaagcaaca actatactgc cttgttaaca caatcagcgt cttggggcta tgttgattat    2520
gtcaaaaatg gtggggagtt agaattagca ccggagagtc caaaaagaat tatttttagga    2580
acttttgaga ataaggttga ggataaaaca attcatcttt tggaaagaga tgcagcgaat    2640
aatccatatt ttgccatttc tccaaataaa gatggaaata gggacgaaat cactccccag    2700
gcaactttct taagaaatgt taaggatatt tctgctcaag ttctagatca aaatggaaat    2760
gttatttggc aaagtaaggt tttaccatct tatcgtaaaa atttccataa taatccaaag    2820
caaagtgatg gtcattatcg tatggatgct cttcagtgga gtggtttaga taaggatggc    2880
aaagttgtag cagatggttt ttatacttat cgcttacgtt acacaccagt agcagaagga    2940
gcaaatagtc aggagtcaga ctttaaagta caagtaagta ctaagtcacc aaatcttcct    3000
tcacgagctc agtttgatga aactaatcga acattaagct tagccatgcc taaggaaagt    3060
agttatgttc ctacatatcg tttacaatta gtttatctc atgttgtaaa agatgaagaa    3120
tatggggatg agacttctta ccattatttc catatagatc aagaaggtaa agtgacactt    3180
cctaaaacgg ttaagatagg agagagtgag gttgcggtag accctaaggc cttgacactt    3240
gttgtggaag ataaagctgg taatttcgca acggtaaaat tgtctgatct cttgaataag    3300
gcagtagtat cagagaaaga aaacgctata gtaatttcta acagtttcaa atattttgat    3360
aacttgaaaa agaacctat gtttatttct aaaaagaaa agtagtaaa caagaatcta    3420
gaagaaataa tattagttaa gccgcaaact acagttacta ctcaatcatt gtctaaagaa    3480
ataactaaat caggaaatga gaaagtcctc acttctacaa acaataatag tagcagagta    3540
gctaagatca tatcacctaa acataacggg gattctgtta accataccct acctagtaca    3600
tcagatagag caacgaatgg tctatttgtt ggtactttgg cattgttatc tagtttactt    3660
ctttatttga aacccaaaaa gactaaaaat aatagtaaa                          3699
```

<210> SEQ ID NO 69
<211> LENGTH: 1233
<212> TYPE: PRT
<213> ORGANISM: Streptococcus agalactiae

<400> SEQUENCE: 69

```
Val Asp Lys His His Ser Lys Lys Ala Ile Leu Lys Leu Thr Leu Ile
  1               5                  10                  15

Thr Thr Ser Ile Leu Leu Met His Ser Asn Gln Val Asn Ala Glu Glu
```

```
                    20                  25                  30
        Gln Glu Leu Lys Asn Gln Glu Gln Ser Pro Val Ile Ala Asn Val Ala
                        35                  40                  45

Gln Gln Pro Ser Pro Ser Val Thr Thr Asn Thr Val Glu Lys Thr Ser
         50                  55                  60

Val Thr Ala Ala Ser Ala Ser Asn Thr Ala Lys Glu Met Gly Asp Thr
         65                  70                  75                  80

Ser Val Lys Asn Asp Lys Thr Glu Asp Glu Leu Leu Glu Glu Leu Ser
                        85                  90                  95

Lys Asn Leu Asp Thr Ser Asn Leu Gly Ala Asp Leu Glu Glu Glu Tyr
                        100                 105                 110

Pro Ser Lys Pro Glu Thr Thr Asn Asn Lys Glu Ser Asn Val Val Thr
                        115                 120                 125

Asn Ala Ser Thr Ala Ile Ala Gln Lys Val Pro Ser Ala Tyr Glu Glu
                        130                 135                 140

Val Lys Pro Glu Ser Lys Ser Ser Leu Ala Val Leu Asp Thr Ser Lys
        145                 150                 155                 160

Ile Thr Lys Leu Gln Ala Ile Thr Gln Arg Gly Lys Gly Asn Val Val
                        165                 170                 175

Ala Ile Ile Asp Thr Gly Phe Asp Ile Asn His Asp Ile Phe Arg Leu
                        180                 185                 190

Asp Ser Pro Lys Asp Lys His Ser Phe Lys Thr Lys Thr Glu Phe
                        195                 200                 205

Glu Glu Leu Lys Ala Lys His Asn Ile Thr Tyr Gly Lys Trp Val Asn
                        210                 215                 220

Asp Lys Ile Val Phe Ala His Asn Tyr Ala Asn Asn Thr Glu Thr Val
        225                 230                 235                 240

Ala Asp Ile Ala Ala Ala Met Lys Asp Gly Tyr Gly Ser Glu Ala Lys
                        245                 250                 255

Asn Ile Ser His Gly Thr His Val Ala Gly Ile Phe Val Gly Asn Ser
                        260                 265                 270

Lys Arg Pro Ala Ile Asn Gly Leu Leu Leu Glu Gly Ala Ala Pro Asn
                        275                 280                 285

Ala Gln Val Leu Leu Met Arg Ile Pro Asp Lys Ile Asp Ser Asp Lys
                        290                 295                 300

Phe Gly Glu Ala Tyr Ala Lys Ala Ile Thr Asp Ala Val Asn Leu Gly
        305                 310                 315                 320

Ala Lys Thr Ile Asn Met Ser Ile Gly Lys Thr Ala Asp Ser Leu Ile
                        325                 330                 335

Ala Leu Asn Asp Lys Val Lys Leu Ala Leu Lys Leu Ala Ser Glu Lys
                        340                 345                 350

Gly Val Ala Val Val Ala Ala Gly Asn Glu Gly Ala Phe Gly Met
                        355                 360                 365

Asp Tyr Ser Lys Pro Leu Ser Thr Asn Pro Asp Tyr Gly Thr Val Asn
                        370                 375                 380

Ser Pro Ala Ile Ser Glu Asp Thr Leu Ser Val Ala Ser Tyr Glu Ser
        385                 390                 395                 400

Leu Lys Thr Ile Ser Glu Val Val Glu Thr Thr Ile Glu Gly Lys Leu
                        405                 410                 415

Val Lys Leu Pro Ile Val Thr Ser Lys Pro Phe Asp Lys Gly Lys Ala
                        420                 425                 430

Tyr Asp Val Val Tyr Ala Asn Tyr Gly Ala Lys Lys Asp Phe Glu Gly
                        435                 440                 445
```

```
Lys Asp Phe Lys Gly Lys Ile Ala Leu Ile Glu Arg Gly Gly Leu
450                 455                 460
Asp Phe Met Thr Lys Ile Thr His Ala Thr Asn Ala Gly Val Val Gly
465                 470                 475                 480
Ile Val Ile Phe Asn Asp Gln Glu Lys Arg Gly Asn Phe Leu Ile Pro
                    485                 490                 495
Tyr Arg Glu Leu Pro Val Gly Ile Ile Ser Lys Val Asp Gly Glu Arg
                500                 505                 510
Ile Lys Asn Thr Ser Ser Gln Leu Thr Phe Asn Gln Ser Phe Glu Val
            515                 520                 525
Val Asp Ser Gln Gly Gly Asn Arg Met Leu Glu Gln Ser Ser Trp Gly
530                 535                 540
Val Thr Ala Glu Gly Ala Ile Lys Pro Asp Val Thr Ala Ser Gly Phe
545                 550                 555                 560
Glu Ile Tyr Ser Ser Thr Tyr Asn Asn Gln Tyr Gln Thr Met Ser Gly
                565                 570                 575
Thr Ser Met Ala Ser Pro His Val Ala Gly Leu Met Thr Met Leu Gln
            580                 585                 590
Ser His Leu Ala Glu Lys Tyr Lys Gly Met Asn Leu Asp Ser Lys Lys
    595                 600                 605
Leu Leu Glu Leu Ser Lys Asn Ile Leu Met Ser Ser Ala Thr Ala Leu
610                 615                 620
Tyr Ser Glu Glu Asp Lys Ala Phe Tyr Ser Pro Arg Gln Gln Gly Ala
625                 630                 635                 640
Gly Val Val Asp Ala Glu Lys Ala Ile Gln Ala Gln Tyr Tyr Ile Thr
                645                 650                 655
Gly Asn Asp Gly Lys Ala Lys Ile Asn Leu Lys Arg Met Gly Asp Lys
                660                 665                 670
Phe Asp Ile Thr Val Thr Ile His Lys Leu Val Glu Gly Val Lys Glu
            675                 680                 685
Leu Tyr Tyr Gln Ala Asn Val Ala Thr Glu Gln Val Asn Lys Gly Lys
    690                 695                 700
Phe Ala Leu Lys Pro Gln Ala Leu Leu Asp Thr Asn Trp Gln Lys Val
705                 710                 715                 720
Ile Leu Arg Asp Lys Glu Thr Gln Val Arg Phe Thr Ile Asp Ala Ser
                725                 730                 735
Gln Phe Ser Gln Lys Leu Lys Glu Gln Met Ala Asn Gly Tyr Phe Leu
                740                 745                 750
Glu Gly Phe Val Arg Phe Lys Glu Ala Lys Asp Ser Asn Gln Glu Leu
            755                 760                 765
Met Ser Ile Pro Phe Val Gly Phe Asn Gly Asp Phe Ala Asn Leu Gln
770                 775                 780
Ala Leu Glu Thr Pro Ile Tyr Lys Thr Leu Ser Lys Gly Ser Phe Tyr
785                 790                 795                 800
Tyr Lys Pro Asn Asp Thr Thr His Lys Asp Gln Leu Glu Tyr Asn Glu
                805                 810                 815
Ser Ala Pro Phe Glu Ser Asn Asn Tyr Thr Ala Leu Leu Thr Gln Ser
                820                 825                 830
Ala Ser Trp Gly Tyr Val Asp Tyr Val Lys Asn Gly Gly Glu Leu Glu
            835                 840                 845
Leu Ala Pro Glu Ser Pro Lys Arg Ile Ile Leu Gly Thr Phe Glu Asn
850                 855                 860
```

```
Lys Val Glu Asp Lys Thr Ile His Leu Leu Glu Arg Asp Ala Ala Asn
865                 870                 875                 880

Asn Pro Tyr Phe Ala Ile Ser Pro Asn Lys Asp Gly Asn Arg Asp Glu
            885                 890                 895

Ile Thr Pro Gln Ala Thr Phe Leu Arg Asn Val Lys Asp Ile Ser Ala
        900                 905                 910

Gln Val Leu Asp Gln Asn Gly Asn Val Ile Trp Gln Ser Lys Val Leu
    915                 920                 925

Pro Ser Tyr Arg Lys Asn Phe His Asn Asn Pro Lys Gln Ser Asp Gly
930                 935                 940

His Tyr Arg Met Asp Ala Leu Gln Trp Ser Gly Leu Asp Lys Asp Gly
945                 950                 955                 960

Lys Val Val Ala Asp Gly Phe Tyr Thr Tyr Arg Leu Arg Tyr Thr Pro
            965                 970                 975

Val Ala Glu Gly Ala Asn Ser Gln Glu Ser Asp Phe Lys Val Gln Val
        980                 985                 990

Ser Thr Lys Ser Pro Asn Leu Pro Ser Arg Ala Gln Phe Asp Glu Thr
    995                 1000                1005

Asn Arg Thr Leu Ser Leu Ala Met Pro Lys Glu Ser Ser Tyr Val Pro
1010                1015                1020

Thr Tyr Arg Leu Gln Leu Val Leu Ser His Val Val Lys Asp Glu Glu
1025                1030                1035                1040

Tyr Gly Asp Glu Thr Ser Tyr His Tyr Phe His Ile Asp Gln Glu Gly
            1045                1050                1055

Lys Val Thr Leu Pro Lys Thr Val Lys Ile Gly Glu Ser Glu Val Ala
        1060                1065                1070

Val Asp Pro Lys Ala Leu Thr Leu Val Val Glu Asp Lys Ala Gly Asn
    1075                1080                1085

Phe Ala Thr Val Lys Leu Ser Asp Leu Leu Asn Lys Ala Val Val Ser
1090                1095                1100

Glu Lys Glu Asn Ala Ile Val Ile Ser Asn Ser Phe Lys Tyr Phe Asp
1105                1110                1115                1120

Asn Leu Lys Lys Glu Pro Met Phe Ile Ser Lys Lys Glu Lys Val Val
            1125                1130                1135

Asn Lys Asn Leu Glu Glu Ile Ile Leu Val Lys Pro Gln Thr Thr Val
        1140                1145                1150

Thr Thr Gln Ser Leu Ser Lys Glu Ile Thr Lys Ser Gly Asn Glu Lys
    1155                1160                1165

Val Leu Thr Ser Thr Asn Asn Ser Ser Arg Val Ala Lys Ile Ile
1170                1175                1180

Ser Pro Lys His Asn Gly Asp Ser Val Asn His Thr Leu Pro Ser Thr
1185                1190                1195                1200

Ser Asp Arg Ala Thr Asn Gly Leu Phe Val Gly Thr Leu Ala Leu Leu
            1205                1210                1215

Ser Ser Leu Leu Leu Tyr Leu Pro Lys Lys Thr Lys Asn Asn Ser
        1220                1225                1230

Lys
```

<210> SEQ ID NO 70
<211> LENGTH: 1203
<212> TYPE: PRT
<213> ORGANISM: Streptococcus agalactiae

<400> SEQUENCE: 70

-continued

```
Glu Glu Gln Glu Leu Lys Asn Gln Glu Gln Ser Pro Val Ile Ala Asn
 1               5                  10                 15
Val Ala Gln Gln Pro Ser Pro Ser Val Thr Thr Asn Thr Val Glu Lys
             20                  25                  30
Thr Ser Val Thr Ala Ala Ser Ala Ser Asn Thr Ala Lys Glu Met Gly
             35                  40                  45
Asp Thr Ser Val Lys Asn Asp Lys Thr Glu Asp Glu Leu Leu Glu Glu
         50                  55                  60
Leu Ser Lys Asn Leu Asp Thr Ser Asn Leu Gly Ala Asp Leu Glu Glu
 65                  70                  75                  80
Glu Tyr Pro Ser Lys Pro Glu Thr Thr Asn Asn Lys Glu Ser Asn Val
                 85                  90                  95
Val Thr Asn Ala Ser Thr Ala Ile Ala Gln Lys Val Pro Ser Ala Tyr
             100                 105                 110
Glu Glu Val Lys Pro Glu Ser Lys Ser Ser Leu Ala Val Leu Asp Thr
             115                 120                 125
Ser Lys Ile Thr Lys Leu Gln Ala Ile Thr Gln Arg Gly Lys Gly Asn
         130                 135                 140
Val Val Ala Ile Ile Asp Thr Gly Phe Asp Ile Asn His Asp Ile Phe
145                 150                 155                 160
Arg Leu Asp Ser Pro Lys Asp Lys His Ser Phe Lys Thr Lys Thr
                 165                 170                 175
Glu Phe Glu Glu Leu Lys Ala Lys His Asn Ile Thr Tyr Gly Lys Trp
             180                 185                 190
Val Asn Asp Lys Ile Val Phe Ala His Asn Tyr Ala Asn Asn Thr Glu
             195                 200                 205
Thr Val Ala Asp Ile Ala Ala Ala Met Lys Asp Gly Tyr Gly Ser Glu
             210                 215                 220
Ala Lys Asn Ile Ser His Gly Thr His Val Ala Gly Ile Phe Val Gly
225                 230                 235                 240
Asn Ser Lys Arg Pro Ala Ile Asn Gly Leu Leu Leu Glu Gly Ala Ala
                 245                 250                 255
Pro Asn Ala Gln Val Leu Leu Met Arg Ile Pro Asp Lys Ile Asp Ser
             260                 265                 270
Asp Lys Phe Gly Glu Ala Tyr Ala Lys Ala Ile Thr Asp Ala Val Asn
         275                 280                 285
Leu Gly Ala Lys Thr Ile Asn Met Ser Ile Gly Lys Thr Ala Asp Ser
             290                 295                 300
Leu Ile Ala Leu Asn Asp Lys Val Lys Leu Ala Leu Lys Leu Ala Ser
305                 310                 315                 320
Glu Lys Gly Val Ala Val Val Ala Ala Gly Asn Glu Gly Ala Phe
             325                 330                 335
Gly Met Asp Tyr Ser Lys Pro Leu Ser Thr Asn Pro Asp Tyr Gly Thr
             340                 345                 350
Val Asn Ser Pro Ala Ile Ser Glu Asp Thr Leu Ser Val Ala Ser Tyr
             355                 360                 365
Glu Ser Leu Lys Thr Ile Ser Glu Val Val Glu Thr Thr Ile Glu Gly
         370                 375                 380
Lys Leu Val Lys Leu Pro Ile Val Thr Ser Lys Pro Phe Asp Lys Gly
385                 390                 395                 400
Lys Ala Tyr Asp Val Val Tyr Ala Asn Tyr Gly Ala Lys Lys Asp Phe
                 405                 410                 415
Glu Gly Lys Asp Phe Lys Gly Lys Ile Ala Leu Ile Glu Arg Gly Gly
```

```
                420             425             430
Gly Leu Asp Phe Met Thr Lys Ile Thr His Ala Thr Asn Ala Gly Val
            435                 440             445
Val Gly Ile Val Ile Phe Asn Asp Gln Glu Lys Arg Gly Asn Phe Leu
        450                 455             460
Ile Pro Tyr Arg Glu Leu Pro Val Gly Ile Ile Ser Lys Val Asp Gly
465                 470              475                 480
Glu Arg Ile Lys Asn Thr Ser Ser Gln Leu Thr Phe Asn Gln Ser Phe
                485                 490             495
Glu Val Val Asp Ser Gln Gly Gly Asn Arg Met Leu Glu Gln Ser Ser
            500                 505             510
Trp Gly Val Thr Ala Glu Gly Ala Ile Lys Pro Asp Val Thr Ala Ser
        515                 520             525
Gly Phe Glu Ile Tyr Ser Ser Thr Tyr Asn Asn Gln Tyr Gln Thr Met
        530                 535             540
Ser Gly Thr Ser Met Ala Ser Pro His Val Ala Gly Leu Met Thr Met
545                 550             555                 560
Leu Gln Ser His Leu Ala Glu Lys Tyr Lys Gly Met Asn Leu Asp Ser
                565             570                 575
Lys Lys Leu Leu Glu Leu Ser Lys Asn Ile Leu Met Ser Ser Ala Thr
            580                 585             590
Ala Leu Tyr Ser Glu Glu Asp Lys Ala Phe Tyr Ser Pro Arg Gln Gln
        595                 600             605
Gly Ala Gly Val Val Asp Ala Glu Lys Ala Ile Gln Ala Gln Tyr Tyr
        610                 615             620
Ile Thr Gly Asn Asp Gly Lys Ala Lys Ile Asn Leu Lys Arg Met Gly
625                 630             635                 640
Asp Lys Phe Asp Ile Thr Val Thr Ile His Lys Leu Val Glu Gly Val
                645             650                 655
Lys Glu Leu Tyr Tyr Gln Ala Asn Val Ala Thr Glu Gln Val Asn Lys
            660                 665             670
Gly Lys Phe Ala Leu Lys Pro Gln Ala Leu Leu Asp Thr Asn Trp Gln
        675                 680             685
Lys Val Ile Leu Arg Asp Lys Glu Thr Gln Val Arg Phe Thr Ile Asp
        690                 695             700
Ala Ser Gln Phe Ser Gln Lys Leu Lys Glu Gln Met Ala Asn Gly Tyr
705                 710             715                 720
Phe Leu Glu Gly Phe Val Arg Phe Lys Glu Ala Lys Asp Ser Asn Gln
                725             730                 735
Glu Leu Met Ser Ile Pro Phe Val Gly Phe Asn Gly Asp Phe Ala Asn
            740                 745             750
Leu Gln Ala Leu Glu Thr Pro Ile Tyr Lys Thr Leu Ser Lys Gly Ser
        755                 760             765
Phe Tyr Tyr Lys Pro Asn Asp Thr Thr His Lys Asp Gln Leu Glu Tyr
        770                 775             780
Asn Glu Ser Ala Pro Phe Glu Ser Asn Asn Tyr Thr Ala Leu Leu Thr
785                 790             795                 800
Gln Ser Ala Ser Trp Gly Tyr Val Asp Tyr Val Lys Asn Gly Gly Glu
                805             810                 815
Leu Glu Leu Ala Pro Glu Ser Pro Lys Arg Ile Ile Leu Gly Thr Phe
            820                 825             830
Glu Asn Lys Val Glu Asp Lys Thr Ile His Leu Leu Glu Arg Asp Ala
        835                 840             845
```

```
Ala Asn Asn Pro Tyr Phe Ala Ile Ser Pro Asn Lys Asp Gly Asn Arg
    850                 855                 860

Asp Glu Ile Thr Pro Gln Ala Thr Phe Leu Arg Asn Val Lys Asp Ile
865                 870                 875                 880

Ser Ala Gln Val Leu Asp Gln Asn Gly Asn Val Ile Trp Gln Ser Lys
                885                 890                 895

Val Leu Pro Ser Tyr Arg Lys Asn Phe His Asn Asn Pro Lys Gln Ser
                900                 905                 910

Asp Gly His Tyr Arg Met Asp Ala Leu Gln Trp Ser Gly Leu Asp Lys
            915                 920                 925

Asp Gly Lys Val Val Ala Asp Gly Phe Tyr Thr Tyr Arg Leu Arg Tyr
        930                 935                 940

Thr Pro Val Ala Glu Gly Ala Asn Ser Gln Glu Ser Asp Phe Lys Val
945                 950                 955                 960

Gln Val Ser Thr Lys Ser Pro Asn Leu Pro Ser Arg Ala Gln Phe Asp
                965                 970                 975

Glu Thr Asn Arg Thr Leu Ser Leu Ala Met Pro Lys Glu Ser Ser Tyr
            980                 985                 990

Val Pro Thr Tyr Arg Leu Gln Leu Val Leu Ser His Val Lys Asp
        995                 1000                1005

Glu Glu Tyr Gly Asp Glu Thr Ser Tyr His Tyr Phe His Ile Asp Gln
    1010                1015                1020

Glu Gly Lys Val Thr Leu Pro Lys Thr Val Lys Ile Gly Glu Ser Glu
1025                1030                1035                1040

Val Ala Val Asp Pro Lys Ala Leu Thr Leu Val Val Glu Asp Lys Ala
                1045                1050                1055

Gly Asn Phe Ala Thr Val Lys Leu Ser Asp Leu Leu Asn Lys Ala Val
            1060                1065                1070

Val Ser Glu Lys Glu Asn Ala Ile Val Ile Ser Asn Ser Phe Lys Tyr
        1075                1080                1085

Phe Asp Asn Leu Lys Lys Glu Pro Met Phe Ile Ser Lys Lys Glu Lys
    1090                1095                1100

Val Val Asn Lys Asn Leu Glu Glu Ile Ile Leu Val Lys Pro Gln Thr
1105                1110                1115                1120

Thr Val Thr Thr Gln Ser Leu Ser Lys Glu Ile Thr Lys Ser Gly Asn
                1125                1130                1135

Glu Lys Val Leu Thr Ser Thr Asn Asn Asn Ser Ser Arg Val Ala Lys
            1140                1145                1150

Ile Ile Ser Pro Lys His Asn Gly Asp Ser Val Asn His Thr Leu Pro
        1155                1160                1165

Ser Thr Ser Asp Arg Ala Thr Asn Gly Leu Phe Val Gly Thr Leu Ala
    1170                1175                1180

Leu Leu Ser Ser Leu Leu Leu Tyr Leu Lys Pro Lys Lys Thr Lys Asn
1185                1190                1195                1200

Asn Ser Lys

<210> SEQ ID NO 71
<211> LENGTH: 1196
<212> TYPE: PRT
<213> ORGANISM: Streptococcus agalactiae

<400> SEQUENCE: 71

Val Asp Lys His His Ser Lys Lys Ala Ile Leu Lys Leu Thr Leu Ile
1               5                   10                  15
```

```
Thr Thr Ser Ile Leu Leu Met His Ser Asn Gln Val Asn Ala Glu Glu
                20                  25                  30

Gln Glu Leu Lys Asn Gln Glu Gln Ser Pro Val Ile Ala Asn Val Ala
         35                  40                  45

Gln Gln Pro Ser Pro Ser Val Thr Thr Asn Thr Val Glu Lys Thr Ser
50                   55                  60

Val Thr Ala Ala Ser Ala Ser Asn Thr Ala Lys Glu Met Gly Asp Thr
65                   70                  75                  80

Ser Val Lys Asn Asp Lys Thr Glu Asp Glu Leu Leu Glu Glu Leu Ser
             85                  90                  95

Lys Asn Leu Asp Thr Ser Asn Leu Gly Ala Asp Leu Glu Glu Glu Tyr
                100                 105                 110

Pro Ser Lys Pro Glu Thr Thr Asn Asn Lys Glu Ser Asn Val Val Thr
            115                 120                 125

Asn Ala Ser Thr Ala Ile Ala Gln Lys Val Pro Ser Ala Tyr Glu Glu
130                 135                 140

Val Lys Pro Glu Ser Lys Ser Ser Leu Ala Val Leu Asp Thr Ser Lys
145                 150                 155                 160

Ile Thr Lys Leu Gln Ala Ile Thr Gln Arg Gly Lys Gly Asn Val Val
                165                 170                 175

Ala Ile Ile Asp Thr Gly Phe Asp Ile Asn His Asp Ile Phe Arg Leu
            180                 185                 190

Asp Ser Pro Lys Asp Lys His Ser Phe Lys Thr Lys Thr Glu Phe
            195                 200                 205

Glu Glu Leu Lys Ala Lys His Asn Ile Thr Tyr Gly Lys Trp Val Asn
    210                 215                 220

Asp Lys Ile Val Phe Ala His Asn Tyr Ala Asn Asn Thr Glu Thr Val
225                 230                 235                 240

Ala Asp Ile Ala Ala Ala Met Lys Asp Gly Tyr Gly Ser Glu Ala Lys
                245                 250                 255

Asn Ile Ser His Gly Thr His Val Ala Gly Ile Phe Val Gly Asn Ser
            260                 265                 270

Lys Arg Pro Ala Ile Asn Gly Leu Leu Leu Glu Gly Ala Ala Pro Asn
            275                 280                 285

Ala Gln Val Leu Leu Met Arg Ile Pro Asp Lys Ile Asp Ser Asp Lys
    290                 295                 300

Phe Gly Glu Ala Tyr Ala Lys Ala Ile Thr Asp Ala Val Asn Leu Gly
305                 310                 315                 320

Ala Lys Thr Ile Asn Met Ser Ile Gly Lys Thr Ala Asp Ser Leu Ile
                325                 330                 335

Ala Leu Asn Asp Lys Val Lys Leu Ala Leu Lys Leu Ala Ser Glu Lys
            340                 345                 350

Gly Val Ala Val Val Ala Ala Gly Asn Glu Gly Ala Phe Gly Met
    355                 360                 365

Asp Tyr Ser Lys Pro Leu Ser Thr Asn Pro Asp Tyr Gly Thr Val Asn
            370                 375                 380

Ser Pro Ala Ile Ser Glu Asp Thr Leu Ser Val Ala Ser Tyr Glu Ser
385                 390                 395                 400

Leu Lys Thr Ile Ser Glu Val Glu Thr Thr Ile Glu Gly Lys Leu
                405                 410                 415

Val Lys Leu Pro Ile Val Thr Ser Lys Pro Phe Asp Lys Gly Lys Ala
            420                 425                 430
```

-continued

```
Tyr Asp Val Val Tyr Ala Asn Tyr Gly Ala Lys Lys Asp Phe Glu Gly
            435                 440                 445

Lys Asp Phe Lys Gly Lys Ile Ala Leu Ile Glu Arg Gly Gly Gly Leu
450                 455                 460

Asp Phe Met Thr Lys Ile Thr His Ala Thr Asn Ala Gly Val Val Gly
465                 470                 475                 480

Ile Val Ile Phe Asn Asp Gln Glu Lys Arg Gly Asn Phe Leu Ile Pro
                485                 490                 495

Tyr Arg Glu Leu Pro Val Gly Ile Ile Ser Lys Val Asp Gly Glu Arg
                500                 505                 510

Ile Lys Asn Thr Ser Ser Gln Leu Thr Phe Asn Gln Ser Phe Glu Val
            515                 520                 525

Val Asp Ser Gln Gly Gly Asn Arg Met Leu Glu Gln Ser Ser Trp Gly
530                 535                 540

Val Thr Ala Glu Gly Ala Ile Lys Pro Asp Val Thr Ala Ser Gly Phe
545                 550                 555                 560

Glu Ile Tyr Ser Ser Thr Tyr Asn Asn Gln Tyr Gln Thr Met Ser Gly
                565                 570                 575

Thr Ser Met Ala Ser Pro His Val Ala Gly Leu Met Thr Met Leu Gln
            580                 585                 590

Ser His Leu Ala Glu Lys Tyr Lys Gly Met Asn Leu Asp Ser Lys Lys
        595                 600                 605

Leu Leu Glu Leu Ser Lys Asn Ile Leu Met Ser Ser Ala Thr Ala Leu
    610                 615                 620

Tyr Ser Glu Glu Asp Lys Ala Phe Tyr Ser Pro Arg Gln Gln Gly Ala
625                 630                 635                 640

Gly Val Val Asp Ala Glu Lys Ala Ile Gln Ala Gln Tyr Tyr Ile Thr
                645                 650                 655

Gly Asn Asp Gly Lys Ala Lys Ile Asn Leu Lys Arg Met Gly Asp Lys
            660                 665                 670

Phe Asp Ile Thr Val Thr Ile His Lys Leu Val Glu Gly Val Lys Glu
        675                 680                 685

Leu Tyr Tyr Gln Ala Asn Val Ala Thr Glu Gln Val Asn Lys Gly Lys
    690                 695                 700

Phe Ala Leu Lys Pro Gln Ala Leu Leu Asp Thr Asn Trp Gln Lys Val
705                 710                 715                 720

Ile Leu Arg Asp Lys Glu Thr Gln Val Arg Phe Thr Ile Asp Ala Ser
                725                 730                 735

Gln Phe Ser Gln Lys Leu Lys Glu Gln Met Ala Asn Gly Tyr Phe Leu
            740                 745                 750

Glu Gly Phe Val Arg Phe Lys Glu Ala Lys Asp Ser Asn Gln Glu Leu
        755                 760                 765

Met Ser Ile Pro Phe Val Gly Phe Asn Gly Asp Phe Ala Asn Leu Gln
    770                 775                 780

Ala Leu Glu Thr Pro Ile Tyr Lys Thr Leu Ser Lys Gly Ser Phe Tyr
785                 790                 795                 800

Tyr Lys Pro Asn Asp Thr Thr His Lys Asp Gln Leu Glu Tyr Asn Glu
                805                 810                 815

Ser Ala Pro Phe Glu Ser Asn Asn Tyr Thr Ala Leu Leu Thr Gln Ser
            820                 825                 830

Ala Ser Trp Gly Tyr Val Asp Tyr Val Lys Asn Gly Gly Glu Leu Glu
        835                 840                 845

Leu Ala Pro Glu Ser Pro Lys Arg Ile Ile Leu Gly Thr Phe Glu Asn
```

```
                850                 855                 860
Lys Val Glu Asp Lys Thr Ile His Leu Leu Glu Arg Asp Ala Ala Asn
865                 870                 875                 880

Asn Pro Tyr Phe Ala Ile Ser Pro Asn Lys Asp Gly Asn Arg Asp Glu
                885                 890                 895

Ile Thr Pro Gln Ala Thr Phe Leu Arg Asn Val Lys Asp Ile Ser Ala
                900                 905                 910

Gln Val Leu Asp Gln Asn Gly Asn Val Ile Trp Gln Ser Lys Val Leu
            915                 920                 925

Pro Ser Tyr Arg Lys Asn Phe His Asn Pro Lys Gln Ser Asp Gly
        930                 935                 940

His Tyr Arg Met Asp Ala Leu Gln Trp Ser Gly Leu Asp Lys Asp Gly
945                 950                 955                 960

Lys Val Val Ala Asp Gly Phe Tyr Thr Tyr Arg Leu Arg Tyr Thr Pro
                965                 970                 975

Val Ala Glu Gly Ala Asn Ser Gln Glu Ser Asp Phe Lys Val Gln Val
            980                 985                 990

Ser Thr Lys Ser Pro Asn Leu Pro Ser Arg Ala Gln Phe Asp Glu Thr
        995                 1000                1005

Asn Arg Thr Leu Ser Leu Ala Met Pro Lys Glu Ser Ser Tyr Val Pro
    1010                1015                1020

Thr Tyr Arg Leu Gln Leu Val Leu Ser His Val Val Lys Asp Glu Glu
1025                1030                1035                1040

Tyr Gly Asp Glu Thr Ser Tyr His Tyr Phe His Ile Asp Gln Glu Gly
                1045                1050                1055

Lys Val Thr Leu Pro Lys Thr Val Lys Ile Gly Glu Ser Glu Val Ala
            1060                1065                1070

Val Asp Pro Lys Ala Leu Thr Leu Val Val Glu Asp Lys Ala Gly Asn
        1075                1080                1085

Phe Ala Thr Val Lys Leu Ser Asp Leu Leu Asn Lys Ala Val Val Ser
    1090                1095                1100

Glu Lys Glu Asn Ala Ile Val Ile Ser Asn Ser Phe Lys Tyr Phe Asp
1105                1110                1115                1120

Asn Leu Lys Lys Glu Pro Met Phe Ile Ser Lys Lys Glu Lys Val Val
                1125                1130                1135

Asn Lys Asn Leu Glu Glu Ile Ile Leu Val Lys Pro Gln Thr Thr Val
            1140                1145                1150

Thr Thr Gln Ser Leu Ser Lys Glu Ile Thr Lys Ser Gly Asn Glu Lys
        1155                1160                1165

Val Leu Thr Ser Thr Asn Asn Asn Ser Ser Arg Val Ala Lys Ile Ile
    1170                1175                1180

Ser Pro Lys His Asn Gly Asp Ser Val Asn His Thr
1185                1190                1195

<210> SEQ ID NO 72
<211> LENGTH: 1166
<212> TYPE: PRT
<213> ORGANISM: Streptococcus agalactiae

<400> SEQUENCE: 72

Glu Glu Gln Glu Leu Lys Asn Gln Glu Gln Ser Pro Val Ile Ala Asn
1               5                   10                  15

Val Ala Gln Gln Pro Ser Pro Ser Val Thr Thr Asn Thr Val Glu Lys
            20                  25                  30
```

```
Thr Ser Val Thr Ala Ala Ser Ala Ser Asn Thr Ala Lys Glu Met Gly
         35                  40                  45
Asp Thr Ser Val Lys Asn Asp Lys Thr Glu Asp Glu Leu Leu Glu Glu
 50                  55                  60
Leu Ser Lys Asn Leu Asp Thr Ser Asn Leu Gly Ala Asp Leu Glu Glu
 65                  70                  75                  80
Glu Tyr Pro Ser Lys Pro Glu Thr Thr Asn Asn Lys Glu Ser Asn Val
             85                  90                  95
Val Thr Asn Ala Ser Thr Ala Ile Ala Gln Lys Val Pro Ser Ala Tyr
                100                 105                 110
Glu Glu Val Lys Pro Glu Ser Lys Ser Ser Leu Ala Val Leu Asp Thr
                 115                 120                 125
Ser Lys Ile Thr Lys Leu Gln Ala Ile Thr Gln Arg Gly Lys Gly Asn
     130                 135                 140
Val Val Ala Ile Ile Asp Thr Gly Phe Asp Ile Asn His Asp Ile Phe
145                 150                 155                 160
Arg Leu Asp Ser Pro Lys Asp Asp Lys His Ser Phe Lys Thr Lys Thr
                 165                 170                 175
Glu Phe Glu Glu Leu Lys Ala Lys His Asn Ile Thr Tyr Gly Lys Trp
             180                 185                 190
Val Asn Asp Lys Ile Val Phe Ala His Asn Tyr Ala Asn Asn Thr Glu
         195                 200                 205
Thr Val Ala Asp Ile Ala Ala Met Lys Asp Gly Tyr Gly Ser Glu
     210                 215                 220
Ala Lys Asn Ile Ser His Gly Thr His Val Ala Gly Ile Phe Val Gly
225                 230                 235                 240
Asn Ser Lys Arg Pro Ala Ile Asn Gly Leu Leu Leu Glu Gly Ala Ala
                 245                 250                 255
Pro Asn Ala Gln Val Leu Leu Met Arg Ile Pro Asp Lys Ile Asp Ser
             260                 265                 270
Asp Lys Phe Gly Glu Ala Tyr Ala Lys Ala Ile Thr Asp Ala Val Asn
         275                 280                 285
Leu Gly Ala Lys Thr Ile Asn Met Ser Ile Gly Lys Thr Ala Asp Ser
     290                 295                 300
Leu Ile Ala Leu Asn Asp Lys Val Lys Leu Ala Leu Lys Leu Ala Ser
305                 310                 315                 320
Glu Lys Gly Val Ala Val Val Ala Ala Gly Asn Glu Gly Ala Phe
                 325                 330                 335
Gly Met Asp Tyr Ser Lys Pro Leu Ser Thr Asn Pro Asp Tyr Gly Thr
             340                 345                 350
Val Asn Ser Pro Ala Ile Ser Glu Asp Thr Leu Ser Val Ala Ser Tyr
         355                 360                 365
Glu Ser Leu Lys Thr Ile Ser Glu Val Val Glu Thr Ile Glu Gly
     370                 375                 380
Lys Leu Val Lys Leu Pro Ile Val Thr Ser Lys Pro Phe Asp Lys Gly
385                 390                 395                 400
Lys Ala Tyr Asp Val Val Tyr Ala Asn Tyr Gly Ala Lys Lys Asp Phe
                 405                 410                 415
Glu Gly Lys Asp Phe Lys Gly Lys Ile Ala Leu Ile Glu Arg Gly Gly
             420                 425                 430
Gly Leu Asp Phe Met Thr Lys Ile Thr His Ala Thr Asn Ala Gly Val
     435                 440                 445
Val Gly Ile Val Ile Phe Asn Asp Gln Glu Lys Arg Gly Asn Phe Leu
```

```
                 450                 455                 460
Ile Pro Tyr Arg Glu Leu Pro Val Gly Ile Ile Ser Lys Val Asp Gly
465                 470                 475                 480

Glu Arg Ile Lys Asn Thr Ser Ser Gln Leu Thr Phe Asn Gln Ser Phe
                485                 490                 495

Glu Val Val Asp Ser Gln Gly Gly Asn Arg Met Leu Glu Gln Ser Ser
                500                 505                 510

Trp Gly Val Thr Ala Glu Gly Ala Ile Lys Pro Asp Val Thr Ala Ser
            515                 520                 525

Gly Phe Glu Ile Tyr Ser Ser Thr Tyr Asn Asn Gln Tyr Gln Thr Met
            530                 535                 540

Ser Gly Thr Ser Met Ala Ser Pro His Val Ala Gly Leu Met Thr Met
545                 550                 555                 560

Leu Gln Ser His Leu Ala Glu Lys Tyr Lys Gly Met Asn Leu Asp Ser
                565                 570                 575

Lys Lys Leu Leu Glu Leu Ser Lys Asn Ile Leu Met Ser Ser Ala Thr
            580                 585                 590

Ala Leu Tyr Ser Glu Glu Asp Lys Ala Phe Tyr Ser Pro Arg Gln Gln
            595                 600                 605

Gly Ala Gly Val Val Asp Ala Glu Lys Ala Ile Gln Ala Gln Tyr Tyr
            610                 615                 620

Ile Thr Gly Asn Asp Gly Lys Ala Lys Ile Asn Leu Lys Arg Met Gly
625                 630                 635                 640

Asp Lys Phe Asp Ile Thr Val Thr Ile His Lys Leu Val Glu Gly Val
                645                 650                 655

Lys Glu Leu Tyr Tyr Gln Ala Asn Val Ala Thr Glu Gln Val Asn Lys
            660                 665                 670

Gly Lys Phe Ala Leu Lys Pro Gln Ala Leu Leu Asp Thr Asn Trp Gln
            675                 680                 685

Lys Val Ile Leu Arg Asp Lys Glu Thr Gln Val Arg Phe Thr Ile Asp
            690                 695                 700

Ala Ser Gln Phe Ser Gln Lys Leu Lys Glu Gln Met Ala Asn Gly Tyr
705                 710                 715                 720

Phe Leu Glu Gly Phe Val Arg Phe Lys Glu Ala Lys Asp Ser Asn Gln
                725                 730                 735

Glu Leu Met Ser Ile Pro Phe Val Gly Phe Asn Gly Asp Phe Ala Asn
            740                 745                 750

Leu Gln Ala Leu Glu Thr Pro Ile Tyr Lys Thr Leu Ser Lys Gly Ser
            755                 760                 765

Phe Tyr Tyr Lys Pro Asn Asp Thr Thr His Lys Asp Gln Leu Glu Tyr
            770                 775                 780

Asn Glu Ser Ala Pro Phe Glu Ser Asn Asn Tyr Thr Ala Leu Leu Thr
785                 790                 795                 800

Gln Ser Ala Ser Trp Gly Tyr Val Asp Tyr Val Lys Asn Gly Gly Glu
                805                 810                 815

Leu Glu Leu Ala Pro Glu Ser Pro Lys Arg Ile Ile Leu Gly Thr Phe
            820                 825                 830

Glu Asn Lys Val Glu Asp Lys Thr Ile His Leu Leu Glu Arg Asp Ala
            835                 840                 845

Ala Asn Asn Pro Tyr Phe Ala Ile Ser Pro Asn Lys Asp Gly Asn Arg
            850                 855                 860

Asp Glu Ile Thr Pro Gln Ala Thr Phe Leu Arg Asn Val Lys Asp Ile
865                 870                 875                 880
```

Ser Ala Gln Val Leu Asp Gln Asn Gly Asn Val Ile Trp Gln Ser Lys
                885                 890                 895

Val Leu Pro Ser Tyr Arg Lys Asn Phe His Asn Pro Lys Gln Ser
        900                 905                 910

Asp Gly His Tyr Arg Met Asp Ala Leu Gln Trp Ser Gly Leu Asp Lys
        915                 920                 925

Asp Gly Lys Val Val Ala Asp Gly Phe Tyr Thr Tyr Arg Leu Arg Tyr
        930                 935                 940

Thr Pro Val Ala Glu Gly Ala Asn Ser Gln Glu Ser Asp Phe Lys Val
945                 950                 955                 960

Gln Val Ser Thr Lys Ser Pro Asn Leu Pro Ser Arg Ala Gln Phe Asp
                965                 970                 975

Glu Thr Asn Arg Thr Leu Ser Leu Ala Met Pro Lys Glu Ser Ser Tyr
            980                 985                 990

Val Pro Thr Tyr Arg Leu Gln Leu Val Leu Ser His Val Lys Asp
            995                 1000                1005

Glu Glu Tyr Gly Asp Glu Thr Ser Tyr His Tyr Phe His Ile Asp Gln
    1010                1015                1020

Glu Gly Lys Val Thr Leu Pro Lys Thr Val Lys Ile Gly Glu Ser Glu
1025                1030                1035                1040

Val Ala Val Asp Pro Lys Ala Leu Thr Leu Val Val Glu Asp Lys Ala
                1045                1050                1055

Gly Asn Phe Ala Thr Val Lys Leu Ser Asp Leu Leu Asn Lys Ala Val
                1060                1065                1070

Val Ser Glu Lys Glu Asn Ala Ile Val Ile Ser Asn Ser Phe Lys Tyr
                1075                1080                1085

Phe Asp Asn Leu Lys Lys Glu Pro Met Phe Ile Ser Lys Lys Glu Lys
    1090                1095                1100

Val Val Asn Lys Asn Leu Glu Glu Ile Ile Leu Val Lys Pro Gln Thr
1105                1110                1115                1120

Thr Val Thr Thr Gln Ser Leu Ser Lys Glu Ile Thr Lys Ser Gly Asn
                1125                1130                1135

Glu Lys Val Leu Thr Ser Thr Asn Asn Asn Ser Ser Arg Val Ala Lys
                1140                1145                1150

Ile Ile Ser Pro Lys His Asn Gly Asp Ser Val Asn His Thr
                1155                1160                1165

<210> SEQ ID NO 73
<211> LENGTH: 2040
<212> TYPE: DNA
<213> ORGANISM: Streptococcus agalactiae

<400> SEQUENCE: 73
atgaaacgta aatactttat tcttaatacg gtgacggttt taacgttagc tgctgcaatg      60
aatactagca gtatctatgc taatagtact gagacaagtg cttcagtagt tcctactaca     120
aatactatcg ttcaaactaa tgacagtaat cctaccgcaa atttgtatc agaatcagga      180 caatctgtaa taggtcaagt aaaaccagat aattctgcgg cgcttacaac agttgacacg     240
cctcatcata tttcagctcc agatgcttta aaaacaactc aatcaagtcc tgtcgttgag     300
agtacttcta ctaagttaac tgaagagact tacaaacaaa agatggtca agatttagcc     360 aacatggtga agtggtca agttactagt gaggaactcg ttaatatggc atacgatatt      420
attgctaaag aaaacccatc tttaaatgca gtcattacta ctagacgcca agaagctatt     480

```
gaagaggcta gaaaacttaa agataccaat cagccgtttt taggtgttcc cttgttagtc      540
aaggggttag ggcacagtat taaaggtggt gaaaccaata atggcttgat ctatgcagat      600
ggaaaaatta gcacatttga cagtagctat gtcaaaaaat ataaagattt aggatttatt      660
attttaggac aaacgaactt tccagagtat gggtggcgta atataacaga ttctaaatta      720
tacggtctaa cgcataatcc ttgggatctt gctcataatg ctggtggctc ttctggtgga      780
agtgcagcag ccattgctag cggaatgacg ccaattgcta gcggtagtga tgctggtggt      840
tctatccgta ttccatcttc ttggacgggc ttggtaggtt taaaaccaac aagaggattg      900
gtgagtaatg aaaagccaga ttcgtatagt acagcagttc attttccatt aactaagtca      960
tctagagacg cagaaacatt attaacttat ctaaagaaaa gcgatcaaac gctagtatca     1020
gttaatgatt taaatctttt accaattgct tatactttga aatcaccaat gggaacagaa     1080
gttagtcaag atgctaaaaa cgctattatg gacaacgtca cattcttaag aaaacaagga     1140
ttcaaagtaa cagagataga cttaccaatt gatggtagag cattaatgcg tgattattca     1200
accttggcta ttggcatggg aggagctttt tcaacaattg aaaaagactt aaaaaaacat     1260
ggttttacta agaagacgt tgatcctatt acttgggcag ttcatgttat ttatcaaaat     1320
tcagataagg ctgaacttaa gaaatctatt atggaagccc aaaaacatat ggatgattat     1380
cgtaaggcaa tggagaagct tcacaagcaa tttcctattt tcttatcgcc aacgaccgca     1440
agtttagccc ctctaaatac agatccatat gtaacagagg aagataaaag agcgatttat     1500
aatatggaaa acttgagcca agaagaaaga attgctctct ttaatcgcca gtgggagcct     1560
atgttgcgta gaacaccttt tacacaaatt gctaatatga caggactccc agctatcagt     1620
atcccgactt acttatctga gtctggttta cccatagggga cgatgttaat ggcaggtgca     1680
aactatgata tggtattaat taaatttgca actttctttg aaaaacatca tggttttaat     1740
gttaaatggc aaagaataat agataaagaa gtgaaaccat ctactggcct aatacagcct     1800
actaactccc tctttaaagc tcattcatca ttagtaaatt tagaagaaaa ttcacaagtt     1860
actcaagtat ctatctctaa aaaatggatg aaatcgtctg ttaaaaataa accatccgta     1920
atggcatatc aaaaagcact tcctaaaaca ggtgatacag aatcaagcct atctccagtt     1980
ttagtagtaa ccctttttatt agcttgtttt agctttgtaa caaaaaagaa tcagaaaagt     2040
```

<210> SEQ ID NO 74
<211> LENGTH: 680
<212> TYPE: PRT
<213> ORGANISM: Streptococcus agalactiae

<400> SEQUENCE: 74

Met Lys Arg Lys Tyr Phe Ile Leu Asn Thr Val Thr Val Leu Thr Leu
1               5                   10                  15

Ala Ala Ala Met Asn Thr Ser Ser Ile Tyr Ala Asn Ser Thr Glu Thr
            20                  25                  30

Ser Ala Ser Val Val Pro Thr Thr Asn Thr Ile Val Gln Thr Asn Asp
        35                  40                  45

Ser Asn Pro Thr Ala Lys Phe Val Ser Glu Ser Gly Gln Ser Val Ile
    50                  55                  60

Gly Gln Val Lys Pro Asp Asn Ser Ala Ala Leu Thr Thr Val Asp Thr
65                  70                  75                  80

Pro His His Ile Ser Ala Pro Asp Ala Leu Lys Thr Thr Gln Ser Ser
                85                  90                  95

Pro Val Val Glu Ser Thr Ser Thr Lys Leu Thr Glu Glu Thr Tyr Lys

-continued

```
                100                 105                 110
Gln Lys Asp Gly Gln Asp Leu Ala Asn Met Val Arg Ser Gly Gln Val
            115                 120                 125
Thr Ser Glu Glu Leu Val Asn Met Ala Tyr Asp Ile Ile Ala Lys Glu
        130                 135                 140
Asn Pro Ser Leu Asn Ala Val Ile Thr Thr Arg Arg Gln Glu Ala Ile
145                 150                 155                 160
Glu Glu Ala Arg Lys Leu Lys Asp Thr Asn Gln Pro Phe Leu Gly Val
                165                 170                 175
Pro Leu Leu Val Lys Gly Leu Gly His Ser Ile Lys Gly Gly Glu Thr
            180                 185                 190
Asn Asn Gly Leu Ile Tyr Ala Asp Gly Lys Ile Ser Thr Phe Asp Ser
        195                 200                 205
Ser Tyr Val Lys Lys Tyr Lys Asp Leu Gly Phe Ile Ile Leu Gly Gln
    210                 215                 220
Thr Asn Phe Pro Glu Tyr Gly Trp Arg Asn Ile Thr Asp Ser Lys Leu
225                 230                 235                 240
Tyr Gly Leu Thr His Asn Pro Trp Asp Leu Ala His Asn Ala Gly Gly
                245                 250                 255
Ser Ser Gly Gly Ser Ala Ala Ala Ile Ala Ser Gly Met Thr Pro Ile
            260                 265                 270
Ala Ser Gly Ser Asp Ala Gly Gly Ser Ile Arg Ile Pro Ser Ser Trp
        275                 280                 285
Thr Gly Leu Val Gly Leu Lys Pro Thr Arg Gly Leu Val Ser Asn Glu
    290                 295                 300
Lys Pro Asp Ser Tyr Ser Thr Ala Val His Phe Pro Leu Thr Lys Ser
305                 310                 315                 320
Ser Arg Asp Ala Glu Thr Leu Leu Thr Tyr Leu Lys Lys Ser Asp Gln
                325                 330                 335
Thr Leu Val Ser Val Asn Asp Leu Lys Ser Leu Pro Ile Ala Tyr Thr
            340                 345                 350
Leu Lys Ser Pro Met Gly Thr Glu Val Ser Gln Asp Ala Lys Asn Ala
        355                 360                 365
Ile Met Asp Asn Val Thr Phe Leu Arg Lys Gln Gly Phe Lys Val Thr
    370                 375                 380
Glu Ile Asp Leu Pro Ile Asp Gly Arg Ala Leu Met Arg Asp Tyr Ser
385                 390                 395                 400
Thr Leu Ala Ile Gly Met Gly Gly Ala Phe Ser Thr Ile Glu Lys Asp
                405                 410                 415
Leu Lys Lys His Gly Phe Thr Lys Glu Asp Val Asp Pro Ile Thr Trp
            420                 425                 430
Ala Val His Val Ile Tyr Gln Asn Ser Asp Lys Ala Glu Leu Lys Lys
        435                 440                 445
Ser Ile Met Glu Ala Gln Lys His Met Asp Tyr Arg Lys Ala Met
    450                 455                 460
Glu Lys Leu His Lys Gln Phe Pro Ile Phe Leu Ser Pro Thr Thr Ala
465                 470                 475                 480
Ser Leu Ala Pro Leu Asn Thr Asp Pro Tyr Val Thr Glu Glu Asp Lys
                485                 490                 495
Arg Ala Ile Tyr Asn Met Glu Asn Leu Ser Gln Glu Glu Arg Ile Ala
            500                 505                 510
Leu Phe Asn Arg Gln Trp Glu Pro Met Leu Arg Arg Thr Pro Phe Thr
        515                 520                 525
```

```
Gln Ile Ala Asn Met Thr Gly Leu Pro Ala Ile Ser Ile Pro Thr Tyr
            530                 535                 540

Leu Ser Glu Ser Gly Leu Pro Ile Gly Thr Met Leu Met Ala Gly Ala
545                 550                 555                 560

Asn Tyr Asp Met Val Leu Ile Lys Phe Ala Thr Phe Phe Glu Lys His
                565                 570                 575

His Gly Phe Asn Val Lys Trp Gln Arg Ile Ile Asp Lys Glu Val Lys
            580                 585                 590

Pro Ser Thr Gly Leu Ile Gln Pro Thr Asn Ser Leu Phe Lys Ala His
        595                 600                 605

Ser Ser Leu Val Asn Leu Glu Glu Asn Ser Gln Val Thr Gln Val Ser
    610                 615                 620

Ile Ser Lys Lys Trp Met Lys Ser Ser Val Lys Asn Lys Pro Ser Val
625                 630                 635                 640

Met Ala Tyr Gln Lys Ala Leu Pro Lys Thr Gly Asp Thr Glu Ser Ser
                645                 650                 655

Leu Ser Pro Val Leu Val Val Thr Leu Leu Ala Cys Phe Ser Phe
            660                 665                 670

Val Thr Lys Lys Asn Gln Lys Ser
        675                 680

<210> SEQ ID NO 75
<211> LENGTH: 642
<212> TYPE: PRT
<213> ORGANISM: Streptococcus agalactiae

<400> SEQUENCE: 75

Thr Thr Asn Thr Ile Val Gln Thr Asn Asp Ser Asn Pro Thr Ala Lys
1               5                   10                  15

Phe Val Ser Glu Ser Gly Gln Ser Val Ile Gly Gln Val Lys Pro Asp
                20                  25                  30

Asn Ser Ala Ala Leu Thr Thr Val Asp Thr Pro His His Ile Ser Ala
            35                  40                  45

Pro Asp Ala Leu Lys Thr Thr Gln Ser Ser Pro Val Val Glu Ser Thr
        50                  55                  60

Ser Thr Lys Leu Thr Glu Glu Thr Tyr Lys Gln Lys Asp Gly Gln Asp
65                  70                  75                  80

Leu Ala Asn Met Val Arg Ser Gly Gln Val Thr Ser Glu Glu Leu Val
                85                  90                  95

Asn Met Ala Tyr Asp Ile Ile Ala Lys Glu Asn Pro Ser Leu Asn Ala
            100                 105                 110

Val Ile Thr Thr Arg Arg Gln Glu Ala Ile Glu Glu Ala Arg Lys Leu
        115                 120                 125

Lys Asp Thr Asn Gln Pro Phe Leu Gly Val Pro Leu Leu Val Lys Gly
    130                 135                 140

Leu Gly His Ser Ile Lys Gly Gly Glu Thr Asn Asn Gly Leu Ile Tyr
145                 150                 155                 160

Ala Asp Gly Lys Ile Ser Thr Phe Asp Ser Ser Tyr Val Lys Lys Tyr
                165                 170                 175

Lys Asp Leu Gly Phe Ile Ile Leu Gly Gln Thr Asn Phe Pro Glu Tyr
            180                 185                 190

Gly Trp Arg Asn Ile Thr Asp Ser Lys Leu Tyr Gly Leu Thr His Asn
        195                 200                 205

Pro Trp Asp Leu Ala His Asn Ala Gly Gly Ser Ser Gly Gly Ser Ala
```

```
              210                 215                 220
Ala Ala Ile Ala Ser Gly Met Thr Pro Ile Ala Ser Gly Ser Asp Ala
225                 230                 235                 240

Gly Gly Ser Ile Arg Ile Pro Ser Ser Trp Thr Gly Leu Val Gly Leu
                245                 250                 255

Lys Pro Thr Arg Gly Leu Val Ser Asn Glu Lys Pro Asp Ser Tyr Ser
                260                 265                 270

Thr Ala Val His Phe Pro Leu Thr Lys Ser Ser Arg Asp Ala Glu Thr
            275                 280                 285

Leu Leu Thr Tyr Leu Lys Lys Ser Asp Gln Thr Leu Val Ser Val Asn
        290                 295                 300

Asp Leu Lys Ser Leu Pro Ile Ala Tyr Thr Leu Lys Ser Pro Met Gly
305                 310                 315                 320

Thr Glu Val Ser Gln Asp Ala Lys Asn Ala Ile Met Asp Asn Val Thr
                325                 330                 335

Phe Leu Arg Lys Gln Gly Phe Lys Val Thr Glu Ile Asp Leu Pro Ile
                340                 345                 350

Asp Gly Arg Ala Leu Met Arg Asp Tyr Ser Thr Leu Ala Ile Gly Met
            355                 360                 365

Gly Gly Ala Phe Ser Thr Ile Glu Lys Asp Leu Lys Lys His Gly Phe
        370                 375                 380

Thr Lys Glu Asp Val Asp Pro Ile Thr Trp Ala Val His Val Ile Tyr
385                 390                 395                 400

Gln Asn Ser Asp Lys Ala Glu Leu Lys Lys Ser Ile Met Glu Ala Gln
                405                 410                 415

Lys His Met Asp Asp Tyr Arg Lys Ala Met Glu Lys Leu His Lys Gln
                420                 425                 430

Phe Pro Ile Phe Leu Ser Pro Thr Thr Ala Ser Leu Ala Pro Leu Asn
            435                 440                 445

Thr Asp Pro Tyr Val Thr Glu Glu Asp Lys Arg Ala Ile Tyr Asn Met
        450                 455                 460

Glu Asn Leu Ser Gln Glu Arg Ile Ala Leu Phe Asn Arg Gln Trp
465                 470                 475                 480

Glu Pro Met Leu Arg Arg Thr Pro Phe Thr Gln Ile Ala Asn Met Thr
                485                 490                 495

Gly Leu Pro Ala Ile Ser Ile Pro Thr Tyr Leu Ser Glu Ser Gly Leu
                500                 505                 510

Pro Ile Gly Thr Met Leu Met Ala Gly Ala Asn Tyr Asp Met Val Leu
            515                 520                 525

Ile Lys Phe Ala Thr Phe Phe Glu Lys His His Gly Phe Asn Val Lys
        530                 535                 540

Trp Gln Arg Ile Ile Asp Lys Glu Val Lys Pro Ser Thr Gly Leu Ile
545                 550                 555                 560

Gln Pro Thr Asn Ser Leu Phe Lys Ala His Ser Ser Leu Val Asn Leu
                565                 570                 575

Glu Glu Asn Ser Gln Val Thr Gln Val Ser Ile Ser Lys Lys Trp Met
                580                 585                 590

Lys Ser Ser Val Lys Asn Lys Pro Ser Val Met Ala Tyr Gln Lys Ala
            595                 600                 605

Leu Pro Lys Thr Gly Asp Thr Glu Ser Ser Leu Ser Pro Val Leu Val
        610                 615                 620

Val Thr Leu Leu Leu Ala Cys Phe Ser Phe Val Thr Lys Lys Asn Gln
625                 630                 635                 640
```

Lys Ser

<210> SEQ ID NO 76
<211> LENGTH: 637
<212> TYPE: PRT
<213> ORGANISM: Streptococcus agalactiae

<400> SEQUENCE: 76

```
Met Lys Arg Lys Tyr Phe Ile Leu Asn Thr Val Thr Val Leu Thr Leu
  1               5                  10                  15
Ala Ala Ala Met Asn Thr Ser Ser Ile Tyr Ala Asn Ser Thr Glu Thr
             20                  25                  30
Ser Ala Ser Val Val Pro Thr Thr Asn Thr Ile Val Gln Thr Asn Asp
         35                  40                  45
Ser Asn Pro Thr Ala Lys Phe Val Ser Glu Ser Gly Gln Ser Val Ile
     50                  55                  60
Gly Gln Val Lys Pro Asp Asn Ser Ala Ala Leu Thr Thr Val Asp Thr
 65                  70                  75                  80
Pro His His Ile Ser Ala Pro Asp Ala Leu Lys Thr Thr Gln Ser Ser
                 85                  90                  95
Pro Val Val Glu Ser Thr Ser Thr Lys Leu Thr Glu Thr Tyr Lys
            100                 105                 110
Gln Lys Asp Gly Gln Asp Leu Ala Asn Met Val Arg Ser Gly Gln Val
        115                 120                 125
Thr Ser Glu Glu Leu Val Asn Met Ala Tyr Asp Ile Ile Ala Lys Glu
    130                 135                 140
Asn Pro Ser Leu Asn Ala Val Ile Thr Thr Arg Arg Gln Glu Ala Ile
145                 150                 155                 160
Glu Glu Ala Arg Lys Leu Lys Asp Thr Asn Gln Pro Phe Leu Gly Val
                165                 170                 175
Pro Leu Leu Val Lys Gly Leu Gly His Ser Ile Lys Gly Gly Glu Thr
            180                 185                 190
Asn Asn Gly Leu Ile Tyr Ala Asp Gly Lys Ile Ser Thr Phe Asp Ser
        195                 200                 205
Ser Tyr Val Lys Lys Tyr Lys Asp Leu Gly Phe Ile Ile Leu Gly Gln
    210                 215                 220
Thr Asn Phe Pro Glu Tyr Gly Trp Arg Asn Ile Thr Asp Ser Lys Leu
225                 230                 235                 240
Tyr Gly Leu Thr His Asn Pro Trp Asp Leu Ala His Asn Ala Gly Gly
                245                 250                 255
Ser Ser Gly Gly Ser Ala Ala Ile Ala Ser Gly Met Thr Pro Ile
            260                 265                 270
Ala Ser Gly Ser Asp Ala Gly Gly Ser Ile Arg Ile Pro Ser Ser Trp
        275                 280                 285
Thr Gly Leu Val Gly Leu Lys Pro Thr Arg Gly Leu Val Ser Asn Glu
    290                 295                 300
Lys Pro Asp Ser Tyr Ser Thr Ala Val His Phe Pro Leu Thr Lys Ser
305                 310                 315                 320
Ser Arg Asp Ala Glu Thr Leu Leu Thr Tyr Leu Lys Lys Ser Asp Gln
                325                 330                 335
Thr Leu Val Ser Val Asn Asp Leu Lys Ser Leu Pro Ile Ala Tyr Thr
            340                 345                 350
Leu Lys Ser Pro Met Gly Thr Glu Val Ser Gln Asp Ala Lys Asn Ala
        355                 360                 365
```

```
Ile Met Asp Asn Val Thr Phe Leu Arg Lys Gln Gly Phe Lys Val Thr
        370                 375                 380

Glu Ile Asp Leu Pro Ile Asp Gly Arg Ala Leu Met Arg Asp Tyr Ser
385                 390                 395                 400

Thr Leu Ala Ile Gly Met Gly Gly Ala Phe Ser Thr Ile Glu Lys Asp
                405                 410                 415

Leu Lys Lys His Gly Phe Thr Lys Glu Asp Val Asp Pro Ile Thr Trp
            420                 425                 430

Ala Val His Val Ile Tyr Gln Asn Ser Asp Lys Ala Glu Leu Lys Lys
        435                 440                 445

Ser Ile Met Glu Ala Gln Lys His Met Asp Asp Tyr Arg Lys Ala Met
450                 455                 460

Glu Lys Leu His Lys Gln Phe Pro Ile Phe Leu Ser Pro Thr Thr Ala
465                 470                 475                 480

Ser Leu Ala Pro Leu Asn Thr Asp Pro Tyr Val Thr Glu Glu Asp Lys
                485                 490                 495

Arg Ala Ile Tyr Asn Met Glu Asn Leu Ser Gln Glu Glu Arg Ile Ala
                500                 505                 510

Leu Phe Asn Arg Gln Trp Glu Pro Met Leu Arg Arg Thr Pro Phe Thr
            515                 520                 525

Gln Ile Ala Asn Met Thr Gly Leu Pro Ala Ile Ser Ile Pro Thr Tyr
        530                 535                 540

Leu Ser Glu Ser Gly Leu Pro Ile Gly Thr Met Leu Met Ala Gly Ala
545                 550                 555                 560

Asn Tyr Asp Met Val Leu Ile Lys Phe Ala Thr Phe Phe Glu Lys His
                565                 570                 575

His Gly Phe Asn Val Lys Trp Gln Arg Ile Ile Asp Lys Glu Val Lys
            580                 585                 590

Pro Ser Thr Gly Leu Ile Gln Pro Thr Asn Ser Leu Phe Lys Ala His
        595                 600                 605

Ser Ser Leu Val Asn Leu Glu Glu Asn Ser Gln Val Thr Gln Val Ser
610                 615                 620

Ile Ser Lys Lys Trp Met Lys Ser Ser Val Lys Asn Lys
625                 630                 635

<210> SEQ ID NO 77
<211> LENGTH: 599
<212> TYPE: PRT
<213> ORGANISM: Streptococcus agalactiae

<400> SEQUENCE: 77

Thr Thr Asn Thr Ile Val Gln Thr Asn Asp Ser Asn Pro Thr Ala Lys
1               5                   10                  15

Phe Val Ser Glu Ser Gly Gln Ser Val Ile Gly Gln Val Lys Pro Asp
            20                  25                  30

Asn Ser Ala Ala Leu Thr Thr Val Asp Thr Pro His His Ile Ser Ala
        35                  40                  45

Pro Asp Ala Leu Lys Thr Thr Gln Ser Ser Pro Val Val Glu Ser Thr
    50                  55                  60

Ser Thr Lys Leu Thr Glu Glu Thr Tyr Lys Gln Lys Asp Gly Gln Asp
65                  70                  75                  80

Leu Ala Asn Met Val Arg Ser Gly Gln Val Thr Ser Glu Glu Leu Val
                85                  90                  95

Asn Met Ala Tyr Asp Ile Ile Ala Lys Glu Asn Pro Ser Leu Asn Ala
```

```
            100                 105                 110
Val Ile Thr Thr Arg Arg Gln Glu Ala Ile Glu Ala Arg Lys Leu
            115                 120                 125
Lys Asp Thr Asn Gln Pro Phe Leu Gly Val Pro Leu Leu Val Lys Gly
            130                 135                 140
Leu Gly His Ser Ile Lys Gly Gly Glu Thr Asn Asn Gly Leu Ile Tyr
145                 150                 155                 160
Ala Asp Gly Lys Ile Ser Thr Phe Asp Ser Ser Tyr Val Lys Lys Tyr
                    165                 170                 175
Lys Asp Leu Gly Phe Ile Ile Leu Gly Gln Thr Asn Phe Pro Glu Tyr
                180                 185                 190
Gly Trp Arg Asn Ile Thr Asp Ser Lys Leu Tyr Gly Leu Thr His Asn
            195                 200                 205
Pro Trp Asp Leu Ala His Asn Ala Gly Gly Ser Ser Gly Gly Ser Ala
            210                 215                 220
Ala Ala Ile Ala Ser Gly Met Thr Pro Ile Ala Ser Gly Ser Asp Ala
225                 230                 235                 240
Gly Gly Ser Ile Arg Ile Pro Ser Ser Trp Thr Gly Leu Val Gly Leu
                    245                 250                 255
Lys Pro Thr Arg Gly Leu Val Ser Asn Glu Lys Pro Asp Ser Tyr Ser
                260                 265                 270
Thr Ala Val His Phe Pro Leu Thr Lys Ser Ser Arg Asp Ala Glu Thr
                275                 280                 285
Leu Leu Thr Tyr Leu Lys Lys Ser Asp Gln Thr Leu Val Ser Val Asn
            290                 295                 300
Asp Leu Lys Ser Leu Pro Ile Ala Tyr Thr Leu Lys Ser Pro Met Gly
305                 310                 315                 320
Thr Glu Val Ser Gln Asp Ala Lys Asn Ala Ile Met Asp Asn Val Thr
                    325                 330                 335
Phe Leu Arg Lys Gln Gly Phe Lys Val Thr Glu Ile Asp Leu Pro Ile
                340                 345                 350
Asp Gly Arg Ala Leu Met Arg Asp Tyr Ser Thr Leu Ala Ile Gly Met
            355                 360                 365
Gly Gly Ala Phe Ser Thr Ile Glu Lys Asp Leu Lys Lys His Gly Phe
            370                 375                 380
Thr Lys Glu Asp Val Asp Pro Ile Thr Trp Ala Val His Val Ile Tyr
385                 390                 395                 400
Gln Asn Ser Asp Lys Ala Glu Leu Lys Lys Ser Ile Met Glu Ala Gln
                    405                 410                 415
Lys His Met Asp Asp Tyr Arg Lys Ala Met Glu Lys Leu His Lys Gln
                420                 425                 430
Phe Pro Ile Phe Leu Ser Pro Thr Thr Ala Ser Leu Ala Pro Leu Asn
            435                 440                 445
Thr Asp Pro Tyr Val Thr Glu Glu Asp Lys Arg Ala Ile Tyr Asn Met
            450                 455                 460
Glu Asn Leu Ser Gln Glu Glu Arg Ile Ala Leu Phe Asn Arg Gln Trp
465                 470                 475                 480
Glu Pro Met Leu Arg Arg Thr Pro Phe Thr Gln Ile Ala Asn Met Thr
                    485                 490                 495
Gly Leu Pro Ala Ile Ser Ile Pro Thr Tyr Leu Ser Glu Ser Gly Leu
                500                 505                 510
Pro Ile Gly Thr Met Leu Met Ala Gly Ala Asn Tyr Asp Met Val Leu
            515                 520                 525
```

Ile Lys Phe Ala Thr Phe Phe Glu Lys His His Gly Phe Asn Val Lys
    530                 535                 540

Trp Gln Arg Ile Ile Asp Lys Glu Val Lys Pro Ser Thr Gly Leu Ile
545                 550                 555                 560

Gln Pro Thr Asn Ser Leu Phe Lys Ala His Ser Ser Leu Val Asn Leu
                565                 570                 575

Glu Glu Asn Ser Gln Val Thr Gln Val Ser Ile Ser Lys Lys Trp Met
            580                 585                 590

Lys Ser Ser Val Lys Asn Lys
        595

<210> SEQ ID NO 78
<211> LENGTH: 1020
<212> TYPE: DNA
<213> ORGANISM: Streptococcus agalactiae

<400> SEQUENCE: 78
atgaaacgta ttgctgtttt aactagtggt ggtgacgccc ctggtatgaa cgctgctatc      60
cgtgcagttg ttcgtaaagc aatttctgaa ggtatggaag tttacggcat caaccaaggt    120
tactatggta tggtgacagg ggatattttc cctttggatg ctaattctgt tggggatact    180
atcaaccgtg gaggaacgtt tttacgttca gcacgttatc ctgaatttgc tgaacttgaa    240
ggtcagctta aagggattga acagcttaaa aaacacggta ttgaaggtgt agtagttatc    300
ggtggtgatg gttcttatca tggtgctatg cgtctaactg agcacggttt cccagctgtt    360
ggtttgccgg gtacaattga taacgatatc gttggcactg actatactat tggttttgac    420
acagcagttg cgacagcagt tgagaatctt gaccgtcttc gtgatacatc agcaagtcat    480
aaccgtactt tgttgttgga ggttatggga agaaatgcag agatatcgc tctttggtca    540 ggtatcgctg caggtgcaga tcaaattatt gttcctgaag aagagttcaa tattgatgaa    600
gttgtctcaa atgttagagc tggctatgca gctggtaaac atcaccaaat catcgtcctt    660
gcagaaggtg ttatgagtgg tgatgagttt gcaaaaacaa tgaaagcagc aggagacgat    720
agcgatcttc gtgtgacgaa tttaggacat ctgctccgtg gtggtagtcc gacggctcgt    780
gatcgtgtct agcatctcg tatgggagcg tacgctgttc aattgttgaa agaaggtcgt    840
ggtggtttag ccgttggtgt ccacaacgaa gaaatggttg aaagtccaat tttaggttta    900
gcagaagaag gtgctttgtt cagcttgact gatgaaggaa aaatcgttgt taataatccg    960
cataaagcgg accttcgctt ggcagcactt aatcgtgacc ttgccaacca agtagtaaa    1020

<210> SEQ ID NO 79
<211> LENGTH: 340
<212> TYPE: PRT
<213> ORGANISM: Streptococcus agalactiae

<400> SEQUENCE: 79

Met Lys Arg Ile Ala Val Leu Thr Ser Gly Gly Asp Ala Pro Gly Met
  1               5                  10                  15

Asn Ala Ala Ile Arg Ala Val Val Arg Lys Ala Ile Ser Glu Gly Met
                20                  25                  30

Glu Val Tyr Gly Ile Asn Gln Gly Tyr Tyr Gly Met Val Thr Gly Asp
            35                  40                  45

Ile Phe Pro Leu Asp Ala Asn Ser Val Gly Asp Thr Ile Asn Arg Gly
        50                  55                  60

Gly Thr Phe Leu Arg Ser Ala Arg Tyr Pro Glu Phe Ala Glu Leu Glu

```
                65                  70                  75                  80
Gly Gln Leu Lys Gly Ile Glu Gln Leu Lys Lys His Gly Ile Glu Gly
                    85                  90                  95

Val Val Val Ile Gly Gly Asp Gly Ser Tyr His Gly Ala Met Arg Leu
                100                 105                 110

Thr Glu His Gly Phe Pro Ala Val Gly Leu Pro Gly Thr Ile Asp Asn
                115                 120                 125

Asp Ile Val Gly Thr Asp Tyr Thr Ile Gly Phe Asp Thr Ala Val Ala
        130                 135                 140

Thr Ala Val Glu Asn Leu Asp Arg Leu Arg Asp Thr Ser Ala Ser His
145                 150                 155                 160

Asn Arg Thr Phe Val Val Glu Val Met Gly Arg Asn Ala Gly Asp Ile
                165                 170                 175

Ala Leu Trp Ser Gly Ile Ala Ala Gly Ala Asp Gln Ile Ile Val Pro
            180                 185                 190

Glu Glu Glu Phe Asn Ile Asp Glu Val Val Ser Asn Val Arg Ala Gly
        195                 200                 205

Tyr Ala Ala Gly Lys His His Gln Ile Ile Val Leu Ala Glu Gly Val
    210                 215                 220

Met Ser Gly Asp Glu Phe Ala Lys Thr Met Lys Ala Ala Gly Asp Asp
225                 230                 235                 240

Ser Asp Leu Arg Val Thr Asn Leu Gly His Leu Leu Arg Gly Gly Ser
                245                 250                 255

Pro Thr Ala Arg Asp Arg Val Leu Ala Ser Arg Met Gly Ala Tyr Ala
            260                 265                 270

Val Gln Leu Leu Lys Glu Gly Arg Gly Gly Leu Ala Val Gly Val His
        275                 280                 285

Asn Glu Glu Met Val Glu Ser Pro Ile Leu Gly Leu Ala Glu Glu Gly
    290                 295                 300

Ala Leu Phe Ser Leu Thr Asp Glu Gly Lys Ile Val Val Asn Asn Pro
305                 310                 315                 320

His Lys Ala Asp Leu Arg Leu Ala Ala Leu Asn Arg Asp Leu Ala Asn
                325                 330                 335

Gln Ser Ser Lys
            340

<210> SEQ ID NO 80
<211> LENGTH: 2070
<212> TYPE: DNA
<213> ORGANISM: Streptococcus agalactiae

<400> SEQUENCE: 80
atgaaaaaga aaattatttt gaaaagtagt gttcttggtt tagtcgctgg gacttctatt      60
atgttctcaa gcgtgttcgc ggaccaagtc ggtgtccaag ttataggcgt caatgacttt     120
catggtgcac ttgacaatac tggaacagca aatatgcctg atggaaaagt tgctaatgct     180
ggtactgctg ctcaattaga tgcttatatg gatgacgctc aaaaagattt caaacaaact     240
aaccctaatg gtgaaagcat tagggttcaa gcaggcgata tggttggagc aagtccagcc     300
aactctgggc ttcttcaaga tgaaccaact gtcaaaaatt ttaatgcaat gaatgttgag     360
tatggcacat tggtaaccat gaatttgat gaagggttgg cagaatataa tcgtatcgtt     420
actggtaaag cccctgctcc agattctaat attaataata ttcgaaaatc ataccccact     480
gaagctgcaa acaagaaat tgtagtggca atgttattg ataaagttaa caacaaaatt     540
```

-continued

| | |
|---|---|
| ccttacaatt ggaagcctta cgctattaaa aatattcctg taaataacaa aagtgtgaac | 600 |
| gttggcttta tcgggattgt caccaaagac atcccaaacc ttgtcttacg taaaaattat | 660 |
| gaacaatatg aattttttaga tgaagctgaa acaatcgtta aatacgccaa agaattacaa | 720 |
| gctaaaaatg tcaaagctat tgtagttctc gcacatgtac ctgcaacaag taaaaatgat | 780 |
| attgctgaag gtgaagcagc agaaatgatg aaaaaagtca atcaactctt ccctgaaaat | 840 |
| agcgtagata ttgtctttgc tggacacaat catcaatata caaatggtct tgttggtaaa | 900 |
| actcgtattg tacaagcgct ctctcaagga aaagcctatg ctgatgtacg tggtgtctta | 960 |
| gatactgata cacaagattt cattgagacc ccttcagcta agtaattgc agttgctcct | 1020 |
| ggtaaaaaaa caggtagtgc cgatattcaa gccattgttg accaagctaa tactatcgtt | 1080 |
| aaacaagtaa cagaagctaa aattggtact gccgaggtaa gtgtcatgat tacgcgttct | 1140 |
| gttgatcaag ataatgttag tccggtaggc agcctcatca cagaggctca actagcaatt | 1200 |
| gctcgaaaaa gctggccaga tatcgatttt gccatgacaa ataatggtgg cattcgtgct | 1260 |
| gacttactca tcaaaccaga tggaacaatc acctggggag ctgcacaagc agttcaacct | 1320 |
| tttggtaata tcttacaagt cgtcgaaatt actggtagag atctttataa agcactcaac | 1380 |
| gaacaatacg accaaaaaca aaatttcttc cttcaaatag ctggtctgcg atacacttac | 1440 |
| acagataata aagagggcgg ggaagaaaca ccatttaaag ttgtaaaagc ttataaatca | 1500 |
| aatggtgagg aaatcaatcc tgatgcaaaa tacaaattag ttatcaatga ctttttattc | 1560 |
| ggtggtggtg atggctttgc aagcttcaga aatgccaaac ttctaggagc cattaacccc | 1620 |
| gatacagagg tatttatggc ctatatcact gatttagaaa aagctggtaa aaaagtgagc | 1680 |
| gttccaaata taaacctaa atctatgtc actatgaaga tggttaatga aactattaca | 1740 |
| caaaatgatg gtacacatag cattattaag aaactttatt tagatcgaca aggaaatatt | 1800 |
| gtagcacaag agattgtatc agacacttta aaccaaacaa aatcaaaatc tacaaaaatc | 1860 |
| aaccctgtaa ctacaattca caaaaaacaa ttacaccaat ttacagctat taaccctatg | 1920 |
| agaaattatg gcaaaccatc aaactccact actgtaaaat caaacaatt accaaaaaca | 1980 |
| aactctgaat atggacaatc attccttatg tctgtctttg gtgttggact tataggaatt | 2040 |
| gctttaaata caaagaaaaa acatatgaaa | 2070 |

<210> SEQ ID NO 81
<211> LENGTH: 690
<212> TYPE: PRT
<213> ORGANISM: Streptococcus agalactiae

<400> SEQUENCE: 81

```
Met Lys Lys Lys Ile Ile Leu Lys Ser Ser Val Leu Gly Leu Val Ala
 1               5                  10                  15

Gly Thr Ser Ile Met Phe Ser Ser Val Phe Ala Asp Gln Val Gly Val
             20                  25                  30

Gln Val Ile Gly Val Asn Asp Phe His Gly Ala Leu Asp Asn Thr Gly
         35                  40                  45

Thr Ala Asn Met Pro Asp Gly Lys Val Ala Asn Ala Gly Thr Ala Ala
     50                  55                  60

Gln Leu Asp Ala Tyr Met Asp Asp Ala Gln Lys Asp Phe Lys Gln Thr
 65                  70                  75                  80

Asn Pro Asn Gly Glu Ser Ile Arg Val Gln Ala Gly Asp Met Val Gly
                 85                  90                  95

Ala Ser Pro Ala Asn Ser Gly Leu Leu Gln Asp Glu Pro Thr Val Lys
```

```
                100             105             110
Asn Phe Asn Ala Met Asn Val Glu Tyr Gly Thr Leu Gly Asn His Glu
            115             120             125

Phe Asp Glu Gly Leu Ala Glu Tyr Asn Arg Ile Val Thr Gly Lys Ala
130             135             140

Pro Ala Pro Asp Ser Asn Ile Asn Ile Thr Lys Ser Tyr Pro His
145             150             155             160

Glu Ala Ala Lys Gln Glu Ile Val Val Ala Asn Val Ile Asp Lys Val
            165             170             175

Asn Lys Gln Ile Pro Tyr Asn Trp Lys Pro Tyr Ala Ile Lys Asn Ile
            180             185             190

Pro Val Asn Asn Lys Ser Val Asn Val Gly Phe Ile Gly Ile Val Thr
            195             200             205

Lys Asp Ile Pro Asn Leu Val Leu Arg Lys Asn Tyr Glu Gln Tyr Glu
            210             215             220

Phe Leu Asp Glu Ala Glu Thr Ile Val Lys Tyr Ala Lys Glu Leu Gln
225             230             235             240

Ala Lys Asn Val Lys Ala Ile Val Val Leu Ala His Val Pro Ala Thr
            245             250             255

Ser Lys Asn Asp Ile Ala Glu Gly Glu Ala Ala Glu Met Met Lys Lys
            260             265             270

Val Asn Gln Leu Phe Pro Glu Asn Ser Val Asp Ile Val Phe Ala Gly
            275             280             285

His Asn His Gln Tyr Thr Asn Gly Leu Val Gly Lys Thr Arg Ile Val
            290             295             300

Gln Ala Leu Ser Gln Gly Lys Ala Tyr Ala Asp Val Arg Gly Val Leu
305             310             315             320

Asp Thr Asp Thr Gln Asp Phe Ile Glu Thr Pro Ser Ala Lys Val Ile
                325             330             335

Ala Val Ala Pro Gly Lys Lys Thr Gly Ser Ala Asp Ile Gln Ala Ile
            340             345             350

Val Asp Gln Ala Asn Thr Ile Val Lys Gln Val Thr Glu Ala Lys Ile
            355             360             365

Gly Thr Ala Glu Val Ser Val Met Ile Thr Arg Ser Val Asp Gln Asp
            370             375             380

Asn Val Ser Pro Val Gly Ser Leu Ile Thr Glu Ala Gln Leu Ala Ile
385             390             395             400

Ala Arg Lys Ser Trp Pro Asp Ile Asp Phe Ala Met Thr Asn Asn Gly
                405             410             415

Gly Ile Arg Ala Asp Leu Leu Ile Lys Pro Asp Gly Thr Ile Thr Trp
                420             425             430

Gly Ala Ala Gln Ala Val Gln Pro Phe Gly Asn Ile Leu Gln Val Val
            435             440             445

Glu Ile Thr Gly Arg Asp Leu Tyr Lys Ala Leu Asn Glu Gln Tyr Asp
450             455             460

Gln Lys Gln Asn Phe Phe Leu Gln Ile Ala Gly Leu Arg Tyr Thr Tyr
465             470             475             480

Thr Asp Asn Lys Glu Gly Gly Glu Glu Thr Pro Phe Lys Val Val Lys
            485             490             495

Ala Tyr Lys Ser Asn Gly Glu Glu Ile Asn Pro Asp Ala Lys Tyr Lys
            500             505             510

Leu Val Ile Asn Asp Phe Leu Phe Gly Gly Asp Gly Phe Ala Ser
            515             520             525
```

```
Phe Arg Asn Ala Lys Leu Leu Gly Ala Ile Asn Pro Asp Thr Glu Val
        530                 535                 540

Phe Met Ala Tyr Ile Thr Asp Leu Glu Lys Ala Gly Lys Lys Val Ser
545                 550                 555                 560

Val Pro Asn Asn Lys Pro Lys Ile Tyr Val Thr Met Lys Met Val Asn
                565                 570                 575

Glu Thr Ile Thr Gln Asn Asp Gly Thr His Ser Ile Ile Lys Lys Leu
            580                 585                 590

Tyr Leu Asp Arg Gln Gly Asn Ile Val Ala Gln Glu Ile Val Ser Asp
        595                 600                 605

Thr Leu Asn Gln Thr Lys Ser Lys Ser Thr Lys Ile Asn Pro Val Thr
    610                 615                 620

Thr Ile His Lys Lys Gln Leu His Gln Phe Thr Ala Ile Asn Pro Met
625                 630                 635                 640

Arg Asn Tyr Gly Lys Pro Ser Asn Ser Thr Thr Val Lys Ser Lys Gln
                645                 650                 655

Leu Pro Lys Thr Asn Ser Glu Tyr Gly Gln Ser Phe Leu Met Ser Val
            660                 665                 670

Phe Gly Val Gly Leu Ile Gly Ile Ala Leu Asn Thr Lys Lys Lys His
        675                 680                 685

Met Lys
    690

<210> SEQ ID NO 82
<211> LENGTH: 650
<212> TYPE: PRT
<213> ORGANISM: Streptococcus agalactiae

<400> SEQUENCE: 82

His Gly Ala Leu Asp Asn Thr Gly Thr Ala Asn Met Pro Asp Gly Lys
1               5                   10                  15

Val Ala Asn Ala Gly Thr Ala Ala Gln Leu Asp Ala Tyr Met Asp Asp
            20                  25                  30

Ala Gln Lys Asp Phe Lys Gln Thr Asn Pro Asn Gly Glu Ser Ile Arg
        35                  40                  45

Val Gln Ala Gly Asp Met Val Gly Ala Ser Pro Ala Asn Ser Gly Leu
    50                  55                  60

Leu Gln Asp Glu Pro Thr Val Lys Asn Phe Asn Ala Met Asn Val Glu
65                  70                  75                  80

Tyr Gly Thr Leu Gly Asn His Glu Phe Asp Glu Gly Leu Ala Glu Tyr
                85                  90                  95

Asn Arg Ile Val Thr Gly Lys Ala Pro Ala Pro Asp Ser Asn Ile Asn
            100                 105                 110

Asn Ile Thr Lys Ser Tyr Pro His Glu Ala Ala Lys Gln Glu Ile Val
        115                 120                 125

Val Ala Asn Val Ile Asp Lys Val Asn Lys Gln Ile Pro Tyr Asn Trp
    130                 135                 140

Lys Pro Tyr Ala Ile Lys Asn Ile Pro Val Asn Asn Lys Ser Val Asn
145                 150                 155                 160

Val Gly Phe Ile Gly Ile Val Thr Lys Asp Ile Pro Asn Leu Val Leu
                165                 170                 175

Arg Lys Asn Tyr Glu Gln Tyr Glu Phe Leu Asp Glu Ala Glu Thr Ile
            180                 185                 190

Val Lys Tyr Ala Lys Glu Leu Gln Ala Lys Asn Val Lys Ala Ile Val
```

-continued

```
            195                 200                 205
Val Leu Ala His Val Pro Ala Thr Ser Lys Asn Asp Ile Ala Glu Gly
210                 215                 220

Glu Ala Ala Glu Met Met Lys Lys Val Asn Gln Leu Phe Pro Glu Asn
225                 230                 235                 240

Ser Val Asp Ile Val Phe Ala Gly His Asn His Gln Tyr Thr Asn Gly
                    245                 250                 255

Leu Val Gly Lys Thr Arg Ile Val Gln Ala Leu Ser Gln Gly Lys Ala
            260                 265                 270

Tyr Ala Asp Val Arg Gly Val Leu Asp Thr Asp Thr Gln Asp Phe Ile
        275                 280                 285

Glu Thr Pro Ser Ala Lys Val Ile Ala Val Ala Pro Gly Lys Lys Thr
    290                 295                 300

Gly Ser Ala Asp Ile Gln Ala Ile Val Asp Gln Ala Asn Thr Ile Val
305                 310                 315                 320

Lys Gln Val Thr Glu Ala Lys Ile Gly Thr Ala Glu Val Ser Val Met
                    325                 330                 335

Ile Thr Arg Ser Val Asp Gln Asp Asn Val Ser Pro Val Gly Ser Leu
            340                 345                 350

Ile Thr Glu Ala Gln Leu Ala Ile Ala Arg Lys Ser Trp Pro Asp Ile
        355                 360                 365

Asp Phe Ala Met Thr Asn Asn Gly Gly Ile Arg Ala Asp Leu Leu Ile
    370                 375                 380

Lys Pro Asp Gly Thr Ile Thr Trp Gly Ala Ala Gln Ala Val Gln Pro
385                 390                 395                 400

Phe Gly Asn Ile Leu Gln Val Val Glu Ile Thr Gly Arg Asp Leu Tyr
                    405                 410                 415

Lys Ala Leu Asn Glu Gln Tyr Asp Gln Lys Gln Asn Phe Phe Leu Gln
            420                 425                 430

Ile Ala Gly Leu Arg Tyr Thr Tyr Thr Asp Asn Lys Glu Gly Gly Glu
        435                 440                 445

Glu Thr Pro Phe Lys Val Val Lys Ala Tyr Lys Ser Asn Gly Glu Glu
    450                 455                 460

Ile Asn Pro Asp Ala Lys Tyr Lys Leu Val Ile Asn Asp Phe Leu Phe
465                 470                 475                 480

Gly Gly Gly Asp Gly Phe Ala Ser Phe Arg Asn Ala Lys Leu Leu Gly
                    485                 490                 495

Ala Ile Asn Pro Asp Thr Glu Val Phe Met Ala Tyr Ile Thr Asp Leu
            500                 505                 510

Glu Lys Ala Gly Lys Lys Val Ser Val Pro Asn Asn Lys Pro Lys Ile
        515                 520                 525

Tyr Val Thr Met Lys Met Val Asn Glu Thr Ile Thr Gln Asn Asp Gly
    530                 535                 540

Thr His Ser Ile Ile Lys Lys Leu Tyr Leu Asp Arg Gln Gly Asn Ile
545                 550                 555                 560

Val Ala Gln Glu Ile Val Ser Asp Thr Leu Asn Gln Thr Lys Ser Lys
                    565                 570                 575

Ser Thr Lys Ile Asn Pro Val Thr Ile His Lys Lys Gln Leu His
            580                 585                 590

Gln Phe Thr Ala Ile Asn Pro Met Arg Asn Tyr Gly Lys Pro Ser Asn
        595                 600                 605

Ser Thr Thr Val Lys Ser Lys Gln Leu Pro Lys Thr Asn Ser Glu Tyr
    610                 615                 620
```

Gly Gln Ser Phe Leu Met Ser Val Phe Gly Val Gly Leu Ile Gly Ile
625                 630                 635                 640

Ala Leu Asn Thr Lys Lys His Met Lys
                645                 650

<210> SEQ ID NO 83
<211> LENGTH: 654
<212> TYPE: PRT
<213> ORGANISM: Streptococcus agalactiae

<400> SEQUENCE: 83

Met Lys Lys Lys Ile Ile Leu Lys Ser Ser Val Leu Gly Leu Val Ala
1               5                   10                  15

Gly Thr Ser Ile Met Phe Ser Ser Val Phe Ala Asp Gln Val Gly Val
                20                  25                  30

Gln Val Ile Gly Val Asn Asp Phe His Gly Ala Leu Asp Asn Thr Gly
            35                  40                  45

Thr Ala Asn Met Pro Asp Gly Lys Val Ala Asn Ala Gly Thr Ala Ala
        50                  55                  60

Gln Leu Asp Ala Tyr Met Asp Asp Ala Gln Lys Asp Phe Lys Gln Thr
65                  70                  75                  80

Asn Pro Asn Gly Glu Ser Ile Arg Val Gln Ala Gly Asp Met Val Gly
                85                  90                  95

Ala Ser Pro Ala Asn Ser Gly Leu Leu Gln Asp Glu Pro Thr Val Lys
                100                 105                 110

Asn Phe Asn Ala Met Asn Val Glu Tyr Gly Thr Leu Gly Asn His Glu
            115                 120                 125

Phe Asp Glu Gly Leu Ala Glu Tyr Asn Arg Ile Val Thr Gly Lys Ala
130                 135                 140

Pro Ala Pro Asp Ser Asn Ile Asn Asn Ile Thr Lys Ser Tyr Pro His
145                 150                 155                 160

Glu Ala Ala Lys Gln Glu Ile Val Val Ala Asn Val Ile Asp Lys Val
                165                 170                 175

Asn Lys Gln Ile Pro Tyr Asn Trp Lys Pro Tyr Ala Ile Lys Asn Ile
            180                 185                 190

Pro Val Asn Asn Lys Ser Val Asn Val Gly Phe Ile Gly Ile Val Thr
        195                 200                 205

Lys Asp Ile Pro Asn Leu Val Leu Arg Lys Asn Tyr Glu Gln Tyr Glu
210                 215                 220

Phe Leu Asp Glu Ala Glu Thr Ile Val Lys Tyr Ala Lys Glu Leu Gln
225                 230                 235                 240

Ala Lys Asn Val Lys Ala Ile Val Val Leu Ala His Val Pro Ala Thr
                245                 250                 255

Ser Lys Asn Asp Ile Ala Glu Gly Glu Ala Ala Glu Met Met Lys Lys
            260                 265                 270

Val Asn Gln Leu Phe Pro Glu Asn Ser Val Asp Ile Val Phe Ala Gly
        275                 280                 285

His Asn His Gln Tyr Thr Asn Gly Leu Val Gly Lys Thr Arg Ile Val
290                 295                 300

Gln Ala Leu Ser Gln Gly Lys Ala Tyr Ala Asp Val Arg Gly Val Leu
305                 310                 315                 320

Asp Thr Asp Thr Gln Asp Phe Ile Glu Thr Pro Ser Ala Lys Val Ile
                325                 330                 335

Ala Val Ala Pro Gly Lys Lys Thr Gly Ser Ala Asp Ile Gln Ala Ile

```
              340                 345                 350
Val Asp Gln Ala Asn Thr Ile Val Lys Gln Val Thr Glu Ala Lys Ile
                355                 360                 365

Gly Thr Ala Glu Val Ser Val Met Ile Thr Arg Ser Val Asp Gln Asp
    370                 375                 380

Asn Val Ser Pro Val Gly Ser Leu Ile Thr Glu Ala Gln Leu Ala Ile
385                 390                 395                 400

Ala Arg Lys Ser Trp Pro Asp Ile Asp Phe Ala Met Thr Asn Asn Gly
                405                 410                 415

Gly Ile Arg Ala Asp Leu Leu Ile Lys Pro Asp Gly Thr Ile Thr Trp
            420                 425                 430

Gly Ala Ala Gln Ala Val Gln Pro Phe Gly Asn Ile Leu Gln Val Val
                435                 440                 445

Glu Ile Thr Gly Arg Asp Leu Tyr Lys Ala Leu Asn Glu Gln Tyr Asp
            450                 455                 460

Gln Lys Gln Asn Phe Phe Leu Gln Ile Ala Gly Leu Arg Tyr Thr Tyr
465                 470                 475                 480

Thr Asp Asn Lys Glu Gly Gly Glu Thr Pro Phe Lys Val Val Lys
                485                 490                 495

Ala Tyr Lys Ser Asn Gly Glu Ile Asn Pro Asp Ala Lys Tyr Lys
                500                 505                 510

Leu Val Ile Asn Asp Phe Leu Phe Gly Gly Asp Gly Phe Ala Ser
            515                 520                 525

Phe Arg Asn Ala Lys Leu Leu Gly Ala Ile Asn Pro Asp Thr Glu Val
            530                 535                 540

Phe Met Ala Tyr Ile Thr Asp Leu Glu Lys Ala Gly Lys Lys Val Ser
545                 550                 555                 560

Val Pro Asn Asn Lys Pro Lys Ile Tyr Val Thr Met Lys Met Val Asn
                565                 570                 575

Glu Thr Ile Thr Gln Asn Asp Gly Thr His Ser Ile Ile Lys Lys Leu
            580                 585                 590

Tyr Leu Asp Arg Gln Gly Asn Ile Val Ala Gln Glu Ile Val Ser Asp
            595                 600                 605

Thr Leu Asn Gln Thr Lys Ser Lys Ser Thr Lys Ile Asn Pro Val Thr
    610                 615                 620

Thr Ile His Lys Lys Gln Leu His Gln Phe Thr Ala Ile Asn Pro Met
625                 630                 635                 640

Arg Asn Tyr Gly Lys Pro Ser Asn Ser Thr Thr Val Lys Ser
                645                 650

<210> SEQ ID NO 84
<211> LENGTH: 614
<212> TYPE: PRT
<213> ORGANISM: Streptococcus agalactiae

<400> SEQUENCE: 84

His Gly Ala Leu Asp Asn Thr Gly Thr Ala Asn Met Pro Asp Gly Lys
1               5                   10                  15

Val Ala Asn Ala Gly Thr Ala Ala Gln Leu Asp Ala Tyr Met Asp Asp
                20                  25                  30

Ala Gln Lys Asp Phe Lys Gln Thr Asn Pro Asn Gly Glu Ser Ile Arg
            35                  40                  45

Val Gln Ala Gly Asp Met Val Gly Ala Ser Pro Ala Asn Ser Gly Leu
    50                  55                  60
```

```
Leu Gln Asp Glu Pro Thr Val Lys Asn Phe Asn Ala Met Asn Val Glu
 65                  70                  75                  80

Tyr Gly Thr Leu Gly Asn His Glu Phe Asp Glu Gly Leu Ala Glu Tyr
                 85                  90                  95

Asn Arg Ile Val Thr Gly Lys Ala Pro Ala Pro Asp Ser Asn Ile Asn
            100                 105                 110

Asn Ile Thr Lys Ser Tyr Pro His Glu Ala Ala Lys Gln Glu Ile Val
        115                 120                 125

Val Ala Asn Val Ile Asp Lys Val Asn Lys Gln Ile Pro Tyr Asn Trp
    130                 135                 140

Lys Pro Tyr Ala Ile Lys Asn Ile Pro Val Asn Asn Lys Ser Val Asn
145                 150                 155                 160

Val Gly Phe Ile Gly Ile Val Thr Lys Asp Ile Pro Asn Leu Val Leu
                165                 170                 175

Arg Lys Asn Tyr Glu Gln Tyr Glu Phe Leu Asp Glu Ala Glu Thr Ile
            180                 185                 190

Val Lys Tyr Ala Lys Glu Leu Gln Ala Lys Asn Val Lys Ala Ile Val
        195                 200                 205

Val Leu Ala His Val Pro Ala Thr Ser Lys Asn Asp Ile Ala Glu Gly
    210                 215                 220

Glu Ala Ala Glu Met Met Lys Lys Val Asn Gln Leu Phe Pro Glu Asn
225                 230                 235                 240

Ser Val Asp Ile Val Phe Ala Gly His Asn His Gln Tyr Thr Asn Gly
                245                 250                 255

Leu Val Gly Lys Thr Arg Ile Val Gln Ala Leu Ser Gln Gly Lys Ala
            260                 265                 270

Tyr Ala Asp Val Arg Gly Val Leu Asp Thr Asp Thr Gln Asp Phe Ile
        275                 280                 285

Glu Thr Pro Ser Ala Lys Val Ile Ala Val Ala Pro Gly Lys Lys Thr
    290                 295                 300

Gly Ser Ala Asp Ile Gln Ala Ile Val Asp Gln Ala Asn Thr Ile Val
305                 310                 315                 320

Lys Gln Val Thr Glu Ala Lys Ile Gly Thr Ala Glu Val Ser Val Met
                325                 330                 335

Ile Thr Arg Ser Val Asp Gln Asp Asn Val Ser Pro Val Gly Ser Leu
            340                 345                 350

Ile Thr Glu Ala Gln Leu Ala Ile Ala Arg Lys Ser Trp Pro Asp Ile
        355                 360                 365

Asp Phe Ala Met Thr Asn Asn Gly Gly Ile Arg Ala Asp Leu Leu Ile
    370                 375                 380

Lys Pro Asp Gly Thr Ile Thr Trp Gly Ala Ala Gln Ala Val Gln Pro
385                 390                 395                 400

Phe Gly Asn Ile Leu Gln Val Glu Ile Thr Gly Arg Asp Leu Tyr
                405                 410                 415

Lys Ala Leu Asn Glu Gln Tyr Asp Gln Lys Asn Phe Phe Leu Gln
            420                 425                 430

Ile Ala Gly Leu Arg Tyr Thr Tyr Thr Asp Asn Lys Glu Gly Glu
        435                 440                 445

Glu Thr Pro Phe Lys Val Val Lys Ala Tyr Lys Ser Asn Gly Glu Glu
        450                 455                 460

Ile Asn Pro Asp Ala Lys Tyr Lys Leu Val Ile Asn Asp Phe Leu Phe
465                 470                 475                 480

Gly Gly Gly Asp Gly Phe Ala Ser Phe Arg Asn Ala Lys Leu Leu Gly
```

```
            485              490              495
Ala Ile Asn Pro Asp Thr Glu Val Phe Met Ala Tyr Ile Thr Asp Leu
            500              505              510

Glu Lys Ala Gly Lys Lys Val Ser Val Pro Asn Asn Lys Pro Lys Ile
            515              520              525

Tyr Val Thr Met Lys Met Val Asn Glu Thr Ile Thr Gln Asn Asp Gly
            530              535              540

Thr His Ser Ile Ile Lys Lys Leu Tyr Leu Asp Arg Gln Gly Asn Ile
545              550              555              560

Val Ala Gln Glu Ile Val Ser Asp Thr Leu Asn Gln Thr Lys Ser Lys
                565              570              575

Ser Thr Lys Ile Asn Pro Val Thr Thr Ile His Lys Lys Gln Leu His
            580              585              590

Gln Phe Thr Ala Ile Asn Pro Met Arg Asn Tyr Gly Lys Pro Ser Asn
            595              600              605

Ser Thr Thr Val Lys Ser
            610

<210> SEQ ID NO 85
<211> LENGTH: 783
<212> TYPE: DNA
<213> ORGANISM: Streptococcus agalactiae

<400> SEQUENCE: 85
atgaaaagat tacataaact gtttataacc gtaattgcta cattaggtat gttggggta      60
atgacctttg gtcttccaac gcagccgcaa acgtaacgc cgatagtaca tgctgatgtc     120
aattcatctg ttgatacgag ccaggaattt caaataatt taaaaatgc tattggtaac     180
ctaccatttc aatatgttaa tggtatttat gaattaaata ataatcagac aaatttaaat     240
gctgatgtca atgttaaagc gtatgttcaa atacaattg acaatcaaca aagactatca     300
actgctaatg caatgcttga tagaaccatt cgtcaatatc aaaatcgcag agataccact     360
cttcccgatg caaattggaa accattaggt tggcatcaag tagctactaa tgaccattat     420
ggacatgcag tcgacaaggg gcatttaatt gcctatgctt tagctggaaa tttcaaaggt     480
tgggatgctt ccgtgtcaaa tcctcaaaat gttgtcacac aaacagctca ttccaaccaa     540
tcaaatcaaa aaatcaatcg tggacaaaat tattatgaaa gcttagttcg taaggcggtt     600
gaccaaaaca acgtgttcg ttaccgtgta actccattgt accgtaatga tactgattta      660
gttccatttg caatgcacct agaagctaaa tcacaagatg gcacattaga atttaatgtt     720
gctattccaa acacacaagc atcatacact atggattatg caacaggaga ataacacta     780
aat                                                                   783

<210> SEQ ID NO 86
<211> LENGTH: 261
<212> TYPE: PRT
<213> ORGANISM: Streptococcus agalactiae

<400> SEQUENCE: 86

Met Lys Arg Leu His Lys Leu Phe Ile Thr Val Ile Ala Thr Leu Gly
1               5                   10                  15

Met Leu Gly Val Met Thr Phe Gly Leu Pro Thr Gln Pro Gln Asn Val
                20                  25                  30

Thr Pro Ile Val His Ala Asp Val Asn Ser Ser Val Asp Thr Ser Gln
            35                  40                  45
```

Glu Phe Gln Asn Asn Leu Lys Asn Ala Ile Gly Asn Leu Pro Phe Gln
 50                  55                  60

Tyr Val Asn Gly Ile Tyr Glu Leu Asn Asn Gln Thr Asn Leu Asn
 65                  70                  75                  80

Ala Asp Val Asn Val Lys Ala Tyr Val Gln Asn Thr Ile Asp Asn Gln
                 85                  90                  95

Gln Arg Leu Ser Thr Ala Asn Ala Met Leu Asp Arg Thr Ile Arg Gln
                100                 105                 110

Tyr Gln Asn Arg Arg Asp Thr Thr Leu Pro Asp Ala Asn Trp Lys Pro
                115                 120                 125

Leu Gly Trp His Gln Val Ala Thr Asn Asp His Tyr Gly His Ala Val
130                 135                 140

Asp Lys Gly His Leu Ile Ala Tyr Ala Leu Ala Gly Asn Phe Lys Gly
145                 150                 155                 160

Trp Asp Ala Ser Val Ser Asn Pro Gln Asn Val Val Thr Gln Thr Ala
                165                 170                 175

His Ser Asn Gln Ser Asn Gln Lys Ile Asn Arg Gly Asn Tyr Tyr
                180                 185                 190

Glu Ser Leu Val Arg Lys Ala Val Asp Gln Asn Lys Arg Val Arg Tyr
                195                 200                 205

Arg Val Thr Pro Leu Tyr Arg Asn Asp Thr Asp Leu Val Pro Phe Ala
210                 215                 220

Met His Leu Glu Ala Lys Ser Gln Asp Gly Thr Leu Glu Phe Asn Val
225                 230                 235                 240

Ala Ile Pro Asn Thr Gln Ala Ser Tyr Thr Met Asp Tyr Ala Thr Gly
                245                 250                 255

Glu Ile Thr Leu Asn
                260

<210> SEQ ID NO 87
<211> LENGTH: 2703
<212> TYPE: DNA
<213> ORGANISM: Streptococcus agalactiae

<400> SEQUENCE: 87

| | |
|---|---:|
| atgagaaaat accaaaaatt tcctaaaata ttgacgttaa gtcttttttg tttgtcgcaa | 60 |
| ataccgctta ataccaatgt tttaggggaa agtaccgtac cggaaaatgg tgctaaagga | 120 |
| aagttagttg ttaaaaagac agatgaccag aacaaaccac tttcaaaagc tacctttgtt | 180 |
| ttaaaaacta ctgctcatcc agaaagtaaa atagaaaaag taactgctga gctaacaggt | 240 |
| gaagctactt ttgataatct catacctgga gattatactt tatcagaaga aacagcgccc | 300 |
| gaaggttata aaaagactaa ccagacttgg caagttaagg ttgagagtaa tggaaaaact | 360 |
| acgatacaaa atagtggtga taaaaattcc acaattggac aaaatcagga gaactagat | 420 |
| aagcagtatc cccccacagg aatttatgaa gatacaaagg aatcttataa acttgagcat | 480 |
| gttaaaggtt cagttccaaa tggaaagtca gaggcaaaag cagttaaccc atattcaagt | 540 |
| gaaggtgagc atataagaga aattccagag ggaacattat ctaaacgtat ttcagaagta | 600 |
| ggtgatttag ctcataataa atataaaatt gagttaactg tcagtggaaa accatagta | 660 |
| aaaccagtgg acaaacaaaa gccgttagat gttgtcttcg tactcgataa ttctaactca | 720 |
| atgaataacg atggcccaaa ttttcaaagg cataataaag ccaagaaagc tgccgaagct | 780 |
| cttgggaccg cagtaaaaga tattttagga gcaaacagtg ataatagggt tgcattagtt | 840 |
| acctatggtt cagatatttt tgatggtagg agtgtagatg tcgtaaaagg atttaaagaa | 900 |

```
gatgataaat attatggcct tcaaactaag ttcacaattc agacagagaa ttatagtcat    960
aaacaattaa caaataatgc tgaagagatt ataaaaagga ttccgacaga agctcctaaa   1020
gctaagtggg gatctactac caatggatta actccagagc aacaaaagga gtactatctt   1080
agtaaagtag gagaaacatt tactatgaaa gccttcatgg aggcagatga tattttgagt   1140
caagtaaatc gaaatagtca aaaaattatt gttcatgtaa ctgatggtgt tcctacgaga   1200
tcatatgcta ttaataattt taaactgggt gcatcatatg aaagccaatt tgaacaaatg   1260
aaaaaaaatg gatatctaaa taaaagtaat tttctactta ctgataagcc cgaggatata   1320
aaaggaaatg gggagagtta cttttttgttt cccttagata gttatcaaac acagataatc   1380
tctgaaaact acaaaaaact tcattattta gatttaaatc ttaattaccc taaaggtaca   1440
atttatcgaa atggaccagt gaagaacat ggaacaccaa ccaaacttta tataaatagt   1500
ttaaaacaga aaattatga cattttaat tttggtatcg atatatctgg ttttagacaa    1560
gtttataatg aggagtataa gaaaatcaa gatggtactt ttcaaaaatt gaaagaggaa   1620
gcttttaaac tttcagatgg agaaatcaca gaactaatga ggtcgttctc ttccaaacct   1680
gagtactaca ccctatcgt aacttcagcc gatacatcta acaatgaaat tttatctaaa   1740
attcagcaac aatttgaaac gatttaaca aaagaaaact caattgttaa tggaactatc   1800
gaagatccta tgggtgataa aatcaattta cagcttggta atggacaaac attacagcca   1860
agtgattata ctttacaggg aaatgatgga agtgtaatga aggatggtat tgcaactggt   1920
gggcctaata atgatggtgg aatacttaag ggggttaaat tagaatacat cggaaataaa   1980
ctctatgtta gaggtttgaa tttaggagaa ggtcaaaaag taacactcac atatgatgtg   2040
aaactagatg acagttttat aagtaacaaa ttctatgaca ctaatggtag aacaacattg   2100
aatcctaagt cagaggatcc taatacactt agagattttc caatccctaa aattcgtgat   2160
gtgagagaat atcctacaat aacgattaaa acgagaagaa gttaggtga aattgaattt   2220
ataaagttg ataagataa taataagttg cttctcaaag gagctacgtt tgaacttcaa   2280
gaatttaatg aagattataa actttattta ccaataaaaa ataataattc aaaagtagtg   2340
acgggagaaa acggcaaaat ttcttacaaa gatttgaaag atggcaaata tcagttaata   2400
gaagcagttt cgccggagga ttatcaaaaa attactaata aaccaatttt aacttttgaa   2460
gtggttaaag gatcgataaa aaatataata gctgttaata aacagatttc tgaatatcat   2520
gaggaaggtg acaagcattt aattaccaac acgcatattc caccaaaagg aattattcct   2580
atgacaggtg ggaaaggaat tctatctttc attttaatag gtggagctat gatgtctatt   2640
gcaggtggaa tttatatttg gaaaggtat aagaaatcta gtgatatgtc catcaaaaaa   2700
gat                                                                2703
```

<210> SEQ ID NO 88
<211> LENGTH: 901
<212> TYPE: PRT
<213> ORGANISM: Streptococcus agalactiae

<400> SEQUENCE: 88

Met Arg Lys Tyr Gln Lys Phe Ser Lys Ile Leu Thr Leu Ser Leu Phe
1               5                   10                  15

Cys Leu Ser Gln Ile Pro Leu Asn Thr Asn Val Leu Gly Glu Ser Thr
            20                  25                  30

Val Pro Glu Asn Gly Ala Lys Gly Lys Leu Val Lys Lys Thr Asp
        35                  40                  45

```
Asp Gln Asn Lys Pro Leu Ser Lys Ala Thr Phe Val Leu Lys Thr Thr
 50                  55                  60

Ala His Pro Glu Ser Lys Ile Glu Lys Val Thr Ala Glu Leu Thr Gly
 65                  70                  75                  80

Glu Ala Thr Phe Asp Asn Leu Ile Pro Gly Asp Tyr Thr Leu Ser Glu
                 85                  90                  95

Glu Thr Ala Pro Glu Gly Tyr Lys Lys Thr Asn Gln Thr Trp Gln Val
            100                 105                 110

Lys Val Glu Ser Asn Gly Lys Thr Thr Ile Gln Asn Ser Gly Asp Lys
            115                 120                 125

Asn Ser Thr Ile Gly Gln Asn Gln Glu Leu Asp Lys Gln Tyr Pro
130                 135                 140

Pro Thr Gly Ile Tyr Glu Asp Thr Lys Glu Ser Tyr Lys Leu Glu His
145                 150                 155                 160

Val Lys Gly Ser Val Pro Asn Gly Lys Ser Glu Ala Lys Ala Val Asn
                165                 170                 175

Pro Tyr Ser Ser Glu Gly Glu His Ile Arg Glu Ile Pro Glu Gly Thr
            180                 185                 190

Leu Ser Lys Arg Ile Ser Glu Val Gly Asp Leu Ala His Asn Lys Tyr
            195                 200                 205

Lys Ile Glu Leu Thr Val Ser Gly Lys Thr Ile Val Lys Pro Val Asp
210                 215                 220

Lys Gln Lys Pro Leu Asp Val Val Phe Val Leu Asp Asn Ser Asn Ser
225                 230                 235                 240

Met Asn Asn Asp Gly Pro Asn Phe Gln Arg His Asn Lys Ala Lys Lys
                245                 250                 255

Ala Ala Glu Ala Leu Gly Thr Ala Val Lys Asp Ile Leu Gly Ala Asn
            260                 265                 270

Ser Asp Asn Arg Val Ala Leu Val Thr Tyr Gly Ser Asp Ile Phe Asp
            275                 280                 285

Gly Arg Ser Val Asp Val Val Lys Gly Phe Lys Glu Asp Asp Lys Tyr
            290                 295                 300

Tyr Gly Leu Gln Thr Lys Phe Thr Ile Gln Thr Glu Asn Tyr Ser His
305                 310                 315                 320

Lys Gln Leu Thr Asn Asn Ala Glu Glu Ile Ile Lys Arg Ile Pro Thr
                325                 330                 335

Glu Ala Pro Lys Ala Lys Trp Gly Ser Thr Thr Asn Gly Leu Thr Pro
            340                 345                 350

Glu Gln Gln Lys Glu Tyr Tyr Leu Ser Lys Val Gly Glu Thr Phe Thr
            355                 360                 365

Met Lys Ala Phe Met Glu Ala Asp Asp Ile Leu Ser Gln Val Asn Arg
            370                 375                 380

Asn Ser Gln Lys Ile Ile Val His Val Thr Asp Gly Val Pro Thr Arg
385                 390                 395                 400

Ser Tyr Ala Ile Asn Asn Phe Lys Leu Gly Ala Ser Tyr Glu Ser Gln
                405                 410                 415

Phe Glu Gln Met Lys Lys Asn Gly Tyr Leu Asn Lys Ser Asn Phe Leu
            420                 425                 430

Leu Thr Asp Lys Pro Glu Asp Ile Lys Gly Asn Gly Glu Ser Tyr Phe
            435                 440                 445

Leu Phe Pro Leu Asp Ser Tyr Gln Thr Gln Ile Ile Ser Gly Asn Leu
450                 455                 460
```

```
Gln Lys Leu His Tyr Leu Asp Leu Asn Leu Asn Tyr Pro Lys Gly Thr
465                 470                 475                 480

Ile Tyr Arg Asn Gly Pro Val Lys Glu His Gly Thr Pro Thr Lys Leu
            485                 490                 495

Tyr Ile Asn Ser Leu Lys Gln Lys Asn Tyr Asp Ile Phe Asn Phe Gly
                500                 505                 510

Ile Asp Ile Ser Gly Phe Arg Gln Val Tyr Asn Glu Glu Tyr Lys Lys
            515                 520                 525

Asn Gln Asp Gly Thr Phe Gln Lys Leu Lys Glu Glu Ala Phe Lys Leu
530                 535                 540

Ser Asp Gly Glu Ile Thr Glu Leu Met Arg Ser Phe Ser Ser Lys Pro
545                 550                 555                 560

Glu Tyr Tyr Thr Pro Ile Val Thr Ser Ala Asp Thr Ser Asn Asn Glu
                565                 570                 575

Ile Leu Ser Lys Ile Gln Gln Phe Glu Thr Ile Leu Thr Lys Glu
                580                 585                 590

Asn Ser Ile Val Asn Gly Thr Ile Glu Asp Pro Met Gly Asp Lys Ile
        595                 600                 605

Asn Leu Gln Leu Gly Asn Gly Gln Thr Leu Gln Pro Ser Asp Tyr Thr
610                 615                 620

Leu Gln Gly Asn Asp Gly Ser Val Met Lys Asp Gly Ile Ala Thr Gly
625                 630                 635                 640

Gly Pro Asn Asn Asp Gly Gly Ile Leu Lys Gly Val Lys Leu Glu Tyr
                645                 650                 655

Ile Gly Asn Lys Leu Tyr Val Arg Gly Leu Asn Leu Gly Glu Gly Gln
            660                 665                 670

Lys Val Thr Leu Thr Tyr Asp Val Lys Leu Asp Ser Phe Ile Ser
                675                 680                 685

Asn Lys Phe Tyr Asp Thr Asn Gly Arg Thr Thr Leu Asn Pro Lys Ser
        690                 695                 700

Glu Asp Pro Asn Thr Leu Arg Asp Phe Pro Ile Pro Lys Ile Arg Asp
705                 710                 715                 720

Val Arg Glu Tyr Pro Thr Ile Thr Ile Lys Asn Glu Lys Lys Leu Gly
                725                 730                 735

Glu Ile Glu Phe Ile Lys Val Asp Lys Asp Asn Asn Lys Leu Leu Leu
            740                 745                 750

Lys Gly Ala Thr Phe Glu Leu Gln Glu Phe Asn Glu Asp Tyr Lys Leu
            755                 760                 765

Tyr Leu Pro Ile Lys Asn Asn Asn Ser Lys Val Val Thr Gly Glu Asn
770                 775                 780

Gly Lys Ile Ser Tyr Lys Asp Leu Lys Asp Gly Lys Tyr Gln Leu Ile
785                 790                 795                 800

Glu Ala Val Ser Pro Glu Asp Tyr Gln Lys Ile Thr Asn Lys Pro Ile
                805                 810                 815

Leu Thr Phe Glu Val Val Lys Gly Ser Ile Lys Asn Ile Ile Ala Val
                820                 825                 830

Asn Lys Gln Ile Ser Glu Tyr His Glu Glu Gly Asp Lys His Leu Ile
        835                 840                 845

Thr Asn Thr His Ile Pro Pro Lys Gly Ile Pro Met Thr Gly Gly
        850                 855                 860

Lys Gly Ile Leu Ser Phe Ile Leu Ile Gly Gly Ala Met Met Ser Ile
865                 870                 875                 880

Ala Gly Gly Ile Tyr Ile Trp Lys Arg Tyr Lys Lys Ser Ser Asp Met
```

Ser Ile Lys Lys Asp
                900

<210> SEQ ID NO 89
<211> LENGTH: 869
<212> TYPE: PRT
<213> ORGANISM: Streptococcus agalactiae

<400> SEQUENCE: 89

Met Arg Lys Tyr Gln Lys Phe Ser Lys Ile Leu Thr Leu Ser Leu Phe
1               5                   10                  15

Cys Leu Ser Gln Ile Pro Leu Asn Thr Asn Val Leu Gly Glu Ser Thr
            20                  25                  30

Val Pro Glu Asn Gly Ala Lys Gly Lys Leu Val Lys Lys Thr Asp
        35                  40                  45

Asp Gln Asn Lys Pro Leu Ser Lys Ala Thr Phe Val Leu Lys Thr Thr
50                  55                  60

Ala His Pro Glu Ser Lys Ile Glu Lys Val Thr Ala Glu Leu Thr Gly
65                  70                  75                  80

Glu Ala Thr Phe Asp Asn Leu Ile Pro Gly Asp Tyr Thr Leu Ser Glu
                85                  90                  95

Glu Thr Ala Pro Glu Gly Tyr Lys Lys Thr Asn Gln Thr Trp Gln Val
            100                 105                 110

Lys Val Glu Ser Asn Gly Lys Thr Thr Ile Gln Asn Ser Gly Asp Lys
        115                 120                 125

Asn Ser Thr Ile Gly Gln Asn Gln Glu Glu Leu Asp Lys Gln Tyr Pro
130                 135                 140

Pro Thr Gly Ile Tyr Glu Asp Thr Lys Glu Ser Tyr Lys Leu Glu His
145                 150                 155                 160

Val Lys Gly Ser Val Pro Asn Gly Lys Ser Glu Ala Lys Ala Val Asn
                165                 170                 175

Pro Tyr Ser Ser Glu Gly Glu His Ile Arg Glu Ile Pro Glu Gly Thr
            180                 185                 190

Leu Ser Lys Arg Ile Ser Glu Val Gly Asp Leu Ala His Asn Lys Tyr
        195                 200                 205

Lys Ile Glu Leu Thr Val Ser Gly Lys Thr Ile Val Lys Pro Val Asp
210                 215                 220

Lys Gln Lys Pro Leu Asp Val Val Phe Val Leu Asp Asn Ser Asn Ser
225                 230                 235                 240

Met Asn Asn Asp Gly Pro Asn Phe Gln Arg His Asn Lys Ala Lys Lys
                245                 250                 255

Ala Ala Glu Ala Leu Gly Thr Ala Val Lys Asp Ile Leu Gly Ala Asn
            260                 265                 270

Ser Asp Asn Arg Val Ala Leu Val Thr Tyr Gly Ser Asp Ile Phe Asp
        275                 280                 285

Gly Arg Ser Val Asp Val Val Lys Gly Phe Lys Glu Asp Asp Lys Tyr
290                 295                 300

Tyr Gly Leu Gln Thr Lys Phe Thr Ile Gln Thr Glu Asn Tyr Ser His
305                 310                 315                 320

Lys Gln Leu Thr Asn Asn Ala Glu Glu Ile Ile Lys Arg Ile Pro Thr
                325                 330                 335

Glu Ala Pro Lys Ala Lys Trp Gly Ser Thr Thr Asn Gly Leu Thr Pro
            340                 345                 350

```
Glu Gln Gln Lys Glu Tyr Tyr Leu Ser Lys Val Gly Glu Thr Phe Thr
                355                 360                 365

Met Lys Ala Phe Met Glu Ala Asp Asp Ile Leu Ser Gln Val Asn Arg
    370                 375                 380

Asn Ser Gln Lys Ile Ile Val His Val Thr Asp Gly Val Pro Thr Arg
385                 390                 395                 400

Ser Tyr Ala Ile Asn Asn Phe Lys Leu Gly Ala Ser Tyr Glu Ser Gln
                405                 410                 415

Phe Glu Gln Met Lys Lys Asn Gly Tyr Leu Asn Lys Ser Asn Phe Leu
            420                 425                 430

Leu Thr Asp Lys Pro Glu Asp Ile Lys Gly Asn Gly Glu Ser Tyr Phe
            435                 440                 445

Leu Phe Pro Leu Asp Ser Tyr Gln Thr Gln Ile Ile Ser Gly Asn Leu
    450                 455                 460

Gln Lys Leu His Tyr Leu Asp Leu Asn Leu Asn Tyr Pro Lys Gly Thr
465                 470                 475                 480

Ile Tyr Arg Asn Gly Pro Val Lys Glu His Gly Thr Pro Thr Lys Leu
                485                 490                 495

Tyr Ile Asn Ser Leu Lys Gln Lys Asn Tyr Asp Ile Phe Asn Phe Gly
            500                 505                 510

Ile Asp Ile Ser Gly Phe Arg Gln Val Tyr Asn Glu Glu Tyr Lys Lys
            515                 520                 525

Asn Gln Asp Gly Thr Phe Gln Lys Leu Lys Glu Glu Ala Phe Lys Leu
            530                 535                 540

Ser Asp Gly Glu Ile Thr Glu Leu Met Arg Ser Phe Ser Ser Lys Pro
545                 550                 555                 560

Glu Tyr Tyr Thr Pro Ile Val Thr Ser Ala Asp Thr Ser Asn Asn Glu
                565                 570                 575

Ile Leu Ser Lys Ile Gln Gln Phe Glu Thr Ile Leu Thr Lys Glu
            580                 585                 590

Asn Ser Ile Val Asn Gly Thr Ile Glu Asp Pro Met Gly Asp Lys Ile
            595                 600                 605

Asn Leu Gln Leu Gly Asn Gly Gln Thr Leu Gln Pro Ser Asp Tyr Thr
            610                 615                 620

Leu Gln Gly Asn Asp Gly Ser Val Met Lys Asp Gly Ile Ala Thr Gly
625                 630                 635                 640

Gly Pro Asn Asn Asp Gly Gly Ile Leu Lys Gly Val Lys Leu Glu Tyr
                645                 650                 655

Ile Gly Asn Lys Leu Tyr Val Arg Gly Leu Asn Leu Gly Glu Gly Gln
            660                 665                 670

Lys Val Thr Leu Thr Tyr Asp Val Lys Leu Asp Asp Ser Phe Ile Ser
            675                 680                 685

Asn Lys Phe Tyr Asp Thr Asn Gly Arg Thr Thr Leu Asn Pro Lys Ser
            690                 695                 700

Glu Asp Pro Asn Thr Leu Arg Asp Phe Pro Ile Pro Lys Ile Arg Asp
705                 710                 715                 720

Val Arg Glu Tyr Pro Thr Ile Thr Ile Lys Asn Glu Lys Lys Leu Gly
                725                 730                 735

Glu Ile Glu Phe Ile Lys Val Asp Lys Asp Asn Lys Leu Leu Leu
            740                 745                 750

Lys Gly Ala Thr Phe Glu Leu Gln Glu Phe Asn Glu Asp Tyr Lys Leu
            755                 760                 765

Tyr Leu Pro Ile Lys Asn Asn Asn Ser Lys Val Val Thr Gly Glu Asn
```

```
                770                 775                 780
Gly Lys Ile Ser Tyr Lys Asp Leu Lys Asp Gly Lys Tyr Gln Leu Ile
785                 790                 795                 800

Glu Ala Val Ser Pro Glu Asp Tyr Gln Lys Ile Thr Asn Lys Pro Ile
                805                 810                 815

Leu Thr Phe Glu Val Val Lys Gly Ser Ile Lys Asn Ile Ile Ala Val
                820                 825                 830

Asn Lys Gln Ile Ser Glu Tyr His Glu Glu Gly Asp Lys His Leu Ile
                835                 840                 845

Thr Asn Thr His Ile Pro Pro Lys Gly Ile Ile Pro Met Thr Gly Gly
                850                 855                 860

Lys Gly Ile Leu Ser
865

<210> SEQ ID NO 90
<211> LENGTH: 5
<212> TYPE: PRT
<213> ORGANISM: Streptococcus agalactiae

<400> SEQUENCE: 90

Ile Pro Met Thr Gly
  1               5

<210> SEQ ID NO 91
<211> LENGTH: 858
<212> TYPE: PRT
<213> ORGANISM: Streptococcus agalactiae

<400> SEQUENCE: 91

Met Arg Lys Tyr Gln Lys Phe Ser Lys Ile Leu Thr Leu Ser Leu Phe
  1               5                  10                  15

Cys Leu Ser Gln Ile Pro Leu Asn Thr Asn Val Leu Gly Glu Ser Thr
                 20                  25                  30

Val Pro Glu Asn Gly Ala Lys Gly Lys Leu Val Lys Lys Thr Asp
                 35                  40                  45

Asp Gln Asn Lys Pro Leu Ser Lys Ala Thr Phe Val Leu Lys Thr Thr
 50                  55                  60

Ala His Pro Glu Ser Lys Ile Glu Lys Val Thr Ala Glu Leu Thr Gly
 65                  70                  75                  80

Glu Ala Thr Phe Asp Asn Leu Ile Pro Gly Asp Tyr Thr Leu Ser Glu
                 85                  90                  95

Glu Thr Ala Pro Glu Gly Tyr Lys Lys Thr Asn Gln Thr Trp Gln Val
                100                 105                 110

Lys Val Glu Ser Asn Gly Lys Thr Thr Ile Gln Asn Ser Gly Asp Lys
                115                 120                 125

Asn Ser Thr Ile Gly Gln Asn Gln Glu Glu Leu Asp Lys Gln Tyr Pro
                130                 135                 140

Pro Thr Gly Ile Tyr Glu Asp Thr Lys Glu Ser Tyr Lys Leu Glu His
145                 150                 155                 160

Val Lys Gly Ser Val Pro Asn Gly Lys Ser Glu Ala Lys Ala Val Asn
                165                 170                 175

Pro Tyr Ser Ser Glu Gly Glu His Ile Arg Glu Ile Pro Glu Gly Thr
                180                 185                 190

Leu Ser Lys Arg Ile Ser Glu Val Gly Asp Leu Ala His Asn Lys Tyr
                195                 200                 205

Lys Ile Glu Leu Thr Val Ser Gly Lys Thr Ile Val Lys Pro Val Asp
```

```
              210                 215                 220
Lys Gln Lys Pro Leu Asp Val Phe Val Leu Asp Asn Ser Asn Ser
225                 230                 235                 240

Met Asn Asn Asp Gly Pro Asn Phe Gln Arg His Asn Lys Ala Lys Lys
                245                 250                 255

Ala Ala Glu Ala Leu Gly Thr Ala Val Lys Asp Ile Leu Gly Ala Asn
                260                 265                 270

Ser Asp Asn Arg Val Ala Leu Val Thr Tyr Gly Ser Asp Ile Phe Asp
            275                 280                 285

Gly Arg Ser Val Asp Val Val Lys Gly Phe Lys Glu Asp Lys Tyr
        290                 295                 300

Tyr Gly Leu Gln Thr Lys Phe Thr Ile Gln Thr Glu Asn Tyr Ser His
305                 310                 315                 320

Lys Gln Leu Thr Asn Asn Ala Glu Glu Ile Ile Lys Arg Ile Pro Thr
                325                 330                 335

Glu Ala Pro Lys Ala Lys Trp Gly Ser Thr Thr Asn Gly Leu Thr Pro
                340                 345                 350

Glu Gln Gln Lys Glu Tyr Tyr Leu Ser Lys Val Gly Glu Thr Phe Thr
            355                 360                 365

Met Lys Ala Phe Met Glu Ala Asp Asp Ile Leu Ser Gln Val Asn Arg
370                 375                 380

Asn Ser Gln Lys Ile Ile Val His Val Thr Asp Gly Val Pro Thr Arg
385                 390                 395                 400

Ser Tyr Ala Ile Asn Asn Phe Lys Leu Gly Ala Ser Tyr Glu Ser Gln
            405                 410                 415

Phe Glu Gln Met Lys Lys Asn Gly Tyr Leu Asn Lys Ser Asn Phe Leu
                420                 425                 430

Leu Thr Asp Lys Pro Glu Asp Ile Lys Gly Asn Gly Ser Tyr Phe
            435                 440                 445

Leu Phe Pro Leu Asp Ser Tyr Gln Thr Gln Ile Ile Ser Gly Asn Leu
450                 455                 460

Gln Lys Leu His Tyr Leu Asp Leu Asn Leu Asn Tyr Pro Lys Gly Thr
465                 470                 475                 480

Ile Tyr Arg Asn Gly Pro Val Lys Glu His Gly Thr Pro Thr Lys Leu
                485                 490                 495

Tyr Ile Asn Ser Leu Lys Gln Lys Asn Tyr Asp Ile Phe Asn Phe Gly
            500                 505                 510

Ile Asp Ile Ser Gly Phe Arg Gln Val Tyr Asn Glu Glu Tyr Lys Lys
            515                 520                 525

Asn Gln Asp Gly Thr Phe Gln Lys Leu Lys Glu Glu Ala Phe Lys Leu
530                 535                 540

Ser Asp Gly Glu Ile Thr Glu Leu Met Arg Ser Phe Ser Ser Lys Pro
545                 550                 555                 560

Glu Tyr Tyr Thr Pro Ile Val Thr Ser Ala Asp Thr Ser Asn Asn Glu
                565                 570                 575

Ile Leu Ser Lys Ile Gln Gln Phe Glu Thr Ile Leu Thr Lys Glu
            580                 585                 590

Asn Ser Ile Val Asn Gly Thr Ile Glu Asp Pro Met Gly Asp Lys Ile
            595                 600                 605

Asn Leu Gln Leu Gly Asn Gly Gln Thr Leu Gln Pro Ser Asp Tyr Thr
            610                 615                 620

Leu Gln Gly Asn Asp Gly Ser Val Met Lys Asp Gly Ile Ala Thr Gly
625                 630                 635                 640
```

```
Gly Pro Asn Asn Asp Gly Gly Ile Leu Lys Gly Val Lys Leu Glu Tyr
                645                 650                 655
Ile Gly Asn Lys Leu Tyr Val Arg Gly Leu Asn Leu Gly Glu Gly Gln
            660                 665                 670
Lys Val Thr Leu Thr Tyr Asp Val Lys Leu Asp Asp Ser Phe Ile Ser
        675                 680                 685
Asn Lys Phe Tyr Asp Thr Asn Gly Arg Thr Thr Leu Asn Pro Lys Ser
    690                 695                 700
Glu Asp Pro Asn Thr Leu Arg Asp Phe Pro Ile Pro Lys Ile Arg Asp
705                 710                 715                 720
Val Arg Glu Tyr Pro Thr Ile Thr Ile Lys Asn Glu Lys Lys Leu Gly
                725                 730                 735
Glu Ile Glu Phe Ile Lys Val Asp Lys Asp Asn Asn Lys Leu Leu Leu
            740                 745                 750
Lys Gly Ala Thr Phe Glu Leu Gln Glu Phe Asn Glu Asp Tyr Lys Leu
        755                 760                 765
Tyr Leu Pro Ile Lys Asn Asn Ser Lys Val Val Thr Gly Glu Asn
    770                 775                 780
Gly Lys Ile Ser Tyr Lys Asp Leu Lys Asp Gly Lys Tyr Gln Leu Ile
785                 790                 795                 800
Glu Ala Val Ser Pro Gly Asp Tyr Gln Lys Ile Thr Asn Lys Pro Ile
                805                 810                 815
Leu Thr Phe Glu Val Val Lys Gly Ser Ile Lys Asn Ile Ile Ala Val
            820                 825                 830
Asn Lys Gln Ile Ser Glu Tyr His Glu Glu Gly Asp Lys His Leu Ile
        835                 840                 845
Thr Asn Thr His Ile Pro Pro Lys Gly Ile
    850                 855

<210> SEQ ID NO 92
<211> LENGTH: 6
<212> TYPE: PRT
<213> ORGANISM: Artificial Sequence
<220> FEATURE:
<223> OTHER INFORMATION: amino acid linker

<400> SEQUENCE: 92

Gly Ser Gly Gly Gly Gly
 1               5

<210> SEQ ID NO 93
<211> LENGTH: 5
<212> TYPE: PRT
<213> ORGANISM: Artificial Sequence
<220> FEATURE:
<223> OTHER INFORMATION: cell wall anchor motif
<221> NAME/KEY: VARIANT
<222> LOCATION: (1)...(5)
<223> OTHER INFORMATION: Xaa = Any Amino Acid

<400> SEQUENCE: 93

Leu Pro Xaa Thr Gly
 1               5
```

IMMUNOGENIC COMPOSITIONS FOR STREPTOCOCCUS AGALACTIAE

This application is a national stage application of co-pending PCT application PCT/US2004/030032 filed Sep. 15, 2004, which was published in English under PCT Article 21(2) on Mar. 31, 2004 and which claims priority to Ser. No. 60/548,789, filed Feb. 26, 2004 and is a continuation-in-part of PCT/US2003/029167, filed on Sep. 15, 2003. Each of these applications is incorporated herein by reference in its entirety.

This application incorporates by reference the contents of a 319 kb text file created on Jan. 15, 2010 and named "SN10568422_sequencelisting.txt," which is the sequence listing for this application.

FIELD OF THE INVENTION

The invention relates to an immunogenic antigen derived from Streptococcus agalactiae ("GBS") and its use in combinations with other GBS antigens to provide for broader coverage among different GBS strains. In particular, the invention relates to a composition comprising a combination of two or more GBS antigens, wherein the combination includes GBS 80 or a fragment thereof. The combination may include GBS 80 and at least one other GBS antigen. For example, the combination may include GBS 80 and up to thirteen GBS antigens. In a preferred embodiment, the combination may include GBS 80 and up to ten GBS antigens. In a more preferred embodiment, the combination may include GBS 80 and up to five GBS antigens. In one embodiment, the combination may consist of two to thirteen GBS antigens selected from an antigen group consisting of GBS 80, GBS 91, GBS 104, GBS 184, GBS 276, GBS 305, GBS 322, GBS 330, GBS 338, GBS 361, GBS 404, GBS 690, and GBS 691. Preferably, the combination includes GBS 80 in combination with one or more of GBS 104 and GBS 322.

BACKGROUND OF INVENTION

GBS has emerged in the last 20 years as the major cause of neonatal sepsis and meningitis that affect 0.5-3 per 1000 live births, and an important cause of morbidity among the older age group affecting 5-8 per 100,000 of the population. Current disease management strategies rely on intrapartum antibiotics and neonatal monitoring which have reduced neonatal case mortality from >50% in the 1970's to less than 10% in the 1990's. Nevertheless, there is still considerable morbidity and mortality and the management is expensive. 15-35% of pregnant women are asymptomatic carriers and at high risk of transmitting the disease to their babies. Risk of neonatal infection is associated with low serotype specific maternal antibodies and high titers are believed to be protective. In addition, invasive GBS disease is increasingly recognized in elderly adults with underlying disease such as diabetes and cancer.

The "B" in "GBS" refers to the Lancefield classification, which is based on the antigenicity of a carbohydrate which is soluble in dilute acid and called the C carbohydrate. Lancefield identified 13 types of C carbohydrate, designated A to O, that could be serologically differentiated. The organisms that most commonly infect humans are found in groups A, B, D, and G. Within group B, strains can be divided into at least 9 serotypes (Ia, Ib, Ia/c, II, m, IV, V, VI, VII and VIII) based on the structure of their polysaccharide capsule. In the past, serotypes Ia, Ib, II, and III were equally prevalent in normal vaginal carriage and early onset sepsis in newborns. Type V GBS has emerged as an important cause of GBS infection in the USA, however, and strains of types VI and VIII have become prevalent among Japanese women.

The genome sequence of a serotype V strain 2603 V/R has been published (Ref. 1) and various polypeptides for use a vaccine antigens have been identified (Ref. 2). The vaccines currently specificity and poor immunogenicity, and so there is a need for effective vaccines against S. agalactiae infection.

It is an object of the invention to provide further and improved compositions for providing immunity against GBS disease and/or infection. The compositions are based on a combination of two or more (e.g., three or more) GBS antigens.

SUMMARY OF THE INVENTION

Applicants have discovered that an immunogenic GBS antigen, GBS 80, is particularly suitable for immunization purposes, especially when used in combination with other GBS antigens. The combination may include GBS 80 and at least one other GBS antigen or up to thirteen other GBS antigens. In a preferred embodiment, the combination may include GBS 80 and up to 10 GBS antigens. In a more preferred embodiment, the combination includes GBS 80 and up to five GBS antigens. In particular, the invention relates to a composition comprising a combination of two or more GBS antigens, wherein the combination includes GBS 80 or a fragment thereof. In one embodiment, the combination may consist of two to thirteen GBS antigens selected from the group consisting of GBS 80, GBS 91, GBS 104, GBS 184, GBS 276, GBS 305, GBS 322, GBS 330, GBS 338, GBS 361, GBS 404, GBS 690, and GBS 691. Preferably, the combination consists of GBS 80, GBS 104 and GBS 322.

Instead of the full length antigen, the combination may comprise an immunogenic fragment of the selected GBS antigen and/or a polypeptide sequence having sequence identity to the selected antigen.

Preferably, the combination of GBS antigens consists of three, four, five, six, seven, eight, nine, or ten GBS antigens. Still more preferably, the combination of GBS antigens consists of three, four, or five GBS antigens.

DETAILED DESCRIPTION OF TEE INVENTION

The practice of the present invention will employ, unless otherwise indicated, conventional methods of chemistry, biochemistry, molecular biology, immunology and pharmacology, within the skill of the art. Such techniques are explained fully in the literature. See, e.g., Remington's Pharmaceutical Sciences, Mack Publishing Company, Easton, Pa., 19th Edition (1995); Methods In Enzymology (S. Colowick and N. Kaplan, eds., Academic Press, Inc.); and Handbook of Experimental Immunology, Vols. I-IV (D. M. Weir and C. C. Blackwell, eds., 1986, Blackwell Scientific Publications); Sambrook, et al., Molecular Cloning: A Laboratory Manual (2nd Edition, 1989); Handbook of Surface and Colloidal Chemistry (Birdi, K. S. ed., CRC Press, 1997); Short Protocols in Molecular Biology, 4th ed. (Ausubel et al. eds., 1999, John Wiley & Sons); Molecular Biology Techniques: An Intensive Laboratory Course, (Ream et al., eds., 1998, Academic Press); PCR (Introduction to Biotechniques Series), 2nd ed. (Newton & Graham eds., 1997, Springer Verlag); Peters and Dalrymple, Fields Virology (2d ed), Fields et al. (eds.), B. N. Raven Press, New York, N.Y.

All publications, patents and patent applications cited herein, are hereby incorporated by reference in their entireties.

GBS Antigens

As discussed above, the invention provides an immunogenic composition comprising a combination of two or more GBS antigens, wherein said combination includes GBS 80 or a fragment thereof.

The combinations of GBS antigens may include polypeptide fragments of the identified GBS antigens. The length of the fragment may vary depending on the amino acid sequence of the specific GBS antigen, but the fragment is preferably at least 7 consecutive amino acids, (e.g. 8, 10, 12, 14, 16, 18, 20, 25, 30, 35, 40, 50, 60, 70, 80, 90, 100, 150, 200 or more). Preferably the fragment comprises one or more epitopes from the sequence. Other preferred fragments include (1) the N-terminal signal peptides of each identified GBS antigen, (2) the identified GBS antigens without their N-terminal signal peptides, and (3) each identified GBS antigen wherein up to 10 amino acid residues (e.g. 1, 2, 3, 4, 5, 6, 7, 8, 9, 10, 15, 20, 25 or more) are deleted from the N-terminus and/or the C-terminus e.g. the N-terminal amino acid residue may be deleted. Other fragments omit one or more domains of the protein (e.g. omission of a signal peptide, of a cytoplasmic domain, of a transmembrane domain, or of an extracellular domain).

The combinations of GBS antigens may include polypeptide sequences having sequence identity to the identified GBS antigens. The degree of sequence identity may vary depending on the amino acid sequence (a) in question, but is preferably greater than 50% (e.g. 60%, 65%, 70%, 75%, 80%, 85%, 90%, 91%, 92%, 93%, 94%, 95%, 96%, 97%, 98%, 99%, 99.5% or more). Polypeptides having sequence identity include homologs, orthologs, allelic variants and functional mutants of the identified GBS antigens. Typically, 50% identity or more between two proteins is considered to be an indication of functional equivalence. Identity between proteins is preferably determined by the Smith-Waterman homology search algorithm as implemented in the MPSRCH program (Oxford Molecular), using an affinity gap search with parameters gap open penalty=12 and gap extension penalty=1.

The polypeptides can, of course, be prepared by various means (e.g. recombinant expression, purification from CBS, chemical synthesis etc.) and in various forms (e.g. native, fusions, glycosylated, non-glycosylated etc.). They are preferably prepared in substantially pure form (i.e. substantially free from other streptococcal or host cell proteins) or substantially isolated form.

GBS 80

As discussed above, the invention relates to the use of GBS 80 in synergistic combination with other GBS antigens. GBS 80 refers to a putative cell wall surface anchor family protein. Nucleotide and amino acid sequence of GBS 80 sequenced from serotype V isolated strain 2603 V/R are set forth in Ref. 2 as SEQ ID 8779 and SEQ ID 8780. These sequences are also set forth below as SEQ ID NOS 1 and 2:

```
                                                   SEQ ID NO: 1
ATGAAATTATCGAAGAGGTTATTGTTTTCGGCTGCTGTTTTAACAATGGT

GGCGGGGTCAACTGTTGAACCAGTAGCTCAGTTTGCGACTGGAATGAGTA

TTGTAAGAGCTGCAGAAGTGTCACAAGAACGCCCAGCGAAAACAACAGTA

AATATCTATAAATTACAAGCTGATAGTTATAAATCGGAAATTACTTCTAA

TGGTGGTATCGAGAATAAAGACGGCGAAGTAATATCTAACTATGCTAAAC

TTGGTGACAATGTAAAAGGTTTGCAAGGTGTACAGTTTAAACGTTATAAA
```

```
-continued
GTCAAGACGGATATTTCTGTTGATGAATTGAAAAAATTGACAACAGTTGA

AGCAGCAGATGCAAAAGTTGGAACGATTCTTGAAGAAGGTGTCAGTCTAC

CTCAAAAAACTAATGCTCAAGGTTTGGTCGTCGATGCTCTGGATTCAAAA

AGTAATGTGAGATACTTGTATGTAGAAGATTTAAAGAATTCACCTTCAAA

CATTACCAAAGCTTATGCTGTACCGTTTGTGTTGGAATTACCAGTTGCTA

ACTCTACAGGTACAGGTTTCCTTTCTGAAATTAATATTTACCCTAAAAAC

GTTGTAACTGATGAACCAAAAACAGATAAAGATGTTAAAAAATTAGGTCA

GGACGATGCAGGTTATACGATTGGTGAAGAATTCAAATGGTTCTTGAAAT

CTACAATCCCTGCCAATTTAGGTGACTATGAAAAATTTGAAATTACTGAT

AAATTTGCAGATGGCTTGACTTATAAATCTGTTGGAAAAATCAAGATTGG

TTCGAAAACACTGAATAGAGATGAGCACTACACTATTGATGAACCAACAG

TTGATAACCAAAATACATTAAAAATTACGTTTAAACCAGAGAAATTTAAA

GAAATTGCTGAGCTACTTAAAGGAATGACCCTTGTTAAAAATCAAGATGC

TCTTGATAAAGCTACTGCAAATACAGATGATGCGGCATTTTTGGAAATTC

CAGTTGCATCAACTATTAATGAAAAAGCAGTTTTAGGAAAAGCAATTGAA

AATACTTTTGAACTTCAATATGACCATACTCCTGATAAAGCTGACAATCC

AAAACCATCTAATCCTCCAAGAAAACCAGAAGTTCATACTGGTGGGAAAC

GATTTGTAAAGAAAGACTCAACAGAAACACAAACACTAGGTGGTGCTGAG

TTTGATTTGTTGGCTTCTGATGGGACAGCAGTAAAATGGACAGATGCTCT

TATTAAAGCGAATACTAATAAAAACTATATTGCTGGAGAAGCTGTTACTG

GGCAACCAATCAAATTGAAATCACATACAGACGGTACGTTTGAGATTAAA

GGTTTGGCTTATGCAGTTGATGCGAATGCAGAGGGTACAGCAGTAACTTA

CAAATTAAAAGAAACAAAAGCACCAGAAGGTTATGTAATCCCTGATAAAG

AAATCGAGTTTACAGTATCACAAACATCTTATAATACAAAACCAACTGAC

ATCACGGTTGATAGTGCTGATGCAACACCTGATACAATTAAAAACAACAA

ACGTCCTTCAATCCCTAATACTGGTGGTATTGGTACGGCTATCTTTGTCG

CTATCGGTGCTGCGGTGATGGCTTTTGCTGTTAAGGGGATGAAGCGTCGT

ACAAAGATAAC

SEQ ID NO: 2
MKLSKKLLFSAAVLTMVAGSTVEPVAQFATGMSIVRAAEVSQERPAKTTV

NIYKLQADSYKSEITSNGGIENKDGEVISNYAKLGDNVKGLQGVQFKRYK

VKTDISVDELKKLTTVEAADAKVGTILEEGVSLPQKTNAQGLVVDALDSK

SNVRYLYVEDLKNSPSNITKAYAVPFVLELPVANSTGTGFLSEINIYPKN

VVTDEPKTDKDVKKLGQDDAGYTIGEEFKWFLKSTIPANLGDYEKFEITD

KFADGLTYKSVGKIKIGSKTLNRDEHYTIDEPTVDNQNTLKITFKPEKFK

EIAELLKGMTLVKNQDALDKATANTDDAAFLEIPVASTINEKAVLGKAIE

NTFELQYDHTPDKADNPKPSNPPRKPEVHTGGKRFVKKDSTETQTLGGAE

FDLLASDGTAVKWTDALIKANTNKNYIAGEAVTGQPIKLKSHTDGTFEIK

GLAYAVDANAEGTAVTYKLKETKAPEGYVIPDKEIEFTVSQTSYNTKPTD

ITVDSADATPDTIKNNKRPSIPNTGGIGTAIFVAIGAAVMAFAVKGMKRR

TKDN
```

As described above, the combinations of the invention may include a fragment of a GBS antigen. In some instances, removal of one or more domains, such as a leader or signal sequence region, a transmembrane region, a cytoplasmic region or a cell wall anchoring motif, may facilitate cloning of the gene encoding the antigen and/or recombinant expression of the GBS protein. In addition, fragments comprising immunogenic epitopes of the cited GBS antigens may be used in the compositions of the invention.

GBS 80 contains an N-terminal leader or signal sequence region which is indicated by the underlined sequence at the beginning of SEQ ID NO: 2 above. In one embodiment, one or more amino acids from the leader or signal sequence region of GBS 80 are removed. An example of such a GBS 80 fragment is set forth below as SEQ ID NO: 3:

```
                                             SEQ ID NO: 3
AEVSQERPAKTTVNIYKLQADSYKSEITSNGGIENKDGEVISNYAKLGDN

VKGLQGVQFKRYKVKTDISVDELKKLTTVEAADAKVGTILEEGVSLPQKT

NAQGLVVDALDSKSNVRYLYVEDLKNSPSNITKAYAVPFVLELPVANSTG

TGFLSEINIYPKNVVTDEPKTDKDVKKLGQDDAGYTIGEEFKWFLKSTIP

ANLGDYEKFEITDKFADGLTYKSVGKIKIGSKTLNRDEHYTIDEPTVDNQ

NTLKITFKPEKFKEIAELLKGMTLVKNQDALDKATANTDDAAFLEIPVAS

TINEKAVLGKAIENTFELQYDHTPDKADNPKPSNPPRKPEVHTGGKRFVK

KDSTETQTLGGAEFDLLASDGTAVKWTDALIKANTNKNYIAGEAVTGQPI

KLKSHTDGTFEIKGLAYAVDANAEGTAVTYKLKETKAPEGYVIPDKEIEF

TVSQTSYNTKPTDITVDSADATPDTIKNNKRPSIPNTGGIGTAIFVAIGA

AVMAFAVKGMKRRTKDN
```

GBS 80 contains a C-terminal transmembrane region which is indicated by the underlined sequence near the end of SEQ ID NO: 2 above. In one embodiment, one or more amino acids from the transmembrane region and/or a cytoplasmic region are removed. An example of such a GBS 80 fragment is set forth below as SEQ ID NO: 4:

```
                                             SEQ ID NO: 4
MKLSKKLLFSAAVLTMVAGSTVEPVAQFATGMSIVRAAEVSQERPAKTTV

NIYKLQADSYKSEITSNGGIENKDGEVISNYAKLGDNVKGLQGVQFKRYK

VKTDISVDELKKLTTVEAADAKVGTILEEGVSLPQKTNAQGLVVDALDSK

SNVRYLYVEDLKNSPSNITKAYAVPFVLELPVANSTGTGFLSEINIYPKN

VVTDEPKTDKDVKKLGQDDAGYTIGEEFKWFLKSTIPANLGDYEKFEITD

KFADGLTYKSVGKIKIGSKYLNRDEHYTIDEPTVDNQNTLKITFKPEKFK

EIAELLKGMTLVKNQDALDKATANTDDAAFLEIPVASTINEKAVLGKAIE

NTFELQYDHTPDKADNPKPSNPPRKPEVHTGGKRFVKKDSTETQTLGGAE

FDLLASDGTAVKETDALIKANTNKNYIAGEAVTGQPIKLKSHTDGTFEIK

GLAYAVDANAEGTAVTYKLKETKAPEGYVIPDKEIEFTVSQTSYNTKPTD

ITVDSADATPDTIKNNKRPSIPNTG
```

GBS 80 contains an amino acid motif indicative of a cell wall anchor: SEQ ID NO: 5 IPNTG (shown in italics in SEQ ID NO: 2 above). In some recombinant host cell systems, it may be preferable to remove this motif to facilitate secretion of a recombinant GBS 80 protein from the host cell. Accordingly, in one preferred fragment of GBS 80 for use in the invention, the transmembrane and/or cytoplasmic regions and the cell wall anchor motif are removed from GBS 80. An example of such a GBS 80 fragment is set forth below as SEQ ID NO: 6.

```
                                             SEQ ID NO: 6
MKLSKKLLFSAAVLTMVAGSTVEPVAQFATGMSIVRAAEVSQERPAKTTV

NIYKLQADSYKSEITSNGGIENKDGEVISNYAKLGDNVKGLQGVQFKRYK

VKTDISVDELKKLTTVEAADAKVGTILEEGVSLPQKTNAQGLVVDALDSK

SNVRYLYVEDLKNSPSNITKAYAVPFVLELPVANSTGTGFLSEINIYPKN

VVTDEPKTDKDVKKLGQDDAGYTIGEEFKWFLKSTIPANLGDYEKFEITD

KFADGLTYKSVGKIKIGSKYLNRDEHYTIDEPTVDNQNTLKITFKPEKFK

EIAELLKGMTLVKNQDALDKATANTDDAAFLEIPVASTINEKAVLGKAIE

NTFELQYDHTPDKADNPKPSNPPRKPEVHTGGKRFVKKDSTETQTLGGAE

FDLLASDGTAVKETDALIKANTNKNYIAGEAVTGQPIKLKSHTDGTFEIK

GLAYAVDANAEGTAVTYKLKETKAPEGYVIPDKEIEFTVSQTSYNTKPTD

ITVDSADATPDTIKNNKRPS
```

Alternatively, in some recombinant host cell systems, it may be preferable to use the cell wall anchor motif to anchor the recombinantly expressed protein to the cell wall. The extracellular domain of the expressed protein may be cleaved during purification or the recombinant protein may be left attached to either inactivated host cells or cell membranes in the final composition.

In one embodiment, the leader or signal sequence region, the transmembrane and cytoplasmic regions and the cell wall anchor motif are removed from the GBS 80 sequence. An example of such a GBS 80 fragment is set forth below as SEQ ID NO: 7.

```
                                             SEQ ID NO: 7
AEVSQERPAKTTVNIYKLQADSYKSEITSNGGIENKDGEVISNYAKLGDN

VKGLQGVQFKRYKVKTDISVDELKKLTTVEAADAKVGTILEEGVSLPQKT

NAQGLVVDALDSKSNVRYLYVEDLKNSPSNITKAYAVPFVLELPVANSTG

TGFLSEINIYPKNVVTDEPKTDKDVKKLGQDDAGYTIGEEFKWFLKSTIP

ANLGDYEKFEITDKFADGLTYKSVGKIKIGSKTLNRDEHYTIDEPTVDNQ

NTLKITFKPEKFKEIAELLKGMTLVKNQDALDKATANTDDAAFLEIPVAS

TINEKAVLGKAIENTFELQYDHTPDKADNPKPSNPPRKPEVHTGGKRFVK

KDSTETQTLGGAEFDLLASDGTAVKWTDALIKANTNKNYIAGEAVTGQPI

KLKSHTDGTFEIKGLAYAVDANAEGTAVTYKLKETKAPEGYVIPDKEIEF

TVSQTSYNTKPTDITVDSADATPDTIKNNKRPS
```

Applicants have identified a particularly immunogenic fragment of the GBS 80 protein. This immunogenic fragment is located towards the N-terminus of the protein and is underlined in the GBS 80 SEQ ID NO: 2 sequence below. The underlined fragment is set forth below as SEQ ID NO: 8.

```
                                             SEQ ID NO: 2
MKLSKKLLFSAAVLTMVAGSTVEPVAQFATGMSIVRAAEVSQERPAKTTV

NIYKLQADSYKSEITSNGGIENKDGEVISNYAKLGDNVKGLQGVQFKRYK
```

VKTDISVDELKKLTTVEAADAKVGTILEEGVSLPQKTNAQGLVVDALDSK

SNVRYLYVEDLKNSPSNITKAYAVPFVLELPVANSTGTGFLSEINIYPKN

VVTDEPKTDKDVKKLGQDDAGYTIGEEFKWFLKSTIPANLGDYEKFEITD

KFADGLTYKSVGKIKIGSKYLNRDEHYTIDEPTVDNQNTLKITFKPEKFK

EIAELLKGMTLVKNQDALDKATANTDDAAFLEIPVASTINEKAVLGKAIE

NTFELQYDHTPDKADNPKPSNPPRKPEVHTGGKRFVKKDSTETQTLGGAE

FDLLASDGTAVKETDALIKANTNKNYIAGEAVTGQPIKLKSHTDGTFEIK

GLAYAVDANAEGTAVTYKLKETKAPEGYVIPDKEIEFTVSQTSYNTKPTD

ITVDSADATPDTIKNNKRPSIPNTGGIGTAIFVAIGAAVMAGAVKGMKRR

TKDN

SEQ ID NO: 8
AEVSQERPAKTTVNIYKLQADSYKSEITSNGGIENKDGEVISNYAKLGDN

VKGLQGVQFKRYKVKTDISVDELKKLTTVEAADAKVGTILEEGVSLPQKT

NAQGLVVDALDSKSNVRYLYVEDLKNSPSNITKAYAVPFVLELPVANSTG

TGFLSEINIYPKNVVTDEPKTDKDVKKLGQDDAGYTIGEEFKWFLKSTIP

ANLGDYEKFEITDKFADGLTYKSVGKIKIGSKTLNRDEHYTIDEPTVDNQ

NTLKITFKPEKFKEIAELLKG

The immunogenicity of the protein encoded by SEQ ID NO: 7 was compared against PBS, GBS whole cell, GBS 80 (full length) and another fragment of GBS 80, located closer to the C-terminus of the peptide (SEQ ID NO: 9, below).

SEQ ID NO: 9
MTLVKNQDALDKATANTDDAAFLEIPVASTINEKAVLGKAIENTFELQYD

HTPDKADNPKPSNPPRKPEVHTGGKRFVKKDSTETQTLGGAEFDLLASDG

TAVKWTDALIKANTNKNYIAGEAVTGQPIKLKSHTDGTFEIKGLAYAVDA

NAEGTAVTYKLKETKAPEGYVIPDKEIEFTVSQTSYNTKPTDITVDSADA

TPDTIKNNKRPS

Both an Active Maternal Immunization Assay and a Passive Maternal Immunization Assay were conducted on this collection of proteins.

As used herein, an Active Maternal Immunization assay refers to an in vivo protection assay where female mice are immunized with the test antigen composition. The female mice are then bred and their pups are challenged with a lethal dose of GBS. Serum titers of the female mice during the immunization schedule are measured as well as the survival time of the pups after challenge.

Specifically, the Active Maternal Immunization assays referred to herein used groups of four CD-1 female mice (Charles River Laboratories, Calco Italy). These mice were immunized intraperitoneally with the selected proteins in Freund's adjuvant at days 1, 21 and 35, prior to breeding. 6-8 weeks old mice received 20 µg protein/dose when immunized with a single antigen, 30-45 µg protein/dose (15 µg each antigen) when immunized with combination of antigens. The immune response of the dams was monitored by using serum samples taken on day 0 and 49. The female mice were bred 2-7 days after the last immunization (at approximately t=36-37), and typically had a gestation period of 21 days. Within 48 hours of birth, the pups were challenged via I.P. with GBS in a dose approximately equal to an amount which would be sufficient to kill 70-90% of unimmunized pups (as determined by empirical data gathered from PBS control groups). The GBS challenge dose is preferably administered in 50 µl of THB medium. Preferably, the pup challenge takes place at 56 to 61 days after the first immunization. The challenge inocula were prepared starting from frozen cultures diluted to the appropriate concentration with THB prior to use. Survival of pups was monitored for 5 days after challenge.

As used herein, the Passive Maternal Immunization Assay refers to an in vivo protection assay where pregnant mice are passively immunized by injecting rabbit immune sera (or control sera) approximately 2 days before delivery. The pups are then challenged with a lethal dose of GBS.

Specifically, the Passive Maternal Immunization Assay referred to herein used groups of pregnant CD1 mice which were passively immunized by injecting 1 ml of rabbit immune sera or control sera via I.P., 2 days before delivery. Newborn mice (24-48 hrs after birth) are challenged via I.P. with a 70-90% lethal dose of GBS serotype III COH1. The challenge dose, obtained by diluting a frozen mid log phase culture, was administered in 50 µl of THB medium.

For both assays, the number of pups surviving GBS infection was assessed every 12 hrs for 4 days. Statistical significance was estimated by Fisher's exact test.

The results of each assay for immunization with SEQ ID NO: 7, SEQ ID NO: 8, PBS and GBS whole cell are set forth in Tables 1 and 2 below.

TABLE 1

Active Maternal Immunization

| Antigen | Alive/total | % Survival | Fisher's exact test |
|---|---|---|---|
| PBS (neg control) | 13/80 | 16% | |
| GBS (whole cell) | 54/65 | 83% | P < 0.00000001 |
| GBS80 (intact) | 62/70 | 88% | P < 0.00000001 |
| GBS80 (fragment) SEQ ID 7 | 35/64 | 55% | P = 0.0000013 |
| GBS80 (fragment) SEQ ID 8 | 13/67 | 19% | P = 0.66 |

TABLE 2

Passive Maternal Immunization

| Antigen | Alive/total | % Survival | Fisher's exact test |
|---|---|---|---|
| PBS (neg control) | 12/42 | 28% | |
| GBS (whole cell) | 48/52 | 92% | P < 0.00000001 |
| GBS80 (intact) | 48/55 | 87% | P < 0.00000001 |
| GBS80 (fragment) SEQ ID 7 | 45/57 | 79% | P = 0.0000006 |
| GBS80 (fragment) SEQ ID 8 | 13/54 | 24% | P = 1 |

As shown in Tables 1 and 2, immunization with the SEQ ID NO: 7 GBS 80 fragment provided a substantially improved survival rate for the challenged pups than the comparison SEQ ID NO: 8 GBS 80 fragment. These results indicate that the SEQ ID NO: 7 GBS 80 fragment may comprise an important immunogenic epitope of GBS 80.

Combinations Including GBS 80

The invention includes combinations of two or more GBS antigens wherein the combination includes GBS 80 or a fragment thereof. Applicants have discovered that GBS 80 is particularly suitable for immunization in combination with other GBS antigens and that these antigen combinations provide for a broader coverage among different GBS strains.

Preferably, the combination of GBS antigens consists of three, four, five, six, seven, eight, nine, or ten GBS antigens.

Still more preferably, the combination of GBS antigens consists of three, four, or five GBS antigens.

Preferably, the combinations of the invention provide for improved immunogenicity over the immunogenicity of the antigens when administered alone. Improved immunogenicity may be measured, for example, by the Active Maternal Immunization Assay. As discussed above, this assay may be used to measure serum titers of the female mice during the immunization schedule as well as the survival time of the pups after challenge. Preferably, immunization with the immunogenic compositions of the invention yield an increase of at least 2 percentage points (preferably at least 3, 4 or 5 percentage points) in the percent survival of the challenged pups as compared to the percent survival from maternal immunization with a single antigen of the composition when administered alone. Preferably, the increase is at least 6, 7, 8, 9, 10, 11, 12, 13, 14, 15, 16, 17, 18, 19, 20, 21, 22, 23, 24, 25, 26, 27, 28, 29 or 30 percentage points. Preferably, the GBS combinations of the invention comprising GBS 80 demonstrate an increase in the percent survival as compared to the percent survival from immunization with a non-GBS 80 antigen alone.

According to one embodiment of the invention, combinations of antigens or fusion proteins containing a portion or portions of the antigens will include GBS 80 or a portion thereof in combination with from one to 10 antigens, preferably one to 10 or less antigens. Such other antigens include by way of example and not limitation, GBS 67, GBS 91, GBS 104, GBS 184, GBS 276, GBS 305, GBS 322, GBS 330, GBS 338, GBS 361, GBS 404, GBS 690, and GBS 691. Still other antigens are identified in U.S. Ser. No. 10/415,182, filed Apr. 28, 2003, hereby incorporated in its entirety.

Combinations, for example, can include GBS 80, GBS 104, GBS 322, and GBS 276; GBS 80, GBS 338, GBS 330; GBS 80, GBS 330, GBS 104; GBS 80, GBS 104, GBS 404; GBS 80, GBS 338, GBS 104; GBS 80, GBS 338, GBS 404; GBS 338, GBS 330, GBS 104; GBS 338, GBS 104, GBS 404; GBS 80, GBS 330, GBS 404; GBS 80, GBS 322, GBS 104; GBS 80, GBS 322, GBS 276; GBS 80, GBS 322, GBS 91; GBS 80, GBS 104, GBS 276; GBS 80, GBS 104, GBS 91; GBS 80, GBS 276, GBS 91; GBS 80, GBS 322, GBS 104; GBS 80, GBS 322, GBS 276; GBS 80, GBS 322, GBS 91; GBS 80, GBS 104, GBS 276; GBS 80, GBS 104, GBS 91; GBS 80, GBS 276, GBS 91; GBS 80, GBS 690, GBS 691; GBS 80, GBS 690, GBS 338; GBS 80, GBS 690, GBS 305; GBS 80, GBS 691, GBS 305; GBS 80, GBS 338, GBS 305; GBS 80, GBS 338, GBS 361; GBS 80, GBS 305, GBS 361; GBS 80, GBS 184, GBS 691; GBS 80, GBS 691, GBS 338; GBS 80, GBS 104, GBS 276, GBS 322; GBS 80, GBS 104, GBS 67, and GBS 322. Examples of combinations of the invention which demonstrate improved immunogenicity are set forth below. A more detailed description of the GBS antigens referred to in these experiments is set forth following the examples.

Example 1

Active Maternal Immunization Assay of GBS 80 Alone vs. in Combination

In this example, the Active Maternal Immunization Assay was used to measure the percent survival of pups challenged with a Type III serotype of GBS (COH1 isolate), at t=56 days. The maternal mice were immunized according to the Active Maternal Immunization Assay schedule discussed above with GBS 80 alone, combinations of GBS antigens (with and without GBS 80), placebo (PBS) or inactivated whole cell GBS isolate as indicated in Table 3 below. In these experiments, the challenge dose for GBS Type III, strain isolate COH1 sufficient to kill 70-90% of unimmunized pups is approximately equal to 10×LD 50% (where LD 50% is the statistically derived Median Lethal Dose).

TABLE 3

Active Maternal Immunization Assay of GBS 80 alone vs. in combination

| α-GBS | I Challenge t = 56 days Type III COH1 10 × LD 50% | |
|---|---|---|
| | Alive/treated | Survival % |
| α-PBS | 3/26 | 11 |
| α-GBS III | 9/20 | 45 |
| 80 | 24/34 | 70 |
| 80 + 338 + 330 | 39/40 | 97 |
| 80 + 330 + 104 | 38/40 | 95 |
| 80 + 104 + 404 | 24/24 | 100 |
| 80 + 338 + 104 | 33/34 | 97 |
| 80 + 338 + 404 | 30/30 | 100 |
| 338 + 330 + 104 | 22/30 | 73 |
| 338 + 104 + 404 | 24/37 | 65 |
| 80 + 330 + 404 | 25/28 | 89 |

As shown in Table 3, combinations of GBS antigens which included GBS 80 demonstrated an improved immunogenicity over the use of the antigens alone. For example, immunization with GBS 80 alone yielded a 70% survival rate among the challenged pups. Immunization with combinations of GBS 80 with GBS 338, GBS 330, GBS 104, and GBS 404 yielded 95 to 100% survival rate among the challenged pups. This is an increase of 25 to 30 percentage points.

By comparison, combinations of these antigens which did not include GBS 80 failed to achieve the % survival of GBS 80 alone. For example, immunization with GBS 338, GBS 104 and GBS 404 yielded a 65% survival rate. Replacement of any one of these antigens with GBS 80 dramatically increased the percent survival rate to between 97 and 100%. This is an increase of 32 to 35 percentage points. (See percent survival rates of GBS 80, 338, 101(97%); GBS 80, 338, 404 (100%) and GBS 80, 104, 404 (100%)). Similarly, immunization with GBS 338, 330 and 104 yielded a 73% survival rate. Replacement of any one of these antigens with GBS 80 increased the percent survival rate to between 95-97%.

These findings indicate that protection from COH1 isolate is increased with use of GBS 80 in combination with other GBS antigens.

Example 2

Active Maternal Immunization Assay of GBS 80, GBS 322 GBS 276. GBS 104 Alone vs. in Combination In this example, the Active Maternal Immunization Assay was used to measure the percent survival of pups challenged with a Type III serotype of GBS (COH1 isolate) at t=56 days. The maternal mice were immunized according to the Active Maternal Immunization Assay schedule discussed above with a single GBS antigen, combinations of GBS antigens with GBS 80, and placebo PBS) as indicated in Table 4 below.

TABLE 4

Active Maternal Immunization Assay of GBS 80, GBS 322,
GBS 276 or GBS 104 alone vs. in combination with GBS 80

| α-GBS | I Challenge t = 56 days Type III COH1 10 × LD 50% | |
|---|---|---|
| | Alive/treated | Survival % |
| 80 + 322 + 104 | 27/27 | 100 |
| 80 + 322 + 276 | 35/38 | 92 |
| 80 + 322 + 91 | 24/24 | 100 |
| 80 + 104 + 276 | 29/30 | 97 |
| 80 + 104 + 91 | 36/40 | 90 |
| 80 + 276 + 91 | 33/40 | 82 |
| GBS 80 | 24/30 | 80 |
| GBS 322 | 7/40 | 17 |
| GBS 276 | 13/37 | 35 |
| GBS 104 | 28/38 | 74 |
| α-PBS | 2/27 | 7 |

As shown in Table 4, the combinations of the antigens with GBS 80 yielded improved immunogenicity over the use of the antigens alone. For example, immunization with GBS 322 alone yielded a 17% survival rate among the challenged pups. Immunization with combinations of GBS 322 with GBS 80 and another GBS antigen yielded survival rates of 92-100%. As another example, immunization with GBS 104 alone yielded a 74% survival rate. Immunization with combinations of GBS 104 with GBS 80 and another GBS antigen yielded survival rates of 90-100%. As another example, immunization with GBS 276 alone yielded a 35% survival rate. Immunization with combinations of GBS 276 with GBS 80 and another GBS antigen yielded survival rates of 82-97%.

Having demonstrated the immunogenicity of the above-described combinations, the duration of the immune response in the mouse model was further analysed. The maternal mice used in the above described Active Maternal Immunization Assay were mated a second time and the resulting pups challenged with a different GBS serotype (Type V, CJB 111 isolate) at a dramatically higher dose (300×LD 50%) at t91 days. The parameters of this second, much stronger challenge were outside those of the standard Active Maternal immunization Assay and were meant to probe the limits of the immunological memory generated from the original maternal immunization in the mouse model. Indication of immunological memory in this model under these conditions is thought to be significant. As shown in Table 5, even under these extreme conditions, increased survival rates were generally achieved, particularly for the combination comprising GBS 80, GBS 322 and GBS 104. It was surprising to note that the percent survival rate for the combination of GBS 80, GBS 233 and GBS 104 was 100% for both the first and second challenges.

TABLE 5

Second generation pups challenged with higher dose of different strain

| α-GBS | II Challenge t = 91 days Type V CJB111 300 × LD 50% | |
|---|---|---|
| | Alive/treated | Survival % |
| 80 + 322 + 104 | 20/20 | 100 |
| 80 + 322 + 276 | 32/37 | 86 |
| 80 + 322 + 91 | 27/30 | 90 |
| 80 + 104 + 276 | 22/37 | 59 |
| 80 + 104 + 91 | 36/39 | 92 |

TABLE 5-continued

Second generation pups challenged with higher dose of different strain

| α-GBS | II Challenge t = 91 days Type V CJB111 300 × LD 50% | |
|---|---|---|
| | Alive/treated | Survival % |
| 80 + 276 + 91 | 23/28 | 82 |
| GBS 80 | 13/30 | 43 |
| GBS 322 | 25/30 | 83 |
| GBS 276 | 18/40 | 45 |
| GBS 104 | 21/39 | 54 |
| α-PBS | 9/36 | 25 |

Example 3

Active Maternal Immunization Assay of combinations of GBS 80 with GBS 690. GBS 691, GBS 338. GBS 305. GBS 361 and GBS 184

In this example additional combinations of GBS antigens were used in the Active Maternal Immunization Assay, again with a GBS Type III COH1 isolate challenge. The maternal mice were immunized according to the Active Maternal Immunization Assay schedule described above with the combinations of GBS antigens set forth in Table 6 below.

TABLE 6

Active Maternal Immunization Assay using combinations of
GBS 80 with GBS 690, GBS 691, GBS 338, GBS 305, GBS 361
and GBS 184

| α-GBS | I Challenge t = 56 days Type III COH1 10 × LD 50% | |
|---|---|---|
| | Alive/treated | Survival % |
| 80 + 690 + 691 | 26/29 | 90 |
| 80 + 690 + 338 | 35/40 | 87 |
| 80 + 690 + 305 | 34/35 | 97 |
| 80 + 691 + 305 | 37/40 | 92 |
| 80 + 338 + 305 | 25/30 | 83 |
| 80 + 338 + 361 | 26/30 | 87 |
| 80 + 305 + 361 | 23/30 | 77 |
| 80 + 184 + 691 | 32/39 | 82 |
| α-PBS | 10/40 | 25 |

The maternal mice in this model were also mated a second time and the resulting pups challenged with the same GBS isolate at a dramatically higher dose (100×LD 50%) at t=84 days. As in the example above, the parameters of this second, much stronger challenge were outside those of the standard Active Maternal Immunization Assay and were meant to probe the limits of the immunological memory generated from the original maternal immunization in the mouse model. As shown in Table 7, even under these extreme conditions, some of the survival rates remained at or above 70%. Surprisingly, the percent survival rates for the combination of GBS 80, GBS 184 and GBS 691 actually increased.

TABLE 7

Second generation pups challenged with higher dose

| α-GBS | II Challenge t = 84 days Type III COH1 100 × LD 50% | |
|---|---|---|
| | Alive/treated | Survival % |
| 80 + 690 + 691 | 19/39 | 49 |
| 80 + 690 + 338 | 21/30 | 70 |
| 80 + 690 + 305 | 23/40 | 57 |
| 80 + 691 + 305 | 22/30 | 73 |
| 80 + 338 + 305 | 18/30 | 60 |
| 80 + 338 + 361 | 25/40 | 62 |
| 80 + 305 + 361 | 21/30 | 70 |
| 80 + 184 + 691 | 35/40 | 87 |
| α-PBS | 4/20 | 20 |

Example 4

Active Maternal Immunization Assay using combinations of GBS 80 with GBS 690, GBS 691. GBS 338. GBS 305, and GBS 361

In this example additional combinations of GBS antigens were used in the Active Maternal Immunization Assay, this time with a GBS Type V, CJB111 isolate challenge. In these experiments, the challenge dose for the GBS Type V, CJB111 isolate sufficient to kill 70-90% of unimmunized pups is approximately equal to 60×LD 50% (where LD 50% is the statistically derived Median Lethal Dose). The maternal mice were immunized according to the Active Maternal Immunization Assay schedule described above with the combinations of GBS antigens set forth in Table 8 below. As shown in Table 8, in this particular challenge study with this specific Type V strain isolate, the survival rates for all of the combinations achieved at least 70%.

TABLE 8

Active Maternal Immunization Assay using combinations of GBS 80 with GBS 690, GBS 691, GBS 338, GBS 305 and GBS 361

| α-GBS | I Challenge t = 56 days Type V CJB111 60 × LD 50% | |
|---|---|---|
| | Alive/treated | Survival % |
| 80 + 690 + 691 | 24/30 | 80 |
| 80 + 690 + 338 | 11/17 | 70 |
| 80 + 691 + 338 | 7/10 | 70 |
| 80 + 691 + 305 | 21/30 | 70 |
| 80 + 338 + 305 | 26/30 | 87 |
| 80 + 338 + 361 | 26/30 | 87 |
| 80 + 305 + 361 | 28/30 | 93 |
| GBS 80 | 21/30 | 70 |
| α-PBS | 5/18 | 28 |

The maternal mice in this model were also mated a second time and the resulting pups challenged with the same GBS isolate at a dramatically higher dose (600×LD 50%) at t=−84 days. As in the example above, the parameters of this second, much stronger challenge were outside those of the standard Active Maternal Immunization Assay and were meant to probe the limits of the immunological memory generated from the original maternal immunization in the mouse model. As shown in Table 9, even under these extreme conditions, some of the survival rates remained above 70%. Surprisingly, the percent survival for two of the antigen groups actually increased (GBS 80, GBS 690 and GBs 338) and (GBS 80, GBS 691 and GBS 338).

TABLE 9

Second generation pups challenged with higher dose

| α-GBS | II Challenge t = 84 days Type V CJB111 600 × LD 50% | |
|---|---|---|
| | Alive/treated | Survival % |
| 80 + 690 + 691 | 27/37 | 73 |
| 80 + 690 + 338 | 15/20 | 75 |
| 80 + 691 + 338 | 27/30 | 90 |
| 80 + 691 + 305 | 23/40 | 57 |
| 80 + 338 + 305 | 12/20 | 60 |
| 80 + 338 + 361 | 24/30 | 80 |
| 80 + 305 + 361 | 24/30 | 80 |
| GBS 80 | 24/30 | 80 |
| α-PBS | ND | ND |

Example 5

Active Maternal Immunization Assay using Combinations of GBS 80 with GBS 104, GBS 276, and GBS 322

In this example an additional combination of GBS antigens was used in the Active Maternal Immunization Assay, this time with an isolate challenge of different GBS strains. In these experiments, the challenge dose for the different GBS strains was sufficient to kill 60-90% of unimmunized pups and is equal to 10×LD 50% (where LD 50% is the statistically derived Median Lethal Dose). The maternal mice were immunized according to the Active Maternal Immunization Assay schedule described above with the combination of GBS 80 antigen with GBS 104, GBS 276, and GBS 322 antigens in the GBS strains set forth in Table 10 below. Survival % was observed with the GBS combination with two different adjuvants, Alum and Freunds. As shown in Tables 10 and 11, in this particular challenge study, the survival rates for the combination in all of the GBS strains achieved up to 96%.

TABLE 10

Active Maternal Immunization Assay using combinations of GBS 80 with GBS 104, GBS 276, and GBS 322 - Alum adjuvant ALUM

| | | Mix = 322 + 80 + 104 + 276 | | PBS | |
|---|---|---|---|---|---|
| GBS strains | Type | Alive/treated | Survival % | Alive/treated | Survival % |
| JM9130013 | VIII | 32/36 | 89 | 18/46 | 40 |
| CJB111 | V | 118/145 | 81 | 21/110 | 19 |
| COH1 | III | 96/115 | 83 | 22/104 | 21 |
| M781 | III | 42/52 | 81 | 18/48 | 38 |
| 2603 | V | 79/145 | 54 | 28/128 | 22 |
| 18RS21 | II | 86/186 | 46 | 24/131 | 18 |
| DK21 | II | 31/140 | 22 | 28/118 | 24 |
| 7357b- | Ib | 25/88 | 28 | 25/106 | 23 |
| A909 | Ia | 4/40 | 10 | 9/60 | 15 |
| 090 | Ia | 2/31 | 6 | 4/53 | 7 |
| SMO53 | VII | 17/54 | 31 | 4/39 | 10 |

TABLE 11

Active Maternal Immunization Assay using combinations of GBS 80 with GBS 104, GBS 276, and GBS 322 - Freund adjuvant

| | | Freund | | PBS | |
|---|---|---|---|---|---|
| | | Mix = 322 + 80 + 104 + 276 | | Alive/ | |
| GBS strains | Type | Alive/treated | Survival % | treated | Survival % |
| JM9130013 | VIII | nd | nd | nd | nd |
| CJB111 | V | 47/49 | 96 | 12/46 | 26 |
| COH1 | III | 47/50 | 94 | 12/50 | 24 |
| M781 | III | 33/50 | 66 | 6/50 | 12 |
| 2603 | V | 28/30 | 93 | 8/48 | 17 |
| 18RS21 | II | 31/78 | 40 | 10/46 | 22 |
| DK21 | II | 37/68 | 54 | 15/60 | 25 |
| H36B | Ib | 8/38 | 21 | 5/60 | 8 |
| 7357b- | Ib | 29/50 | 58 | 5/50 | 10 |
| A909 | Ia | 18/49 | 37 | 6/49 | 12 |

Accordingly, the invention therefore includes compositions comprising combinations of two or more GBS antigens, wherein the combination includes GBS 80 or a fragment thereof or a polypeptide sequence having sequence identity thereto.

In one embodiment, the combination may consist of two to thirteen GBS antigens, including GBS 80. As an example, the combination may contain GBS 80 and other GBS antigens selected from the group consisting of GBS 80, GBS 91, GBS 104, GBS 184, GBS 276, GBS 305, GBS 322, GBS 330, GBS 338, GBS 361, GBS 404, GBS 690, and GBS 691. Preferably, the combination includes GBS 80 in combination with one or more of GBS 104 and GBS 322. For example, the combination may include GBS 80, GBS 104, GBS 322 and GBS 67.

Instead of the full length antigen, the combination may comprise an immunogenic fragment of the selected GBS antigen and/or a polypeptide sequence having sequence identity to the selected antigen.

Preferably, the combination of GBS antigens consists of three, four, five, six, seven, eight, nine, or ten GBS antigens. Still more preferably, the combination of GBS antigens consists of three, four, or five GBS antigens.

Details of examples of CBS antigens for use in combination with GBS 80 are set forth below.

GBS 91

GBS 91 refers to a GBS C3 binding polypeptide. Nucleotide and amino acid sequences of GBS 91 sequenced from serotype V isolated strain 2603 V/R are set forth in Ref. 2 as SEQ ID 8937 and SEQ ID 8938. These sequences are set forth below as SEQ ID NOS 10 and 11:

```
                                                SEQ ID NO. 10
ATGAAAAAAGGACAAGTAAATGATACTAAGCAATCTTACTCTCTACGTAA

ATATAAATTTGGTTTAGCATCAGTAATTTTAGGGTCATTCATAATGGTCA

CAAGTCCTGTTTTTGCGGATCAAACTACATCGGTTCAAGTTAATAATCAG

ACAGGCACTAGTGTGGATGCTAATAATTCTTCCAATGAGACAAGTGCGTC

AAGTGTGATTACTTCCAATAATGATAGTGTTCAAGCGTCTGATAAAGTTG

TAAATAGTCAAAATACGGCAACAAAGGACATTACTACTCCTTTAGTAGAG

ACAAAGCCAATGGTGGAAAAAACATTACCTGAACAAGGGAATTATGTTTA

TAGCAAAGAAACCGAGGTGAAAAATACACCTTCAAAATCAGCCCCAGTAG

CTTTCTATGCAAAGAAAGGTGATAAAGTTTTCTATGACCAAGTATTTAAT

AAAGATAATGTGAAATGGATTTCATATAAGTCTTTTTGTGGCGTACGTCG

ATACGCAGCTATTGAGTCACTAGATCCATCAGGAGGTTCAGAGACTAAAG

CACCTACTCCTGTAACAAATTCAGGAAGCAATAATCAAGAGAAAATAGCA

ACGCAAGGAAATTATACATTTTCACATAAAGTAGAAGTAAAAAATGAAGC

TAAGGTAGCGAGTCCAACTCAATTTACATTGGACAAAGGAGACAGAATTT

TTTACGACCAAATACTAACTATTGAAGGAAATCAGTGGTTATCTTATAAA

TCATTCAATGGTGTTCGTCGTTTTGTTTTGCTAGGTAAAGCATCTTCAGT

AGAAAAAACTGAAGATAAAGAAAAAGTGTCTCCTCAACCACAAGCCCGTA

TTACTAAAACTGGTAGACTGACTATTTCTAACGAAACAACTACAGGTTTT

GATATTTTAATTACGAATATTAAAGATGATAACGGTATCGCTGCTGTTAA

GGTACCGGTTTGGACTGAACAAGGAGGGCAAGATGATATTAAATGGTATA

CAGCTGTAACTACTGGGGATGGCAACTACAAAGTAGCTGTATCATTTGCT

GACCATAAGAATGAGAAGGGTCTTTATAATATTCATTTATACTACCAAGA

AGCTAGTGGGACACTTGTAGGTGTAACAGGAACTAAAGTGACAGTAGCTG

GAACTAATTCTTCTCAAGAACCTATTGAAAATGGTTTAGCAAAGACTGGT

GTTTATAATATTATCGGAAGTACTGAAGTAAAAAATGAAGCTAAAATATC

AAGTCAGACCCAATTTACTTTAGAAAAAGGTGACAAAATAAATTATGATC

AAGTATTGACAGCAGATGGTTACCAGTGGATTTCTTACAAATCTTATAGT

GGTGTTCGTCGCTATATTCCTGTGAAAAAGCTAACTACAAGTAGTGAAAA

AGCGAAAGATGAGGCGACTAAACCGACTAGTTATCCCAACTTACCTAAAA

CAGGTACCTATACATTTACTAAAACTGTAGATGTGAAAAGTCAACCTAAA

GTATCAAGTCCAGTGGAATTTAATTTTCAAAAGGGTGAAAAAATACATTA

TGATCAAGTGTTAGTAGTAGATGGTCATCAGTGGATTTCATACAAGAGTT

ATTCCGGTATTCGTCGCTATATTGAAATT

SEQ ID NO. 11
MKKGQVNDTKQSYSLRKYKFGLASVILGSFIMVTSPVFADQTTSVQVNNQ

TGTSVDANNSSNETSASSVITSNNDSVQASDKVVNSQNTATKDITTPLVE

TKPMVEKTLPEQGNYVYSKETEVKNTPSKSAPVAFYAKKGDKVFYDQVFN

KDNVKWISYKSFCGVRRYAAIESLDPSGGSETKAPTPVTNSGSNNQEKIA

TQGNYTFSHKVEVKNEAKVASPTQFTLDKGDRIFYDQILTIEGNQWLSYK

SFNGVRRFVLLGKASSVEKTEDKEKVSPQPQARITKTGRLTISNETTTGF

DILITNIKDDNGIAAVKVPVWTEQGGQDDIKWYTAVTTGDGNYKVAVSFA

DHKNEKGLYNIHLYYQEASGTLVGVTGTKVTVAGTNSSQEPIENGLAKTG

VYNIIGSTEVKNEAKISSQTQFTLEKGDKINYDQVLTADGYQWISYKSYS

GVRRYIPVKKLTTSSEKAKDEATKPTSYPNLPKTGTYTFTKTVDVKSQPK

VSSPVEFNFQKGEKIHYDQVLVVDGHQWISYKSYSGIRRYIEI
```

GBS 91 contains an N-terminal leader or signal sequence region which is indicated by the underlined sequence at the beginning of SEQ ID NO: 11 above. In one embodiment, one or more amino acids from this leader or signal sequence region of GBS 91 are removed. An example of such a GBS 91 fragment is set forth below as SEQ ID NO: 12.

SEQ ID NO: 12
DQTTSVQVNNQTGTSVDANNSSNETSASSVITSNNDSVQASDKVVNSQNT
ATKDITTPLVETKPMVEKTLPEQGNYVYSKETEVKNTPSKSAPVAFYAKK
GDKVFYDQVFNKDNVKWISYKSFCGVRRYAAIESLDPSGGSETKAPTPVT
NSGSNNQEKIATQGNYTFSHKVEVKNEAKVASPTQFTLDKGDRIFYDQIL
TIEGNQWLSYKSFNGVRRFVLLGKASSVEKTEDKEKVSPQPQARITKTGR
LTISNETTTGFDILITNIKDDNGIAAVKVPVWTEQGGQDDIKWYTAVTTG
DGNYKVAVSFADHKNEKGLYNIHLYYQIASGTLVGVTGTKVTVAGTNSSQ
EPIENGLAKTGVYNIIGSTEVKNEAKISSQTQFTLEKGDKINYDQVLTAD
GYQWISYKSYSGVRRYIPVKKLTTSSEKAKDEATKPTSYPNLPKTGTYTF
TKTVDVKSQPKVSSPVEFNFQKGEKIHYDQVLVVDGHQWISYKSYSGIRR
YIEI

GBS 91 contains a C-terminal transmembrane region which may be located within the underlined region near the end of SEQ ID NO: 11 above. In one embodiment, one or more amino acids from the transmembrane and cytoplasmic regions are removed. An example of such a GBS 91 fragment is set forth below as SEQ ID NO: 13.

SEQ ID NO: 13
MKKGQVNDTKQSYSLRKYKFGLASVILGSFIMVTSPVFADQTTSVQVNNQ
TGTSVDANNSSNETSASSVITSNNDSVQASDKVVNSQNTATKDITTPLVE
TKPMVEKTLPEQGNYVYSKETEVKNTPSKSAPVAFYAKKGDKVFYDQVFN
KDNVKWISYKSFCGVRRYAAIESLDPSGGSETKAPTPVTNSGSNNQEKIA
TQGNYTFSHKVEVKNEAKVASPTQFTLDKGDRIFYDQILTIEGNQWLSYK
SFNGVRRFVLLGKASSVEKTEDKEKVSPQPQARITKTGRLTISNETTTGF
DILITNIKDDNGIAAVKVPVWTEQGGQDDIKWYTAVTTGDGNYKVAVSFA
DHKNEKGLYNIHLYYQEASGTLVGVTGTKVTVAGTNSSQEPIENGLAKTG
VYNIIGSTEVKNEAKISSQTQFTLEKGDKINYDQVLTADGYQWISYKSYS
GVRRYIPVKKLTTSSEKAKDEATKPTSYPNLPKTG

GBS 91 contains an amino acid motif indicative of a cell wall anchor: SEQ ID NO: 14 LTKTG (shown in italics in SEQ ID NO: 11 above). In one embodiment, both the transmembrane domain and the cell wall anchor motif are removed from GBS 91. An example of such a GBS 91 fragment is set forth below as SEQ ID NO: 15.

SEQ ID NO: 15
MKKGQVNDTKQSYSLRKYKFGLASVILGSFIMVTSPVFADQTTSVQVNNQ
TGTSVDANNSSNETSASSVITSNNDSVQASDKVVNSQNTATKDITTPLVE
TKPMVEKTLPEQGNYVYSKETEVKNTPSKSAPVAFYAKKGDKVFYDQVFN
KDNVKWILSYKSFCGVRRYAAIESLDPSGGSETKAPTPTNSGSNNQEKIA
TQGNYTGSHKVEVKNEAKVASPTQFTLDKGDRIFYDQILTIEGNQWLSYK
SFNGVRRFVLLGKASSVEDTEDKEKVSPQPQARITKTGRLTISNETTTFG
DIDITNIKDDNGIAAVKVPVWTEQGGQDDIKWYTAVTTGDGNYKVAVSFA
DHKNEKGLYNIHLYYQEASGTLVGVTGTKVTVAGTNSSQEPIENGLAKTG
VYNIIGSTEVKNEAKISSQTQFTLEKGDKINYDQVLTADGYQWISYKSYS
GVRRYIPVKKLTTSSEKAKDEATKPTSYPN

In one embodiment, one or more amino acids from the leader or signal sequence region and one or more amino acids from the transmembrane and cytoplasmic regions are removed from the GBS 91 sequence. An example of such a GBS 91 fragment is set forth below as SEQ ID NO: 16.

SEQ ID NO: 16
DQTTSVQVNNQTGTSVDANNSSNETSASSVITSNNDSVQASDKVVNSQNT
ATKDITTPLVETKPMVEKTLPEQGNYVYSKETEVKNTPSKSAPVAFYAKK
GDKVFYDQVFNKDNVKWISYKSFCGVRRYAAIESLDPSGGSETKAPTPVT
NSGSNNQEKIATQGNYTFSHKVEVKNEAKVASPTQFTLDKGDRIFYDQIL
TIEGNQWLSYKSFNGVRRFVLLGKASSVEKTEDKEKVSPQPQARITKTGR
LTISUETTTGFDILITNIKDDNGIAAVKVPVWTEQGGQDDIKWYTAVTTG
DGNYKVAVSFADHKNEKGLYNYHLYYQEASGTLVGVTGTKVTVAGTNSSQ
EPIENGLAKTGVYNIIGSTEVKNEAKISSQTQFTLEKGDKINYDQVLTAD
GYQWISYKSYSGVRRYIPVKKLTTSSEKAKDEATKPTSYPNLPKTG

In another embodiment, the leader or signal sequence region, the transmembrane and cytoplasmic regions, and the cell wall anchor motif are all removed from the GBS 91 sequence. An example of such a GBS 91 fragment is set forth below as SEQ ID NO: 17.

SEQ ID NO: 17
DQTTSVQVNNQTGTSVDANNSSNETSASSVITSNNDSVQASDKVVNSQNT
ATKDITTPLVETKPMVEKTLPEQGNYVYSKETEVKNTPSKSAPVAFYAKK
GDKVFYDQVFNKDNVKWISYKSFCGVRRYAAIESLDPSGGSETKAPTPVT
NSGSNNQEKIATQGNYTFSHKVEVKNEAKVASPTQFTLDKGDRIFYDQIL
TIEGNQWLSYKSFNGVRRFVLLGKASSVEKTEDKEKVSPQPQARITKTGR
LTISNETTTGFDILITNIKDDNGIAAVKVPVWTEQGGQDDIKWYTAVTTG
DGNYKVAVSFADHKNEKGLYNIHLYYQEASGTLVGVTGTKVTVAGTNSSQ
EPIENGLAKTGVYNIIGSTEVKNEAKISSQTQFTLEKGDKINYDQVLTAD
GYQWISYKSYSGVRRYIPVKKLTTSSEKAKDEATKPTSYPN

Further information regarding GBS 91 can be found in WO 01/25440 (C3 binding polypeptide), WO 01/32882 (ID-65), WO 02/31156 (BVH) and Reinscheid et al., *Microbiology* (2002) 148: 3245-3254 (bsp gene), each of which are incorporated herein by reference in their entirety.

GBS 104

GBS 104 refers to a putative cell wall surface anchor family protein. It has been referred to as emaA protein. Nucleotide and amino acid sequences of GBS 104 sequenced from serotype V isolated strain 2603 V/R are set forth in Ref. 2 as SEQ ID 8777 and SEQ ID 8778. These sequences are set forth below as SEQ ID NOS 18 and 19:

SEQ ID NO. 18
ATGAAAAAGAGACAAAAAATATGGAGAGGGTTATCAGTTACTTTACTAAT
CCTGTCCCAAATTCCATTTGGTATATTGGTACAAGGTGAAACCCAAGATA

-continued

```
CCAATCAAGCACTTGGAAAAGTAATTGTTAAAAAAACGGGAGACAATGCT

ACACCATTAGGCAAAGCGACTTTTGTGTTAAAAAATGACAATGATAAGTC

AGAAACAAGTCACGAAACGGTAGAGGGTTCTGGAGAAGCAACCTTTGAAA

ACATAAAACCTGGAGACTACACATTAAGAGAAGAAACAGCACCAATTGGT

TATAAAAAAACTGATAAAACCTGGAAAGTTAAAGTTGCAGATAACGGAGC

AACAATAATCGAGGGTATGGATGCAGATAAAGCAGAGAAACGAAAAGAAG

TTTTGAATGCCCAATATCCAAAATCAGCTATTTATGAGGATACAAAAGAA

AATTACCCATTAGTTAATGTAGAGGGTTCCAAAGTTGGTGAACAATACAA

AGCATTGAATCCAATAAATGGAAAAGATGGTCGAAGAGAGATTGCTGAAG

GTTGGTTATCAAAAAAAATTACAGGGGTCAATGATCTCGATAAGAATAAA

TATAAAATTGAATTAACTGTTGAGGGTAAAACCACTGTTGAAACGAAAGA

ACTTAATCAACCACTAGATGTCGTTGTGCTATTAGATAATTCAAATAGTA

TGAATAATGAAAGAGCCAATAATTCTCAAAGAGCATTAAAAGCTGGGGAA

GCAGTTGAAAAGCTGATTGATAAAATTACATCAAATAAAGACAATAGAGT

AGCTCTTGTGACATATGCCTCAACCATTTTTGATGGTACTGAAGCGACCG

TATCAAAGGGAGTTGCCGATCAAAATGGTAAAGCGCTGAATGATAGTGTA

TCATGGGATTATCATAAAACTACTTTTACAGCAACTACACATAATTACAG

TTATTTAAATTTAACAAATGATGCTAACGAAGTTAATATTCTAAAGTCAA

GAATTCCAAAGGAAGCGGAGCATATAAATGGGGATCGCACGCTCTATCAA

TTTGGTGCGACATTTACTCAAAAAGCTCTAATGAAAGCAAATGAAATTTT

AGAGACACAAAGTTCTAATGCTAGAAAAAAACTTATTTTTCACGTAACTG

ATGGTGTCCCTACGATGTCTTATGCCATAAATTTTAATCCTTATATATCA

ACATCTTACCAAAACCAGTTTAATTCTTTTTTAAATAAAATACCAGATAG

AAGTGGTATTCTCCAAGAGGATTTTATAATCAATGGTGATGATTATCAAA

TAGTAAAAGGAGATGGAGAGAGTTTTAAACTGTTTTCGGATAGAAAAGTT

CCTGTTACTGGAGGAACGACACAAGCAGCTTATCGAGTACCGCAAAATCA

ACTCTCTGTAATGAGTAATGAGGGATATGCAATTAATAGTGGATATATTT

ATCTCTATTGGAGAGATTACAACTGGGTCTATCCATTTGATCCTAAGACA

AAGAAAGTTTCTGCAACGAAACAAATCAAAACTCATGGTGAGCCAACAAC

ATTATACTTTAATGGAAATATAAGACCTAAAGGTTATGACATTTTTACTG

TTGGGATTGGTGTAAACGGAGATCCTGGTGCAACTCCTCTTGAAGCTGAG

AAATTTATGCAATCAATATCAAGTAAAACAGAAATTATACTAATGTTGA

TGATACAAATAAATTTATGATGAGCTAAATAAATACTTTAAAACAATTG

TTGAGGAAAAACATTCTATTGTTGATGGAAATGTGACTGATCCTATGGGA

GAGATGATTGAATTCCAATTAAAAAATGGTCAAAGTTTTACACATGATGA

TTACGTTTTGGTTGGAAATGATGGCAGTCAATTAAAAAATGGTGTGGCTC

TTGGTGGACCAAACAGTGATGGGGAATTTTAAAAGATGTTACAGTGACT

TATGATAAGACATCTCAAACCATCAAAATCATTTGAACTTAGGAAG

TGGACAAAAAGTAGTTCTTACCTATGATGTACGTTTAAAAGATAACTATA

TAAGTAACAAATTTTACAATACAAATAATCGTACAACGCTAAGTCCGAAG
```

```
AGTGAAAAAGAACCAAATACTATTCGTGATTTCCCAATTCCCAAAATTCG

TGATGTTCGTGAGTTTCCGGTACTAACCATCAGTAATCAGAAGAAAATGG

GTGAGGTTGAATTTATTAAAGTTAATAAAGACAAACATTCAGAATCGCTT

TTGGGAGCTAAGTTTCAACTTCAGATAGAAAAGATTTTTCTGGGTATAA

GCAATTTGTTCCAGAGGGAAGTGATGTTACAACAAAGAATGATGGTAAAA

TTTATTTTAAAGCACTTCAAGATGGTAACTATAAATTATATGAAATTTCA

AGTCCAGATGGCTATATAGAGGTTAAAACGAAACCTGTTGTGACATTTAC

AATTCAAAATGGAGAAGTTACGAACCTGAAAGCAGATCCAAATGCTAATA

AAAATCAAATCGGGTATCTTGAAGGAAATGGTAAACATCTTATTACCAAC

ACTCCCAAACGCCCACCAGGTGTTTTTCCTAAAACAGGGGGAATTGGTAC

AATTGTCTATATATTAGTTGGTTCTACTTTTATGATACTTACCATTTGTT

CTTTCCGTCGTAAACAATTG
```

SEQ ID NO. 19

<u>MKKRQKIWRGLSVTLLILSQIPFGILV</u>QGETQDTNQALGKVIVKKTGDNA
TPLGKATFVLKNDNDKSETSHETVEGSGEATFENIKPGDYTLREETAPIG
YKKTDKTWKVKVADNGATIIEGMDADKAEKRKEVLNAQYPKSAIYEDTKE
NYPLVNVEGSKVGEQYKALNPINGKDGREEIAEGWLSKKITGVNDLDKNK
YKIELTVEGKTTVETKELNQPLDVVVLLDNSNSMNNERANNSQRALKAGE
AVEKLIDKITSNKDNRVALVTYASTIFDGTEATVSKGVADQNGKALNDSV
SWDYHKTTFTATTHNYSYLNLTNDANEVNILKSRIPKEAEHINGDRTLYQ
FGATFTQKALMKANEILETQSSNARKKLIFHVTDGVPTMSYAINFNPYIS
TSYQNQFNSFLNKIPDRSGILQEDFIINGDDYQIVKGDGESFKLFSDRKV
PVTGGTTQAAYRVPQNQLSVMSNEGYAINSGYIYLYWRDYNWVYPFDPKT
KKVSATKQIKTHGEPTTLYFNGNIRPKGYDIFTVGIGVNGDPGATPLEAE
KFMQSISSKTENYTNVDDTNKIYDELNKYFDTIVEEKHSIVDGNVTDPMG
EMIEFQLKNGQSFTHDDYVLVGNDGSQLKNGVALGGPNSDGGILKDVTVT
YDKTSQTIKINHLNLGSGQKVVLTYDVRLKDNYISNKFYNTNNRTTLSPK
SEKEPNTIRDFPIPKIRDVREFPVLTISNQKKMGEVEFIKVNKDKHSESL
LGAKFQLQIEKDFSGYKQFVPEGSDVTTKNDGKIYFKALQDGNYKLYEIS
SPDGYIEVKTKPVVTFTIQNGEVTNLKADPNANKNQIGYLEGNGKHLITN
<u>TPKRPPGVFPKTGGIGTIVYILVGSTFMILTICSFRRKQL</u>

GBS 104 contains an N-terminal leader or signal sequence region which is indicated by the underlined sequence at the beginning of SEQ ID NO 19 above. In one embodiment, one or more amino acid sequences from the leader or signal sequence region of GBS 104 are removed. An example of such a GBS 104 fragment is set forth below as SEQ ID NO 20.

SEQ ID NO 20

GETQDTNQALGKVIVKKTGDNATPLGKATFVLKNDNDKSETSHETVEGSG
EATFENIKPGDYTLREETAPIGYKKTDKTWKVKVADNGATIIEGMDADKA
EKRKEVLNAQYPKSAIYEDTKENYPLVNVEGSKVGEQYKALNPINGKDGR
REIAEGWLSKKITGVNDLDKNKYKIELTVEGKTTVETKELNQPLDVVVLL
DNSNSMNNERANNSQRALKAGEAVEKLIDKITSNKDNRVALVTYASTIFD

```
                                                      SEQ ID NO: 22
GETQDTNQALGKVIVKKTGDNATPLGKATFVLKNDNDKSETSHETVEGSG

EATFENIKPGDYTLREETAPIGYKKTDKTWKVKVADNGATIIEGMDADKA

EKRKEVLNAQYPKSAIYEDTKENYPLVNVEGSKVGEQYKALNPINGKDGR

REIAEGWLSKKITGVNDLDKNKYKIELTVEGKTTVETKELNQPLDVVVLL

DNSNSMNNERANNSQRALKAGEAVEKLIDKITSNKDNRVALVTYALTIFD

GTEATVSKGVADQNGKALNDSVSWDYHKTTFTATTHNYSYLNLTNDANEV

NILKSRIPKEAEHINGDRTLYQFGATGTQKALMKANEILETQSSNARKKL

IFHVTDGVPTMSYAINFNPYISTSYQNQFNSFLNKIPDRSGILQEDFIIN

GDDYQIVKGDGESFKLFSDRKVPVTGGTTQAAYRVPQNQLSVMSNEGYAI

NSGYIYLYWRDYNWVYPFDPKTKKVSATKQIKTHGEPTTLYFNGNIRPKG

YDIFTVGIGVNGDPGATPLEAEKFMQSISSKTENYTNVDDTNKIYDELNK

YFKTIVEEKHSIVDGNVTDPMGEMIEFQLKNGQSFTHDDYVLVGNDGSQL

KNGVALGGPNSDGGILKDVTVTYDKTSQTIKINHLNLGSGQKVVLTYDVR

LKCNYISNKFYNTNNRTTLSPKSEKEPNTIRDFPIPKIRDVREFPVLTIS

NQKKMGEVEFIKVNKDKHSESLLGAKFQLQIEKDFSGYKQFVPEGSDVTT

KNDGKIYFKALQDGNYKLYEISSPDGYIEVKTKPVVTFTIQNGEVTNLKA

DPNANKNQIGYLEGNGKHLITNT
```

In other embodiments, additional fragments of GBS 104 are provided including an 830 amino acid fragment of GBS 104 of amino acids 28-858, a 359 amino acid fragment of GBS 104 of amino acids 28-387, a 581 amino acid fragment of GBS 104 of amino acids 28-609, or a 740 amino acid fragment of GBS 104 of amino acids 28-768.

GBS 184

GBS 184 refers to a putative lipoprotein. Nucleotide and amino acid sequences of GBS 184 sequenced from serotype V isolated strain 2603 V/R are set forth in Ref. 2 as SEQ ID 1977 and SEQ ID 1978. These sequences are also set forth below as SEQ ID NOS 23 and 24.

```
                                                      SEQ ID NO: 23
ATGAAAAAACAAAAACTATTACTGCTTATTGGAGGCTTATTAATAATGAT

AATGATGACAGCATGTAAGGATTCAAAAATCCCAGAAAACCGCACAAAGG

AAGAGTACCAAGCTGAACAAAATTTTAAACCGTTTTTTGAGTTTTTAGCA

CAAAAAGATAAAGATTTGAGCAAAATACAAAAATACTTACTATTAGTATC

GGATTCAGGTGATGCATTAGATTTAGAATATTTCTATAGTATTCAAGATT

TAAAAAAAAATAAGGATTTAGGGAAGTTTGAAACAAGAAAAAGTCAAATA

GAAAAGCCGGGTGGCTATAATGAGTTAGAAAATAAAGAGGTCCCATTTGA

ATATTTTAAAAATAATATAGTTTATCCAAAAGGAAAACCGAATATTACAT

TTGATGACTTTATTATCGGAGCAATGGATACTAAAGAATTAAAAGAATTA

AAAAAATTAAAAGTAAAAAGTTATTTATTAAAACATCCGGAAACTGAGTT

GAAAGATATAACATATGAATTGCCGACACAGTCGAAGCTTATTAAAAAA
```

```
                                                      SEQ ID NO: 24
MKKQKLLLLIGGLLIMIMMTACKDSKIPENRTKEEYQAEQNFKPFFEFLA

QKDKDLSKIQKYLLLVSDSGDALDLEYFYSIQDLKKNKDLGKFETRKSQI
```

```
EKPGGYNELENKEVPFEYFKNNIVYPKGKPNITFDDFIIGAMDTKELKEL

KKLKVKSYLLKHPETELKDITYELPTQSKLIKK
```

GBS 184 contains a N-terminal leader or signal sequence region which is indicated by the underlined sequence at the beginning of SEQ ID NO 24, above. In one embodiment, one or more amino acids from the leader or signal sequence are removed from GBS 184. An example of such a GBS 184 fragment is set forth below as SEQ ID NO: 25.

```
                                          SEQ ID NO: 25
KDSKIPENRTKEEYQAEQNFKPFFEFLAQKDKDLSKIQKYLLLVSDSGDA

LDLEYFYSIQDLKKNKDLGKFETRKSQIEKPGGYNELENKEVPFEYFKNN

IVYPKGKPNITFDDFIIGAMDTKELKELKKLKVKSYLLKHPETELKDITY

ELPTQSKLIKK
```

GBS 276

GBS 276 refers to a C5a peptidase. Nucleotide and amino acid sequences of GBS 276 sequenced from serotype V isolated strain 2603 V/R are set forth in Ref. 2 as SEQ ID 8941 and SEQ ID 8942. These sequences are set forth below as SEQ ID NOS 26 and 27:

```
                                          SEQ ID NO. 26
TTGCGTAAAAAACAAAAACTACCATTTGATAAACTTGCCATTGCGCTTAT

ATCTACGAGCATCTTGCTCAATGCACAATCAGACATTAAAGCAAATACTG

TGACAGAAGACACTCCTGCTACCGAACAAGCCGTAGAACCCCCACAACCA

ATAGCAGTTTCTGAGGAATCACGATCATCAAAGGAAACTAAAACCTCACA

AACTCCTAGTGATGTAGGAGAAACAGTAGCAGATGACGCTAATGATCTAG

CCCCTCAAGCTCCTGCTAAAACTGCTGATACACCAGCAACCTCAAAAGCG

ACTATTAGGGATTTGAACGACCCTTCTCATGTCAAAACCCTGCAGGAAAA

AGCAGGCAAGGGAGCTGGGACCGTTGTTGCAGTGATTGATGCTGGTTTTG

ATAAAAATCATGAAGCGTGGCGCTTAACAGACAAAACTAAAGCACGTTAC

CAATCAAAAGAAAATCTTGAAAAAGCTAAAAAAGAGCACGGTATTACCTA

TGGCGAGTGGGTCAATGATAAGGTTGCTTATTACCACGACTATAGTAAAG

ATGGTAAAAACGCTGTTGATCAAGAACACGGCACACACGTGTCAGGGATC

TTGTCAGGAAATGCTCCATCTGAAATGAAAGAACCTTACCGCCTAGAAGG

TGCGATGCCTGAGGCTCAATTGCTTTTGATGCGTGTCGAAATTGTAAATG

GACTAGCAGACTATGCTCGTAACTACGCTCAAGCTATCAGAGATGCTGTC

AACTTGGGAGCTAAGGTGATTAATATGAGCTTTGGTAATGCTGCACTAGC

TTACGCCAACCTTCCAGACGAAACCAAAAAAGCCTTTGACTATGCCAAAT

CAAAAGGTGTTAGCATTGTGACCTCAGCTGGTAATGATAGTAGCTTTGGG

GGCAAGCCCCGTCTACCTCTAGCAGATCATCCTGATTATGGGGTGGTTGG

GACACCTGCAGCGGCAGATTCAACATTGACAGTTGCTTCTTACAGCCCAG

ATAAACAGCTCACTGAAACTGCTACGGTCAAAACAGACGATCATCAAGAT

AAAGAAATGCCTGTTATTTCAACAAACCGTTTTGAGCCAAACAAGGCTTA

CGACTATGCTTATGCTAATCGTGGTACGAAAGAGGATGATTTTAAGGATG

TCGAAGGTAAGATTGCCCTTATTGAACGTGGCGATATTGATTTCAAAGAT

AAGATTGCAAACGCTAAAAAAGCTGGTGCTGTAGGGGTCTTGATCTATGA

CAATCAAGACAAGGGCTTCCCGATTGAATTGCCAAATGTTGACCAGATGC

CTGCGGCCTTTATCAGTCGAAGAGACGGTCTCTTATTAAAAGACAATCCC

CCAAAAACCATTACCTTCAATGCGACACCTAAGGTATTGCCAACAGCAAG

TGGCACCAAACTAAGCCGCTTCTCAAGCTGGGGTCTGACAGCTGACGGCA

ATATTAAACCGGATATTGCAGCACCCGGCCAAGATATTTTGTCATCAGTG

GCTAACAACAAGTATGCCAAACTTTCTGGAACTAGTATGTCTGCACCATT

GGTAGCGGGTATCATGGGACTGTTGCAAAAGCAATATGAGACACAGTATC

CTGATATGACACCATCAGAGCGTCTTGATTTAGCTAAGAAAGTATTGATG

AGCTCAGCAACTGCCCTATATGATGAAGATGAAAAAGCTTATTTTTCTCC

TCGCCAACAGGGAGCAGGAGCAGTCGATGCTAAAAAAGCTTCAGCAGCAA

CGATGTATGTAACAGATAAGGACAATACCTCAAGCAAGGTTCACCTGAAC

AATGTTTCTGATAAATTTGAAGTAACAGTAACAGTTCACAACAAATCTGA

TAAACCTCAAGAGTTGTATTACCAAGTAACTGTTCAAACAGATAAAGTAG

ATGGAAAACACTTTGCCTTGGCTCCTAAAGCATTGTATGAGACATCATGG

CAAAAAATCACAATTCCAGCCAATAGCAGCAAACAAGTCACCGTTCCAAT

CGATGCTAGTCGATTTAGCAAGGACTTGCTTGCCCAAATGAAAAATGGCT

ATTTCTTAGAAGGTTTTGTTCGTTTCAAACAAGATCCTACAAAAGAAGAG

CTTATGAGCATTCCATATATTGGTTTCCGAGGTGATTTTGGCAATCTGTC

AGCCTTAGAAAAACCAATCTATGATAGCAAAGACGGTAGCAGCTACTATC

ATGAAAGCAATAGTGATGCCAAAGACCAATTAGATGGTGATGGATTACAG

TTTTACGCTCTGAAAAATAACTTTACAGCACTTACCACAGAGTCTAACCC

ATGGACGATTATTAAAGCTGTCAAAGAAGGGGTTGAAAACATAGAGGATA

TCGAATCTTCAGAGATCACAGAAACCATTTTTGCAGGTACTTTTGCAAAA

CAAGACGATGATAGCCACTACTATATCCACCGTCACGCTAATGGCAAACC

ATATGCTGCGATCTCTCCAAATGGGGACGGTAACAGAGATTATGTCCAAT

TCCAAGGTACTTTCTTGCGTAATGCTAAAAACCTTGTGGCTGAAGTCTTG

GACAAAGAAGGAAATGTTGTTTGGACAAGTGAGGTAACCGAGCAAGTTGT

TAAAAACTACAACAATGACTTGGCAAGCACACTTGGTTCAACCCGTTTTG

AAAAAACGCGTTGGGACGGTAAAGATAAAGACGGCAAAGTTGTTGCTAAC

GGAACCTACACCTATCGTGTTCGCTACACGCCGATTAGCTCAGGTGCAAA

AGAACAACACACTGATTTTGATGTGATTGTAGACAATACGACACCTGAAG

TCGCAACATCGGCAACATTCTCAACAGAAGATAGTCGTTTGACACTTGCA

TCTAAACCAAAAACCAGCCAACCGGTTTACCGTGAGCGTATTGCTTACAC

TTATATGGATGAGGATCTGCCAACAACAGAGTATATTTCTCCAAATGAAG

ATGGTACCTTTACTCTTCCTGAAGAGGCTGAAACAATGGAAGGCGCTACT

GTTCCATTGAAAATGTCAGACTTTACTTATGTTGTTGAAGATATGGCTGG

TAACATCACTTATACACCAGTGACTAAGCTATTGGAGGGCCACTCTAATA

AGCCAGAACAAGACGGTTCAGATCAAGCACCAGACAAGAAACCAGAAGCT

AAACCAGAACAAGACGGTTCAGGTCAAACACCAGATAAAAAAAAGAAAC
```

```
TAAACCAGAAAAAGATAGTTCAGGTCAAACACCAGGTAAAACTCCTCAAA

AAGGTCAATCTTCTCGTACTCTAGAGAAACGATCTTCTAAGCGTGCTTTA

GCTACAAAAGCATCAACAAGAGATCAGTTACCAACGACTAATGACAAGGA

TACAAATCGTTTACATCTCCTTAAGTTAGTTATGACCACTTTCTTCTTGG

GA
```

```
                                            SEQ ID NO. 27
MRKKQKLPFDKLAIALISTSILLNAQSDIKANTVTEDTPATEQAVEPPQP

IAVSEESRSSKETKTSQTPSDVGETVADDANDLAPQAPAKTADTPATSKA

TIRDLNDPSHVKTLQEKAGKGAGTVVAVIDAGFDKNHEAWRLTDKTKARY

QSKENLEKAKKEHGITYGEWVNDKVAYYHDYSKDGKNAVDQEHGTHVSGI

LSGNAPSEMKEPYRLEGAMPEAQLLLMRVEIVNGLADYARNYAQAIRDAV

NLGAKVINMSFGNAALAYANLPDETKKAFDYAKSKGVSIVTSAGNDSSFG

GKPRLPLADHPDYGVVGTPAAADSTLTVASYSPDKQLTETATVKTDDHQD

KEMPVISTNRFEPNKAYDYAYANRGTKEDDFKDVEGKIALIERGDIDFKD

KIANAKKAGAVGVLIYDNQDKGFPIELPNVDQMPAAFISRRDGLLLKDNP

PKTITFNATPKVLPTASGTKLSRFSSWGLTADGNIKPDIAAPGQDILSSV

ANNKYAKLSGTSMSAPLVAGIMGLLQKQYETQYPDMTPSERLDLAKKVLM

SSATALYDEDEKAYFSPRQQGAGAVDAKKASAATMYVTDKDNTSSKVHLN

NVSDKFEVTVTVHNKSDKPQELYYQVTVQTDKVDGKHFALAPKALYETSW

QKITIPANSSKQVTVPIDASRFSKDLLAQMKNGYFLEGFVRFKQDPTKEE

LMSIPYIGFRGDFGNLSALEKPIYDSKDGSSYYHEANSDAKDQLDGDGLQ

FYALKNNFTALTTESNPWTIIKAVKEGVENIEDIESSEITETIFAGTFAK

QDDDSHYYIHRHANGKPYAAISPNGDGNRDYVQFQGTFLRNAKNLVAEVL

DKEGNVVWTSEVTEQVVKNYNNDLASTLGSTRFEKTRWDGKDKDGKVVAN

GTYTYRVRYTPISSGAKEQHTDFDVIVDNTTPEVATSATFSTEDSRLTLA

SKPKTSQPVYRERIAYTYMDEDLPTTEYISPNEDGTFTLPEEAETMEGAT

VPLKMSDFTYVVEDMAGNITYTPVTKLLEGHSNKPEQDGSDQAPDKKPEA

KPEQDGSGQTPDKKKETKPEKDSSGQTPGKTPQKGQSSRTLEKRSSKRAL

ATKASTRDQLPTTNDKDTNRLHLLKLVMTTFFLG
```

GBS 276 contains an N-terminal leader or signal sequence region which is indicated by the underlined sequence at the beginning of SEQ ID NO: 27 above. In one embodiment, one or more amino acids from the leader or signal sequence region of GBS 276 are removed. An example of such a GBS 276 fragment is set forth below as SEQ ID NO: 28.

```
                                            SEQ ID NO: 28
QSDIKANTVTEDTPATEQAVEPPQPIAVSEESRSSKETKTSQTPSDVGET

VADDANDLAPQAPAKTADTPATSKATIRDLNDPSHVKTLQEKAGKGAGTV

VAVIDAGFDKNHEAWRLTDKTKARYQSKENLEKAKKEHGITYGEWVUDKV

AYYHDYSKDGKNAVDQEHGTHVSGILSGNAPSEMKEPYRLEGAMPEAQLL

LMRVEIVNGLADYARNYAQAIRDAVNLGAKVINMSFGNAALAYANLPDET

KKAFDYAKSKGVSIVTSAGNDSSFGGKPRLPLADHPDYGVVGTPAAADST

LTVASYSPDkQLTETATVKTDDHQDKEMPVISTNRFEPNKAYDYAYANRG
```

```
TKEDDFKDVEGKIALIERGDIDFKDKIANAKKAGAVGVLIYDNQDKGFPI

ELPNVDQMPAAFISRRDGLLLKDNPPKTITFUATPKVLPTASGTKLSRFS

SWGLTADGNIKPDIAAPGQDILSSVANNKYAKLSGTSMSAPLVAGIMGLL

QKQYETQYPDMTPSERLDLAKKVLMSSATALYDEDEKAYFSPRQQGAGAV

DAKKASAATMYVTDKDNTSSKVHLNUVSDKFEVTVTVHNKSDKPQELYYQ

VTVQTDKVDGKHFALAPKALYETSWQKITIPANSSKQVTVPIDASRFSKD

LLAQMKNGYFLEGFVRFKQDPTKEELMSIPYIGFRGDFGNLSALEKPIYD

SKDGSSYYHEANSDAKDQLDGDGLQFYALNKKFTALTTESNPWTIIKAVK

EGVENIEDIESSEITETIFAGTFAKQDDDSHYYIHRHANGKPYAAISPNG

DGNRDYVQFQGTFLRNAKNLVAEVLDKEGNVVWTSEVTEQVVKNYNNDLA

STLGSTRFEKTRWDGKDKDGKVVANGTYTYRVRYTPISSGAKEQHTDFDV

IVDNTTPEVATSATFSTEDSRLTLASKPKTSQPVYRERIAYTYMDEDLPT

TEYISPNEDGTFTLPEEAETMEGATVPLKMSDFTYVVEDMAGNITYTPVT

KLLEGHSNKPEQDGSDQAPDKKPEAKPEQDGSGQTPDKKKETKPEKDSSG

QTPGKTPQKGQSSRTLEKRSSKRALATKASTRDQLPTTNDKDTNRLHLLK

LVMTTFFLG
```

GBS 276 contains a C-terminal transmembrane and/or cytoplasmic region which is indicated by the underlined sequence near the end of SEQ ID NO: 27 above. In one embodiment, one or more amino acids from the transmembrane or cytoplasmic regions of GBS 276 are removed. An example of such a GBS 276 fragment is set forth below as SEQ ID NO: 29.

```
                                            SEQ ID NO: 29
MRKKQKLPFDKLAIALISTSILLNAQSDIKANTVTEDTPATEQAVEPPQP

IAVSEESRSSKETKTSQTPSDVGETVADDANDLAPQAPAKTADTPATSKA

TIRDLNDPSHVKTLQEKAGKGAGTVVAVIDAGFDKNHEAWRLTDKTKARY

QSKENLEKAKKEHGITYGEWVNDKVAYYHDYSKDGKNAVDQEHGTHVSGI

LSGNAPSEMKEPYRLEGAMPEAQLLLMRVEIVNGLADYARNYAQAIRDAV

NLGAKVINMSFGNAALAYANLPDETKKAFDYAKSKGVSIVTSAGNDSSFG

GKPRLPLADHPDYGVVGTPAAADSTLTVASYSPDKQLTETATVKTDDHQD

KEMPVISTNRGEPNKAYDYAYANRGTKEDDFKDVEGKIALIERGDIDFKD

KIANAKKAGAVGVLIYDNQDKGFPIELPNVDQMPAAFISRRDGLLLKDNP

PKTITFNATPKVLPTASGTKLSRFSSWGLTADGNIKPDIAAPGQDILSSV

ANNKYAKLSGTSMSAPLVAGIMGLLQKQYETQYPDMTPSERLDLAKKVLM

SSATALYDEDEKAYFSPRQQGAGAVDAKKASAATMYVTDKDNTSSKVHLN

NVSDKFEVTVTVHNKSDKPQELYYQVTVQTDKVDGKHFALAPKALYETSW

QKITIPANSSKQVTVPIDASRFSKDLLAQMKNGYFLEGFVRFKQDPTKEE

LMSIPYIGFRGDFGNLSALEKPIYDSKDGSSYYHEANSDAKDQLDGDGLQ

FYALKNNFTALTTESNPWTIIKAVKEGVENIEDIESSEITETIFAGTFAK

QDDDSHYYIHRHANGKPYAAISPNGDGNRDYVQFQGTFLRNAKNLVAEVL

DKEGNVVWTSEVTEQVVKNYNNDLASTLGSTRFEKTRWDGKDKDGKVVAN
```

```
-continued
GTYTYRVRYTPISSGAKEQHTDFDVIVDNTTPEVATSATGSTEDSRLTLA

SKPKTSQPVYRERIAYTYMDEDLPTTEYISPNEDGTFTLPEEAETMEGAT

VPLKMSDFTYVVEDMAGNITYTPVTKLLEGHSNKPEQDGSDQAPDKKPEA

KPEQDGSGQTPDKKKETKPEKDSSGQTPGKTPQKGQSSRTLEKRSSKRAL

ATK
```

In one embodiment, one or more amino acids from the leader or signal sequence region and one or more amino acids from the transmembrane or cytoplasmic regions of GBS 276 are removed. An example of such a GBS 276 fragment is set forth below as SEQ ID NO: 30.

```
                             SEQ ID NO: 30
QSDIKANTVTEDTPATEQAVEPPQPIAVSEESRSSKETKTSQTPSDVGET

VADDANDLAPQAPAKTADTPATSKATIRDLNDPSHVKTLQEKAGKGAGTV

VAVIDAGFDKNHEAWRETDKTKARYQSKENLEKAKKEHGITYGEWVNDKV

AYYHDYSKDGKNAVDQEHGTHVSGILSGNAPSEMKEPYRLEGAMPEAQLL

LMRVEIVNGLADYARNYAQAIRDAVNLGAKVINMSFGNAALAYANLPDET

KKAFDYAKSKGVSIVTSAGNDSSFGGKPRLPLADHPDYGVVGTPAAADST

LTVASYSPDKQLTETATVKTDDHQDKEMPVISTNRFEPNKAYDYAYANRG

TKEDDFKDVEGKIALIERGDIDFKDKIANAKKAGAVGVLIYDNQDKGFPI

ELPNVDQMPAAFISRRDGLLLKDNPPKTITFNATPKVLPTASGTKLSRFS

SWGLTADGUIKFDIAAPGQDILSSVANNKYAKLSGTSMSAPLVAGIMGLL

QKQYETQYPDMTPSERLDLAKKVLMSSATALYDEDEKAYFSPRQQGAGAV

DAKKASAATMYVTDKDNTSSKVHLNNVSDKFEVTVTVHNKSDKPQELYYQ

VTVQTDKVDGKHFALAPKALYETSWQKITIPANSSKQVTVPIDASRFSKD

LLAQMKNGYFLEGFVRFKQDPTKEELMSIPYIGFRGDFGNLSALEKPIYD

SKDGSSYYHEANSDAKDQLDGDGLQFYALKNNFTALTTESNPWTIIKAVK

EGVENIEDIESSEITETIFAGTFAKQDDDSHYYIHRHANGKPYAAISPNG

DGNRDYVQFQGTFLRNAKNLVAEVLDKEGNVVWTSEVTEQVVKNYNNDLA

STLGSTRFEKTRWDGKDKDGKVVANGTYTYRVRYTPISSGAKEQHTDFDV

IVDNTTPEVATSATFSTEDSRLTLASKPKTSQPVYRERIAYTYMDEDLPT

TEYISPNEDGTFTLPEEAETMEGATVPLKMSDFTYVVEDMAGNITYTPVT

KLLEGHSNKPEQDGSDQAPDKKPEAKPEQDGSGQTPDKKKETKPEKDSSG

QTPGKTPQKGQSSRTLEKRSSKRALATK
```

Further description of GBS 276 can be found in the following references: Qi Chen et al., "Immunization with C5a Peptidase or Peptidase-Type III Polysaccharide conjugate Vaccines Enhances Clearance of Group B Streptococci from Lungs of Infected Mice", Infection and Immunity (2002) 70 (11):6409-6415; Beckmann et al., "Identification of Novel Adhesions from Group B Streptococci by Use of Phage Display Reveals that C5a Peptidase Mediates Fibronectin Binding" Infection and Immunity (2002) 70(6):2869-2876; Cheng et al., "The Group B Streptococcal C5a Peptidase Is Both a Specific Protease and an Invasin" Infection and Immunity (2002) 70(5) 2408-2413; and Cheng et al., "Antibody against Surface-Bound C5a Peptidase Is Opsonic and Initiates Macrophage Killing of Group B Streptococci" Infection and Immunity (2001) 69(4):2302-2308.

GBS 305

GBS 305 refers to a UDP-N-acetylmuramoylalanine—D-glutamate ligase, also referred to as Mur D. Nucleotide and amino acid sequences of GBS 305 sequenced from serotype V isolated strain 2603 V/R are set forth in Ref. 2 as SEQ ID 207 and SEQ ID 208. These sequences are set forth below as SEQ ID NOS 31 and 32:

```
                                    SEQ ID NO. 31
ATGGGACGAGTAATGAAAACAATAACAACATTTGAAAATAAAAAAGTTTT

AGTCCTTGGTTTAGCACGATCTGGAGAAGCTGCTGCACGTTTGTTAGCTA

GGTTAGGAGCAATAGTGACAGTTAATGATGGCAAACCATTTGATGAAAAT

CCAACAGCACAGTCTTTGTTGGAAGAGGGTATTAAAGTGGTTTGTGGTAG

TCATCCTTTAGAATTGTTAGATGAGGATTTTTGTTACATGATTAAAAATC

CAGGAATACCTTATAACAATCCTATGGTCAAAAAAGCATTAGAAAAACAA

ATCCCTGTTTTGACTGAAGTGGAATTAGCATACTTAGTTTCAGAATCTCA

GCTAATAGGTATTACAGGCTCTAACGGGAAAACGACAACGACAACGATGA

TTGCAGAAGTCTTAAATGCTGGAGGTCAGAGAGGTTTGTTAGCTGGGAAT

ATCGGCTTTCCTGCTAGTGAAGTTGTTCAGGCTGCGAATGATAAAGATAC

TCTAGTTATGGAATTATCAAGTTTTCAGCTAATGGGAGTTAAGGAATTTC

GTCCTCATATTGCAGTAATTACTAATTTAATGCCAACTCATTTAGATTAT

CATGGGTCTTTTGAAGATTATGTTGCTGCAAAATGGAATATCCAAAATCA

AATGTCTTCATCTGATTTTTTGGTACTTAATTTTAATCAAGGTATTTCTA

AAGAGTTAGCTAAAACTACTAAAGCAACAATCGTTCCTTTCTCTACTACG

GAAAAAGTTGATGGTGCTTACGTACAAGACAAGCAACTTTTCTATAAAGG

GGAGAATATTATGTCAGTAGATGACATTGGTGTCCCAGGAAGCCATAACG

TAGAGAATGCTCTAGCAACTATTGCGGTTGCTAAACTGGCTGGTATCAGT

AATCAAGTTATTAGAGAAACTTTAAGCAATTTTGGAGGTGTTAAACACCG

CTTGCAATCACTCGGTAAGGTTCATGGTATTAGTTTCTATAACGACAGCA

AGTCAACTAATATATTGGCAACTCAAAAAGCATTATCTGGCTTTGATAAT

ACTAAAGTTATCCTAATTGCAGGAGGTCTTGATCGCGGTAATGAGTTTGA

TGAATTGATACCAGATATCACTGGACTTAAACATATGGTTGTTTTAGGGG

AATCGGCATCTCGAGTAAAACGTGCTGCACAAAAAGCAGGAGTAACTTAT

AGCGATGCTTTAGATGTTAGAGATGCGGTACATAAAGCTTATGAGGTGGC

ACAACAGGGCGATGTTATCTTGCTAAGTCCTGCAAATGCATCATGGGACA

TGTATAAGAATTTCGAAGTCCGTGGTGATGAATTCATTGATACTTTCGAA

AGTCTTAGAGGAGAG

SEQ ID NO. 32
MGRVMKTITTFENKKVLVLGLARSGEAAARLLAKLGAIVTVNDGKPFDEN

PTAQSLLEEGIKVVCGSHPLELLDEDFCYMIKNPGIPYNNPMVKKALEKQ

IPVLTEVELAYLVSESQLIGITGSNGKTTTTTMIAEVLNAGGQRGLLAGN

IGFPASEVVQAANDKDTLVMELSSFQLMGVKEFRPHIAVITNLMPTHLDY

HGSFEDYVAAKWNIQNQMSSSDFLVLNFNQGISKELAKTTKATIVPFSTT

EKVDGAYVQDKQLFYKGENIMSVDDIGVPGSHNVENALATIAVAKLAGIS

NQVIRETLSNFGGVKHRLQSLGKVHGISFYNDSKSTNILATQKALSGFDN
```

TKVILIAGGLDRGNEFDELIPDITGLKHMVVLGESASRVKRAAQKAGVTY

SDALDVRDAVHKAYEVAQQGDVILLSPANASWDMYKNFEVRGDEFIDTFE

SLRGE

GBS 305 contains an N-terminal leader or signal sequence region which is indicated by the underlined sequence at the beginning of SEQ ID NO: 32 above. In one embodiment, one or more amino acids from the leader or signal sequence region are removed from GBS 305. An example of such a GBS 305 fragment is set forth below as SEQ ID NO: 33.

SEQ ID NO: 33
ITTFENKKVLVLGLARSGEAAARLLAKLGAIVTVNDGKPFDENPTAQSLL

EEGIKVVCGSHPLELLDEDFCYMIKNPGIPYNNPMVKKALEKQIPVLTEV

ELAYLVSESQLIGITGSNGKTTTTTMIAEVLNAGGQRGLLAGNIGFPASE

VVQANNDKDTLVMELSSFQLMGVKEFRPHIAVITNLMPTHLDYHGSFEDY

VAAKWNIQNQMSSSDFLVLNFNQGISKELAKTTKATIVPFSTTEKVDGAY

VQDKQLFYKGENIMSVDDIGVPGSHNVENALATIAVAKLAGISNQVIRET

LSNFGGVKHRLQSLGKVHGISFYNDSKSTNILATQKALSGFDNTKVILIA

GGLDRGNEFDELIPDITGLKHMVVLGESASRVKRAAQKAGVTYSDALDVR

DAVHKAYEVAQQGDVILLSPANASWDMYKNFEVRGDEFIDTFESLRGE

GBS 305 contains a C-terminal transmembrane or cytoplasmic region indicated by the underlined sequence near the end of SEQ ID NO: 32 above. In one embodiment, one or more amino acids from the transmembrane or cytomplasmic regions are removed from GBS 305. An example of such a GBS 305 fragment is set forth below as SEQ ID NO: 34.

SEQ ID NO: 34
MGRVMKTITTFENKKVLVLGLARSGEAAARLLAKLGAIVTVNDGKPFDEN

PTAQSLLEEGIKVVCGSHPLELLDEDFCYMIKNPGIPYNNPMVKKALEKQ

IPVLTEVELAYLVSESQLIGITGSNGKTTTTTMIAEVLNAGGQRGLLAGN

IGFPASEVVQAANDKDTLVMELSSFQLMGVKEFRPHIAVITNLMPTHLDY

HGSFEDYVAAKWNIQNQMSSSDFLVLNFNQGISKELAKTTKATIVPFSTT

EKVDGAYVQDKQLFYKGENIMSVDDIGVPGSHNVENALATIAVAKLAGIS

NQVIRETLSNFGGVKHRLQSLGKVHGISFYNDSK

In one embodiment one or more amino acids from the leader or signal sequence region and one or more amino acids from the transmembrane or cytoplasmic regions are removed from GBS 305. An example of such a GBS 305 fragment is set forth below as SEQ ID NO: 35.

SEQ ID NO: 35
ITTFENKKVLVLGLARSGEAAARLLAKLGAIVTVNDGKPFDENPTAQSL

LEEGIKVVCGSHPLELLDEDFCYMIKNPGIPYNNPMVKKALEKQIPVLT

EVELAYLVSESQLIGITGSNGKTTTTTMIAEVLNAGGQRGLLAGNIGFP

ASEVVQAANDKDTLVMELSSFQLMGVKEFRPHIAVITNLMPTHLDYHGS

FEDYVAAKWNIQNQMSSSDFLVLNFNQGISKELAKTTKATIVPFSTTEK

VDGAYVQDKQLFYKGENIMSVDDIGVPGSHNVENALATIAVAKLAGISN

QVIRETLSNFGGVKHRLQSLGKVHGISFYNDSK

GBS 322

GBS 322 refers to a surface immunogenic protein, also referred to as "sip". Nucleotide and amino acid sequences of GBS 322 sequenced from serotype V isolated strain 2603 V/R are set forth in Ref. 2 as SEQ ID 8539 and SEQ ID 8540. These sequences are set forth below as SEQ ID NOS 36 and 37:

SEQ ID NO. 36
ATGAATAAAAAGGTACTATTGACATCGACAATGGCAGCTTCGCTATTATC

AGTCGCAAGTGTTCAAGCACAAGAAACAGATACGACGTGGACAGCACGTA

CTGTTTCAGAGGTAAAGGCTGATTTGGTAAAGCAAGACAATAAATCATCA

TATACTGTGAAATATGGTGATACACTAAGCGTTATTTCAGAAGCAATGTC

AATTGATATGAATGTCTTAGCAAAAATAAATAACATTGCAGATATCAATC

TTATTTATCCTGAGACAACACTGACAGTAACTTACGATCAGAAGAGTCAT

ACTGCCACTTCAATGAAAATAGAAACACCAGCAACAAATGCTGCTGGTCA

AACAACAGCTACTGTGGATTTGAAAACCAATCAAGTTTCTGTTGCAGACC

AAAAAGTTTCTCTCAATACAATTTCGGAAGGTATGACACCAGAAGCAGCA

ACAACGATTGTTTCGCCAATGAAGACATATTCTTCTGCGCCAGCTTTGAA

ATCAAAAGAAGTATTAGCACAAGAGCAAGCTGTTAGTCAAGCAGCAGCTA

ATGAACAGGTATCACCAGCTCCTGTGAAGTCGATTACTTCAGAAGTTCCA

GCAGCTAAAGAGGAAGTTAAACCAACTCAGACGTCAGTCAGTCAGTCAAC

AACAGTATCACCAGCTTCTGTTGCCGCTGAAACACCAGCTCCAGTAGCTA

AAGTAGCACCGGTAAGAACTGTAGCAGCCCCTAGAGTGGCAAGTGTTAAA

GTAGTCACTCCTAAAGTAGAAACTGGTGCATCACCAGAGCATGTATCAGC

TCCAGCAGTTCCTGTGACTACGACTTCACCAGCTACAGACAGTAAGTTAC

AAGCGACTGAAGTTAAGAGCGTTCCGGTAGCACAAAAAGCTCCAACAGCA

ACACCGGTAGCACAACCAGCTTCAACAACAAATGCAGTAGCTGCACATCC

TGAAAATGCAGGGCTCCAACCTCATGTTGCAGCTTATAAAGAAAAAGTAG

CGTCAACTTATGGAGTTAATGAATTCAGTACATACCGTGCGGGAGATCCA

GGTGATCATGGTAAAGGTTTAGCAGTTGACTTTATTGTAGGTACTAATCA

AGCACTTGGTAATAAAGTTGCACAGTACTCTACACAAAATATGGCAGCAA

ATAACATTTCATATGTTATCTGGCAACAAAAGTTTTACTCAAATACAAAC

AGTATTTATGGACCTGCTAATACTTGGAATGCAATGCCAGATCGTGGTGG

CGTTACTGCCAACCACTATGACCACGTTCACGTATCATTTAACAAATAAT

ATAAAAAGGAAGCTATTTGGCTTCTTTTTTATATGCCTTGAATAGACTT

TCAAGGTTCTTATATAATTTTTATTA

SEQ ID NO. 37
MNKKVLLTSTMAASLLSVASVQAQETDTTWTARTVSEVKADLVKQDNKSS

YTVKYGDTLSVISEAMSIDMNVLAKINNIADINLIYPETTLTVTYDQKSH

TATSMKIETPATNAAGQTTATVDLKTNQVSVADQKVSLNTISEGMTPEAA

TTIVSPMKTYSSAPALKSKEVLAQEQAVSQAAANEQVSPAPVKSITSEVP

-continued

AAKEEVKPTQTSVSQSTTVSPASVAAETPAPVAKVAPVRTVAAPRVASVK

VVTPKVETGASPEHVSAPAVPVTTTSPATDSKLQATEVKSVPVAQKAPTA

TPVAQPASTTNAVAAHPENAGLQPHVAAYKEKVASTYGVNEFSTYRAGDP

GDHGKGLAVDFIVGTNQALGNKVAQYSTQNMAANNISYVIWQQKFYSNTN

SIYGPANTWNAMPDRGGVTANHYDHVHVSFNK

GBS 322 contains an N-terminal leader or signal sequence region which is indicated by the underlined sequence near the beginning of SEQ ID NO: 37. In one embodiment, one or more amino acids from the leader or signal sequence region of GBS 322 are removed. An example of such a GBS 322 fragment is set forth below as SEQ ID NO: 38.

SEQ ID NO: 38
DLVKQDNKSSYTVKYGDTLSVISEAMSIDMNVLAKINNIADINLIYFETT

LTVTYDQKSHTATSMKIETPATNAAGQTTATVDLKTNQVSVADQKVSLNT

ISEGMTPEAATTIVSPMKTYSSAPALKSKEVLAQEQAVSQAAANEQVSPA

PVKSITSEVPAAKEEVKPTQTSVSQSTTVSPASVAAETPAPVAKVAPVRT

VAAPRVASVKVVTPKVETGASPEHVSAPAVPVTTTSPATDSKLQATEVKS

VPVAQKAPTATPVAQPASTTNAVAAHPENAGLQPHVAAYKEKVASTYGVN

EFSTYRAGDPGDHGKGLAVDFIVGTNQALGNKVAQYSTQNMAANNISYVI

WQQKFYSNTNSIYGPANTWNAMPDRGGVTANHYDHVHVSFNK

GBS 330

GBS 330 refers to a pyruvate kinase, also referred to as "pyk". Nucleotide and amino acid sequences of GBS 330 sequenced from serotype V isolated strain 2603 V/R are set forth in Ref. 2 as SEQ ID 8791 and SEQ ID 8792. These sequences are set forth below as SEQ ID NOS 39 and 40:

SEQ ID NO. 39
ATGAATAAACGCGTAAAAATCGTTGCAACACTTGGTCCTGCGGTTGAATT

CCGTGGTGGTAAGAAGTTTGGTGAGTCTGGATACTGGGGTGAAAGCCTTG

ACGTAGAAGCTTCAGCAGAAAAAATTGCTCAATTGATTAAAGAAGGTGCT

AACGTTTTCCGTTTCAACTTCTCACATGGAGATCATGCTGAGCAAGGAGC

TCGTATGGCTACTGTTCGTAAAGCAGAAGAGATTGCAGGACAAAAAGTTG

GCTTCCTCCTTGATACTAAAGGACCTGAAATTCGTACAGAACTTTTTGAA

GATGGTGCAGATTTCCATTCATATACAACAGGTACAAAATTACGTGTTGC

TACTAAGCAAGGTATCAAATCAACTCCAGAAGTGATTGCATTGAATGTTG

CTGGTGGACTTGACATCTTTGATGACGTTGAAGTTGGTAAGCAAATCCTT

GTTGATGATGGTAAACTAGGTCTTACTGTGTTTGCAAAAGATAAAGACAC

TCGTGAATTTGAAGTAGTTGTTGAGAATGATGGCCTTATTGGTAAACAAA

AAGGTGTAAACATCCCTTATACTAAAATTCCTTTCCCAGCACTTGCAGAA

CGCGATAATGCTGATATCCGTTTTGGACTTGAGCAAGGACTTAACTTTAT

TGCTATCTCATTTGTACGTACTGCTAAAGATGTTAATGAAGTTCGTGCTA

TTTGTGAAGAAACTGGSMATGGACACGTTAAGTTGTTTGCTAAAATTGAA

AATCAACAAGGTATCGATAATATTGATGAGATTATCGAAGCAGCAGATGG

-continued
TATTATGATTGCTCGTGGTGATATGGGTATCGAAGTTCCATTTGAAATGG

TTCCAGTTTACCAAAAAATGATCATTACTAAAGTTAATGCAGCTGGTAAA

GCAGTTATTACAGCAACAAATATGCTTGAAACAATGACTGATAAACCACG

TGCGACTCGTTCAGAAGTATCTGATGTCTTCAATGCTGTTATTGATGGTA

CTGATGCTACAATGCTTTCAGGTGAGTCAGCTAATGGTAAATACCCAGTT

GAGTCAGTTCGTACAATGGCTACTATTGATAAAAATGCTCAAACATTACT

CAATGAGTATGGTCGCTTAGACTCATCTGCATTCCCACGTAATAACAAAA

CTGATGTTATTGCATCTGCGGTTAAAGATGCAACACACTCAATGGATATC

AAACTTGTTGTAACAATTACTGAAACAGGTAATACAGCTCGTGCCATTTC

TAAATTCCGTCCAGATGCAGACATTTTGGCTGTTACATTTGATGAAAAAG

TACAACGTTCATTGATGATTAACTGGGGTGTTATCCCTGTCCTTGCAGAC

AAACCAGCATCTACAGATGATATGTTTGAGGTTGCAGAACGTGTAGCACT

TGAAGCAGGATTTGTTGAATCAGGCGATAATATCGTTATCGTTGCAGGTG

TTCCTGTAGGTACAGGTGGAACTAACACAATGCGTGTTCGTACTGTTAAA

SEQ ID NO. 40
MNKRVKIVATLGPAVEFRGGKKFGESGYWGESLDVEASAEKIAQLIKEGA

NVFRFNFSHGDHAEQGARMATVRKAEEIAGQKVGFLLDTKGPEIRTELFE

DGADFHSYTTGTKLRVATKQGIKSTPEVIALNVAGGLDIFDDVEVGKQIL

VDDGKLGLTVFAKDKDTREFEVVVENDGLIGKQKGVNIPYTKIPFPALAE

RDNADIRFGLEQGLNFIAISFVRTAKDVNEVRAICEETGXGHVKLFAKIE

NQQGIDNIDEIIEAADGIMIARGDMGIEVPFEMVPVYQKMIITKVNAAGK

AVITATNMLETMRDKPRATRSEVSDVFNAVIDGTDATMLSGESANGKYPV

ESVRTMATIDKNAQTLLNEYGRLDSSAFPRNNKTDVIASAVKDATHSMDI

KLVVTITETGNTARAISKFRPDADILAVTFDEKVQRSLMINWGVIPVLAD

KPASTDDMFEVAERVALEAGFVESGDNIVIVAGVPVGTGGTNTMRVRTVK

GBS 338

GBS 338 refers to a Sat D protein. Nucleotide and amino acid sequences of GBS 338 sequenced from serotype V isolated strain 2603 V/R are set forth in Ref. 2 as SEQ ID 8637 and SEQ ID 8638. These sequences are set forth below as SEQ ID NOS 41 and 42:

SEQ ID NO. 41
TTGTCTGCTATAATAGACAAAAAGGTGGTGATATTTATGTATTTAGCATT

AATCGGTGATATCATTAATTCAAAACAGATACTTGAACGTGAAACTTTCC

AACAGTCTTTTCAGCAACTAATGACCGAACTATCTGATGTATATGGTGAA

GAGCTGATTTCTCCATTCACTATTACAGCTGGTGATGAATTTCAAGCTTT

ATTGAAACCATCAAAAAAGGTATTTCAAATTATTGACCATATTCAACTAG

CTCTAAAACCTGTTAATGTAAGGTTCGGCCTCGGTACAGGAAACATTATA

ACATCCATCAATTCAAATGAAAGTATCGGTGCTGATGGTCCTGCCTACTG

GCATGCTCGCTCAGCTATTAATCATATACATGATAAAAATGATTATGGAA

CAGTTCAAGTAGCTATTTGCCTTGATGATGAAGACCAAAACCTTGAATTA

ACACTAAATAGTCTCATTTCAGCTGGTGATTTTATCAAGTCAAAATGGAC

TACAAACCATTTTCAAATGCTTGAGCACTTAATACTTCAAGATAATTATC

AAGAACAATTTCAACATCAAAAGTTAGCCCAACTGGAAAATATTGAACCT

AGTGCGCTGACTAAACGCCTTAAAGCAAGCGGTCTGAAGATTTACTTAAG

AACGAGAACACAGGCAGCCGATCTATTAGTTAAAAGTTGCACTCAAACTA

AAGGGGGAAGCTATGATTTC

SEQ ID NO.42
MSAIIDKKVVIFMYLALIGDIINSKQILERETFQQSFQQLMTELSDVYGE

ELISPFTITAGDEFQALLKPSKKVFQIIDHIQLALKPVNVRFGLGTGNII

TSINSNESIGADGPAYWHARSAINHIHDKNDYGTVQVAICLDDEDQNLEL

TLUSLISAGDFIKSKWTTNHFQMLEHLILQDNYQEQFQEQKLAQLENIEP

SALTKRLKASGLKIYLRTRTQAADLLVKSCTQTKGGSYDF

GBS 338 may contain an N-terminal leader or signal sequence region which is indicated by the underlined sequence at the beginning of SEQ ID NO: 42 above. In one embodiment, one or more amino acids from the leader or signal sequence region are removed from GBS 338. An example of such a GBS 338 fragment is set forth below as SEQ ID NO: 43.

SEQ ID NO: 43
MYLALIGDIINSKQILERETFQQSFQQLMTELSDVYGEELISPFTITAGD

EFQALLKPSKKVFQIIDHIQLALKPVNVRFGLGTGNIITSINSNESIGAD

GPAYWHARSAINHIHDKNDYGTVQVAICLDDEDQNLELTLNSLISAGDFI

KSKWTTNHFQMLEHLILQDNYQEQFQHQKLAQLENIEPSALTKRLKASGL

KIYLRTRTQAADLLVKSCTQTKGGSYDF

GBS 361

GBS 361 refers to a cylI protein. Nucleotide and amino acid sequences of GBS 361 sequenced from serotype V isolated strain 2603 V/R are set forth in Ref. 2 as SEQ ID 8769 and SEQ ID 8770. These sequences are set forth below as SEQ ID NOS 44 and 45:

SEQ ID NO. 44
ATGAGCGTATATGTTAGTGGAATAGGAATTATTTCTTCTTTGGGAAAGAA

TTATAGCGAGCATAAACAGCATCTCTTCGACTTAAAAGAAGGAATTTCTA

AACATTTATATAAAAATCACGACTCTATTTTAGAATCTTATACAGGAAGC

ATAACTAGTGACCCAGAGGTTCCTGAGCAATACAAAGATGAGACACGTAA

TTTTAAATTTGCTTTTACCGCTTTTGAAGAGGCTCTTGCTTCTTCAGGTG

TTAATTTAAAAGCTTATCATAATATTGCTGTGTGTTTAGGGACCTCACTT

GGGGGAAAGAGTGCTGGTCAAAATGCCTTGTATCAATTTGAAGAAGGAGA

GCGTCAAGTAGATGCTAGTTTATTAGAAAAAGCATCTGTTTACCATATTG

CTGATGAATTGATGGCTTATCATGATATTGTGGGAGCTTCGTATGTTATT

TCAACCGCCTGTTCTGCAAGTAATAATGCCGTAATATTAGGAACACAATT

ACTTCAAGATGGCGATTGTGATTTAGCTATTTGTGGTGGCTGTGATGAGT

TAAGTGATATTTCTTTAGCAGGCTTCACATCACTAGGAGCTATTAATACA

GAAATGGCATGTCAGCCCTATTCTTCTGGAAAAGGAATCAATTTGGGTGA

GGGCGCTGGTTTTGTTGTTCTTGTCAAAGATCAGTCCTTAGCTAAATATG

GAAAAATTATCGGTGGTCTTATTACTTCAGATGGTTATCATATAACAGCA

CCTAAGCCAACAGGTGAAGGGGCGGCACAGATTGCAAAGCAGCTAGTGAC

TCAAGCAGGTATTGACTACAGTGAGATTGACTATATTAACGGTCACGGTA

CAGGTACTCAAGCTAATGATAAAATGGAAAAAAATATGTATGGTAAGTTT

TTCCCGACAACGACATTGATCAGCAGTACCAAGGGGCAAACGGGTCATAC

TCTAGGGGCTGCAGGTATTATCGAATTGATTAATTGTTTAGCGGCAATAG

AGGAACAGACTGTACCAGCAACTAAAAATGAGATTGGGATAGAAGGTTTT

CCAGAAAATTTTGTCTATCATCAAAAGAGAGAATACCCAATAAGAAATGC

TTTAAATTTTTCGTTTGCTTTTGGTGGAAATAATAGTGGTGTCTTATTGT

CATCTTTAGATTCACCTCTAGAAACATTACCTGCTAGAGAAAATCTTAAA

ATGGCTATCTTATCATCTGTTGCTTCCATTTCTAAGAATGAATCACTTTC

TATAACCTATGAAAAAGTTGCTAGTAATTTCAACGACTTTGAAGCATTAC

GCTTTAAAGGGGCTAGACCACCCAAAACTGTCAACCCAGCACAATTTAGG

AAAATGGATGATTTTTCCAAAATGGTTGCCGTAACAACAGCTCAAGCACT

AATAGAAAGCAATATTAATCTAAAAAAACAAGATACTTCAAAAGTAGGAA

TTGTATTTACAACACTTTCTGGACCAGTTGAGGTTGTTGAAGGTATTGAA

AAGCAAATCACAACAGAAGGATATGCACATGTTTCTGCTTCACGATTCCC

GTTTACAGTAATGAATGCAGCAGCTGGTATGCTTTCTATCATTTTTAAAA

TAACAGGTCCTTTATCTGTCATTTCGACAAATAGTGGAGCGCTTGATGGT

ATACAATATGCCAAGGAAATGATGCGTAACGATAATCTAGACTATGTGAT

TCTTGTTTCTGCTAATCAGTGGACAGACATGAGTTTTATGTGGTGGCAAC

AATTAAACTATGATAGTCAAATGTTTGTCGGTTCTGATTATTGTTCAGCA

CAAGTCCTCTCTCGTCAAGCATTGGATAATTCTCCTATAATATTAGGTAG

TAAACAATTAAAATATAGCCATAAAACATTCACAGATGTGATGACTATTT

TTGATGCTGCGCTTCAAAATTTATTATCAGACTTAGGACTAACCATAAAA

GATATCAAAGGTTTCGTTTGGAATGAGCGGAAGAAGGCAGTTAGTTCAGA

TTATGATTTCTTAGCGAACTTGTCTGAGTATTATAATATGCCAAACCTTG

CTTCTGGTCAGTTTGGATTTTCATCTAATGGTGCTGGTGAAGAACTGGAC

TATACTGTTAATGAAAGTATAGAAAAGGGCTATTATTTAGTCCTATCTTA

TTCGATCTTCGGTGGTATCTCTTTTGCTATTATTGAAAAAAGG

SEQ ID NO. 45
MSVYVSGIGIISSLGKNYSEHKQHLFDLKEGISKHLYKNHDSILESYTGS

ITSDPEVPEQYKDETRNFKFAFTAFEEALASSGVNLKAYHNIAVCLGTSL

GGKSAGQNALYQFEEGERQVDASLLEKASVYHIADELMAYHDIVGASYVI

STACSASNNAVILGTQLLQDGDCDLAICGGCDELSDISLAGFTSLGAINT

EMACQPYSSGKGINLGEGAGFVVLVKDQSLAKYGKIIGGLITSDGYHITA

PKPTGEGAAQIAKQLVTQAGIDYSEIDYINGHGTGTQANDKMEKNMYGDF

FPTTTLISSTKGQTGHTLGAAGIIELINCLAAIEEQTVPATKNEIGIEGF

PENFVYHQKREYPIRNALNGSFAFGGNNSGVLSSLDSPLETLRARENTLK

MAILSSVASISKNESLSITYEKVASNFNDFEALRFKGARPPKTVNPAQFR

KMDDFSKMVAVTTAQALIESNINLKKODTSKVGIVFTTLSGPVEVVEGIE

KQITTEGYAHVSASRFPFTVMNAAAGMLSIIFKITGPLSVISTNSGALDG

IQYAKEMMRNDNLDYVILVSANQWTDMSFMWWQQLNYDSQMFVGSDYCSA

QVLSRQALDNSPIILGSKQLKYSHKTFTDVMTIFDAALQNLLSDLGLTIK

DIKGFVWNERKKAVSSDYDFLANLSEYYNMPNLASGQFGFSSNGAGEELD

YTVNESDIEKGYYLVLSYSIGGISFAIIEKR

GBS 361 may contain an N-terminal leader or signal sequence region which is indicated by the underlined sequence at the beginning of SEQ ID NO: 45 above. In one embodiment, one or more amino acids from the leader or signal sequence region are removed from GBS 361. An example of such a GBS 361 fragment is set forth below as SEQ ID NO: 46.

SEQ ID NO: 46
VSGIGIISSLGKNYSEHKQHLFDLKEGISKHLYKNHDSILESYTGSITSD

PEVPEQYKDETRNFKFAFTAFEEALASSGVNLKAYHNIAVCLGTSLGGKS

AGQNALYQFEEGERQVDASLLEKASVYHIADELMAYHDIVGASYVISTAC

SASNNAVILGTQLLQDGDCDLAICGGCDELSDISLAGFTSLGAINTEMAC

OPYSSGKGINLGEGAGFVVLVKDQSLAKYGKIIGGLITSDGYHITAPKPT

GEGAAQIAKQLVTQAGIDYSEIDYINGHGTGTQANDKMEKNMYGDFFPTT

TLISSTKGQTGHTLGAAGIIELINCLAAIEEQTVPATKNEIGIEGFPENF

VYHQKREYPIRNALNGSFAFGGNNSGVLSSLDSPLETLRARENTLKMAIL

SSVASISKNESLSITYEKVASNFNDFEALRFKGARPPKTVNPAQFRKMDD

FSKMVAVTTAQALIESNINLKKODTSKVGIVFTTLSGPVEVVEGIEKQIT

TEGYAHVSASRFPFTVMNAAAGMLSIIFKITGPLSVISTNSGALDGIQYA

KEMMRNDNLDYVILVSANQWTDMSFMWWQQLNYDSQMFVGSDYCSAQVLS

RQALDNSPIILGSKQLKYSHKTFTDVMTIFDAALQNLLSDLGLTIKDIKG

FVWNERKKAVSSDYDFLANLSEYYNMPNLASGQFGFSSNGAGEELDYTVN

ESDIEKGYYLVLSYSIGGISFAIIEKR

GBS 404

Nucleotide and amino acid sequences of GBS 404 sequenced from serotype V isolated strain 2603 V/R are set forth in Ref. 2 as SEQ ID 8799 and SEQ ID 8800. These sequences are set forth below as SEQ ID NOS 47 and 48:

SEQ ID NO. 47
ATGAAAATAGATGACCTAAGAAAAAGCGACAATGTTGAAGATCGTCGCTC

CAGTAGCGGAGGTTCATTCTCTAGCGGAGGAAGTGGATTACCGATTCTTC

AACTTTTATTGCTGCGAGGGAGTTGGAAAACCAAGCTTGTGGTTTTAATC

ATCTTACTGCTACTTGGCGGAGGGGGACTAACCAGCATTTTTAATGACTC

ATCCTCACCTTCTAGTTACCAATCTCAGAATGTCTCACGTTCTGTTGATA

ATAGCGCAACGAGAGAACAAATCGATTTCGTTAATAAAGTCCTTGGCTCA

ACTGAGGATTTCTGGTCACAAGAATTCCAAACCCAAGGTTTTGGAAATTA

TAAGGAACCAAAACTTGTTCTTTACACCAATTCAATTCAAACAGGTTGTG

GTATAGGTGAATCTGCTTCAGGACCATTTTATTGTTCAGCAGATAAAAAA

ATCTATCTTGATATTTCTTTTTACAATGAATTATCACATAAATATGGTGC

TACTGGTGATTTTGCTATGGCCTACGTCATCGCCCACGAAGTTGGTCACC

ACATTCAAACAGAGTTAGGCATTATGGATAAGTATAATAGAATGCGACAC

GGACTTACTAAGAAAGAAGCAAATGCTTTAAATGTTCGGCTAGAACTTCA

AGCAGATTATTATGCAGGGGTATGGGCTCACTACATCAGGGGAAAAAATC

TCTTAGAACAAGGAGACTTTGAAGAGGCCATGAATGCTGCCCACGCCGTC

GGAGACGATACCCTTCAGAAAGAAACCTACGGAAAATTAGTGCCTGATAG

CTTTTACCCATGGAACAGCTGAACAACGCCAACGTTGGTTTAACAAAGGCT

TTCAATATGGTGACATCCAACACGGTGATACTTTCTCCGTAGAACATCTA

SEQ ID NO. 48
MKIDDLRKSDNVEDRRSSSGGGSFSSGGSGLPILQLLLLRGSWKTKLVVLI

ILLLLGGGGLTSIFNDSSSPSSYQSQNVSRSVDNSATREQIDFVNKVLGS

TEDFWSQEFQTQGFGNYKEPKLVLYTNSIQTGCGIGESASGPFYCSADKK

IYLDISFYNELSHKYGATGDFAMAYVIAHEVGHHIQTELGIMDKYNRMRH

GLTKKEANALNVRLELQADYYAGVWAHYIRGKNLLEQGDFEEAMNAAHAV

GDDTLQKETYGKLVPDSFTHGTAEQRQRWFNKGFQYGDIQHGDTFSVEHL

GBS 690

Nucleotide and amino acid sequences of GBS 690 sequenced from serotype V isolated strain 2603 V/R are set forth in Ref. 2 as SEQ ID 9965 and SEQ ID 9966. These sequences are set forth as SEQ ID NOS 49 and 50 below:

SEQ ID NO. 49
ATGAGTAAACGACAAAATTTAGGAATTAGTAAAAAAGGAGCAATTATATC

AGGGCTCTCAGTGGCACTAATTGTAGTAATAGGTGGCTTTTTATGGGTAC

AATCTCAACCTAATAAGAGTGCAGTAAAAACTAACTACAAAGTTTTTAAT

GTTAGAGAAGGAAGTGTTTCGTCCTCAACTCTTTTGACAGGAAAAGCTAA

GGCTAATCAAGAACAGTATGTGTATTTTGATGCTAATAAAGGTAATCGAG

CAACTGTCACAGTTAAAGTGGGTGATAAAATCACAGCTGGTCAGCAGTTA

GTTCAATATGATCAACAACTGCACAAGCAGCCTACGACACTGCTAATCG

TCAATTAAATAAAGTAGCGCGTCAGATTAATAATCTAAAGACAACAGGAA

GTCTTCCAGCTATGGAATCAAGTGATCAATCTTCTTCATCATCACAAGGA

CAAGGGACTCAATCGACTAGTGGTGCGACGAATCGTCTACAGCAAAATTA

TCAAAGTCAAGCTAATGCTTCATACAACCAACAACTTCAAGATTTGAATG

ATGCTTATGCAGATGCACAGGCAGAAGTAAATAAAGCACAAAAAGCATTG

AATGATACTGTTATTACAAGTGACGTATCAGGGACAGTTGTTGAAGTTAA

TAGTGATATTGATCCAGCTTCAAAAACTAGTCAAGTACTTGTCCATGTAG

CAACTGAAGGTAAACTCCAAGTACAAGGAACGATGAGTGAGTATGATTTG

GCTAATGTTAAAAAAGACCAGGCTGTTAAAATAAAATCTAAGGTCTATCC

TGACAAGGAATGGGAAGGTAAAATTTCATATATCTCAAATTATCCAGAAG

CAGAAGCAAACAACAATGACTCTAATAACGGCTCTAGTGCTGTAAATTAT

AAATATAAAGTAGATATTACTAGCCCTCTCGATGCATTAAAACAAGGTTT

TACCGTATCAGTTGAAGTAGTTAATGGAGATAAGCACCTTATTGTCCCTA

CAAGTTCTGTGATAAACAAAGATAATAAACACTTTGTTTGGGTATACAAT

```
GATTCTAATCGTAAAATTTCCAAAGTTGAAGTCAAAATTGGTAAAGCTGA

TGCTAAGACACAAGAAATTTTATCAGGTTTGAAAGCAGGACAAATCGTGG

TTACTAATCCAAGTAAAACCTTCAAGGATGGGCAAAAAATTGATAATATT

GAATCAATCGATCTTAACTCTAATAAGAAATCAGAGGTGAAA
```

SEQ ID NO. 50
```
MSKRQNLGISKKGAIISGLSVALIVVIGGFLWVQSQPNKSAVKTNYKVFN

VREGSVSSSTLLTGKAKANQEQYVYFDANKGNRATVTVKVGDKITAGQQL

VQYDTTTAQAAYDTANRQLNKVARQINNLKTTGSLPAMESSDQSSSSSQG

QGTQSTSGATNRLQQNYQSQANASYNQQLQDLNDAYADAQAEVNKAQKAL

NDTVITSDVSGTVVEVNSDIDPASKTSQVLVHVATEGKLQVQGTMSEYDL

ANVKKDQAVKIKSKVYPDKEWEGKISYISNYPEAEANNNDSNNGSSAVNY

KYKVDITSPLDALKQGFTVSVEVVNGDKHLIVPTSSVINKDNKHFVWVYN

DSNRKISKVEVKIGKADAKTQEILSGLKAGQIVVTNPSKTFKDGQKIDNI

ESIDLNSNKKSEVK
```

GBS 690 contains an N-terminal leader or signal sequence region which is indicated by the underlined sequence at the beginning of SEQ ID NO: 50 above. In one embodiment, one or more amino acids from the leader or signal sequence region of GBS 690 are removed. An example of such a GBS 690 fragment is set forth below as SEQ ID NO: 51.

SEQ ID NO: 51
```
FLWVQSQPNKSAVKTNYKVFNVREGSVSSSTLLTGKAKANQEQYVYFDAN

KGNRATVTVKVGDKITAGQQLVQYDTTTAQAAYDTANRQLNKVARQINNL

KTTGSLPAMESSDQSSSSSQGQGTQSTSGATNRLQQNYQSQANASYNQQL

QDLNDAYADAQAEVNKAQKALNDTVITSDVSGTVVEVNSDIDPASKTSQV

LVHVATEGKLQVQGTMSEYDLANVKKDQAVKIKSKVYPDKEWEGKISYIS

NYPEAEANNNDSNNGSSAVNYKYKVDITSPLDALKQGFTVSVEVVNGDKH

LIVPTSSVINKDNKHFVWVYNDSNRKISKVEVKIGKADAKTQEILSGLKA

GQIVVTNPSKTFKDGQKIDNIESIDLNSNKKSEVK
```

GBS 691

GBS 691 refers to an iron compound ABC transporter, or a substrate binding protein. Nucleotide and amino acid sequences of GBS 691 sequenced from serotype V isolated strain 2603 V/R are set forth in Ref. 2 as SEQ ID 3691 and SEQ ID 3692. These sequences are set forth as SEQ ID NOS 52 and 53 below:

SEQ ID NO. 52
```
ATGAAAAAAATTGGAATTATTGTCCTCACACTACTGACCTTCTTTTTGGT

ATCTTGCGGACAACAAACTAAACAAGAAAGCACTAAAACAACTATTTCTA

AAATGCCTAAAATTGAAGGCTTCACCTATTATGGAAAAATTCCTGAAAAT

CCGAAAAAAGTAATTAATTTTACATATTCTTACACTGGGTATTTATTAAA

ACTAGGTGTTAATGTTTCAAGTTACAGTTTAGACTTAGAAAAAGATAGCC

CCGTTTTTGGTAAACAACTGAAAGAAGCTAAAAAATTAACTGCTGATGAT

ACAGAAGCTATTGCCGCACAAAAACCTGATTTAATCATGGTTTTCGATCA

AGATCCAAACATCAATACTCTGAAAAAAATTGCACCAACTTTAGTTATTA

AATATGGTGCACAAAATTATTTAGATATGATGCCAGCCTTGGGGAAAGTA

TTCGGTAAAGAAAAAGAAGCTAATCAGTGGGTTAGCCAATGGAAAACTAA

AACTCTCGCTGTCAAAAAAGATTTACACCATATCTTAAAGCCTAACACTA

CTTTTACTATTATGGATTTTTATGATAAAAATATCTATTTATATGGTAAT

AATTTTGGACGCGGTGGAGAACTAATCTATGATTCACTAGGTTATGCTGC

CCCAGAAAAAGTCAAAAAAGATGTCTTTAAAAAAGGGTGGTTTACCGTTT

CGCAAGAAGCAATCGGTGATTACGTTGGAGATTATGCCCTTGTTAATATA

AACAAAACGACTAAAAAAGCAGCTTCATCACTTAAAGAAAGTGATGTCTG

GAAGAATTTACCAGCTGTCAAAAAAGGGCACATCATAGAAAGTAACTACG

ACGTGTTTTATTTCTCTGACCCTCTATCTTTAGAAGCTCAATTAAAATCA

TTTACAAAGGCTATCAAAGAAAATACAAAT
```

SEQ ID NO. 53
```
MKKIGIIVLTLLTFFLVSCGQQTKQESTKTTISKMPKIEGFTYYGKIPEN

PKKVINFTYSYTGYLLKLGVNVSSYSLDLEKDSPVFGKQLKEAKKLTADD

TEAIAAQKPDLIMVFDQDPNINTLKKIAPTLVIKYGAQNYLDMMPALGKV

FGKEKEANQWVSQWKTKTLAVKKDLHHILKPNTTFTIMDFYDKNIYLYGN

NFGRGGELIYDSLGYAAPEKVKKDVFKKGWFTVSQEAIGDYVGDYALVNI

NKTTKKAASSLKESDVWKNLPAVKKGHIIESNYDVFYFSPLSLEAQLKSF

TKAIKENTN
```

GBS 691 contains an N-terminal leader or signal sequence region which is indicated by the underlined sequence at the beginning of SEQ ID NO: 53 above. In one embodiment, one or more amino acids are removed from the leader or signal sequence region of GBS 691. An example of such a GBS 691 fragment is set forth below as SEQ ID NO: 54.

SEQ ID NO: 54
```
EGFTYYGKIPENPKKVINFTYSYTGYLLKLGVNVSSYSLDLEKDSPVFGK

QLKEAKKLTADDTEAIAAQKPDLIMVFDQDPNINTLKKIAPTLVIKYGAQ

NYLDMMPALGKVFGKEKEANQWVSQWKTKTLAVKKDLHHILKPNTTFTIM

DFYDKUIYLYGNNFGRGGELIYDSLGYAAPEKVKKDVFKKGWFTVSQEAI

GDYVGDYALVNINKTTKKAASSLKESDVWKNLPAVKKGHIIESNYDVFYF

SDPLSLEAQLKSFTKAIKENTN
```

GBS 691 contains a C-terminal transmembrane or cytosplasmic region which is indicated by the underlined sequence at the end of SEQ ID NO: 53 above. In one embodiment, one or more amino acids are removed from the transmembrane or cytoplasmic region of GBS 691. An example of such a GBS 691 fragment is set forth below as SEQ ID NO: 55.

SEQ ID NO: 55
```
MKKIGIIVLTLLTFFLVSCGQQTKQESTKTTISKMPKIEGFTYYGKIPEN

PKKVINFTYSYTGYLLKLGVNVSSYSLDLEKDSPVFGKQLKEAKKLTADD

TEAIAAQKPDLIMVFDQDPNINTLKKIAPTLVIKYGAQNYLDMMPALGKV

FGKEKEANQWVSQWKTKTLAVKKDLHHILKPNTTFTIMDFYDKNIYLYGN
```

NFGRGGELIYDSLGYAAPEKVKKDVFKKGWFTVSQEAIGDYVGDYALVNI

NKTTKKAASSLKESDVWKNLPAVKKGHIIESNYDVFYFSPLSLEAQLK

SFT

In one embodiment, one or more amino acids from the leader or signal sequence region and one or more amino acids from the transmembrane or cytoplasmic region are removed from GBS 691. One example of such a GBS 691 fragment is set forth below as SEQ ID NO: 56

SEQ ID NO: 56
EGFTYYGKIPENPKKVINFTYSYTGYLLKLGVNVSSYSLDLEKDSPVFGK

QLKEAKKLTADDTEAIAAQKPDLIMVFDQDPNINTLKKIAPTLVIKYGAQ

NYLDMMPALGKVFGKEKEANQWVSQWKTKTLAVKKDLHHILKPNTTFTIM

DFYDKUIYLYGNNFGRGGELIYDSLGYAAPEKVKKDVFKKGWFTVSQEAI

GDYVGDYALVNINKTTKKAASSLKESDVWKNLPAVKKGHIIESNYDVFYF

SDPLSLEAQLKSFT

Additional examples of GBS antigens which may be used in combination with GBS 80 are set forth below.
GBS 4

GBS 4 refers to another putative cell wall surface anchor family protein. Nucleotide and amino acid sequences of GBS 4 sequenced from serotype V isolated strain 2603 V/R are set forth in Ref. 2 as SEQ ID 1 and SEQ ID 2. These sequences are also set forth below as SEQ ID NOS 57 and 58:

SEQ ID NO. 57
ATGAAAGTGAAAAATAAGATTTTAACGATGGTAGCACTTACTGTCTTAAC

ATGTGCTACTTATTCATCAATCGGTTATGCTGATACAAGTGATAAGAATA

CTGACACGAGTGTCGTGACTACGACCTTATCTGAGGAGAAAAGATCAGAT

GAACTAGACCAGTCTAGTACTGGTTCTTCTTCTGAAAATGAATCGAGTTC

ATCAAGTGAACCAGAAACAAATCCGTCAACTAATCCACCTACAACAGAAC

CATCGCAACCCTCACCTAGTGAAGAGAACAAGCCTGATGGTAGAACGAAG

ACAGAAATTGGCAATAATAAGGATATTTCTAGTGGAACAAAAGTATTAAT

TTCAGAAGATAGTATTAAGAATTTTAGTAAAGCAAGTAGTGATCAAGAAG

AAGTGGATCGCGATGAATCATCATCTTCAAAAGCAAATGATGGGAAAAAA

GGCCACAGTAAGCCTAAAAAGGAACTTCCTAAAACAGGAGATAGCCACTC

AGATACTGTAATAGCATCTACGGGAGGGATTATTCTGTTATCATTAAGTT

TTTACAATAAGAAAATGAAACTTTAT

SEQ ID NO. 58
<u>MKVKNKILTMVALTVLTCATYSSIGYA</u>DTSDKNTDTSVVTTTLSEEKRSD

ELDQSSTGSSSENESSSSSEPETNPSTNPPTTEPSQPSPSEENKPDGRTK

TEIGNNKDISSGTKVLISEDSIKNFSKASSDQEEVDRDESSSSKANDGKK

GHSKPKKE<u>LPKTGDSHSDTVIASTGGIILLSLSFYNKKMKLY</u>

GBS 4 contains an N-terminal leader or signal sequence which is underlined at the beginning of SEQ ID NO: 58 above. In one embodiment, one or more amino acids from the N-terminal leader or signal peptide domain of GBS 4 are removed. An example of such a GBS 4 fragment is set forth below as SEQ ID NO 59.

SEQ ID NO 59
DTSDKNTDTSVVTTTLSEEKRSDELDQSSTGSSSENESSSSSEPETNPST

NPPTTEPSQPSPSEENKPDGRTKTEIGNNKDISSGTKVLISEDSIKNFSK

ASSDQEEVDRDESSSSKANDGKKGHSKPKKELPKTGDSHSDTVIASTGGI

ILLSLSFYNKKMKLY

A further N-terminal section of GBS 4 may be removed to facilitate recombinant expression. An example of such a GBS 4 fragment is set forth below as SEQ ID NO: 60.

SEQ ID NO: 60
DQSSTGSSSENESSSSSEPETNPSTNPPTTEPSQPSPSEENKPDGRTKTE

IGNNKDISSGTKVLISEDSIKNFSKASSDQEEVDRDESSSSKANDGKKGH

SKPKKELPKTGDSHSDTVIASTGGIILLSLSFYNKKMKLY

GBS 4 contains an C-terminal transmembrane region which is underlined at the end of SEQ ID NO: 58 above. In one embodiment, one or more amino acids from the C-terminal transmembrane region is removed. An example of such a GBS 4 fragment is set forth below as SEQ ID NO: 61.

SEQ ID NO: 61
MKVKNKILTMVALTVLTCATYSSIGYADTSDKNTDTSVVTTTLSEEKRSD

ELDQSSTGSSSENESSSSSEPETNPSTNPPTTEPSQPSPSEENKPDGRTK

TEIGNNKDISSGTKVLISEDSIKNFSKASSDQEEVDRDESSSSKANDGKK

GHSKPKKE

In one embodiment, both the N-terminal leader or signal domain and the C-terminal transmembrane domain are removed from the GBS 4 sequence. An example of such a GBS 4 fragment is set forth below as SEQ ID NO: 62.

SEQ ID NO: 62
DTSDKNTDTSVVTTTLSEEKRSDELDQSSTGSSSENESSSSSEPETNPST

NPPTTEPSQPSPSEENKPDGRTKTEIGNNKDISSGTKVLISEDSIKNGSD

ASSDQEEVDRDESSSSKANDGKKGHSKPKKE

In yet another embodiment, the N-terminal leader or signal domain, a further N-terminal region and the C-terminal transmembrane domain are removed from the GBS 4 sequence. An example of such a GBS 4 fragment is set forth below as SEQ ID NO: 63.

SEQ ID NO: 63
DQSSTGSSSENESSSSSEPETNPSTNPPTTEPSQPSPSEENKPDGRTKTE

IGNNKDISSGTKVLISEDSIKNFSKASSDQEEVDRDESSSSKANDGKKGH

SKPKKE

GBS 22

GBS 22 refers to a putative adhesion lipoprotein. Nucleotide and amino acid sequences of GBS 22 sequenced from serotype V isolated strain 2603 V/R are set forth in Ref. 2 as SEQ 8583 and SEQ ID 8584. These sequences are set forth below as SEQ ID NOS 64 and 65:

SEQ ID NO. 64
ATGAAAAGGATACGGAAAAGCCTTATTTTTGTTCTCGGAGTAGTTACCCT
AATTTGCTTATGTGCTTGTACTAAACAAAGCCAGCAAAAAAATGGCTTGT
CAGTACTGACTAGCTTTTATCCAGTATATTCCATTACAAAAGCAGTTTCT
GGTGATTTGAATGATATTAAAATGATTCGATCACAGTCAGGTATTCATGG
TTTTGAACCCTCATCAAGTGATGTTGCTGCCATTTATGATGCTGATCTAT
TTCTTTATCATTCGCACACACTAGAAGCTTGGGCGAGACGTTTGGAACCT
AGTTTGCATCACTCTAAAGTATCTGTAATTGAAGCTTCAAAAGGTATGAC
TTTGGATAAAGTTCATGGCTTAGAAGATGTAGAGGCAGAAAAAGGAGTAG
ATGAGTCAACCTTGTATGACCCTCACACTTGGAATGACCCTGTAAAAGTA
TCTGAGGAAGCACAACTCATCGCTACACAATTAGCTAAAAAGGATCCTAA
AAACGCTAAGGTTTATCAAAAAAATGCTGATCAATTTAGTGACAAGGCAA
TGGCTATTGCAGAGAAGTATAAGCCAAAATTTAAAGCTGCAAAGTCTAAA
TACTTTGTGACTTCACATACAGCATTCTCATACTTAGCTAAGCGATACGG
ATTGACTCAGTTAGGTATTGCAGGTGTCTCACCGAGCAAGAACCTAGTGC
TAAAAAATTAGCCGAAATTCAGGAGTTTGTGAAAACATATAAGGTTAAGA
CTATTTTTGTTGAAGAAGGAGTCTCACCTAAATTAGCTCAAGCAGTAGCT
TCAGCTACTCGAGTTAAAATTGCAAGTTTAAGTCCCTTARAAGCAGTTCC
CAAAAACAATAAAGATTACTTAGAAAATTTGGAAACTAATCTTAAGGTAC
TTGTCAAATCGTTAAATCAATAG

SEQ ID NO. 65
MKRIRKSLIFVLGVVTLICLCACTKQSQQKNGLSVVTSFYPVYSITKAVS
GDLNDIKMIRSQSGIHGFEPSSSDVAAIYDADLFLYSHSTLEAWARRLEP
SLHHSKVSVIEASKGMTLDKVHGLEDVEAEKGVDESTLYDPHTWNDPVKV
SEEAQLIATQLAKKDPKNAKVYQKNADQFSDKAMAIAEKYKPKFKAAKSK
YFVTSHTAFSYLAKRYGLTQLGIAGVSTEQEPSAKKLAIEQEFVKTYKVK
TIGVEEGVSPKLAQAVASATRVKIASLSPLXAVPKNNKDYLENLETNLKV
LVKSLNQ

GBS 85
GBS 85 refers to a putative cell division protein (DivIB). Nucleotide and amino acid sequences of GBS 85 sequenced from serotype V isolated strain 2603 V/R are set forth in Ref. 2 as SEQ ID 215 and SEQ ID 216. These sequences are set forth below as SEQ ID NOS 66 and 67:

SEQ ID NO. 66
ATGCCTAAGAAGAAATCAGATACCCCAGAAAAGAAGAAGTTGTCTTAAC
GGAATGGCAAAAGCGTAACCTTGAATTTTTAAAAAAACGCAAAGAAGATG
AAGAAGAACAAAAACGTATTAACGAAAAATTACGCTTAGATAAAAGAAGT
AAATTAAATATTTCTTCTCCTGAAGAACCTCAAAATACTACTAAAATTAA
GAAGCTTCATTTTCCAAAGATTTCAAGACCTAAGATTGAAAAGAAACAGA
AAAAAGAAAAAATAGTCAACAGCTTAGCCAAAACTAATCGCATTAGAACT
GCACCTATATTTGTAGTAGCATTCCTAGTCATTTTAGTTTCCGTTTTCCT
ACTAACTCCTTTTAGTAAGCAAAAAACAATAACAGTTAGTGGAAATCAGC
ATACACCTGATGATATTTTGATAGAGAAACGAATATTCAAAAAAACGAT
TATTTCTTTTCTTTAATTTTTAAACATAAAGCTATTGAACAACGTTTAGC
TGCAGAAGATGTATGGGTAAAAACAGCTCAGATGACTTATCAATTTCCCA
ATAAGTTTCATATTCAAGTTCAAGAAAATAAGATTATTGCATATGCACAT
ACAAAGCAAGGATATCAACCTGTCTTGGAAACTGGAAAAAAGGCTGATCC
TGTAAATAGTTCAGAGCTACCAAAGCACTTCTTAACAATTAACCTTGATA
AGGAAGATAGTATTAAGCTATTAATTAAAGATTTAAAGGCTTTAGACCCT
GATTTAATAAGTGAGATTCAGGTGATAAGTTTAGCTGATTCTAAAACGAC
ACCTGACCTCCTGCTGTTAGATATGCACGATGGAAATAGTATTAGAATAC
CATTATCTAAATTTAAAGAAAGACTTCCTTTTTACAAACAAATTAAGAAG
AACCTTAAGGAACCTTCTATTGTTGATATGGAAGTGGGAGTTTACACAAC
AACAAATACCATTGAATCAACCCCTGTTAAAGCAGAAGATACAAAAAATA
AATCAACTGATAAAACACAAACACAAAATGGTCAGGTTGCGGAAAATAGT
CAAGGACAAACAAATAACTCAAATACTAATCAACAAGGACAACAGATAGC
AACAGAGCAGGCACCTAACCCTCAAAATGTTAAT

SEQ ID NO. 67
MPKKKSDTPEKEEVVLTEWQKRNLEFLKKRKEDEEEQKRINEKLRLDKRS
KLNISSPEEPQNTTKIKKLHFPKISRPKIEKKQKKEKIVNSLAKTNRIRT
APIFVVAFLVILVSVFLLTPFSKQKTITVSGNQHTPDDILIEKTNIQKND
YFFSLIFKHKAIEQRLAAEDVWVKTAQMTYQFPNKFHIQVQENKIIAYAH
TKQGYQPVLETGKKADPVNSSELPKHFLTINLDKEDSIKLLIKDLKALDP
DLISEIQVISLADSKTTPDLLLLDMHDGNSIRIPLSKFKERLPFYKQIKK
NLKEPSIVDMEVGVYTTTNTIESTPVKAEDTKNKSTDKTQTQNGQVAENS
QGQTNNSNTNQQGQQIATEQAPNPQNVN

GBS 147
GBS 147 refers to a putative protease. Nucleotide and amino acid sequences of GBS 147 sequenced from serotype V isolated strain 2603 V/R are set forth in Ref. 2 as SEQ ID 8525 and SEQ ID 8526. These sequences are set forth below as SEQ ID NOS 68 and 69.

SEQ ID NO. 68
GTGGATAAACATCACTCAAAAAAGGCTATTTTAAAGTTAACACTTATAAC
AACTAGTATTTTATTAATGCATAGCAATCAAGTGAATGCAGAGGAGCAAG
AATTAAAAAACCAAGAGCAATCACCTGTAATTGCTAATGTTGCTCAACAG
CCATCGCCATCGGTAACTACTAATACTGTTGAAAAAACATCTGTAACAGC
TGCTTCTGCTAGTAATACAGCGAAAGAAATGGGTGATACATCTGTAAAAA
ATGACAAAACAGAAGATGAATTATTAGAAGAGTTATCTAAAAACCTTGAT
ACGTCTAATTTGGGGGCTGATCTTGAAGAAGAATATCCCTCTAAACCAGA
GACAACCAACAATAAAGAAAGCAATGTAGTAACAAATGCTTCAACTGCAA
TAGCACAGAAAGTTCCCTCAGCATATGAAGGGTGAAGCCAGAAAGCAAG
TCATCGCTTGCTGTTCTTGATACATCTAAAATAACAAAATTACAAGCCAT
AACCCAAAGAGGAAAGGGAAATGTAGTAGCTATTATTGATACTGGCTTTG
ATATTAACCATGATATTTTTCGTTTAGATAGCCCAAAAGATGATAAGCAC

```
AGCTTTAAAACTAAGACAGAATTTGAGGAATTAAAAGCAAAACATAATAT
CACTTATGGGAAATGGGTTAACGATAAGATTGTTTTTGCACATAACTACG
CCAACAATACAGAAACGGTGGCTGATATTGCAGCAGCTATGAAAGATGGT
TATGGTTCAGAAGCAAAGAATATTTCGCATGGTACACACGTTGCTGGTAT
TTTTGTAGGTAATAGTAAACGTCCAGCAATCAATGGTCTTCTTTTAGAAG
GTGCAGCGCCAAATGCTCAAGTCTTATTAATGCGTATTCCAGATAAAATT
GATTCGGACAAATTTGGTGAAGCATATGCTAAAGCAATCACAGACGCTGT
TAATCTAGGAGCAAAAACGATTAATATGAGTATTGGAAAAACAGCTGATT
CTTTAATTGCTCTCAATGATAAAGTTAAATTAGCACTTAAATTAGCTTCT
GAGAAGGGCGTTGCAGTTGTTGTGGCTGCCGGAAATGAAGGCGCATTTGG
TATGGATTATAGCAAACCATTATCAACTAATCCTGACTACGGTACGGTTA
ATAGTCCAGCTATTTCTGAAGATACTTTGAGTGTTGCTAGCTATGAATCA
CTTAAAACTATCAGTGAGGTCGTTGAAACAACTATTGAAGGTAAGTTAGT
TAAGTTGCCGATTGTGACTTCTAAACCTTTTGACAAAGGTAAGGCCTACG
ATGTGGTTTATGCCAATTATGGTGCAAAAAAAGACTTTGAAGGTAAGGAC
TTTAAAGGTAAGATTGCATTAATTGAGCGTGGTGGTGGACTTGATTTTAT
GACTAAAATCACTCATGCTACAAATGCAGGTGTTGTTGGTATCGTTATTT
TTAACGATCAAGAAAAACGTGGAAATTTTCTAATTCCTTACCGTGAATTA
CCTGTGGGATTATTAGTAAAGTAGATGGCGAGCGTATAAAAAATACTTC
AAGTCAGTTAACATTTAACCAGAGTTTTGAAGTAGTTGATAGCCAAGGTG
GTAATCGTATGCTGGAACAATCAAGTTGGGCGTGACAGCTGAAGGAGCA
ATCAAGCCTGATGTAACAGCTTCTGGCTTTGAAATTTATTCTTCAACCTA
TAATAATCAATACCAAACAATGTCTGGTACAAGTATGGCTTCACCACATG
TTGCAGGATTAATGACAATGCTTCAAAGTCATTTGGCTGAGAAATATAAA
GGGATGAATTTAGATTCTAAAAAATTGCTAGAATTGTCTAAAAACATCCT
CATGAGCTCAGCAACAGCATTATATAGTGAAGAGGATAAGGCGTTTTATT
CACCACGTCAGCAAGGTGCAGGTGTAGTTGATGCTGAAAAAGCTATCCAA
GCTCAATATTATATTACTGGAAACGATGGCAAAGCTAAAATTAATCTCAA
ACGAATGGGAGATAAATTTGATATCACAGTTACAATTCATAAACTTGTAG
AAGGTGTCAAAGAATTGTATTATCAAGCTAATGTAGCAACAGAACAAGTA
AATAAAGGTAAATTTGCCCTTAAACCACAAGCCTTGCTAGATACTAATTG
GCAGAAAGTAATTCTTCGTGATAAAGAAACACAAGTTCGATTTACTATTG
ATGCTAGTCAATTTAGTCAGAAATTAAAAGAACAGATGGCAAATGGTTAT
TTCTTAGAAGGTTTTGTACGTTTTAAAGAAGCCAAGGATAGTAATCAGGA
GTTAATGAGTATTCCTTTTGTAGGATTTAATGGTGATTTTGCGAACTTAC
AAGCACTTGAAACACCGATTTATAAGACGCTTTCTAAAGGTAGTTTCTAC
TATAAACCAAATGATACAACTCATAAAGACCAATTGGAGTACAATGAATC
AGCTCCTTTTGAAAGCAACAATTACACTGCCTTGTTAACACAATCAGCGT
CTTGGGGCTATGTTGATTATGTCAAAAATGGTGGGGAGTTAGAATTAGCA
CCGGAGAGTCCAAAAAGAATTATTTTAGGAACTTTTGAGAATAAGGTTGA
GGATAAAACAATTCATCTTTTTGGAAAGAGATGCAGCGAATAATCCATATT
TTGCCATTTCTCCAAATAAAGATGGAAATAGGGACGAAATCACTCCCCAG
GCAACTTTCTTAAGAAATGTTAAGGATATTTCTGCTCAAGTTCTAGATCA
AAATGGAAATGTTATTTGGCAAAGTAAGGTTTTACCATCTTATCGTAAAA
ATTTCCATAATAATCCAAAGCAAAGTGATGGTCATTATCGTATGGATGCT
CTTCAGTGGAGTGGTTTAGATAAGGATGGCAAAAGTTGTGCAGATGGTTT
TTATACTTATCGCTTACGTTACACACCAGTAGCAGAAGGAGCAAATAGTC
AGGAGTCAGACTTTAAAGTACAAGTAAGTACTAAGTCACCAAATCTTCCT
TCACGAGCTCAGTTTGATGAAACTAATCGAACATTAAGCTTAGCCATGCC
TAAGGAAAGTAGTTATGTTCCTACATATCGTTTACAATTAGTTTTATCTC
ATGTTGTAAAAGATGAAGAATATGGGGATGAGACTTCTTACCATTATTTC
CATATAGATCAAGAAGGTAAAGTGACACTTCCTAAAACGGTTAAGATAGG
AGAGAGTGAGGTTGCGGTAGACCCTAAGGCCTTGACACTTGTTGTGGAAG
ATAAAGCTGGTAATTTCGCAACGGTAAAATTGTCTGATCTCTTGAATAAG
GCAGTAGTATCAGAGAAAGAAAACGCTATAGTAATTTCTAACAGTTTCAA
ATATTTTGATAACTTGAAAAAAGAACCTATGTTTATTTCTAAAAAAGAAA
AAGTAGTAAACAAGAATCTAGAAGAATAATATTAGTTAAGCCGCAAACT
ACAGTTACTACTCAATCATTGTCTAAAGAAATAACTAAATCAGGAAATGA
GAAAGTCCTCACTTCTACAAACAATAATAGTAGCAGAGTAGCTAAGATCA
TATCACCTAAACATAACGGGGATTCTGTTAACCATACCTTACCTAGTACA
TCAGATAGAGCAACGAATGGTCTATTTGTTGGTACTTTGGCATTGTTATC
TAGTTTACTTCTTTATTTGAAACCCAAAAAGACTAAAAATAATAGTAAA
                                                SEQ ID NO. 69
VDKHHSKKAILKLTLITTSILLMHSNQVNAEEQELKNQEQSPVIANVAQQ
PSPSVTTNTVEKTSVTAASASNTAKEMGDTSVKNDKTEDELLEELSKNLD
TSNLGADLEEEYPSKPETTNNKESVNNTNASTAIAQKVPSAYEEVKPESK
SSLAVLDTSKITKLQAITQRGKGNVVAIIDTGFDINHDIFRLDSPKDDKH
SFKTKTEFEELKAKHNITYGKWVNDKIVFAHNYANNTETVADIAAAMKDG
YGDEAKNISHGTHVAGIFVGNSKRPAINGLLLEGAAPNAQVLLMRIPDKI
DSDKFGEAYAKAITDAVNLGAKTINMSIGKTADSLIALNDKVKLALKLAS
EKGVAVVVAAGNEGAFGMDYSKPLSTNPDYGTVNSPAISEDTLSVASYES
LKTISEVVETTIEGKLVKLPIVTSKPFDKGKAYDVVYANYGAKKDFEGKD
FKGKIALIERGGGLDFMTKITHATNAGVVGIVIGNDQEKRGNFLIPYREL
PVGIISKVDGERIKNTSSQLTFNQSFEVVDSQGGNRMLEQSSWGVTAEGA
IKPDVTASGFEIYSSTYNNQYQTMSGTSMASPHVAGLMTMLQSHLAEKYK
GMNLDSKKLLELSKNILMSSATALYSEEDKAFYSPRQQGAGVVDAEKAIQ
AQYYITGNDGKAKINLKRMGDKFDITVTIHKLVEGVKELYYQANVATEQV
NKGKFALKPQALLDTNWQKVILRDKETQVRFTIDASQFSQKLKEQMANGY
GLEGFVRGKEAKDSNQELMSIPFVGFNGDFANLQALETPIYKTLSKGSFY
YKPNDTTHKDQLEYNESAPFESNNYTALLTQSASWGYVDYVKNGGELELA
PESPKRIILGTFENKVEDKTIHLLERDAANNPYFAISPNKDGNRDEITPQ
```

```
ATFLRNVKDISAQVLDQNGNVIWQSKVLPSYRKNFHNNPKQSDGHYRMDA

LQWSGLDKDGKVVADGFYTYRLRYTPVAEGANSQESDGKVQVSTKSPNLP

SRAQFDETNRTLSLAMPKESSYVPTYLQLVLSHVVKDEEYGDETSYHYFH

IDQEGKVTLPKTTVKIGESEVAVDPKALTLVVEDKAGNFATVKLSDLLNK

AVVSEKANAIVISNSFKYFDNLKKEPMFISKKEKVVNKNLEEIILVKPQT

TVTTQSLSKEITKSGNEKVLTSTNNNSSRVAKIISPKHNGDSVNHTLPST

SDRATNGLFVGTLALLSSLLLYLKPKKTKNNSK
```

GBS 147 contains an N-terminal leader or signal sequence region which is indicated by the underlined sequence at the beginning of SEQ ID NO 69 above. In one embodiment, one or more amino acids from the leader or signal sequence region of GBS 147 are removed. An example of such a GBS 147 fragment is set forth below as SEQ ID NO: 70.

```
                                           SEQ ID NO: 70
EEQELKNQEQSPVIANVAQQPSPSVTTNTVEKTSVTAASASNTAKEMGDT

SVKNDKTEDELLEELSKNLDTSNLGADLEEEYPSKPETTNNKESNVVTNA

STAIAQKVPSAYEEVKPESKSSLAVLDTSKITKLQAITQRGKGNVVAIID

TGFDINHDIFRLDSPKDDKHSFKTKTEFEELKAKHNITYGKWVNDKIVFA

HNYANNTETVADIAAAMKDGYGDEAKNISHGTHVAGIFVGNSKRPAINGL

LLEGAAPNAQVLLMRIPDKIDSDKFGEAYAKAITDAVNLGAKTINMSIGK

TADSLIALNDKVKLALKLASEKGVAVVVAAGNEGAFGMDYSKPLSTNPDY

GTVNSPAISEDTLSVASYESLKTISEVVETTIEGKLVKLPIVTSKPFDKG

KAYDVVYANYGAKKDFEGKDFKGKIALIERGGGLDFMTKITHATNAGVVG

IVIGNDQERKGNFLIPYRELPVGIISKVDGERIKNTSSQLTFNQSFEVVD

SQGGNRMLEQSSWGVTAEGAIKPDVTASGFEIYSSTYNNQYQTMSGTSMA

SPHVAGLMTMLQSHLAEKYKGMNLDSKKLLELSKNILMSSATALYSEEDK

AFYSPRQQGAGVVDAEKAIQAQYYITGNDGKAKINLKRMGDKFDITVTIH

KLVEGVKELYYQANVATEQVNKGKFALKPQALLDTNWQKVILRDKETQVR

FTIDASQFSQKLKEQMANGYFLEGFVRFKEAKDSNQELMSIPFVGFNGDF

ANLQALETPIYKTLSKGSFYYKPNDTTHKDQLEYNESAPFESNNYTALLT

QSASWGYVDYVKNGGELELAPESPKRIILGTFENKVEDKTIHLLERDAAN

NPYFAISPNKDGNRDEITPQATFLRNVKDISAQVLDQNGNVIWQSKVLPS

YRKNFHNNPKQSDGHYRMDALQWSGLDKDGKVVADGFYTYRLRYTPVAEG

ANSQESDFKVQVSTKSPNLPSRAQFDETNRTLSLAMPKESSYVPTYRLQL

VLSHVVKDEEYGDETSYHYFHIDQEGKVTLPKTVKIGESEVAVDPKALTL

VVEDKAGNFATVKLSDLLNKAVVDEKENAIVISNSFKYFDNLKKEPMFIS

KKEKVVNKNLEEIILVKPQTTVTTQSLSKEITKSGNEKVLTSTNNNSSRV

AKIISPKHNGDSVNHTLPSTSDRATNGLFVGTLALLSSLLLYLKPKKTKN

NSK
```

GBS 147 also contains a C-terminal transmembrane and/or cytoplasmic region which may be located within the underlined sequence near the end of SEQ ID NO: 69 above. In one embodiment, one or more amino acids from the transmembrane and/or cytoplasmic region are removed. An example of such a GBS 147 fragment is set forth below as SEQ ID NO: 71.

```
                                           SEQ ID NO: 71
VDKHHSKKAILKLTLITTSILLMHSNQVNAEEQELKNQEQSPVEANVAQQ

PSPSVTTNTVEKTSVTAASASNTAKEMGDTSVKNDKTEDELLEELSKNLD

TSNLGADLEEEYPSKPETTNNKESNVVTNASTAIAQKVPSAYEEVKPESK

SSLAVLDTSKITKLQAITQRGKGNVVAIIDTGFDINHDIFRLDSPKDDKH

SFKTKTEFEELKAKHNITYGKWVNDKIVFAHNYANNTETVADIAAAMKDG

YGSEAKNISHGTHVAGIFVGNSKRPAINGLLLEGAAPNAQVLLMRIPDKI

DSDKFGEAYAKAITDAVNLGAKTINMSIGKTADSLIALNDKVKLALKLAS

EKGVAVVVAAGNEGAFGMDYSKPLSTNPDYGTVNSPAISEDTLSVASYES

LKTISEVVETTIEGKLVKLPIVTSKPFDKGKAYDVVYANYGAKKDFEGKD

FKGKIALIERGGGLDFMTHITHATNAGVVGIVIFNDQEKRGNFLIPYREL

PVGIISKVDGERIKNTSSQLTFNQSFEVVDSQGGNRMLEQSSWGVTAEGA

IKPDVTASGFEIYSSTYNNQYQTMSGTSMASPHVAGLMTMLQSHLAEKYK

GMNLDSKKLLELSKNILMSSATALYSEEDKAFYSPRQQGAGVVDAEKAIQ

AQYYITGNDGKAKINLKRMGDKFDITVTIHKLVEGVKELYYQANVATEQV

NKGKFALKPQALLDTNWQKVILRDKETQVRFTIDASQFSQKLKEQMANGY

FLEGFVRFKEAKDSNQELMSIPFVGFNGDFANLQALETPIYKTLSKGSFY

YKPNDTTHKDQLEYNESAPFESNNYTALLTQSASWGYVDYVKNGGELELA

PESPKRIILGTFENKVEDKTIHLLERDAANNPYFAISPNKDGNRDEITPQ

ATFLRNVKDISAQVLDQNGNVIWQSKVLPSYRKNFHNNPKQSDGHYRMDA

LQWSGLDKDGKVVADGFYTYRLRYTPVAEGANSQESDFKVQVSTKSPNLP

SRAQFDETNRTLSLAMPKESSYVPTYRLQLVLSHVVKDEEYGDETSYHYF

HIDQEGKVTLPKTVKIGESEVAVDPKALTLVVEDKAGNFATVKLSDLLNK

AVVDEKENAIVISNSFKYFDNLKKEPMFISKKEKVVNKNLEEIILVKPQT

TVTTQSLSKEITKSGNEKVLTSTNNNSSRVAKIISPKHNGDSVNHT
```

In one embodiment, one or more amino acids from the leader or signal sequence region and one or more amino acids from the transmembrane or cytoplasmic region are removed from the GBS 147 sequence. An example of such a GBS 147 fragment is set forth below as SEQ ID NO 72.

```
                                           SEQ ID NO: 72
EEQELKNQEQSPVIANVAQQPSPSVTTNTVEKTSVTAASASNTAKEMGDT

SVKNDKTEDELLEELSKNLDTSNLGADLEEEYPSKPETTNNKESNVVTNA

STAIAQKVPSAYEEVKPESKSSLAVLDTSKITKLQAITQRGKGNVVAIID

TGFDINHDIFRLDSPKDDKHSFKTKTEFEELKAKHNITYGKWVNDKIVFA

HNYANNTETVADIAAAMKDGYGSEAKNISHGTHVAGIFVGNSKRPAINGL

LLEGAAPNAQVLLMRIPDKIDSDKFGEAYAKAITDAVNLGAKTINMSIGK

TADSLIALNDKVKLALKLASEKGVAVVVAAGNEGAFGMDYSKPLSTNPDY

GTVNSPAISEDTLSVASYESLKTISEVVETTIEGKLVKLPIVTSKPFDKG

KAYDVVYANYGAKKDFEGKDFKGKIALIERGGGLDFMTKITHATNAGVVF
```

IVIFNDQEKRGNFLIPYRELPVGIISKVDGERIKNTSSQLTFNQSFEVVD

SQGGNRMLEQSSWGVTAEGAIKPDVTASGFEIYSSTYNNQYQTMSGTSMA

SPHVAGLMTMLQSHLAEKYKGMNLDSKKLLELSKNILMSSATALYSEEDK

AFYSPRQQGAGVVDAEKAIQAQYYITGNDGKAKINLKRMGDKFDITVTIH

KLVEGVKELYYQANVATEQVNKGKFALKPQALLDTNWQKVILRDKETQVR

FTIDASQFSQKLKEQMANGYFLEGFVRFKEAKDSNQELMSIPFVGFNGDF

ANLQALETPIYKTLSKGSFYYKPNDTTHKDQLEYNESAPFESNNYTALLT

QSASWGYVDYVKNGGELELAPESPKRIILGTFENKVEDKTIHLLERDAAN

NPYFAISPNKDGNRDEITPQATFLRNVKDISAQVLDQNGNVIWQSKVLPS

YRKNFHNNPKQSDGHYRMDALQWSGLDKDGKVVADGFYTYRLRYTPVAEG

ANSQESDFKVQVSTKSPNLPSRAQFDETNRTLSLAMPKESSYVPTYRLQL

VLSHVVKDEEYGDETSYHYFHIDQEGKVTLPKTVKIGESEVAVDPKALTL

VVEDKAGNFATVKLSDLLNKAVVSEKENAIVISNSFKYFDNLKKEPMFIS

KKEKVVNKNLEEIILVKPQTTVTTQSLSKEITKSGNEKVLTSTNNNSSRV

AKIISPKHNGDSVNHT

GBS 173

GBS 173 refers to an amidase family protein. Nucleotide and amino acid sequences of GBS 173 sequenced from serotype V isolated strain 2603 V/R are set forth in Ref. 2 as SEQ ID 8787 and SEQ ID 8788. These sequences are set forth below as SEQ ID NOS 73 and 74:

SEQ ID NO. 73
ATGAAACGTAAATACTTTATTCTTAATACGGTGACGGTTTTAACGTTAGC

TGCTGCAATGAATACTAGCAGTATCTATGCTAATAGTACTGAGACAAGTG

CTTCAGTAGTTCCTACTACAAATACTATCGTTCAAACTAATGACAGTAAT

CCTACCGCAAAATTTGTATCAGAATCAGGACAATCTGTAATAGGTCAAGT

AAAACCAGATAATTCTGCGGCGCTTACAACAGTTGACACGCCTCATCATA

TTTCAGCTCCAGATGCTTTAAAAACAACTCAATCAAGTCCTGTCGTTGAG

AGTACTTCTACTAAGTTAACTGAAGAGACTTACAAACAAAAAGATGGTCA

AGATTTAGCCAACATGGTGAGAAGTGGTCAAGTTACTAGTGAGGAACTCG

TTAATATGGCATACGATATTATTGCTAAAGAAAACCCATCTTTAAATGCA

GTCATTACTACTAGACGCCAAGAAGCTATTGAAGAGGCTAGAAAACTTAA

AGATACCAATCAGCCGTTTTTAGGTGTTCCCTTGTTAGTCAAGGGGTTAG

GGCACAGTATTAAAGGTGGTGAAACCAATAATGGCTTGATCTATGCAGAT

GGAAAAATTAGCACATTTGACAGTAGCTATGTCAAAAAATATAAAGATTT

AGGATTTATTATTTTAGGACAAACGAACTTTCCAGAGTATGGGTGGCGTA

ATATAACAGATTCTAAATTATACGGTCTAACGCATAATCCTTGGGATCTT

GCTCATAATGCTGGTGGCTCTTCTGGTGGAAGTGCAGCAGCCATTGCTAG

CGGAATGACGCCAATTGCTAGCGGTAGTGATGCTGGTGGTTCTATCCGTA

TTCCATCTTCTTGGACGGGCTTGGTAGGTTTAAAACCAACAAGAGGATTG

GTGAGTAATGAAAAGCCAGATTCGTATAGTACAGCAGTTCATTTTCCATT

AACTAAGTCATCTAGAGACGCAGAAACATTATTAACTTATCTAAAGAAAA

GCGATCAAACGCTAGTATCAGTTAATGATTTAAAATCTTTACCAATTGCT

TATACTTTGAAATCACCAATGGGAACAGAAGTTAGTCAAGATGCTAAAAA

CGCTATTATGGACAACGTCACATTCTTAAGAAAACAAGGATTCAAAGTAA

CAGAGATAGACTTACCAATTGATGGTAGAGCATTAATGCGTGATTATTCA

ACCTTGGCTATTGGCATGGGAGGAGCTTTTTCAACAATTGAAAAAGACTT

AAAAAAACATGGTTTTACTAAAGAAGACGTTGATCCTATTACTTGGGCAG

TTCATGTTATTTATCAAAATTCAGATAAGGCTGAACTTAAGAAATCTATT

ATGGAAGCCCAAAAACATATGGATGATTATCGTAAGGCAATGGAGAAGCT

TCACAAGCAATTTCCTATTTTCTTATCGCCAACGACCGCAAGTTTAGCCC

CTCTAAATACAGATCCATATGTAACAGAGGAAGATAAAAGAGCGATTTAT

AATATGGAAAACTTGAGCCAAGAAGAAAGAATTGCTCTCTTTAATCGCCA

GTGGGAGCCTATGTTGCGTAGAACACCTTTTACACAAATTGCTAATATGA

CAGGACTCCCAGCTATCAGTATCCCGACTTACTTATCTGAGTCTGGTTTA

CCCATAGGGACGATGTTAATGGCAGGTGCAAACTATGATATGGTATTAAT

TAAATTTGCAACTTTCTTTGAAAAACATCATGGTTTTAATGTTAAATGGC

AAAGAATAATAGATAAAGAAGTGAAACCATCTACTGGCCTAATACAGCCT

ACTAACTCCCTCTTTAAAGCTCATTCATCATTAGTAAATTTAGAAGAAAA

TTCACAAGTTACTCAAGTATCTATCTCTAAAAAATGGATGAAATCGTCTG

TTAAAAATAAACCATCCGTAATGGCATATCAAAAAGCACTTCCTAAAACA

GGTGATACAGAATCAAGCCTATCTCCAGTTTTAGTAGTAACCCTTTTATT

AGCTTGTTTTAGCTTTGTAACAAAAAAGAATCAGAAAAGT

SEQ ID NO. 74
<u>MKRKYFILNTVTVLTLAAAMNTSSIYANSTETSASVVP</u>TTNTIVQTNDSN

PTAKFVSESGQSVIGQVKPDNSAALTTVDTPHHISAPDALKTTQSSPVVE

STSTKLTEETYKQKDGQDKANMVRSGQVTSEELVNMAYDIIAKENPSLNA

VITTRRQEAIEEARKLKDTNQPFLGVPLLVKGLGHSIKGGETNNGLIYAD

GKISTFDSSYVKKYKDLGFIILGQTNFPEYGWRNITDSKLYGLTHNPWDL

AHNAGGSSGGSAAAIASGMTPIASGSDAGGSIRIPSSWTGLVGLKPTRGL

VSNEKPDSYSTAVHFPLTKSSRDAETLLTYLKKVDQTLVSVNDLKSLPIA

YTLKSPMGTEVSQDAKNAIMDNVTFLRKQGFKVTEIDLPIDGRALMRDYS

TLAIGMGGAGSTIEKDLKKHGFTKEDVDPITWAVHVIYQNSDKAELKKSI

MEAQKHMDDYRKAMEKLHKQFPIFLSPTTASLAPLNTDPYVTEEDKRAIY

NMENLSQEERIALFNRQWEPMLRRTPFTQIANMTGLPAISIPTYLSESGL

PIGTMLMAGANYDMVLIKFATFFEKHHGFNVKWQRIIDKEVKPSTGLIQP

TNSLFKAHSSLVNLEENSQVTQVSISKKWMKSSVKNK<u>PSVMAYQKALPKT

GDTESSLSPVLVVTLLLACFSFVTKKNQKS</u>

GBS 173 contains an N-terminal leader or signal sequence region which is indicated by the underlined sequences at the beginning of SEQ ID NO: 74 above. In one embodiment, one or more amino acids from the leader or signal sequence of GBS 173 are removed. An example of such a GBS 173 fragment is set forth below as SEQ ID NO: 75.

SEQ ID NO: 75
TTNTIVQTNDSNPTAKFVSESGQSVIGQVKPDNSAALTTVDTPHHISAPD
ALKTTQSSPVVESTSTKLTEETYKQKDGQDLANMVRSGQVTSEELVNMAY
DIIAKENPSLNAVITTRRQEAIEEARKLKDTNQPFLGVPLLVKGLGHSIK
GGETNNGLIYADGKISTFDSSYVKKYKDLGFIILGQTNFPEYGWRNITDS
KLYGLTHNPWDLAHNAGGSSGGSAAAIASGMTPIASGSDAGGSIRIPSSW
TGLVGLKPTRGLVSNEKPDSYSTAVHFPLTKSSRDAETLLTYLKKSDQTL
VSVNDLKSLPIAYTLKSPMGTEVSQDAKNAIMDNVTFLRKQGFKVTEIDL
PIDGRALMRDYSTLAIGMGGAFSTIEKDLKKHGFTKEDVDPITWAVHVIY
QNSDKAELKKSIMEAQKHMDDYRKAMEKLHKQFPIFLSPTTASLAPLNTD
PYVTEEDKRAIYNMENLSQEERIALFNRQWEPMLRRTPFTQIANMTGLPA
ISIPTYLSESGLPIGTMLMAGANYDMVLIKFATFFEKHHGFNVKWQRIID
KEVKPSTGLIQPTNSLFKAHSSLVNLEENSQVTQVSISKKWMKSSVKNKP
SVMAYQKALPKTGDTESSLSPVLVVTLLLAVFSFVTKKNQKS

GBS 173 may also contain a C-terminal transmembrane and/or cytoplasmic region which may be located within the underlined region near the end of SEQ ID NO: 74 above. In one embodiment, one or more amino acids from the transmembrane or cytoplasmic region of GBS 173 are removed. An example of such a GBS 173 fragment is set forth below as SEQ ID NO: 76.

SEQ ID NO: 76
MKRKYFILNTVTVLTLAAAMNTSSIYANSTETSASVVPTTNTIVQTNDSN
PTAKFVSESGQSVIGQVKPDNSAALTTVDTPHHISAPDALKTTQSSPVVE
STSTKLTEETYKQKDGQDKANMVRSGQVTSEELVNMAYDIIAKENPSLNA
VITTRRQEAIEEARKLKDTNQPFLGVPLLVKGLGHSIKGGETNNGLIYAD
GKISTFDSSYVKKYKDLGFIILGQTNFPEYGWRNITDSKLYGLTHNPWDL
AHNAGGSSGGSAAAIASGMTPIASGSDAGGSIRIPSSWTGLVGLKPTRGL
VSNEKPDSYSTAVHFPLTKSSRDAETLLTYLKKVDQTLVSVNDLKSLPIA
YTLKSPMGTEVSQDAKNAIMDNVTFLRKQGFKVTEIDLPIDGRALMRDYS
TLAIGMGGAGSTIEKDLKKHGFTKEDVDPITWAVHVIYQNSDKAELKKSI
MEAQKHMDDYRKAMEKLHKQFPIFLSPTTASLAPLNTDPYVTEEDKRAIY
NMENLSQEERIALFNRQWEPMLRRTPFTQIANMTGLPAISIPTYLSESGL
PIGTMLMAGANYDMVLIKFATFFEKHHGFNVKWQRIIDKEVKPSTGLIQP
TNSLFKAHSSLVNLEENSQVTQVSISKKWMKSSVKNK

In one embodiment, one or more amino acids from the leader or signal sequence region and one or more amino acids from the transmembrane or cytoplasmic region are removed. An example of such a GBS 173 fragment is set forth below as SEQ ID NO: 77.

SEQ ID NO: 77
TTNTIVQTNDSNPTAKFVSESGQSVIGQVKPDNSAALTTVDTPHHISAPD
ALKTTQSSPVVESTSTKLTEETYKQKDGQDLANMVRSGQVTSEELVNMAY
DIIAKENPSLNAVITTRRQEAIEEARKLKDTNQPFLGVPLLVKGLGHSIK
GGETNNGLIYADGKISTFDSSYVKKYKDLGFIILGQTNFPEYGWRNITDS
KLYGLTHNPWDLAHNAGGSSGGSAAAIASGMTPIASGSDAGGSIRIPSSW
TGLVGLKPTRGLVSNEKPDSYSTAVHFPLTKSSRDAETLLTYLKKSDQTL
VSVNDLKSLPIAYTLKSPMGTEVSQDAKNAIMDNVTFLRKQGFKVTEIDL
PIDGRALMRDYSTLAIGMGGAFSTIEKDLKKHGFTKEDVDPITWAVHVIY
QNSDKAELKKSIMEAQKHMDDYRKAMEKLHKQFPIFLSPTTASLAPLNTD
PYVTEEDKRAIYNMENLSQEERIALFNRQWEPMLRRTPFTQIANMTGLPA
ISIPTYLSESGLPIGTMLMAGANYDMVLIKFATFFEKHHGFNVKWQRIID
KEVKPSTGLIQPTNSLFKAHSSLVNLEENSQVTQVSISKKWMKSSVKNK

GBS 313

Nucleotide and amino acid sequences of GBS 313 sequenced from serotype V isolated strain 2603 V/R are set forth in Ref. 2 as SEQ ID 4089 and SEQ ID 4090. These sequences are set forth as SEQ D NOS 78 and 79 below:

SEQ ID NO. 78
ATGAAACGTATTGCTGTTTTAACTAGTGGTGGTGACGCCCCTGGTATGAA
CGCTGCTATCCGTGCAGTTGTTCGTAAAGCAATTTCTGAAGGTATGGAAG
TTTACGGCATCAACCAAGGTTACTATGGTATGGTGACAGGGGATATTTTC
CCTTTGGATGCTAATTCTGTTGGGGATACTATCAACCGTGGAGGAACGTT
TTTACGTTCAGCACGTTATCCTGAATTTGCTGAACTTGAAGGTCAGCTTA
AAGGGATTGAACAGCTTAAAAAACACGGTATTGAAGGTGTAGTAGTTATC
GGTGGTGATGGTTCTTATCATGGTGCTATGCGTCTAACTGAGCACGGTTT
CCCAGCTGTTGGTTTGCCGGGTACAATTGATAACGATATCGTTGGCACTG
ACTATACTATTGGTTTTGACACAGCAGTTGCGACAGCAGTTGAGAATCTT
GACCGTCTTCGTGATACATCAGCAAGTCATAACCGTACTTTTGTTGTTGA
GGTTATGGGAAGAAATGCAGGAGATATCGCTCTTTGGTCAGGTATCGCTG
CAGGTGCAGATCAAATTATTGTTCCTGAAGAAGAGTTCAATATTGATGAA
GTTGTCTCAAATGTTAGAGCTGGCTATGCAGCTGGTAAACATCACCAAAT
CATCGTCCTTGCAGAAGGTGTTATGAGTGGTGATGAGTTTGCAAAAACAA
TGAAAGCAGCAGGAGACGATAGCGATCTTCGTGTGACGAATTTAGGACAT
CTGCTCCGTGGTGGTAGTCCGACGGCTCGTGATCGTGTCTTAGCATCTCG
TATGGGAGCGTACGCTGTTCAATTGTTGAAAGAAGGTCGTGGTGGTTTAG
CCGTTGGTGTCCACAACGAAGAAATGGTTGAAAGTCCAATTTTAGGTTTA
GCAGAAGAAGGTGCTTTGTTCAGCTTGACTGATGAAGGAAAAATCGTTGT
TAATAATCCGCATAAAGCGGACCTTCGCTTGGCAGCACTTAATCGTGACC
TTGCCAACCAAAGTAGTAAA

SEQ ID NO. 79
MKRIAVLTSGGDAPGMNAAIRAVVRKAISEGMEVYGINQGYYGMVTGDIF
PLDANSVGDTINRGGTFLRSARYPEFAELEGQLKGIEQLKKHGIEGVVVI
GGDGSYHGAMRLTEHGFPAVGLPGTIDNDIVGTDYTIGFDTAVATAVENL
DRLRDTSASHNRTFVVEVMGRNAGDIALWSGIAAGADQIIVPEEEFNIDE
VVSNVRAGYAAGKHHQIIVLAEGVMSGDEFAKTMKAAGDDSDLRVTNLGH

LLRGGSPTARDRVLASRMGAYAVQLLKEGRGGLAVGVHNEEMVESPILGL

AEEGALFSLTDEGKIVVNNPHKADLRLAALNRDLANQSSK

GBS 328

GBS 328 belongs to the 5'-nucleotidase family. Nucleotide and amino acid sequences of GBS 328 sequenced from serotype V isolated strain 2603 V/R are set forth in Ref. 2 as SEQ ID 6015 and SEQ ID 6016. These sequences are set forth below as SEQ ID NOS 80 and 81:

SEQ ID NO. 80
ATGAAAAAGAAAATTATTTTGAAAAGTAGTGTTCTTGGTTTAGTCGCTGG

GACTTCTATTATGTTCTCAAGCGTGTTCGCGGACCAAGTCGGTGTCCAAG

TTATAGGCGTCAATGACTTTCATGGTGCACTTGACAATACTGGAACAGCA

AATATGCCTGATGGAAAAGTTGCTAATGCTGGTACTGCTGCTCAATTAGA

TGCTTATATGGATGACGCTCAAAAAGATTTCAAACAAACTAACCCTAATG

GTGAAAGCATTAGGGTTCAAGCAGGCGATATGGTTGGAGCAAGTCCAGCC

AACTCTGGGCTTCTTCAAGATGAACCAACTGTCAAAAATTTTAATGCAAT

GAATGTTGAGTATGGCACATTGGGTAACCATGAATTTGATGAAGGGTTGG

CAGAATATAATCGTATCGTTACTGGTAAAGCCCCTGCTCCAGATTCTAAT

ATTAATAATATTACGAAATCATACCCACATGAAGCTGCAAAACAAGAAAT

TGTAGTGGCAAATGTTATTGATAAAGTTAACAAACAAATTCCTTACAATT

GGAAGCCTTACGCTATTAAAAATATTCCTGTAAATAACAAAAGTGTGAAC

GTTGGCTTTATCGGATTGTCACCAAAGACATCCCAAACCTTGTCTTACG

TAAAAATTATGAACAATATGAATTTTTAGATGAAGCTGAAACAATCGTTA

AATACGCCAAAGAATTACAAGCTAAAAATGTCAAAGCTATTGTAGTTCTC

GCACATGTACCTGCAACAAGTAAAAATGATATTGCTGAAGGTGAAGCAGC

AGAAATGATGAAAAAGTCAATCAACTCTTCCCTGAAAATAGCGTAGATA

TTGTCTTTGCTGGACACAATCATCAATATACAAATGGTCTTGTTGGTAAA

ACTCGTATTGTACAAGCGCTCTCTCAAGGAAAAGCCTATGCTGATACG

TGGTGTCTTAGATACTGATACACAAGATTTCATTGAGACCCCTTCAGCTA

AAGTAATTGCAGTTGCTCCTGGTAAAAAAACAGGTAGTGCCGATATTCAA

GCCATTGTTGACCAAGCTAATACTATCGTTAAACAAGTAACAGAAGCTAA

AATTGGTACTGCCGAGGTAAGTGTCATGATTACGCGTTCTGTTGATCAAG

ATAATGTTAGTCCGGTAGGCAGCCTCATCACAGAGGCTCAACTAGCAATT

GCTCGAAAAGCTGGCCAGATATCGATTTTGCCATGACAAATAATGGTGG

CATTCGTGCTGACTTACTCATCAAACCAGATGGAACAATCACCTGGGGAG

CTGCACAAGCAGTTCAACCTTTTGGTAATATCTTACAAGTCGTCGAAATT

ACTGGTAGAGATCTTTATAAAGCACTCAACGAACAATACGACCAAAAACA

AAATTTCTTCCTTCAAATAGCTGGTCTGCGATACACTTACACAGATAATA

AAGAGGGCGGGGAAGAAACACCATTTAAAGTTGTAAAAGCTTATAAATCA

AATGGTGAGGAAATCAATCCTGATGCAAAATACAAATTAGTTATCAATGA

CTTTTTATTCGGTGGTGGTGATGGCTTTGCAAGCTTCAGAAATGCCAAAC

TTCTAGGAGCCATTAACCCCGATACAGAGGTATTTATGGCCTATATCACT

GATTTAGAAAAAGCTGGTAAAAAAGTGAGCGTTCCAAATAATAAACCTAA

AATCTATGTCACTATGAAGATGGTTAATGAAACTATTACACAAAATGATG

GTACACATAGCATTATTAAGAAACTTTATTTAGATCGACAAGGAAATATT

GTAGCACAAGAGATTGTATCAGACACTTTAAACCAAACAAAATCAAATC

TACAAAAATCAACCCTGTAACTACAATTCACAAAAAACAATTACACCAAT

TTACAGCTATTAACCCTATGAGAAATTATGGCAAACCATCAAACTCCACT

ACTGTAAAATCAAAACAATTACCAAAAACAAACTCTGAATATGGACAATC

ATTCCTTATGTCTGTCTTTGGTGTTGGACTTATAGGAATTGCTTTAAATA

CAAAGAAAAAACATATGAAA

SEQ ID NO. 81
<u>MKKKIILKSSVLGLVAGTSIMFSSVFAD</u>QVGVQVIGVN<u>D</u>FHGALDNTGTA

NMPDGKVANAGTAAQLDAYMDDAQKDFKQTNPNGESIRVQAGDMVGASPA

NSGLLQDEPTVKNFNAMNVEYGTLGNHEFDEGLAEYNRIVTGKAPAPDSN

INNITKSYPHEAAKQEIVVANVIDKVNKQIPYNWKPYAIKNIPVNNKSVN

VGFIGIVTKDIPNLVLRKNYEQYEFLDEAETIVKYAKELQAKNVKAIVVL

AHVPATSKNDIAEGEAAEMMKKVNQLFPENSVDIVFAGHNHQYTNGLVGK

TRIVQALSQGKAYADVRGVLDTDTQDFIETPSAKVIAVAPGKKTGSADIQ

AIVDQANTIVKQVTEAKIGTAEVSVMITRSVDQDNVSPVGSLITEAQLAI

ARKSWPDIDFAMTNNGGIRADLLIKPDGTITWGAAQAVQPFGNILQVVEI

TGRDLYKALNEQYDQKQNFFLQIAGLRYTYTDNKEGGEETPFKVVKAYKS

NGEEINPDAKYKLVINDFLFGGGDGFASFRNAKLLGAINPDTEVFMAYIT

DLEKAGKKVSVPNNKPKIYVTMKMVNETITQNDGTHSIIKKLYLDRQGNI

VAQEIVSDTLNQTKSKSTKINPVTTIHKKQLHQFTAINPMRNYGKPSNST

TVKS<u>KQLPKTNSEYGQSFLMSVFGVGLIGIALNTKKKHMK</u>

GBS 328 may contain an N-terminal leader or signal sequence region which is indicated by the underlined sequence at the beginning of SEQ ID NO: 81 above. In one embodiment, one or more amino acids from the leader or signal sequence region of GBS 328 are removed. An example of such a GBS 328 fragment is set forth below as SEQ ID NO: 82.

SEQ ID NO: 82
HGALDNTGTANMPDGKVANAGTAAQLDAYMDDAQKDFDQTNPNGESIRVQ

AGDMVGASPANSGLLQDEPTVKNFNAMNVEYGTLGNHEFDEGLAEYNRIV

TGKAPAPDSNINNITKSYPHEAAKQEIVVANVIDKVNKQIPYNWKPYAIK

NIPVNNKSVNVGFIGIVTKDIPNLVLRKNYEQYEFLDEAETIVKYAKELQ

AKNVKAIVVLAHVPATSKNDIAEGEAAEMMKKVNQLFPENSVDIVFAGHN

HQYTNGLVGKTRIVQALSQGKAYADVRGVLDTDTQDFIETPSAKVIAVAP

GKKTGSADIQAIVDQANTIVKQVTEAKIGTAEVSVMITRSVDQDNVSPVG

SLITEAQLAIARRKSWPDIDFAMTNNGGIRADLLIKPDGTITWGAAQVQP

FGNILQVVEITGRDLYKALNEQYDQKQNFFLQIAGLRYTYTDNKEGGEET

PFKVVKAYKSNGEEINPDAKYKLVINDFLFGGGDGFASFRNAKLLGAINP

DTEVFMAYITDLEKAGKKVSVPNNKPKIYVTMKMVNETITQNDGTHSIIK

-continued
KLYLDRQGNIVAQEIVSDTLNQTKSKSTKINPVTTIHKKQLHQFTAINPM

RNYGKPSNSTTVKSKQLPKTNSEYGQSFLMSVFGVGLIGIALNTKKKHMK

GBS 328 may also contain a transmembrane and/or cytoplasmic domain region. In one embodiment, one or more amino acids from the transmembrane and/or cytoplasmic domain region of GBS 328 are removed. An example of such a GBS 328 fragment is set forth below as SEQ ID NO: 83.

SEQ ID NO: 83
MKKKIILKSSVLGLVAGTSIMFSSVFADQVGVQVIGVNDFHGALDNTGTA

NMPDGKVANAGTAAQLDAYMDDAQKDFKQTNPNGESIRVQAGDMVGASPA

NSGLLQDEPTVKNFNAMNVEYGTLGNHEFDEGLAEYNRIVTGKAPAPDSN

INNITKSYPHEAAKQEIVVANVIDKVNKQIPYNWKPYAIKNIPVNNKSVN

VGFIGIVTKDIPNLVLRKNYEQYEFLDEAETIVKYAKELQAKNVKAIVVL

AHVPATSKNDIAEGEAAEMMKKVNQLFPENSVDIVFAGHNHQYTNGLVGK

TRIVQALSQGKAYADVRGVLDTDTQDFIETPSAKVIAVAPGKKTGSADIQ

AIVDQANTIVKQVTEAKIGTAEVSVMITRSVDQDNVSPVGSLITEAQLAI

ARKSWPDIDFAMTNNGGIRADLLIKPDGTITWGAAQAVQPFGNILQVVEI

TGRDLYKALNEQYDQKQNFFLQIAGLRYTYTDNKEGGEETPFKVVKAYKS

NGEEINPDAKYKLVINDFLFGGGDGFASFRNAKLLGAINPDTEVFMAYIT

DLEKAGKKVSVPNNKPKIYVTMKMVNETITQNDGTHSIIKKLYLDRQGNI

VAQEIVSDTLNQTKSKSTKINPVTTIHKKQLHQFTAINPMRNYGKPSNST

TVKS

In one embodiment, one or more amino acids from the leader or signal sequence region and one or more amino acids from the transmembrane or cytoplasmic region of GBS 328 are removed. An example of such a GBS 328 fragment is set forth below as SEQ ID NO: 84.

SEQ ID NO: 84
HGALDNTGTANMPDGKVANAGTAAQLDAYMDDAQKDFDQTNPNGESIRVQ

AGDMVGASPANSGLLQDEPTVKNFNAMNVEYGTLGNHEFDEGLAEYNRIV

TGKAPAPDSNINNITKSYPHEAAKQEIVVANVIDKVNKQIPYNWKPYAIK

NIPVNNKSVNVGFIGIVTKDIPNLVLRKNYEQYEFLDEAETIVKYAKELQ

AKNVKAIVVLAHVPATSKNDIAEGEAAEMMKKVNQLFPENSVDIVFAGHN

HQYTNGLVGKTRIVQALSQGKAYADVRGVLDTDTQDFIETPSAKVIAVAP

GKKTGSADIQAIVDQANTIVKQVTEAKIGTAEVSVMITRSVDQDNVSPVG

SLITEAQLAIARRKSWPDIDFAMTNNGGIRADLLIKPDGTITWGAAQVQP

FGNILQVVEITGRDLYKALNEQYDQKQNFFLQIAGLRYTYTDNKEGGEET

PFKVVKAYKSNGEEINPDAKYKLVINDFLFGGGDGFASFRNAKLLGAINP

DTEVFMAYITDLEKAGKKVSVPNNKPKIYVTMKMVNETITQNDGTHSIIK

KLYLDRQGNIVAQEIVSDTLNQTKSKSTKINPVTTIHKKQLHQFTAINPM

RNYGKPSNSTTVKS

GBS 656

GBS 656 refers to a putative DNA-entry nuclease. Nucleotide and amino acid sequences of GB S 656 sequenced from serotype V isolated strain 2603 V/R are set forth in Ref. 2 as SEQ ID 9323 and SEQ ID 9324. These sequences are set forth below as SEQ ID NOS 85 and 86:

SEQ ID NO. 85
ATGAAAAGATTACATAAACTGTTTATAACCGTAATTGCTACATTAGGTAT

GTTGGGGGTAATGACCTTTGGTCTTCCAACGCAGCCGCAAAACGTAACGC

CGATAGTACATGCTGATGTCAATTCATCTGTTGATACGAGCCAGGAATTT

CAAAATAATTTAAAAAATGCTATTGGTAACCTACCATTTCAATATGTTAA

TGGTATTTATGAATTAAATAATAATCAGACAAATTTAAATGCTGATGTCA

ATGTTAAAGCGTATGTTCAAAATACAATTGACAATCAACAAAGACTATCA

ACTGCTAATGCAATGCTTGATAGAACCATTCGTCAATATCAAAATCGCAG

AGATACCACTCTTCCCGATGCAAATTGGAAACCATTAGGTTGGCATCAAG

TAGCTACTAATGACCATTATGGACATGCAGTCGACAAGGGGCATTTAATT

GCCTATGCTTTAGCTGGAAATTTCAAAGGTTGGGATGCTTCCGTGTCAAA

TCCTCAAAATGTTGTCACACAAACAGCTCATTCCAACCAATCAAATCAAA

AAATCAATCGTGGACAAAATTATTATGAAAGCTTAGTTCGTAAGGCGGTT

GACCAAAACAAACGTGTTCGTTACCGTGTAACTCCATTGTACCGTAATGA

TACTGATTTAGTTCCATTTGCAATGCACCTAGAAGCTAAATCACAAGATG

GCACATTAGAATTTAATGTTGCTATTCCAAACACACAAGCATCATACACT

ATGGATTATGCAACAGGAGAAATAACACTAAAT

SEQ ID NO. 86
MKRLHKLFITVIATLGMLGVMTFGLPTQPQNVTPIVHADVNSSVDTSQEF

QNNLKNAIGNLPFQYVNGIYELNNNQTNLNADVNVKAYVQNTIDNQQRLS

TANAMLDRTIRQYQNRRDTTLPDANWKPLGWHQVATNDHYGHAVDKGHLI

AYALAGNFKGWDASVSNPQNVVTQTAHSNQSNQKINRGQNYYESLVRKAV

DQNKRVRYRVTPLYRNDTDLVPFAMHLEAKSQDGTLEFNVAIPNTQASYT

MDYATGEITLN

GBS 67

The following offers examples of preferred GBS 67 fragments. Nucleotide and amino acid sequence of GBS 67 sequences from serotypeV isolated strain 2603 are set forth below as SEQ ID NOS: 87 and 88.

SEQ ID NO: 87
ATGAGAAAATACCAAAAATTTTCTAAAATATTGACGTTAAGTCTTTTTTG

TTTGTCGCAAATACCGCTTAATACCAATGTTTTAGGGGAAAGTACCGTAC

CGGAAAATGGTGCTAAAGGAAAGTTAGTTGTTAAAAAGACAGATGACCAG

AACAAACCACTTTCAAAAGCTACCTTTGTTTTAAAAACTACTGCTCATCC

AGAAAGTAAAATAGAAAAAGTAACTGCTGAGCTAACAGGTGAAGCTACTT

TTGATAATCTCATACCTGGAGATTATACTTTATCAGAAGAAACAGCGCCC

GAAGGTTATAAAAAGACTAACCAGACTTGGCAAGTTAAGGTTGAGAGTAA

TGGAAAAACTACGATACAAAATAGTGGTGATAAAAATTCCACAATTGGAC

AAAATCAGGAAGAACTAGATAAGCAGTATCCCCCCACAGGAATTTATGAA

GATACAAAGGAATCTTATAAACTTGAGCATGTTAAAGGTTCAGTTCCAAA

TGGAAAGTCAGAGGCAAAAGCAGTTAACCCATATTCAAGTGAAGGTGAGC

```
ATATAAGAGAAATTCCAGAGGGAACATTATCTAAACGTATTTCAGAAGTA
GGTGATTTAGCTCATAATAAATATAAAATTGAGTTAACTGTCAGTGGAAA
AACCATAGTAAAACCAGTGGACAAACAAAAGCCGTTAGATGTTGTCTTCG
TACTCGATAATTCTAACTCAATGAATAACGATGGCCCAAATTTTCAAAGG
CATAATAAAGCCAAGAAAGCTGCCGAAGCTCTTCGGACCGCAGTAAAAGA
TATTTTAGGAGCAAACAGTGATAATAGGGTTGCATTAGTTACCTATGGTT
CAGATATTTTTGATGGTAGGAGTGTAGATGTCGTAAAAGGATTTAAAGAA
GATGATAAATATTATGGCCTTCAAACTAAGTTCACAATTCAGACAGAGAA
TTATAGTCATAAACAATTAACAAATAATGCTGAAGAGATTATAAAAAGGA
TTCCGACAGAAGCTCCTAAAGCTAAGTGGGGATCTACTACCAATGGATTA
ACTCCAGAGCAACAAAAGGAGTACTATCTTAGTAAAGTAGGAGAAACATT
TACTATGAAAGCCTTCATGGAGGCAGATGATATTTTGAGTCAAGTAAATC
GAAATAGTCAAAAAATTATTGTTCATGTAACTGATGGTGTTCCTACGAGA
TCATATGCTATTAATAATTTTAAACTGGGTGCATCATATGAAAGCCAATT
TGAACAAATGAAAAAAAATGGATATCTAAATAAAAGTAATTTTCTACTTA
CTGATAAGCCCGAGGATATAAAAGGAAATGGGGAGAGTTACTTTTTGTTT
CCCTTAGATAGTTATCAAACACAGATAATCTCTGGAAACTTACAAAAACT
TCATTATTTAGATTTAAATCTTAATTACCCTAAAGGTACAATTTATCGAA
ATGGACCAGTGAAAGAACATGGAACACCAACCAAACTTTATATAAATAGT
TTAAAACAGAAAAATTATGACATTTTTAATTTTGGTATCGATATATCTGG
TTTTAGACAAGTTTATAATGAGGAGTATAAGAAAAATCAAGATGGTACTT
TTCAAAAATTGAAAGAGGAAGCTTTTAAACTTTCAGATGGAGAAATCACA
GAACTAATGAGGTCGTTCTCTTCCAAACCTGAGTACTACACCCCTATCGT
AACTTCAGCCGATACATCTAACAATGAAATTTTATCTAAAATTCAGCAAC
AATTTGAAACGATTTTAACAAAAGAAAACTCAATTGTTAATGGAACTATC
GAAGATCCTATGGGTGATAAAAATCAATTTACAGCTTGGTAATGGACAAAC
ATTACAGCCAAGTGATTATACTTTACAGGGAAATGATGGAAGTGTAATGA
AGGATGGTATTGCAACTGGTGGGCCTAATAATGATGGTGGAATACTTAAG
GGGGTTAAATTAGAATACATCGGAAATAAACTCTATGTTAGAGGTTTGAA
TTTAGGAGAAGGTCAAAAAGTAACACTCACATATGATGTGAAACTAGATG
ACAGTTTTATAAGTAACAAATTCTATGACACTAATGGTAGAACAACATTG
AATCCTAAGTCAGAGGATCCTAATACACTTAGAGATTTTCCAATCCCTAA
AATTCGTGATGTGAGAGAATATCCTACAATAACGATTAAAAACGAGAAGA
AGTTAGGTGAAATTGAATTTATAAAAGTTGATAAAGATAATAATAAGTTG
CTTCTCAAAGGAGCTACGTTTGAACTTCAAGAATTTAATGAAGATTATAA
ACTTTATTTACCAATAAAAAATAATAATTCAAAAGTAGTGACGGGAGAAA
ACGGCAAATTTCTTACAAAGATTTGAAAGATGGCAAATATCAGTTAATA
GAAGCAGTTTCGCCGGAGGATTATCAAAAAATTACTAATAAACCAATTTT
AACTTTTGAAGTGGTTAAAGGATCGATAAAAAATATAATAGCTGTTAATA
AACAGATTTCTGAATATCATGAGGAAGGTGACAAGCATTTAATTACCAAC
ACGCATATTCCACCAAAAGGAATTATTCCTATGACAGGTGGGAAAGGAAT
TCTATCTTTCATTTTAATAGGTGGAGCTATGATGTCTATTGCAGGTGGAA
TTTATATTTGGAAAAGGTATAAGAAATCTAGTGATATGTCCATCAAAAAA
GAT
```

SEQ ID NO: 88
MRKYQKFSKILTLSLFCLSQIPLNTNVLGESTVPENGAKGKLVVKKTDDQ
NKPLSKATFVLKTTAHPESKIEKVTAILTGEATFDNLIPGDYTLSEETAP
EGYKKTNQTWQVKVESNGKTTIQNSGDKNSTIGQNQEELDKQYPPTGIYE
DTKESYLKEHVKGSVPNGKSEAKAVNPYSSEGEHIREIPEGTLSKRISEV
GDLAHNKYKIELTVSGKTIVKPVDKQKPLDVVFVLDNSNSMNNDGPNFQR
HNKAKKAAEALGTAVKDILGANSDNRVALVTYGSDIFDGRSVDVVKGFKE
DDKYYGLQTKFTIQTENYSHKQLTNNAEEIIKRIPTEAPKAKWGSTTNGL
TPEQQKEYYLSKVGETFTMKAFMEADDILSQVNRNSQKIIVHVTDGVPTR
SYAINNFKLGASYESQGEQMKKNGYLNKSNFLLTDKPEDIKGNGESYFLF
PLDSYQTQIISGNLQKLHYLDLNLNYPKGTIYRNGPVKEHGTPTKLYINS
LKQKNYDIFNFGIGISGFRQVYNEEYKKNQDGTFQKLKEEAFKLSDGEIT
ELMRSFSSKPEYYTPIVTSADTSNNEILSKIQQQFETILTKENSIVNGTI
EDPMGDKINLQLGNGQTLQPSDYTLQGNDGSVMKDGIATGGPNNDGGILK
GVKLEYIGNKLYVRGLNLGEGQKVTLTYDVKLDDSFISNKFYDTNGRTTL
NPKSEDPNTLRDFPIPKIRDVREYPTITIKNEKKLGEIEFIKVDKDNNKL
LLKGATFELQEFNEDYKLYPIKNNNSKKVVTGENGKISYKDLKDGKYQLI
EAVSPEDYQKITNKPILTFEVVKGSIKNIIAVNKQISEYHEEGDKHLITN
THIPPKGIIPMTGGKGILS<u>FILIGGAMMSIAGGIYI</u>WKRYKKSSDMSI
KKD

GBS 67 contains a C-terminus transmembrane region which is indicated by the underlined region closest to the C-terminus of SEQ ID NO: 88 above. In one embodiment; one or more amino acids from the transmembrane region is removed and or the amino acid is truncated before the transmembrane region. An example of such a GBS 67 fragment is set forth below as SEQ ID NO: 89.

SEQ ID NO: 89
MRKYQKFSKILTLSLFCLSQIPLNTNVLGESTVPENGAKGKLVVKKTDDQ
NKPLSKATFVLKTTAHPESKIEKVTAILTGEATFDNLIPGDYTLSEETAP
EGYKKTNQTWQVKVESNGKTTIQNSGDKNSTIGQNQEELDKQYPPTGIYE
DTKESYLKEHVKGSVPNGKSEAKAVNPYSSEGEHIREIPEGTLSKRISEV
GDLAHNKYKIELTVSGKTIVKPVDKQKPLDVVFVLDNSNSMNNDGPNFQR
HNKAKKAAEALGTAVKDILGANSDNRVALVTYGSDIFDGRSVDVVKGFKE
DDKYYGLQTKFTIQTENYSHKQLTNNAEEIIKRIPTEAPKAKWGSTTNGL
TPEQQKEYYLSKVGETFTMKAFMEADDILSQVNRNSQKIIVHVTDGVPTR
SYAINNFKLGASYESQGEQMKKNGYLNKSNFLLTDKPEDIKGNGESYFLF
PLDSYQTQIISGNLQKLHYLDLNLNYPKGTIYRNGPVKEHGTPTKLYINS
LKQKNYDIFNFGIGISGFRQVYNEEYKKNQDGTFQKLKEEAFKLSDGEIT
ELMRSFSSKPEYYTPIVTSADTSNNEILSKIQQQFETILTKENSIVNGTI

-continued

EDPMGDKINLQLGNGQTLQPSDYTLQGNDGSVMKDGIATGGPNNDGGILK

GVKLEYIGNKLYVRGLNLGEGQKVTLTYDVKLDDSFISNKFYDTNGRTTL

NPKSEDPNTLRDFPIPKIRDVREYPTITIKNEKKLGEIEFIKVDKDNNKL

LLKGATFELQEFNEDYKLYPIKNNNSKKVVTGENGKISYKDLKDGKYQLI

EAVSPEDYQKITNKPILTFEVVKGSIKNIIAVNKQISEYHEEGDKHLITN

THIPPKGIIPMTGGKGILS

GBS 67 contains an amino acid motif indicative of a cell wall anchor (an LPXTG motif) (SEQ ID NO:93): SEQ ID NO: 90 IPMTG. (shown in italics in SEQ ID NO: 88 above). In some recombinant host cell systems, it may be preferable to remove this motif to facilitate secretion of a recombinant GBS 67 protein from the host cell. Accordingly, in one preferred fragment of GBS 67 for use in the invention, the transmembrane and the cell wall anchor motif are removed from GBS 67. An example of such a GBS 67 fragment is set forth below as SEQ ID NO: 91.

SEQ ID NO: 91
MRKYQKFSKILTLSLFCLSQIPLNTNVLGESTVPENGAKGKLVVKKTDDQ

NKPLSKATFVLKTTAHPESKIEKVTAILTGEATFDNLIPGDYTLSEETAP

EGYKKTNQTWQVKVESNGKTTIQNSGDKNSTIGQNQEELDKQYPPTGIYE

DTKESYLKEHVKGSVPNGKSEAKAVNPYSSEGEHIREIPEGTLSKRISEV

GDLAHNKYKIELTVSGKTIVKPVDKQKPLDVVFVLDNSNSMNNDGPNFQR

HNKAKKAAEALGTAVKDILGANSDNRVALVTYGSDIFDGRSVDVVKGFKE

DDKYYGLQTKFTIQTENYSHKQLTNNAEEIIKRIPTEAPKAKWGSTTNGL

TPEQQKEYYLSKVGETFTMKAFMEADDILSQVNRNSQKIIVHVTDGVPTR

SYAINNFKLGASYESQGEQMKKNGYLNKSNFLLTDKPEDIKGNGESYFLF

PLDSYQTQIISGNLQKLHYLDLNLNYPKGTIYRNGPVKEHGTPTKLYINS

LKQKNYDIFNFGIGISGFRQVYNEEYKKNQDGTFQKLKEEAFKLSDGEIT

ELMRSFSSKPEYYTPIVTSADTSNNEILSKIQQQFETILTKENSIVNGTI

EDPMGDKINLQLGNGQTLQPSDYTLQGNDGSVMKDGIATGGPNNDGGILK

GVKLEYIGNKLYVRGLNLGEGQKVTLTYDVKLDDSFISNKFYDTNGRTTL

NPKSEDPNTLRDFPIPKIRDVREYPTITIKNEKKLGEIEFIKVDKDNNKL

LLKGATFELQEFNEDYKLYPIKNNNSKKVVTGENGKISYKDLKDGKYQLI

EAVSPEDYQKITNKPILTFEVVKGSIKNIIAVNKQISEYHEEGDKHLITN

THIPPKGI

The compositions of the invention may also include combinations including one or more known GBS antigens in combination with GBS 80.

There is an upper limit to the number of GBS antigens which will be in the compositions of the invention. Preferably, the number of GBS antigens in a composition of the invention is less than 20, less than 19, less than 18, less than 17, less than 16, less than 15, less than 14, less than 13, less than 12, less than 11, less than 10, less than 9, less than 8, less than 7, less than 6, less than 5, less than 4, or less than 3. Still more preferably, the number of GBS antigens in a composition of the invention is less than 6, less than 5, or less than 4. Still more preferably, the number of GBS antigens in a composition of the invention is 3.

The GBS antigens used in the invention are preferably isolated, i.e., separate and discrete, from the whole organism with which the molecule is found in nature or, when the polynucleotide or polypeptide is not found in nature, is sufficiently free of other biological macromolecules so that the polynucleotide or polypeptide can be used for its intended purpose.

Fusion Proteins

The GBS antigens used in the invention may be present in the composition as individual separate polypeptides, but it is preferred that at least two (i.e. 2, 3, 4, 5, 6, 7, 8, 9, 10, 11, 12, 13, 14, 15, 16, 17, or 18) of the antigens are expressed as a single polypeptide chain (a "hybrid" or "fusion" polypeptide). Such fusion polypeptides offer two principal advantages: first, a polypeptide that may be unstable or poorly expressed on its own can be assisted by adding a suitable fusion partner that overcomes the problem; second, commercial manufacture is simplified as only one expression and purification need be employed in order to produce two polypeptides which are both antigenically useful.

The fusion polypeptide may comprise two or more polypeptide sequences from the group consisting of GBS 80, GBS 91, GBS 104, GBS 184, GBS 276, GBS 305, GBS 322, GBS 330, GBS 338, GBS 361, GBS 404, GBS 690 and GBS 691. Preferably, the polypeptide sequences are selected from the group consisting of GBS 80, GBS 104 and GBS 322. Most preferably, the fusion peptide includes a polypeptide sequence from GBS 80. Accordingly, the invention includes a fusion peptide comprising a first amino acid sequence and a second amino acid sequence, wherein said first and second amino acid sequences are selected from a GBS antigen or a fragment thereof of the above antigen group. Preferably, the first and second amino acid sequences in the fusion polypeptide comprise different epitopes.

Example 7

Examples of Fragments for Fusion Proteins from GBS 80 with GBS 104, and GBS 322

Examples of GBS fragments for fusion proteins are provided from GBS 322, GBS 104, and GBS 80. One example of a fragment of GBS 322 in a fusion protein is a 407 amino acid fragment with the signal peptide removed. Fragments of GBS 104 may also be incorporated in fusion proteins. An example of GBS 104 fragments includes an 830 amino acid fragment, a 359 amino acid fragment from near the N-terminus, a 581 amino acid fragment from near the N-terminus, and a 740 amino acid fragment from near the N-terminus. Examples of GBS 80 fragments include a 446 amino acid fragment and a 235 amino acid fragment. Table 13 below summarizes the examples of fragments for fusion proteins and their locations within the corresponding full length GBS protein.

TABLE 13

Active Maternal Immunization Assay using combinations of GBS 80 with GBS 104 and GBS 322

| GBS | Size (AA) | SEQ ID NO | From . . . to |
|---|---|---|---|
| 322 | 407 | 92 | 25-432 |
| 104 | 830 | 96 | 28-858 |
| 104 N1 | 359 | 97 | 28-387 |
| 104 N2 | 581 | 98 | 28-609 |
| 104 N3 | 740 | 99 | 28-768 |
| 80 | 446 | 100 | 37-483 |
| 80N | 235 | 101 | 37-272 |

Hybrids (or fusions) consisting of amino acid sequences from two, three, four, five, six, seven, eight, nine, or ten GBS antigens are preferred. In particular, hybrids consisting of amino acid sequences from two, three, four, or five GBS antigens are preferred.

Different hybrid polypeptides may be mixed together in a single formulation. Within such combinations, a GBS antigen may be present in more than one hybrid polypeptide and/or as a non-hybrid polypeptide. It is preferred, however, that an antigen is present either as a hybrid 6r as a non-hybrid, but not as both.

Hybrid polypeptides can be represented by the formula $NH_2$-A-$\{$-X-L-$\}_n$-B—COOH, wherein: X is an amino acid sequence of a GBS antigen or a fragment thereof from the antigen group set forth above; L is an optional linker amino acid sequence; A is an optional N-terminal amino acid sequence; B is an optional C-terminal amino acid sequence; and n is 2, 3, 4, 5, 6, 7, 8, 9, 10, 11, 12, 13, 14 or 15.

If a -X- moiety has a leader peptide sequence in its wild-type form, this may be included or omitted in the hybrid protein. In some embodiments, the leader peptides will be deleted except for that of the -X- moiety located at the N-terminus of the hybrid protein i.e. the leader peptide of $X_1$ will be retained, but the leader peptides of $X_2 \ldots X_n$ will be omitted. This is equivalent to deleting all leader peptides and using the leader peptide of $X_1$ as moiety -A-.

For each n instances of $\{$-X-L-$\}$, linker amino acid sequence -L- may be present or absent. For instance, when n=2 the hybrid may be $NH_2$-$X_1$-$L_1$-$X_2$-$L_2$-COOH, $NH_2$—$X_1$—$X_2$—COOH, $NH_2$—$X_1$-$L_1$-$X_2$—COOH, $NH_2$—$X_1$—$X_2$-$L_2$-COOH, etc. Linker amino acid sequence(s)-L- will typically be short (e.g. 20 or fewer amino acids i.e. 19, 18, 17, 16, 15, 14, 13, 12, 11, 10, 9, 8, 7, 6, 5, 4, 3, 2, 1). Examples comprise short peptide sequences which facilitate cloning, poly-glycine linkers (i.e. comprising $Gly_n$ where n=2, 3, 4, 5, 6, 7, 8, 9, 10 or more), and histidine tags (i.e. $His_n$ where n=3, 4, 5, 6, 7, 8, 9, 10 or more). Other suitable linker amino acid sequences will be apparent to those skilled in the art. A useful linker is GSGGGG (SEQ ID NO:92), with the Gly-Ser dipeptide being formed from a BamHI restriction site, thus aiding cloning and manipulation, and the $(Gly)_4$ tetrapeptide being a typical poly-glycine linker.

-A- is an optional N-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking, or short peptide sequences which facilitate cloning or purification (e.g. histidine tags i.e. $His_n$ where n=3, 4, 5, 6, 7, 8, 9, 10 or more). Other suitable N-terminal amino acid sequences will be apparent to those skilled in the art. If $X_1$ lacks its own N-terminus methionine, -A- is preferably an oligopeptide (e.g. with 1, 2, 3, 4, 5, 6, 7 or 8 amino acids) which provides a N-terminus methionine.

-B- is an optional C-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include sequences to direct protein trafficking, short peptide sequences which facilitate cloning or purification (e.g. comprising histidine tags i.e. $His_n$ where n=3, 4, 5, 6, 7, 8, 9, 10 or more), or sequences which enhance protein stability. Other suitable C-terminal amino acid sequences will be apparent to those skilled in the art. Most preferably, n is 2 or 3.

Example 8

Active Maternal Immunization Assay using fusion proteins of Fragments of GBS 80, GBS 67, and GBS 322

In this example, fusion proteins of GBS antigens was used in the Active Maternal Immunization Assay with an isolate challenge of different GBS strains. In these experiments, the challenge dose for the different GBS strains was sufficient to kill approximately 70-90% of unimmunized pups and is equal to 10×LD 50% (where LD 50% is the statistically derived Median Lethal Dose). The maternal mice were immunized according to the Active Maternal Immunization Assay schedule described above with the fusion proteins of a GBS 80 antigen with GBS 322 antigen in the GBS strains set forth in Table 14 below. Survival % was observed with the GBS fusion proteins. As shown in Table 14, in this particular challenge study, the survival rates for the fusion proteins in all of the GBS strains achieved up to 79%.

TABLE 14

Active Maternal Immunization Assay using fusion proteins of GBS 80 with GBS 322

| | COH1 (III) | | CJB111 (V) | | 515 (Ia) | | DK21 (II) | | 2603 (V) | |
|---|---|---|---|---|---|---|---|---|---|---|
| GBS | Dead/treated | Survival % | Dead/treated | Survival % | Dead/treated | Survival % | Dead/treated | Survival % | Dead/treated | Survival % |
| 80N-322 | 16/40 | 60 | 8/39 | 79 | 12/28 | 57 | 7/19 | 63 | 8/37 | 78 |
| 80 | 4/24 | 83 | | | | | | | | |
| PBS | 35/40 | 12 | 27/35 | 23 | 32/39 | 18 | 31/40 | 22 | 33/40 | 17 |
| 80-322 | 12/27 | 55 | | | | | | | 12/38 | 68 |
| 80 | 0/33 | 100 | 28/40 | 30 | | | | | | |
| 322 | | | | | | | | | 1/16 | 94 |
| PBS | 19/20 | 5 | 38/39 | 2 | 25/29 | 14 | | | 19/26 | 27 |

Nucleic Acids

The invention also provides nucleic acid encoding the GBS antigens and/or the hybrid fusion polypeptides of the invention. Furthermore, the invention provides nucleic acid which can hybridise to these nucleic acids, preferably under "high stringency" conditions (e.g. 65° C. in a 0.1×SSC, 0.5% SDS solution).

Polypeptides of the invention can be prepared by various means (e.g. recombinant expression, purification from cell culture, chemical synthesis, etc.) and in various forms (e.g. native, fusions, non-glycosylated, lipidated, etc.). They are preferably prepared in substantially pure form (i.e. substantially free from other GAS or host cell proteins).

Nucleic acid according to the invention can be prepared in many ways (e.g. by chemical synthesis, from genomic or cDNA libraries, from the organism itself, etc.) and can take various forms (e.g. single stranded, double stranded, vectors, probes, etc.). They are preferably prepared in substantially pure form (ie. substantially free from other GBS or host cell nucleic acids).

The term "nucleic acid" includes DNA and RNA, and also their analogues, such as those containing modified backbones (e.g. phosphorothioates, etc.), and also peptide nucleic acids (PNA), etc. The invention includes nucleic acid comprising sequences complementary to those described above (e.g. for antisense or probing purposes).

The invention also provides a process for producing a polypeptide of the invention, comprising the step of culturing a host cell transformed with nucleic acid of the invention under conditions which induce polypeptide expression.

The invention provides a process for producing a polypeptide of the invention, comprising the step of synthesising at least part of the polypeptide by chemical means.

The invention provides a process for producing nucleic acid of the invention, comprising the step of amplifying nucleic acid using a primer-based amplification method (e.g. PCR).

The invention provides a process for producing nucleic acid of the invention, comprising the step of synthesising at least part of the nucleic acid by chemical means.

Purification and Recombinant Expression

The GBS antigens of the invention may be isolated from *Streptococcus agalactiae*, or they may be recombinantly produced, for instance, in a heterologous host. Preferably, the GBS antigens are prepared using a heterologous host. The heterologous host may be prokaryotic (e.g. a bacterium) or eukaryotic. It is preferably *E. coli*, but other suitable hosts include *Bacillus subtilis, Vibrio cholerae, Salmonella typhi, Salmonella typhimurium, Neisseria lactamica, Neisseria cinerea, Mycobacteria* (e.g. *M. tuberculosis*), yeasts, etc.

Recombinant production of polypeptides is facilitated by adding a tag protein to the GBS antigen to be expressed as a fusion protein comprising the tag protein and the GBS antigen. Such tag proteins can facilitate purification, detection and stability of the expressed protein. Tag proteins suitable for use in the invention include a polyarginine tag (Arg-tag), polyhistidine tag (His-tag), FLAG-tag, Strep-tag, c-myc-tag, S-tag, calmodulin-binding peptide, cellulose-binding domain, SBP-tag, chitin-binding domain, glutathione S-transferase-tag (GST), maltose-binding protein, transcription termination anti-terminiantion factor (NusA), *E. coli* thioredoxin (TrxA) and protein disulfide isomerase I (DsbA). Preferred tag proteins include His-tag and GST. A full discussion on the use of tag proteins can be found at Ref. 3.

After purification, the tag proteins may optionally be removed from the expressed fusion protein, i.e., by specifically tailored enzymatic treatments known in the art. Commonly used proteases include enterokinase, tobacco etch virus (TEV), thrombin, and factor $X_a$.

GBS Polysaccharides

The compositions of the invention may be further improved by including GBS polysaccharides. Preferably, the GBS antigen and the saccharide each contribute to the immunological response in a recipient. The combination is particularly advantageous where the saccharide and polypeptide provide protection from different GBS serotypes.

The combined antigens may be present as a simple combination where separate saccharide and polypeptide antigens are administered together, or they may be present as a conjugated combination, where the saccharide and polypeptide antigens are covalently linked to each other.

Thus the invention provides an immunogenic composition comprising (i) one or more GBS polypeptide antigens and (ii) one or more GBS saccharide antigens. The polypeptide and the polysaccharide may advantageously be covalently linked to each other to form a conjugate.

Between them, the combined polypeptide and saccharide antigens preferably cover (or provide protection from) two or more GBS serotypes (e.g. 2, 3, 4, 5, 6, 7, 8 or more serotypes). The serotypes of the polypeptide and saccharide antigens may or may not overlap. For example, the polypeptide might protect against serogroup II or V, while the saccharide protects against either serogroups Ia, Ib, or III. Preferred combinations protect against the following groups of serotypes: (1) serotypes Ia and Ib, (2) serotypes Ia and II, (3) serotypes Ia and III, (4) serotypes Ia and IV, (5) serotypes Ia and V, (6) serotypes Ia and VI, (7) serotypes Ia and VII, (8) serotypes Ia and VIII, (9) serotypes Ib and II, (10) serotypes Ib and III, (11) serotypes Ib and IV, (12) serotypes Ib and V, (13) serotypes Ib and VI, (14) serotypes Ib and VII, (15) serotypes Ib and VIII, 16) serotypes II and III, (17) serotypes II and IV, (18) serotypes II and V, (19) serotypes II and VI, (20) serotypes II and VII, (21) serotypes II and VII, (22) serotypes III and IV, (23) serotypes III and V, (24) serotypes III and VI, (25) serotypes III and VII, (26) serotypes III and VIII, (27) serotypes IV and V, (28) serotypes IV and VI, (29) serotypes IV and VII, (30) serotypes IV and VIII, (31) serotypes V and VI, (32) serotypes V and VII, (33) serotypes V and VIII, (34) serotypes VI and VII, (35) serotypes VI and VIII, and (36) serotypes VII and VIII.

Still more preferably, the combinations protect against the following groups of serotypes: (1) serotypes Ia and II, (2) serotypes Ia and V, (3) serotypes Ib and II, (4) serotypes Ib and V, (5) serotypes III and II, and (6) serotypes III and V. Most preferably, the combinations protect against serotypes III and V.

Protection against serotypes II and V is preferably provided by polypeptide antigens. Protection against serotypes Ia, Ib and/or III may be polypeptide or saccharide antigens.

In one embodiment, the immunogenic composition comprises a GBS saccharide antigen and at least two GBS polypeptide antigens or fragments thereof, wherein said GBS saccharide antigen comprises a saccharide selected from GBS serotype Ia, Ib, and III, and wherein said GBS polypeptide antigens comprise a combination of at least two polypeptide or a fragment thereof selected from the antigen group consisting of GBS 80, GBS 91, GBS 104, GBS 184, GBS 276, GBS 305, GBS 322, GBS 330, GBS 338, GBS 361, GBS 404, GBS 690, and GBS 691. Preferably, the combination includes one or more of GBS 80, GBS 104 and GBS 322. Still more preferably, the combination includes GBS 80 or a fragment thereof.

In certain embodiments, the compositions of the invention do not include a GBS polysaccharide. In certain embodiments, the combination does not include one or more of the GBS antigens selected from the group consisting of GBS 4, GBS 22, GBS 85, GBS 338 and GBS 361.

Immunogenic Compositions and Medicaments

Compositions of the invention are preferably immunogenic compositions, and are more preferably vaccine compositions. The pH of the composition is preferably between 6 and 8, preferably about 7. The pH may be maintained by the use of a buffer. The composition may be sterile and/or pyrogen-free. The composition may be isotonic with respect to humans.

Vaccines according to the invention may either be prophylactic (i.e. to prevent infection) or therapeutic (i.e. to treat infection), but will typically be prophylactic. Accordingly, the invention includes a method for the therapeutic or prophylactic treatment of a *Streptococcus agalactiae* infection in an animal susceptible to streptococcal infection comprising administering to said animal a therapeutic or prophylactic amount of the immunogenic compositions of the invention.

The invention also provides a composition of the invention for use as a medicament. The medicament is preferably able to raise an immune response in a mammal (i.e. it is an immunogenic composition) and is more preferably a vaccine.

The invention also provides the use of the compositions of the invention in the manufacture of a medicament for raising an immune response in a mammal. The medicament is preferably a vaccine.

The invention also provides for a kit comprising a first component comprising a combination of GBS antigens.

The invention also provides a delivery device pre-filled with the immunogenic compositions of the invention.

The invention also provides a method for raising an immune response in a mammal comprising the step of administering an effective amount of a composition of the invention. The immune response is preferably protective and preferably involves antibodies and/or cell-mediated immunity. The method may raise a booster response.

The mammal is preferably a human. Where the vaccine is for prophylactic use, the human is preferably a female (either of child bearing age or a teenager). Alternatively, the human may be elderly (e.g., over the age of 50, 55, 60, 65, 70 or 75) and may have an underlying disease such as diabetes or cancer. Where the vaccine is for therapeutic use, the human is preferably a pregnant female or an elderly adult.

These uses and methods are preferably for the prevention and/or treatment of a disease caused by *Streptococcus agalactiae*. The compositions may also be effective against other streptococcal bacteria.

One way of checking efficacy of therapeutic treatment involves monitoring GBS infection after administration of the composition of the invention. One way of checking efficacy of prophylactic treatment involves monitoring immune responses against the GBS antigens in the compositions of the invention after administration of the composition.

Compositions of the invention will generally be administered directly to a patient. Direct delivery may be accomplished by parenteral injection (e.g. subcutaneously, intraperitoneally, intradermally, intravenously, intramuscularly, or to the interstitial space of a tissue), or by rectal, oral (e.g. tablet, spray), vaginal, topical, transdermal {e.g. see ref. 4} or transcutaneous {e.g. see refs. 5 & 6}, intranasal {e.g. see ref. 7}, ocular, aural, pulmonary or other mucosal administration. The invention may be used to elicit systemic and/or mucosal immunity.

Dosage treatment can be a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc.

The compositions of the invention may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition). The composition may be prepared for topical administration e.g. as an ointment, cream or powder. The composition may be prepared for oral administration e.g. as a tablet or capsule, as a spray, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops. The composition may be in kit form, designed such that a combined composition is reconstituted just prior to administration to a patient. Such kits may comprise one or more antigens in liquid form and one or more lyophilised antigens.

Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials.

Further Components of the Composition

The composition of the invention will typically, in addition to the components mentioned above, comprise one or more 'pharmaceutically acceptable carriers', which include any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. A thorough discussion of pharmaceutically acceptable excipients is available in reference 8.

Vaccines of the invention may be administered in conjunction with other immunoregulatory agents. In particular, compositions will usually include an adjuvant.

Preferred further adjuvants include, but are not limited to, one or more of the following set forth below:

A. Mineral Containing Compositions

Mineral containing compositions suitable for use as adjuvants in the invention include mineral salts, such as aluminium salts and calcium salts. The invention includes mineral salts such as hydroxides (e.g. oxyhydroxides), phosphates (e.g. hydroxyphoshpates, orthophosphates), sulphates, etc. {e.g. see chapters 8 & 9 of ref. 9}), or mixtures of different mineral compounds, with the compounds taking any suitable form (e.g. gel, crystalline, amorphous, etc.), and with adsorption being preferred. The mineral containing compositions may also be formulated as a particle of metal salt. See ref. 10.

B. Oil-Emulsions

Oil-emulsion compositions suitable for use as adjuvants in the invention include squalene-water emulsions, such as MF59® (5% Squalene, 0.5% TWEEN® 80, and 0.5% SPAN® 85, formulated into submicron particles using a microfluidizer). See WO90/14837. See also, Frey et al., "Comparison of the safety, tolerability, and immunogenicity of a MF59®-adjuvanted influenza vaccine and a non-adjuvanted influenza vaccine in non-elderly adults", Vaccine (2003) 21:4234-4237.

Particularly preferred adjuvants for use in the compositions are submicron oil-in water emulsions. Preferred submicron oil-in-water emulsions for use herein are squalene/water emulsions optionally containing varying amounts of MFP-PE, such as a submicron oil-in-water emulsion containing 4-5% w/v squalene, 0.25-1.0% w/v TWEEN® 80 (polyoxyethylenesorbitan monooleate), and/or 0.25-1.0% SPAN® 85 (sorbitan trioleate), and, optionally, N-acetylmuramyl-L-alanyl-D-isogluatminyl-L-alanine-2-(1'-2'-dipalmitoyl-sn-glycero-3-huydroxyphosphoryloxy)-ethylamine (MTP-PE), for example, the submicron oil-in-water emulsion known as "MF59®" (International Publication No. WO 90/14837; U.S. Pat. Nos. 6,299,884 and 6,451,325, incorporated herein by reference in their entireties; and Ott et al., "MF59—Design and Evaluation of a Safe and Potent Adjuvant for Human Vaccines" in *Vaccine Design: The Subunit and Adjuvant Approach* (Powell, M. F. and Newman, M. J. eds.) Plenum Press, New York, 1995, pp. 277-296). MF59® contains 4-5% w/v Squalene (e.g., 4.3%), 0.25-0.5% w/v TWEEN® 80, and 0.5% w/v SPAN® 85 and optionally contains various amounts of MTP-PE, formulated into submicron particles using a microfluidizer such as Model 110Y microfluidizer (Microfluidics, Newton, Mass.). For example, MRP-PE may be present in an amount of about 0-500 µg/dose, more preferably 0-250 µg/dose and most preferably, 0-100 µg/dose. As used herein, the term "MF59-0" refers to the above submicron oil-in-water emulsion lacking MTP-PE, while the term MF59-MTP denotes a formulation that contains MTP-PE. For instance, "MF59® MF59 100" contains 100 µg MTP-PE per dose, and so on. MF69, another submicron oil-in-water emulsion for use herein, contains 4.3% w/v squalene, 0.25% w/v TWEEN® 80, and 0.75% w/v SPAN® 85 and optionally MRP-PE. Yet another submicron oil-in-water emulsion is MF75, also known as SAF, containing 10% squalene, 0.4% TWEEN® 80, 5% PLURONIC®-blocked polymer L121, and thr-MDP, also microfluidized into a submicron emulsion. MF75-MTP denotes an MF75 formulation that includes MTP, such as from 100-400 µg MTP-PE per dose.

Submicron oil-in-water emulsions, methods of making the same and immunostimulating agents, such as muramyl peptides, for use in the compositions, are described in detail in International Publication No. WO 90114837 and U.S. Pat. Nos. 6,299,884 and 6,451,325, incorporated herein by reference in their entireties.

Complete Freund's adjuvant (CFA) and incomplete Freund's adjuvant (IFA) may also be used as adjuvants in the invention.

C. Saponin Formulations

Saponin formulations, may also be used as adjuvants in the invention. Saponins are a heterologous group of sterol glycosides and triterpenoid glycosides that are found in the bark, leaves, stems, roots and even flowers of a wide range of plant species. Saponin from the bark of the Quillaia *saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs.

Saponin compositions have been purified using High Performance Thin Layer Chromatography (HP-LC) and Reversed Phase High Performance Liquid Chromatography (RP-HPLC). Specific purified fractions using these techniques have been identified, including QS7, QS17, QS18, QS21, QH-A, QH-B and QH-C. Preferably, the saponinis QS21. A method of production of QS21 is disclosed in U.S. Pat. No. 5,057,540. Saponin formulations may also comprise a sterol, such as cholesterol (see WO 96/33739).

Combinations of saponins and cholesterols can be used to form unique particles called Immunostimulating Complexes (ISCOMs). ISCOMs typically also include a phospholipid such as phosphatidylethanolamine or phosphatidylcholine. Any known saponin can be used in ISCOMs. Preferably, the ISCOM includes one or more of Quil A, QHA and QHC. ISCOMs are further described in EP 0 109 942, WO 96/11711 and WO 96/33739. Optionally, the ISCOMS may be devoid of additional detergent. See ref. 11.

A review of the development of saponin based adjuvants can be found at ref. 12.

C. Virosomes and Virus Like Particles (VLPs)

Virosomes and Virus Like Particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HUV, RNA-phages, QB-phage (such as coat proteins), GA-phage, fr-phage, AP205 phage, and Ty (such as retrotransposon Ty protein p1). VLPs are discussed further in WO 03/024480, WO 03/024481, and Refs. 13, 14, 15 and 16. Virosomes are discussed further in, for example, Ref. 17

D. Bacterial or Microbial Derivatives

Adjuvants suitable for use in the invention include bacterial or microbial derivatives such as:

(1) Non-Toxic Derivatives of Enterobacterial Lipopolysaccharide (LPS)

Such derivatives include Monophosphoryl lipid A (MPL) and 3-O-deacylated MPL (3dMPL). 3dMPL is a mixture of 3 De-O-acylated monophosphoryl lipid A with 4, 5 or 6 acylated chains. A preferred "small particle" form of 3 De-O-acylated monophosphoryl lipid A is disclosed in EP 0 689 454. Such "small particles" of 3dMPL are small enough to be sterile filtered through a 0.22 micron membrane (see EP 0 689 454). Other non-toxic LPS derivatives include monophosphoryl lipid A mimics, such as aminoalkyl glucosaminide phosphate derivatives e.g. RC-529. See Ref. 18.

(2) Lipid A Derivatives

Lipid A derivatives include derivatives of lipid A from *Escherichia coli* such as OM-174. OM-174 is described for example in Ref. 19 and 20.

(3) Immunostimulatory Oligonucleotides

Immunostimulatory oligonucleotides suitable for use as adjuvants in the invention include nucleotide sequences containing a CpG motif (a sequence containing an unmethylated cytosine followed by guanosine and linked by a phosphate bond). Bacterial double stranded RNA or oligonucleotides containing palindromic or poly(dG) sequences have also been shown to be immunostimulatory.

The CpG's can include nucleotide modifications/analogs such as phosphorothioate modifications and can be double-stranded or single-stranded. Optionally, the guanosine may be replaced with an analog such as 2'-deoxy-7-deazaguanosine. See ref. 21, WO 02/26757 and WO 99/62923 for examples of possible analog substitutions. The adjuvant effect of CpG oligonucleotides is further discussed in Refs. 22, 23, WO 98/40100, U.S. Pat. No. 6,207,646, U.S. Pat. No. 6,239,116, and U.S. Pat. No. 6,429,199.

The CpG sequence may be directed to TLR9, such as the motif GTCGTT or TTCGTT. See ref. 24. The CpG sequence may be specific for inducing a Th1 immune response, such as a CpG-A ODN, or it may be more specific for inducing a B cell response, such a CpG-B ODN. CpG-A and CpG-B ODNs are discussed in refs. 25, 26 and WO 01/95935. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, refs. 27, 28, 29 and WO 03/035836.

(4) ADP-Ribosylating Toxins and Detoxified Derivatives Thereof.

Bacterial ADP-ribosylating toxins and detoxified derivatives thereof may be used as adjuvants in the invention. Preferably, the protein is derived from E. coli (i.e., E. coli heat labile enterotoxin "LT"), cholera ("CT"), or pertussis ("PT"). The use of detoxified ADP-ribosylating toxins as mucosal adjuvants is described in WO 95/17211 and as parenteral adjuvants in WO 98/42375. Preferably, the adjuvant is a detoxified LT mutant such as LT-K63.

E. Human Immunomodulators

Human immunomodulators suitable for use as adjuvants in the invention include cytokines, such as interleukins (e.g. IL-1, IL-2, IL-4, IL-5, IL-6, IL-7, IL-12, etc.), interferons (e.g. interferon-γ), macrophage colony stimulating factor, and tumor necrosis factor.

F. Bioadhesives and Mucoadhesives

Bioadhesives and mucoadhesives may also be used as adjuvants in the invention. Suitable bioadhesives include esterified hyaluronic acid microspheres (Ref. 30) or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention. E.g., ref. 31.

G. Microparticles

Microparticles may also be used as adjuvants in the invention. Microparticles (i.e. a particle of ~100 nm to –150 μm in diameter, more preferably 200 nm to –30 μm in diameter, and most preferably –500-nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

H. Liposomes

Examples of liposome formulations suitable for use as adjuvants are described in U.S. Pat. No. 6,090,406, U.S. Pat. No. 5,916,588, and EP 0 626 169.

I. Polyoxyethylene ether and Polyoxyethylene Ester Formulations

Adjuvants suitable for use in the invention include polyoxyethylene ethers and polyoxyethylene esters. Ref. 32. Such formulations further include polyoxyethylene sorbitan ester surfactants in combination with an octoxynol Ref. 33) as well as polyoxyethylene alkyl ethers or ester surfactants in combination with at least one additional non-ionic surfactant such as an octoxynol (Ref. 34).

Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

J. Polyphosphazene (PCPP)

PCPP formulations are described, for example, in Ref. 35 and 36.

K. Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

L. Imidazoguinolone Compounds.

Examples of imidazoquinolone compounds suitable for use adjuvants in the invention include Imiquimod and its homologues, described further in Ref 37 and 38.

The invention may also comprise combinations of aspects of one or more of the adjuvants identified above. For example, the following adjuvant compositions may be used in the invention:

(1) a saponin and an oil-in-water emulsion (ref. 39);
(2) a saponin (e.g., QS21)+a non-toxic LPS derivative (e.g., 3dMPL) (see WO 94/00153);
(3) a saponin (e.g., QS21)+a non-toxic LPS derivative (e.g., 3dMPL)+a cholesterol;
(4) a saponin (e.g. QS21)+3dMPL+IL-12 (optionally+a sterol) (Ref. 40);
(5) combinations of 3dMPL with, for example, QS21 and/or oil-in-water emulsions (Ref. 41);
(6) SAF, containing 10% Squalane, 0.4% TWEEN® 80, 5% PLURONIC®-block polymer L121, and thr-MDP, either microfluidized into a submicron emulsion or vortexed to generate a larger particle size emulsion.
(7) RIBI™ adjuvant system (RAS), (Ribi Immunochem) containing 2% Squalene, 0.2% TWEEN® 80, and one or more bacterial cell wall components from the group consisting of monophosphorylipid A (MPL), trehalose dimycolate (TDM), and cell wall skeleton (CWS), preferably MPL+CWS (DETOX™); and
(8) one or more mineral salts (such as an aluminum salt)+a non-toxic derivative of LPS (such as 3dPML).

Aluminium salts and MF59 are preferred adjuvants for parenteral immunisation. Mutant bacterial toxins are preferred mucosal adjuvants.

The composition may include an antibiotic.

Further Antigens

The compositions of the invention may further comprise one or more additional non-GBS antigens, including additional bacterial, viral or parasitic antigens.

In another embodiment, the GBS antigen combinations of the invention are combined with one or more additional, non-GBS antigens suitable for use in a vaccine designed to protect elderly or immunocomprised individuals. For example, the GBS antigen combinations may be combined with an antigen derived from the group consisting of *Enterococcus faecalis, Staphylococcus aureus, Staphylococcus epidermis, Pseudomonas aeruginosa, Legionella pneumophila, Listeria monocytogenes, Neisseria meningitides*, influenza, and Parainfluenza virus ('PIV').

Where a saccharide or carbohydrate antigen is used, it is preferably conjugated to a carrier protein in order to enhance immunogenicity {e.g. refs. 42 to 51}. Preferred carrier proteins are bacterial toxins or toxoids, such as diphtheria or tetanus toxoids. The CRM$_{197}$ diphtheria toxoid is particularly preferred {52}. Other carrier polypeptides include the *N. meningitidis* outer membrane protein {53}, synthetic peptides {54, 55}, heat shock proteins {56, 57}, pertussis proteins {58, 59}, protein D from *H. influenzae* {60}, cytokines {61}, lymphokines, hormones, growth factors, toxin A or B from *C. difficile* {62}, iron-uptake proteins {63}, etc. Where a mixture comprises capsular saccharides from both serogroups A and C, it may be preferred that the ratio (w/w) of MenA saccharide:MenC saccharide is greater than 1 (e.g. 2:1, 3:1, 4:1, 5:1, 10:1 or higher). Different saccharides can be conjugated to the same or different type of carrier protein. Any suitable conjugation reaction can be used, with any suitable linker where necessary.

Toxic protein antigens may be detoxified where necessary e.g. detoxification of pertussis toxin by chemical and/or genetic means.

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens.

Antigens in the composition will typically be present at a concentration of at least 1 µg/ml each. In general, the concentration of any given antigen will be sufficient to elicit an immune response against that antigen.

As an alternative to using protein antigens in the composition of the invention, nucleic acid encoding the antigen may be used {e.g. refs. 64 to 72}. Protein components of the compositions of the invention may thus be replaced by nucleic acid (preferably DNA e.g. in the form of a plasmid) that encodes the protein.

DEFINITIONS

The term "comprising" means "including" as well as "consisting" e.g. a composition "comprising" X may consist exclusively of X or may include something additional e.g. X+Y.

The term "about" in relation to a numerical value x means, for example, X±10%.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of reference 73. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in reference 74.

REFERENCES

The Contents of which are Hereby Incorporated by Reference

[1] Tettelin et al. (2002) *Proc. Natl. Acad. Sci. USA,* 10.1073/pnas.182380799.
[2] International patent application WO02/34771.
3 Terpe et al., "Overview of tag protein fusions: from molecular and biochemical fundamentals to commercial systems", Appl Microbiol Biotechnol (2003) 60:523-533.
4. WO99/27961.
5. WO02/074244.
6. WO02/064162.
7. WO03/028760.
8. Gennaro (2000) *Remington: The Science and Practice of Pharmacy.* 20th ed., ISBN: 0683306472.
9. Vaccine design: the subunit and adjuvant approach (1995) Powell & Newman. ISBN 0-306-44867-X.
10. WO00/23105.
11. WO00/07621.
12. Barr, et al., "ISCOMs and other saponin based adjuvants", Advanced Drug Delivery Reviews (1998) 32:247-271. See also Sjolander, et al., "Uptake and adjuvant activity of orally delivered saponin and ISCOM vaccines", Advanced Drug Delivery Reviews (1998) 32:321-338.
13. Niikura et al., "Chimeric Recombinant Hepatitis E Virus-Like Particles as an Oral Vaccine Vehicle Presenting Foreign Epitopes", Virology (2002) 293:273-280.
14. Lenz et al., "Papillomarivurs-Like Particles Induce Acute Activation of Dendritic Cells", Journal of Immunology (2001) 5246-5355.
15. Pinto, et al., "Cellular Immune Responses to Human Papillomavirus (HPV)-16 L1 Healthy Volunteers Immunized with Recombinant HPV-16 L1 Virus-Like Particles", Journal of Infectious Diseases (2003) 188:327-338.
16. Gerber et al., "Human Papillomavrisu Virus-Like Particles Are Efficient Oral Immunogens when Coadministered with *Escherichia coli* Heat-Labile Entertoxin Nutant R192G or CpG", Journal of Virology (2001) 75(10):4752-4760.
17. Gluck et al., "New Technology Platforms in the Development of Vaccines for the Future", Vaccine (2002) 20:B10-B16.
18. Johnson et al. (1999) *Bioorg Med Clem Lett* 9:2273-2278.
19. Meraldi et al., "OM-174, a New Adjuvant with a Potential for Human Use, Induces a Protective Response with Administered with the Synthetic C-Terminal Fragment 242-310 from the circumsporozoite protein of *Plasmodium berghei*", Vaccine (2003) 21:2485-2491.
20. Pajak, et al., "The Adjuvant OM-174 induces both the migration and maturation of murine dendritic cells in vivo", Vaccine (2003) 21:836-842.
21. Kandimalla, et al., "Divergent synthetic nucleotide motif recognition pattern: design and development of potent immunomodulatory oligodeoxyribonucleotide agents with distinct cytokine induction profiles", Nucleic Acids Research (2003) 31(9): 2393-2400.
22. Krieg, "CpG motifs: the active ingredient in bacterial extracts?", Nature Medicine (2003) 9(7): 831-835.
23. McCluskie, et al., "Parenteral and mucosal prime-boost immunization strategies in mice with hepatitis B surface antigen and CpG DNA", FEMS Immunology and Medical Microbiology (2002) 32:179-185.
24. Kandimalla, et al., "Toll-like receptor 9: modulation of recognition and cytokine induction by novel synthetic CpG DNAs", Biochemical Society Transactions (2003) 31 (part 3): 654-658.
25. Blackwell, et al., "CpG-A-Induced Monocyte IFN-gamma-Inducible Protein-10 Production is Regulated by Plasmacytoid Dendritic Cell Derived IFN-alpha", J. Immunol. (2003) 170(8):4061-4068.
26. Krieg, "From A to Z on CpG", TRENDS in Immunology (2002) 23(2): 64-65.
27. Kandimalla, et al., "Secondary structures in CpG oligonucleotides affect immunostimulatory activity", BBRC (2003) 306:948-953.

28. Kandimalla, et al., "Toll-like receptor 9: modulation of recognition and cytokine induction by novel synthetic GpG DNAs", Biochemical Society Transactions (2003) 31(part 3):664-658.
29. Bhagat et al., "CpG penta- and hexadeoxyribonucleotides as potent immunomodulatory agents" BBRC (2003) 300: 853-861.
30. Singh et al. (2001) *J. Cont. Rele.* 70:267-276.
31. WO99/27960.
32. WO99/52549.
33. WO01/21207.
34. WO01/21152.
35. Andrianov et al., "Preparation of hydrogel microspheres by coacervation of aqueous polyphophazene solutions", Biomaterials (1998) 19(1-3):109-115.
36. Payne et al., "Protein Release from Polyphosphazene Matrices", Adv. Drug. Delivery Review (1998) 31(3):185-196.
37. Stanley, "Imiquimod and the imidazoquinolones: mechanism of action and therapeutic potential" Clin Exp Dermatol (2002) 27(7):571-577.
38. Jones, "Resiquimod 3M", Curr Opin Investig Drugs (2003) 4(2):214-218.
39. WO99/11241.
40. WO98/57659.
41. European patent applications 0835318, 0735898 and 0761231.
42. Ramsay et al. (2001) *Lancet* 357(9251):195-196.
43. Lindberg (1999) *Vaccine* 17 Suppl 2:S28-36.
44. Buttery & Moxon (2000) *J R Coll Physicians Lond* 34:163-168.
45. Ahmad & Chapnick (1999) *Infect Dis Clin North Am* 13:113-133, vii.
46. Goldblatt (1998) *J. Med. Microbiol.* 47:563-567.
47. European patent 0 477 508.
48. U.S. Pat. No. 5,306,492.
49. International patent application WO98/42721.
50. Conjugate Vaccines (eds. Cruse et al.) ISBN 3805549326, particularly vol. 10:48-114.
51. Hermanson (1996) Bioconjugate Techniques ISBN: 0123423368 or 012342335X.
52. Research Disclosure, 453077 (January 2002)
53. EP-A-0372501
54. EP-A-0378881
55. EP-A-0427347
56. WO93/17712
57. WO94/03208
58. WO98/58668
59. EP-A-0471177
60. WO00/56360
61. WO91/01146
62. WO00/61761
63. WO01/72337
64. Robinson & Torres (1997) *Seminars in Immunology* 9:271-283.
65. Donnelly et al. (1997) *Annu Rev Immunol* 15:617-648.
66. Scott-Taylor & Dalgleish (2000) *Expert Opin Investig Drugs* 9:471-480.
67. Apostolopoulos & Plebanski (2000) *Curr Opin Mol Ther* 2:441-447.
68. Ilan (1999) *Curr Opin Mol Ther* 1:116-120.
69. Dubensky et al. (2000) *Mol Med* 6:723-732.
70. Robinson & Pertner (2000) *Adv Virus Res* 55:1-74.
71. Donnelly et al. (2000) *Am J Respir Crit. Care Med* 162(4 Pt 2):S190-193.
72. Davis (1999) *Mt. Sinai J. Med.* 66:84-90.
73. *Current Protocols in Molecular Biology* (F. M. Ausubel et al., eds., 1987) Supplement 30.
74. Smith & Waterman (1981) *Adv. Appl. Math.* 2: 482-489.

What is claimed is:

1. A composition comprising:
   (1) a Group B *Streptococcus* (GBS) antigen combination GBS, wherein the antigen combination consists of:
      a first isolated Group B *Streptococcus* (GBS) polypeptide antigen, wherein the first isolated GBS polypeptide antigen is a GBS 80 polypeptide antigen comprising an amino acid sequence selected from the group consisting of SEQ ID NO:2, SEQ ID NO:3, SEQ ID NO:4, and SEQ ID NO:6, or an isolated fragment thereof comprising at least seven consecutive amino acids of SEQ ID NO:2, SEQ ID NO:3, SEQ ID NO:4, or SEQ ID NO:6; and
      a second isolated GBS polypeptide antigen, wherein the second isolated GBS polypeptide antigen is a GBS 322 polypeptide antigen comprising the amino acid sequence of SEQ ID NO:38 or an isolated fragment of thereof comprising at least seven consecutive amino acids of SEQ ID NO:38; and
   (2) adjuvant comprising a submicron oil-in-water emulsion of 5% squalene, 0.5% polyoxyethylene sorbitan monooleate, and 0.5% sorbitan trioleate.

2. The composition of claim 1, wherein the GBS 80 polypeptide antigen comprises the amino acid sequence of SEQ ID NO:3 or the fragment thereof comprising the least seven consecutive amino acids of SEQ ID NO:3.

3. The composition of claim 1, wherein the GBS polypeptide antigen is the isolated fragment, wherein the isolated fragment comprises the amino acid sequence of SEQ ID NO:7, SEQ ID NO:8, or SEQ ID NO:9.

4. A composition comprising:
   (1) a Group B *Streptococcus* (GBS) antigen combination, wherein the antigen combination consists of:
      a first isolated GBS polypeptide antigen comprising the amino acid sequence of SEQ ID NO:7; and
      a second isolated GBS polypeptide antigen comprising the amino acid sequence of SEQ ID NO:38; and
   (2) an adjuvant comprising a submicron oil-in-water emulsion of 5% squalene, 0.5% polyoxyethylene sorbitan monooleate, and 0.5% sorbitan trioleate.

5. The composition of claim 4, wherein the first isolated GBS polypeptide antigen comprises the amino acid sequence of SEQ ID NO:3.

6. A method of producing the composition of claim 1 for raising an immune response against the GBS comprising combining the first isolated GBS polypeptide antigen, the second isolated polypeptide antigen, and the adjuvant to produce the composition.

7. A method of raising an immune response against *Streptococcus agalactiae* in a mammal, comprising administering to the mammal the composition of claim 1.

8. The method of claim 7, wherein the GBS 80 polypeptide antigen comprises the amino acid sequence of SEQ ID NO:3 or the fragment thereof comprising the at least seven consecutive amino acids of SEQ ID NO:3.

9. The method of claim 8, wherein the GBS 80 polypeptide antigen comprises the amino acid sequence of SEQ ID NO:3.

10. The method of claim 7, wherein the GBS 322 polypeptide antigen comprises the amino acid sequence of SEQ ID NO:38.

* * * * *